(12) United States Patent
Medoff

(10) Patent No.: US 9,700,868 B2
(45) Date of Patent: Jul. 11, 2017

(54) PROCESSING BIOMASS AND PETROLEUM CONTAINING MATERIALS

(71) Applicant: Xyleco, Inc., Wakefield, MA (US)

(72) Inventor: Marshall Medoff, Brookline, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

(21) Appl. No.: 15/182,155

(22) Filed: Jun. 14, 2016

(65) Prior Publication Data

US 2016/0289705 A1    Oct. 6, 2016

Related U.S. Application Data

(63) Continuation of application No. 14/879,051, filed on Oct. 8, 2015, now Pat. No. 9,409,140, which is a (Continued)

(51) Int. Cl.
*B01J 19/08*   (2006.01)
*C12P 5/00*    (2006.01)
(Continued)

(52) U.S. Cl.
CPC ............ *B01J 19/08* (2013.01); *B01J 19/081* (2013.01); *B01J 19/085* (2013.01); *C08B 1/00* (2013.01); *C10G 3/00* (2013.01); *C10G 11/00* (2013.01); *C10G 15/10* (2013.01); *C10G 47/00* (2013.01); *C10L 1/02* (2013.01); *C10L 1/04* (2013.01); *C12P 5/00* (2013.01); *C12P 5/02* (2013.01); *C12P 5/023* (2013.01); *C12P 7/02* (2013.01); *C12P 7/04* (2013.01); *C12P 7/10* (2013.01); *C12P 7/14* (2013.01); *C12P 7/16* (2013.01); *C12P 19/02* (2013.01); *C12P 19/14* (2013.01); (Continued)

(58) Field of Classification Search
CPC ...... C12P 5/00; C12P 5/04; C12P 7/16; C12P 2203/00; C10L 1/02; C10L 2200/0469; C10L 2290/26
See application file for complete search history.

(56) References Cited

U.S. PATENT DOCUMENTS 2,896,922 A    7/1959   Pohlman
2,905,610 A    9/1959   Wigner
(Continued)

FOREIGN PATENT DOCUMENTS

CA    2673060    7/2008
GB    866752     4/1961
(Continued)

OTHER PUBLICATIONS

Yang, S-T. (2007). Bioprocessing for Value-Added Products from Renewable Resources, Elsevier, 684 pgs [Office action cites pp. 9-10].*

(Continued)

*Primary Examiner* — Brian McCaig
(74) *Attorney, Agent, or Firm* — Leber IP Law

(57) ABSTRACT

Biomass (e.g., plant biomass, animal biomass, and municipal waste biomass) is processed to produce useful products, such as fuels. For example, systems can use feedstock materials, such as cellulosic and/or lignocellulosic materials and/or starchy materials, to produce ethanol and/or butanol, e.g., by fermentation.

10 Claims, 81 Drawing Sheets

Related U.S. Application Data continuation of application No. 14/853,764, filed on Sep. 14, 2015, now Pat. No. 9,352,294, which is a continuation of application No. 14/688,393, filed on Apr. 16, 2015, now Pat. No. 9,138,715, which is a continuation of application No. 13/798,961, filed on Mar. 13, 2013, now Pat. No. 9,023,183, which is a continuation of application No. 13/042,692, filed on Mar. 8, 2011, now Pat. No. 8,454,803, which is a continuation of application No. 12/417,699, filed on Apr. 3, 2009, now Pat. No. 7,931,784.

(60) Provisional application No. 61/049,406, filed on Apr. 30, 2008, provisional application No. 61/073,665, filed on Jun. 18, 2008.

(51) Int. Cl.

| | |
|---|---|
| C12P 7/04 | (2006.01) |
| C12P 7/16 | (2006.01) |
| C10L 1/02 | (2006.01) |
| C10L 1/04 | (2006.01) |
| C10G 3/00 | (2006.01) |
| C10G 11/00 | (2006.01) |
| C10G 15/10 | (2006.01) |
| C10G 47/00 | (2006.01) |
| C12P 19/14 | (2006.01) |
| C12P 7/14 | (2006.01) |
| C08B 1/00 | (2006.01) |
| C12P 7/10 | (2006.01) |
| C12P 19/02 | (2006.01) |
| H01M 8/22 | (2006.01) |
| H01M 8/1007 | (2016.01) |
| H01M 8/1011 | (2016.01) |
| C12P 5/02 | (2006.01) |
| C12P 7/02 | (2006.01) |
| H01M 8/16 | (2006.01) |

(52) U.S. Cl.
CPC ....... *H01M 8/1007* (2016.02); *H01M 8/1013* (2013.01); *H01M 8/16* (2013.01); *H01M 8/22* (2013.01); *B01J 2219/08* (2013.01); *B01J 2219/0879* (2013.01); *C10G 2300/1011* (2013.01); *C10L 2200/0469* (2013.01); *C10L 2270/02* (2013.01); *C10L 2270/04* (2013.01); *C10L 2290/02* (2013.01); *C10L 2290/06* (2013.01); *C10L 2290/26* (2013.01); *C10L 2290/34* (2013.01); *C10L 2290/36* (2013.01); *C10L 2290/543* (2013.01); *C12P 2201/00* (2013.01); *C12P 2203/00* (2013.01); *Y02E 50/16* (2013.01); *Y02E 50/343* (2013.01); *Y02P 30/20* (2015.11); *Y02T 50/678* (2013.01)

(56) References Cited

U.S. PATENT DOCUMENTS

| | | | |
|---|---|---|---|
| 3,100,182 A | 8/1963 | Erdman et al. | |
| 3,107,206 A | 10/1963 | Ducros et al. | |
| 3,108,890 A | 10/1963 | Beaver | |
| 3,144,552 A | 8/1964 | Schonberg et al. | |
| 3,711,389 A | 1/1973 | Hook et al. | |
| 4,143,299 A | 3/1979 | Sprangle et al. | |
| 4,398,920 A * | 8/1983 | Guibet | C12P 7/28 44/438 |
| 4,537,734 A | 8/1985 | Morganstern | |
| 4,751,170 A | 6/1988 | Mimura et al. | |
| 4,769,082 A | 9/1988 | Kumakura et al. | |
| 4,956,219 A | 9/1990 | Legras et al. | |
| 5,128,543 A | 7/1992 | Reed et al. | |
| 5,417,824 A | 5/1995 | Greenbaum | |
| 5,473,165 A | 12/1995 | Stinnett et al. | |
| 5,532,495 A | 7/1996 | Bloomquist et al. | |
| 5,562,777 A * | 10/1996 | Farone | C08B 15/02 127/1 |
| 5,900,443 A | 5/1999 | Stinnett et al. | |
| 6,315,871 B1 | 11/2001 | Daulton et al. | |
| 6,454,944 B1 * | 9/2002 | Raven | C12M 21/04 210/180 |
| 6,600,164 B1 | 7/2003 | Badura et al. | |
| 6,638,895 B1 | 10/2003 | Karapetrov et al. | |
| 7,175,816 B2 | 2/2007 | Golden | |
| 7,932,065 B2 | 4/2011 | Medoff | |
| 8,052,848 B2 | 11/2011 | Kropf | |
| 8,323,458 B2 * | 12/2012 | O'Connor | C10G 1/00 204/157.15 |
| 2004/0129394 A1 | 7/2004 | Graveson et al. | |
| 2006/0145088 A1 | 7/2006 | Ma | |
| 2007/0031918 A1 | 2/2007 | Dunson et al. | |
| 2008/0047872 A1* | 2/2008 | Iaccino | C07C 2/76 208/66 |
| 2008/0057541 A1 | 3/2008 | Hill et al. | |
| 2008/0067452 A1 | 3/2008 | Moriyama et al. | |
| 2008/0299622 A1* | 12/2008 | Paulson | C12N 9/16 435/99 |
| 2008/0311637 A1 | 12/2008 | Navapanich et al. | |
| 2008/0313954 A1 | 12/2008 | Lee et al. | |
| 2009/0124839 A1* | 5/2009 | Dumesic | C07D 307/08 585/251 |
| 2010/0021980 A1* | 1/2010 | McDonald | C12P 5/023 435/161 |
| 2010/0051444 A1 | 3/2010 | Zaikin et al. | |
| 2011/0039308 A1* | 2/2011 | Slupska | C12N 9/2414 435/101 |
| 2012/0064574 A1* | 3/2012 | Tokuyasu | C12P 7/10 435/72 |
| 2012/0267544 A1 | 10/2012 | Ueda | |
| 2012/0305384 A1 | 12/2012 | Zaikin et al. | |

FOREIGN PATENT DOCUMENTS

| | | |
|---|---|---|
| JP | 928220 | 2/1997 |
| KR | 10-0873700 | 5/2008 |
| RU | 2071992 | 1/1997 |
| RU | 2154654 | 8/2000 |
| WO | 0126569 | 4/2001 |
| WO | 0126569 | 9/2002 |
| WO | 2006102543 | 9/2006 |
| WO | 2008014526 | 1/2008 |
| WO | 2008134836 | 11/2008 |

OTHER PUBLICATIONS

Lacerda, L.G. et al. (2009). Brazilian Archives of Biology and Technology, 52, 143-150.*
Moreschi, S.R.M. et al. (2004). Journal of Agricultural and Food Chemistry, 52, 1753-1758.*
Stern, M., "Electron Beam Processing of Plastics: An Alternative to Chemical Additives," in ANTEC 2000 Plastics: The Magical Solution, vol. 2, Society of Plastics Engineers, 2000, pp. 1772-1776.
Loveland, W.D. et al., "Reactors and Accelerators", Modern Nuclear Chemistry, Wiley, 2006, pp. 383-405.
Woiciechowski, A.L. et al., "Acid and Enzymatic Hydrolysis to Recover Reducing Sugars from Cassava Bagasse: an Economic Study", Brazilian Archives of Biology and Technology, 45(3), Sep. 2002, pp. 393-400.
Mussatto, S.I. et al., "Lignocellulose as Raw Material in Fermentation Processes", Current Research, Technology and Education: Topics in Applied Microbiology and Microbial Technology, vol. 2, 2010, pp. 897-907.
Kumar, P. et al., "Methods for Pretreatment of Lignocellulosic Biomass for Efficient Hydrolysis and Biofuel Production", Industrial & Engineering Chemistry Research, Vol. 48, 2009, pp. 3713-3729.
Iller et al., "Electron-Beam Stimulation of the Reactivity of Cellulose Pulps for Production of Derivatives", Radiation Physics and Chemistry, vol. 63, 2002, pp. 253-257.

(56) References Cited

OTHER PUBLICATIONS

Written Opinion for PCT/US2009/041896, mailed Jan. 28, 2010, 9 pages.
Scharf, W. et al., "Electron Accelerators for Industrial Processing—A Review", Waraw University of Technology, Nowowiejska Street 15/19, PL 00-665, Warsaw, Poland, 19 pages, Date unknown.
Cleland, M.R., "Industrial Application of Electron Accelerators," presented at the CERN Accelerator School Small Accelerator Course, May 24-Jun. 2, 2005, 135 pgs.
Zhou et al., "Effects of Ion Beam Irradiation on Adventitious Shoot Regeneration from In Vitro Leaf Explants of Saintpaulia Ionahta", Nucl. Instr. and Meth. in Phys. Res. B, vol. 244, 2006, pp. 349-353.
Moroz et al., "Optical Alteration of Complex Organics Induced by Ion Irradiation: 1. Laboratory Experiments Suggest Unusual Space Weathering Trend," Icarus, Elsevier, [Online] vol. 170, Mar. 27, 2004, pp. 214-228, XP002557447.
Dong et al., "The Influence of Carbon Ion Irradiation on Sweet Sorghum Seeds," Nuclear Instruments and Methods in Physics Research, Section B: Beam Interactions with Materials and Atoms, Elsevier, Amsterdam, NL, vol. 266, No. 1, Nov. 1, 2007, pp. 123-126, XP022409319.
Blouin et al., "Thermal Neutron Irradiation of Cotton," Textile Research Journal, 1961, vol. 31, pp. 597-602.
PCT Invitation for PCT/US2009/041896, mailed Sep. 29, 2009, 6 pages.
ISR for PCT/US2009/041896, mailed Jan. 28, 2010, 5 pages.
Biermann, C., "Pulping Fundamentals", Handbook of Pulp and Papermaking, 2nd ed. Elsevier, 841 pgs. (Chapter 3), 1996.
Orkla Stock Exchange Release of Jan. 12, 2004 [see http://www.orkla.com/Investor-relations/GA-General-Archive/Press-and-stock-exchange-releases/Stock-exchange-releases/Borregaard-sells-book-paper-and-mechanical-pulp-business].
Kumakura, M. et al., "Effect of Radiation Pretreatment of Bagasse on Enzymatic and Acid Hydrolysis", Biomass, vol. 3 (3), 1983, pp. 199-208.
Scharf, W., "Particle Accelerators and Their Uses", 3rd ed. Routledge, 1986, 1050 pgs.
Wilson, E.J.N., "Applications of Accelerators", An Introduction to Particle Accelerators, Oxford University Press, 2001, 272 pgs. (Chapter 13).
Emmett, P.H., Catalysis, vol. 2, Reinhold Publishing, 1955, 473 pgs. (p. 25).
Zimek et al., "Short Pulse Electron Accelerator for Pulse Radiolysis Study", Proceedings of the EPAC, Vienne Austria, 2000, pp. 2379-2381.
Jongen, Y. et al., "Rhodotron Accelerators for Industrial Electron-Beam Processing: A Progress Report", Proceedings of the EPAC, Bristol, U.K., 1996, pp. 2687-2692.
Defrise, D. et al., "Technical Status of the First Industrial Unit of the 10 MeV, 100 kW Rhodotron", Radiation Physics and Chemistry, vol. 46-4-6, 1995, pp. 473-476.
Bassaler, J.M. et al., "Rhodotron: an Accelerator for Industrial Irradiation", Nuclear Instruments and Methods in Physics Research B, vol. 68, 1992, pp. 92-95.
Martinez, J.M. et al., "Hydrolytic Pretreatment of Softwood and Almond Shells. Degree of Polymerization and Enzymatic Digestibility of the Cellulose Fraction", Ing. Eng. Chem. Res. vol. 36, 1997, pp. 688-696.
Hawley's Condensed Chemical Dictionary, 14th ed. "Fuel", John Wiley & Sons, 2002.
Yamaguchi, H. et al., "Mutation Induced with Ion Beam Irradiation in Rose", Nuclear Instruments and Methods in Physics Research, B 206 (2003), pp. 561-564.
Ershov, B.G., "Radiation-Chemical Degradation of Cellulose and other Polysaccharides," Russian Chemical Reviews, 67(4) 315-334 (1998).
Seymour and Carraher, Polymer Chemistry: An Introduction 3rd ed., Marcel Dekker Inc., 1992, Chapter 15, p. 420, para. 7, lines 1-6.
Zekonyte et al., "Mechanisms of Argon Ion-Beam Surface Modification of Polystyrene," Surface Science (2003), vol. 532-535, pp. 1040-1044.
Ermer et al., "Deuterium Depth Profiling in Polymers Using Heavy Ion Elastic Recoil Detection," Nuclear Instruments and Methods in Physics Research B, vol. 134 (1998), pp. 237-248.
Lee et al., "Microstructure and Adhesion of Au Deposited on Parylene-c Substrate with Surface Modification for Potential Immunoassay Application," IEEE Transactions on Plasma Science, vol. 32, No. 2, Apr. 2004.
Alberti, A. et al., "Electron Beam Irradiated Textile Cellulose Fibres, ESR Studies and Derivatisation with Glycidyl Methacrylate (GMA)", European Polymer Journal, vol. 41, 2005, pp. 1787-1797.
Office Action, Corresponding U.S. Appl. No. 14/879,051, dated Feb. 26, 2016, 20 pages.
Kumakura, M. et al., "Radiation-Induced Decomposition and Enzymatic Hydrolysis of Cellulose", Biotechnology and Bioengineering, vol. 20, No. 8, 1978, pp. 1309-1315.
Office Action, Corresponding U.S. Appl. No. 14/853,764, dated Dec. 23, 2015, 16 pages.
Han, Y.W. et al., "Effect of High-Energy Radiation on Lignocellulose Conversion", Annual Reports on Fermentation Processes, vol. 6, 1983, pp. 299-322.

* cited by examiner

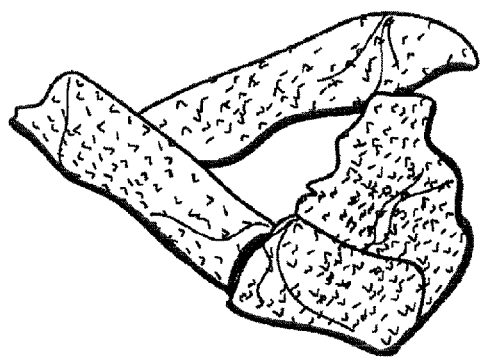
FIG. 7A
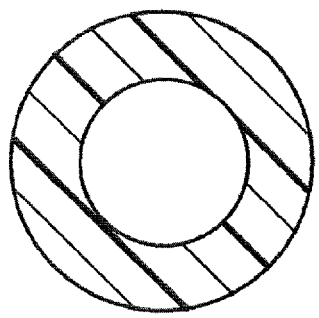 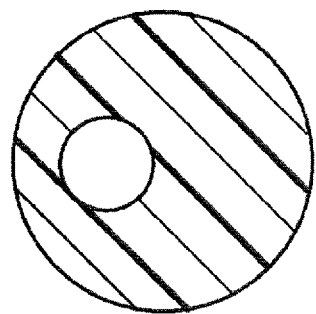
FIG. 7B  FIG. 7C
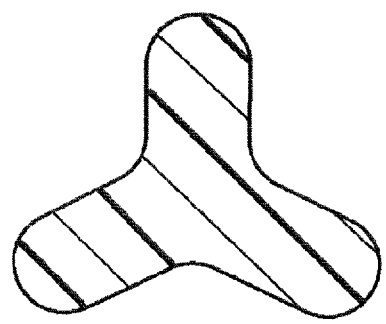
FIG. 7D

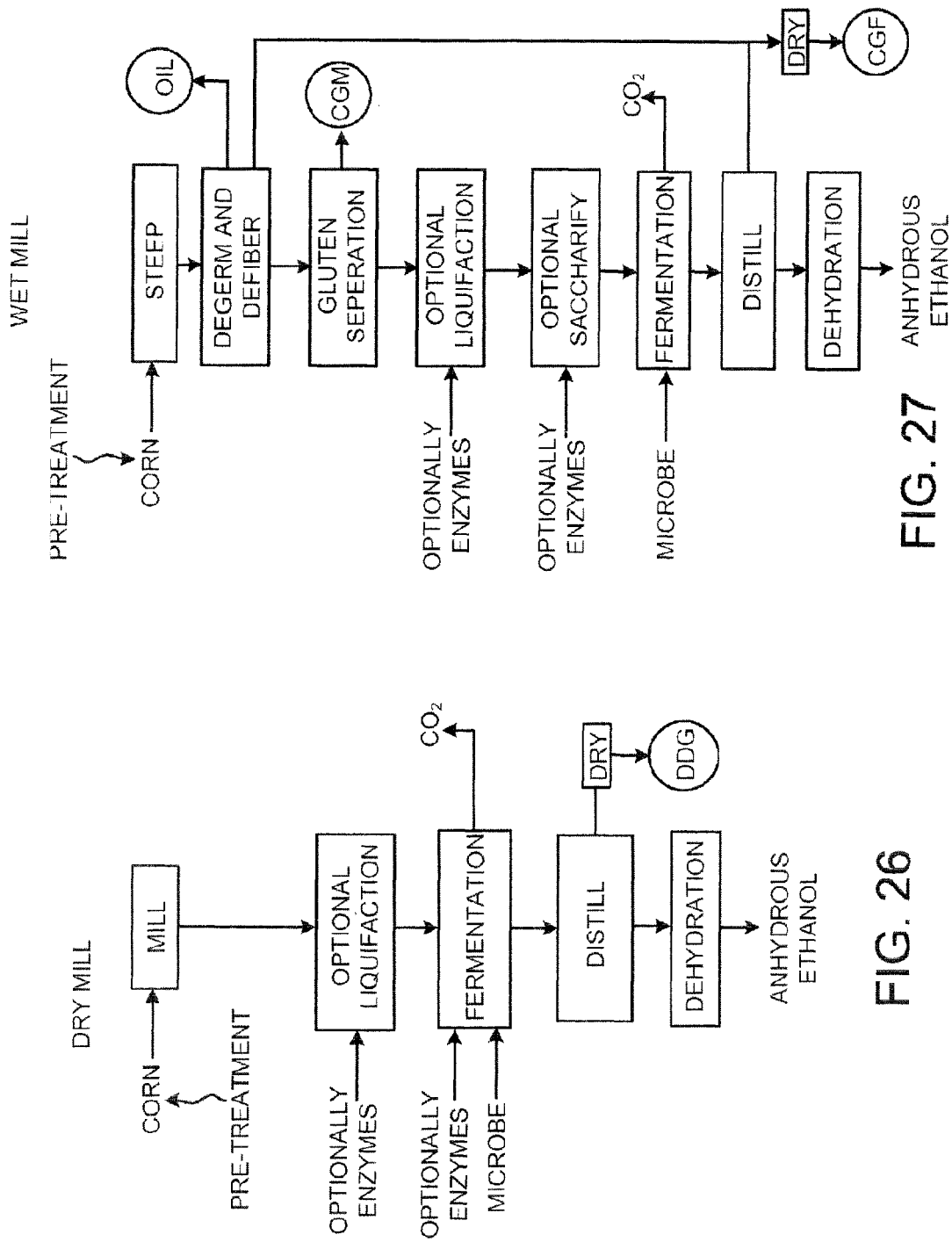

Sample Data
    ID1.................................................P30E
    Sample Size..........................1.00g.

End Points

Det U   Det U.1
    Ep1.....................49.8 mV........0.6415 mL
Results
    Res01.......................................0.000

Det U.1 - Det U

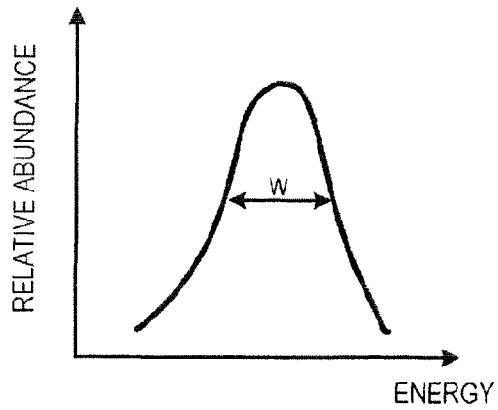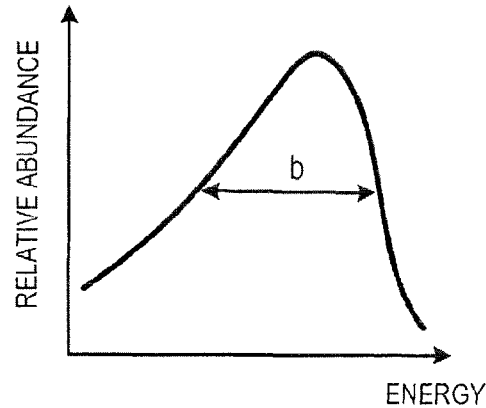
FIG. 56A  FIG. 56B
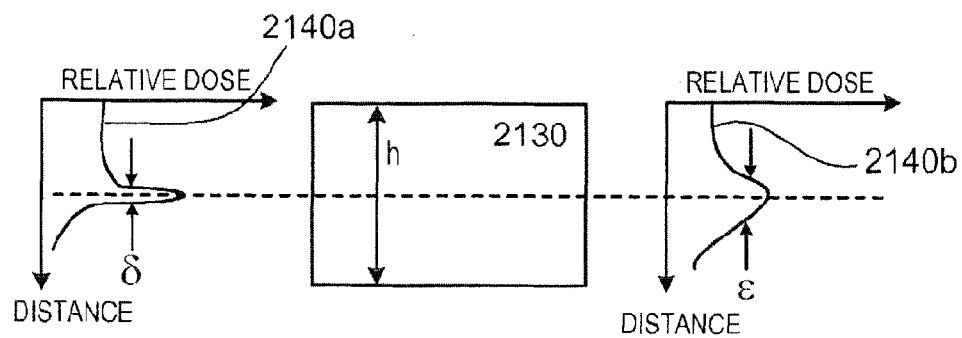
FIG. 56C
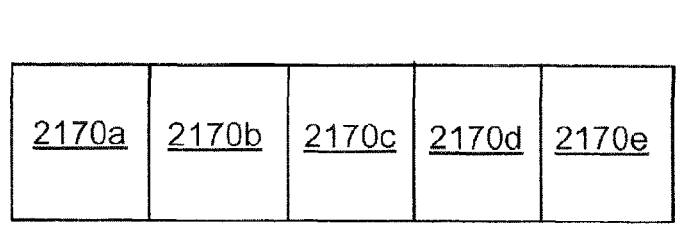
FIG. 57

PROCESSING BIOMASS AND PETROLEUM CONTAINING MATERIALS

RELATED APPLICATIONS

This application is a continuation of U.S. Ser. No. 14/879,051 filed on Oct. 8, 2015, now U.S. Pat. No. 9,409,140, issued Aug. 9, 2016, which is a continuation of U.S. Ser. No. 14/853,764, filed Sep. 14, 2015, now U.S. Pat. No. 9,352,294, issued May 31, 2016, which is a continuation of U.S. Ser. No. 14/688,393, filed Apr. 16, 2015, now U.S. Pat. No. 9,138,715, issued Sep. 22, 2105, which is a continuation of U.S. Ser. No. 13/798,961, filed Mar. 13, 2013, now U.S. Pat. No. 9,023,183, issued on May 5, 2015, which is a continuation of U.S. Ser. No. 13/042,692, filed Mar. 8, 2011, now U.S. Pat. No. 8,454,803, issued on Jun. 4, 2013, which is a continuation of U.S. Ser. No. 12/417,699, filed Apr. 3, 2009, now U.S. Pat. No. 7,931,784, issued on Apr. 26, 2011, which claims priority from U.S. Provisional Application Ser. Nos. 61/049,406, filed Apr. 30, 2008, and 61/073,665, filed Jun. 18, 2008. The full disclosure of each of these applications is incorporated by reference herein.

TECHNICAL FIELD

This invention relates to processing biomass and petroleum-containing materials.

BACKGROUND

Biomass, particularly biomass waste, is abundantly available. It would be useful to derive materials and fuel, such as ethanol, from biomass.

It would also be useful to more efficiently process petroleum-containing materials to obtain fuels and other products.

SUMMARY

Biomass can be processed to alter its structure at one more levels. The processed biomass can then be used as source of materials and fuel.

Many embodiments of this application use Natural Force™ Chemistry. Natural Force™ Chemistry methods use the controlled application and manipulation of physical forces, such as particle beams, gravity, light, etc., to create intended structural and chemical molecular change. In preferred implementations, Natural Force™ Chemistry methods alter molecular structure without chemicals or microorganisms. By applying the processes of Nature, new useful matter can be created without harmful environmental interference.

A method for changing a molecular and/or a supramolecular structure of any biomass material includes treating the biomass material with radiation. In particular, the radiation can include particles, particularly charged particles. Charged particles include ions, such as positively charged ions, such as protons, carbon or oxygen ions. For example, the charged particles typically are heavier than an electron or have a different charge than an electron (e.g., a positron). The radiation can be applied in an amount sufficient to change the molecular structure and/or supramolecular structure of the biomass material. The biomass material can include carbohydrates or materials that include carbohydrates, e.g., cellulosic materials, lignocellulosic materials, starchy materials, or mixtures of any biomass materials. The radiation-treated material can be used to produce a product.

Particles having a different charge than electrons and/or particles heavier than electrons can be utilized for the irradiation. For example, protons, helium nuclei, argon ions, silicon ions, neon ions, carbon ions, phoshorus ions, oxygen ions or nitrogen ions can be utilized to modify the structure of the biomass, e.g., breakdown the molecular weight or increase the molecular weight of the biomass. In some embodiments, heavier particles can induce higher amounts of chain scission in comparison to electrons or photons. In addition, in some instances, positively charged particles can induce higher amounts of chain scission than negatively charged particles due to their acidity.

A method for making and processing materials from biomass can include functionalizing materials with one or more desired types and amounts of functional groups, and products made from the structurally changed materials. For example, many of the methods described herein can provide cellulosic and/or lignocellulosic materials that have a lower molecular weight and/or crystallinity relative to a native material. Many of the methods provide materials that can be more readily utilized by a variety of microorganisms to produce useful products, such as hydrogen, alcohols (e.g., ethanol or butanol), organic acids (e.g., acetic acid), hydrocarbons, co-products (e.g., proteins) or mixtures of any of these.

In some instances, functionalized biomass is more soluble and more readily utilized by microorganisms in comparison to un-functionalized biomass. In addition, many of the functionalized materials described herein are less prone to oxidation and can have enhanced long-term stability (e.g., oxidation in air under ambient conditions). Many of the products obtained, such as ethanol or n-butanol, can be utilized as a fuel for powering cars, trucks, tractors, ships or trains, e.g., as an internal combustion fuel or as a fuel cell feedstock. Many of the products obtained can also be utilized to power aircraft, such as planes, e.g., having jet engines or helicopters. In addition, the products described herein can be utilized for electrical power generation, e.g., in a conventional steam generating plant or in a fuel cell plant.

In some embodiments, materials include a cellulosic or lignocellulosic material.

In one aspect, the invention features methods of changing a molecular and/or a supramolecular structure of any biomass material that include pretreating the biomass material with radiation including charged particles (e.g., accelerated charged particles), such as those heavier than an electron or having a different charge than an electron (e.g., a positron), to change the molecular structure and/or supramolecular structure of the biomass material, and processing the pretreated biomass material to produce a product. Prior to pretreating, the biomass material can be optionally prepared by reducing one or more dimensions of individual pieces of the biomass material. Charged particles include ions, such as positively charged ions, such as protons, carbon or oxygen ions. Charged particles that are used to pretreat biomass can have velocities of, e.g., from 0.05 c to about 0.9999 c, where c represents the vacuum velocity of light.

In another aspect, the invention features methods of making a product from biomass, such as a combustible fuel or a fuel for a fuel cell, such as ethanol, butanol, hydrogen, hydrocarbons or mixtures of any of these, that include providing a material that includes a carbohydrate, such as oligomeric and/or monomeric carbohydrates or derivative and analogs thereof, produced by a process that includes pretreating a biomass feedstock with radiation that includes charged particles heavier than an electron, such as ions, such as positively charged ions, such as protons or carbon ions, optionally together with one or more other pretreatments selected from the group consisting of photonic radiation, sonication, pyrolysis, and oxidation, and contacting the material that includes the carbohydrate with a microorganism, such as a blend of bacteria, having the ability to convert at least a portion, e.g., at least about 1, 2, 3, 4, or 5 percent by weight, of the material to the product, such as the combustible fuel.

The dose of radiation utilized depends upon the type and degree of modification that is desired and the kind of radiation employed. For example, to break down structures with electrons can require, e.g., greater than about 10 MRad, whereas protons, which are more massive than an electron and can deliver a larger effective dose, may require only 1 MRad.

In one aspect, the invention features a method that includes exposing a biomass material to charged particles having a mass greater than or equal to the mass of a proton, wherein exposing the biomass material comprises directing the charged particles to pass through a fluid, and then directing the charged particles to be incident on the biomass material.

In some implementations the fluid is selected from the group consisting of air, oxygen, hydrogen, and reactive gases.

In another aspect, the invention features a method of treating biomass, the method including: forming a plurality of negatively charged ions, and accelerating the negatively charged ions to a first energy; removing a plurality of electrons from at least some of the negatively charged ions to form positively charged ions; accelerating the positively charged ions to a second energy, and directing the positively charged ions to be incident on the biomass.

Some embodiments may include one or more of the following features. Removing the plurality of electrons from at least some of the negatively charged ions can include directing the negatively charged ions to be incident on a metal foil. Accelerating the negatively charged ions to a first energy can include directing the ions to pass through a plurality of electrodes at different electrostatic potentials. The method can further include altering trajectories of the positively charged ions before the ions are accelerated to the second energy.

In yet another aspect, the invention features a method of treating biomass that includes generating a plurality of charged particles; accelerating the plurality of charged particles by directing each of the charged particles to make multiple passes through an accelerator cavity comprising a time-dependent electric field; and exposing the biomass to the accelerated charged particles.

Some embodiments may include one or more of the following features. An orientation of the electric field can be selected to correspond to a direction of motion of the charged particles in the accelerator cavity.

In a further aspect, the invention features a method of treating biomass that includes generating a plurality of charged particles; accelerating the plurality of charged particles by directing the charged particles to pass through an acceleration cavity comprising multiple electrodes at different potentials; and exposing the biomass to the accelerated charged particles.

In another aspect, the invention features a method of treating biomass that includes generating a plurality of charged particles; accelerating the plurality of charged particles by directing the charged particles to pass through an accelerator comprising multiple waveguides, wherein each waveguide comprises an electromagnetic field; and exposing the biomass to the accelerated charged particles.

Some embodiments include one or more of the following features. The electromagnetic field in each of the waveguides can be a time-varying field. The electromagnetic field in each of the waveguides can be generated by a microwave field source. The electromagnetic fields in each of the waveguides can be generated to coincide with passage of the charged particles through each of the waveguides.

Any of the methods discussed herein can include one or more of the following features. Some embodiments may include one or more of the following features. The charged particles may include ions, in some cases two or more different types of ions. The charged particles may be negatively charged. The charged particles can be selected from the group consisting of hydrogen ions, carbon ions, oxygen ions, nitrogen ions, halogen ions, and noble gas ions. The method can further include exposing the biomass to a plurality of electrons.

In yet another aspect, the invention features a method that includes exposing a petroleum-containing material to an ion beam, and processing the petroleum-containing material to extract a hydrocarbon component from the petroleum-containing material.

Some implementations may include one or more of the following features. The ion beam can include positively charged ions. The ion beam can include at least one of protons, carbon ions, oxygen ions, and noble gas ions. In some cases, the ion beam includes at least one of platinum ions, palladium ions, rhenium ions, iridium ions, ruthenium ions, aluminum ions, nickel ions, and osmium ions. The petroleum-containing material can include crude oil, in which case the crude oil can in some cases be exposed to the ion beam before the crude oil is refined. Processing the petroleum containing material can include refining at least a portion of the material in at least one step selected from the group consisting of a catalytic cracking process, a catalytic reforming process, a catalytic hydrocracking process, and an alkylation process. The method can further include exposing the material to an electron beam, and/or exposing the material to a reactive gas, such as ozone, during exposure of the material to the ion beam. Exposing the material to the ion beam can include exposing the material to a first type of ions from a first ion beam, and exposing the material from a second type of ions from a second ion beam. In some cases, the first and second types of ions have different charges, and/or different masses. During exposure to the ion beam the material can be flowing.

In another aspect, the invention features methods of changing a molecular and/or a supramolecular structure of a biomass feedstock that include 1) irradiating the biomass feedstock with radiation, such as photons, electrons or ions of sufficient energy to ionize the biomass feedstock, to provide a first level of radicals; and 2) quenching the radicals to an extent that the radicals are at a second level lower than the first level. The irradiated biomass feedstock can be processed to produce a product. The first level of radicals may be detectable, e.g., with an electron spin resonance spectrometer. For example, the second level can be detectably less than the first level, or a level that that is no longer detectable with the electron spin resonance spectrometer, e.g., such as at a level of less than about $10^{14}$ spins. If desired, prior to irradiation and/or after irradiation, the biomass feedstock can be prepared by reducing one or more dimensions of individual pieces of the biomass feedstock.

In another aspect, the invention features methods of making a product, such as a fuel, such as a combustible fuel, such as a motor, an aviation fuel or a fuel cell fuel, e.g., for generating electricity, that include a) providing a material that includes a carbohydrate produced by a process comprising 1) irradiating a biomass feedstock with ionizing radiation to provide a first level of radicals, and 2) quenching the radicals to an extent that the radicals are present at a second level lower than the first level. The material can then be contacted with a microorganism, e.g., to convert the material, for example to a product such as a combustible fuel. The microorganism can have the ability to convert at least a portion, e.g., at least about 1, 2, 3, 4, or 5 percent by weight, of the biomass to the product.

Examples of biomass feedstock include paper, paper products, paper waste, wood, particle board, sawdust, agricultural waste, sewage, silage, grasses, rice hulls, bagasse, cotton, jute, hemp, flax, bamboo, sisal, abaca, straw, corn cobs, corn stover, switchgrass, alfalfa, hay, rice hulls, coconut hair, cotton, synthetic celluloses, seaweed, algae, or mixtures of these. The biomass can be or can include a natural or a synthetic material.

Examples of fuels include one or more of hydrogen, alcohols, and hydrocarbons. For example, the alcohols can be ethanol, n-propanol, isoproanol, n-butanol, or mixtures of these.

In some examples, the biomass feedstock can be prepared by shearing a biomass fiber source to provide a fibrous material. For example, the shearing can be performed with a rotary knife cutter. The fibers of the fibrous material can have, e.g., an average length-to-diameter ratio of greater than 5/1. The fibrous material can have, e.g., a BET surface area of greater than 0.25 $m^2/g$.

In some embodiments, the pretreated biomass material can further include a buffer, such as sodium bicarbonate or ammonium chloride, an electrolyte, such as potassium chloride or sodium chloride a growth factor, such as biotin and/or a base pair such as uracil, a surfactant, a mineral, or a chelating agent.

In some embodiments, the biomass is sheared, and the sheared biomass can include discrete fibers having a length-to-diameter ratio (L/D) of greater than about 5/1. For example, the biomass can have internal fibers, and the biomass has been sheared to an extent that its internal fibers are substantially exposed. For example, the biomass has been sheared to an extent that it has a bulk density of less than about 0.35 $g/cm^3$. Low bulk density materials can be deeply penetrated by charged particles. For example, for electrons at an average energy of 5 MeV and a material with a bulk density of 0.35 $g/cm^3$, electron penetration depths can be 5-7 inches or more.

In still another aspect, the invention features a system that includes: one or more of: (1) a biomass reservoir, (2) a particle beam source (e.g., an accelerator), and (3) a delivery module for moving biomass from the biomass reservoir into range of the particle beam. The system can be designed for continuous processing of biomass. See e.g., conveyance and processing methods described in Ser. No. 61/049,404. In certain cases, the particle beam source provides a beam of at least 20, 40, or 60 cm in length and biomass (e.g., switchgrass, stover, or other plant waste) is located in the beam.

To further aid in the reduction of the molecular weight of the cellulose, an enzyme, e.g., a cellulolytic enzyme, or a chemical, e.g., sodium hypochlorite, an acid, a base or a swelling agent, can be utilized with any method described herein. The enzyme and/or chemical treatment can occur before, during or after sonication.

In some embodiments, no chemicals, e.g., no swelling agents, are added to the biomass prior to irradiation. For example, alkaline substances (such as sodium hydroxide, potassium hydroxide, lithium hydroxide and ammonium hydroxides), acidifying agents (such as mineral acids (e.g., sulfuric acid, hydrochloric acid and phosphoric acid)), salts, such as zinc chloride, calcium carbonate, sodium carbonate, benzyltrimethylammonium sulfate, or basic organic amines, such as ethylene diamine, is added prior to irradiation or other processing. In some cases, no additional water is added. For example, the biomass prior to processing can have less than 0.5 percent by weight added chemicals, e.g., less than 0.4, 0.25, 0.15 or 0.1 percent by weight added chemicals. In some instances, the biomass has no more than a trace, e.g., less than 0.05 percent by weight added chemicals, prior to irradiation. In other instances, the biomass prior to irradiation has substantially no added chemicals or swelling agents. Avoiding the use of such chemicals can also be extended throughout, e.g., at all times prior to fermentation, or at all times.

When a microorganism is utilized, it can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures may be utilized. Generally, various microorganisms can produce a number of useful products, such as a fuel, by operating on, e.g., fermenting the materials. For example, alcohols, organic acids, hydrocarbons, hydrogen, proteins or mixtures of any of these materials can be produced by fermentation or other processes.

In some embodiments, the method may include passing sheared material through one or more screens, e.g., a screen having an average opening size of 1.59 mm or less (0.0625 inch). Screening separates the material according to size. For example, in one embodiment, the method includes: shearing the fiber source to produce a sheared fiber source; passing the sheared fiber source through a first screen to produce a screened fiber source; shearing the screened fiber source to produce a second sheared fiber source; passing the second sheared fiber source through a second screen having an average opening size less than the first screen to provide a second screened fiber source; and steam exploding the second screened fiber source to produce the fibrous material. The method may further include shearing the second screened fiber source to produce a third sheared fiber source, and then steam exploding the third sheared fibers source to produce the fibrous material.

It is also possible to shear the fiber source and concurrently pass it through a screen.

The methods may also further include encapsulating the fibrous material in a substantially gas impermeable material to remove entrapped gas and densify the fibrous material. The substantially gas impermeable material may be soluble in water, and may be provided in the form of a bag.

Examples of products that may be produced include mono- and polyfunctional C1-C6 alkyl alcohols, mono- and poly-functional carboxylic acids, C1-C6 hydrocarbons, and combinations thereof. Specific examples of suitable alcohols include methanol, ethanol, propanol, isopropanol, butanol, ethylene glycol, propylene glycol, 1,4-butane diol, glycerin, and combinations thereof. Specific example of suitable carboxylic acids include formic acid, acetic acid, propionic acid, butyric acid, valeric acid, caproic acid, palmitic acid, stearic acid, oxalic acid, malonic acid, succinic acid, glutaric acid, oleic acid, linoleic acid, glycolic acid, lactic acid, γ-hydroxybutyric acid, and combinations thereof. Examples of suitable hydrocarbons include methane, ethane, propane, pentane, n-hexane, and combinations thereof. Many of these products may be used as fuels.

The term "fibrous material," as used herein, is a material that includes numerous loose, discrete and separable fibers. For example, a fibrous material can be prepared from a bleached Kraft paper fiber source by shearing, e.g., with a rotary knife cutter.

The term "screen," as used herein, means a member capable of sieving material according to size. Examples of screens include a perforated plate, cylinder or the like, or a wire mesh or cloth fabric.

The term "pyrolysis," as used herein, means to break bonds in a material by the application of heat energy. Pyrolysis can occur while the subject material is under vacuum, or immersed in a gaseous material, such as an oxidizing gas, e.g., air or oxygen, or a reducing gas, such as hydrogen.

Oxygen content is measured by elemental analysis by pyrolyzing a sample in a furnace operating at 1300° C. or above.

For the purposes of this disclosure, carbohydrates are materials that are composed entirely of one or more saccharide units or that include one or more saccharide units. The saccharide units can be functionalized about the ring with one or more functional groups, such as carboxylic acid groups, amino groups, nitro groups, nitroso groups or nitrile groups and still be considered carbohydrates. Carbohydrates can be polymeric (e.g., equal to or greater than 10-mer, 100-mer, 1,000-mer, 10,000-mer, or 100,000-mer), oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different.

Examples of polymeric carbohydrates include cellulose, xylan, pectin, and starch, while cellobiose and lactose are examples of dimeric carbohydrates. Examples of monomeric carbohydrates include glucose and xylose.

Carbohydrates can be part of a supramolecular structure, e.g., covalently bonded into the structure. Examples of such materials include lignocellulosic materials, such as that found in wood.

A starchy material is one that is or includes significant amounts of starch or a starch derivative, such as greater than about 5 percent by weight starch or starch derivative. For purposes of this disclosure, a starch is a material that is or includes an amylose, an amylopectin, or a physical and/or chemical mixture thereof, e.g., a 20:80 or 30:70 percent by weight mixture of amylose to amylopectin. For example, rice, corn, and mixtures thereof are starchy materials. Starch derivatives include, e.g., maltodextrin, acid-modified starch, base-modified starch, bleached starch, oxidized starch, acetylated starch, acetylated and oxidized starch, phosphate-modified starch, genetically-modified starch and starch that is resistant to digestion.

For purposes of this disclosure, a low molecular weight sugar is a carbohydrate or a derivative thereof that has a formula weight (excluding moisture) that is less than about 2,000, e.g., less than about 1,800, 1,600, less than about 1,000, less than about 500, less than about 350 or less than about 250. For example, the low molecular weight sugar can be a monosaccharide, e.g., glucose or xylose, a disaccharide, e.g., cellobiose or sucrose, or a trisaccharide.

A combustible fuel is a material capable of burning in the presence of oxygen. Examples of combustible fuels include ethanol, n-propanol, n-butanol, hydrogen and mixtures of any two or more of these.

Swelling agents as used herein are materials that cause a discernable swelling, e.g., a 2.5 percent increase in volume over an unswollen state of cellulosic and/or lignocellulosic materials, when applied to such materials as a solution, e.g., a water solution. Examples include alkaline substances, such as sodium hydroxide, potassium hydroxide, lithium hydroxide and ammonium hydroxides, acidifying agents, such as mineral acids (e.g., sulfuric acid, hydrochloric acid and phosphoric acid), salts, such as zinc chloride, calcium carbonate, sodium carbonate, benzyltrimethylammonium sulfate, and basic organic amines, such as ethylene diamine.

A "sheared material," as used herein, is a material that includes discrete fibers in which at least about 50% of the discrete fibers, have a length/diameter (L/D) ratio of at least about 5, and that has an uncompressed bulk density of less than about 0.6 g/cm$^3$. A sheared material is thus different from a material that has been cut, chopped or ground.

Changing a molecular structure of a biomass feedstock, as used herein, means to change the chemical bonding arrangement, such as the type and quantity of functional groups or conformation of the structure. For example, the change in the molecular structure can include changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or an changing an overall domain size.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

In any of the methods disclosed herein, radiation may be applied from a device that is in a vault.

This application incorporates by reference herein the entire contents of International Application No. PCT/US2007/022719, filed Oct. 26, 2007. The full disclosures of each of the following U.S. patent applications, which are being filed concurrently herewith, are hereby incorporated by reference herein: Ser. Nos. 12/417,707, 12/417,720, 12/417,840, 12/417,731, 12/417,900, 12/417,880, 12/417,723, 12/417,786 and 12/417,904.

The entire contents of each of the following publications are incorporated herein by reference: J. R. Adney et al., IEEE Transactions on Nuclear Science, Vol. NS-32, pp. 1841-1843 (1985); J. R. Adney et al., Proceedings of the 1989 IEEE Particle Accelerator Conference, Vol. 1, pp. 348-350 (1989); J. A. Ferry et al., Nuclear Instruments and Methods in Physics Research, Vol. B64, pp. 309-312 (1992); J. Ferry, in Handbook of Accelerator Physics and Engineering, pp. 16-17 (1999); J. A. Ferry et al., Nuclear Instruments and Methods in Physics Research A, Vol. 382, pp. 316-320 (1996); J. A. Ferry, Nuclear Instruments and Methods in Physics Research A, Vol. 328, pp. 28-33 (1993); T. M. Hauser et al., Nuclear Instruments and Methods in Physics Research B, Vol. 249, pp. 932-934 (2006); R. G. Herb, in Encyclopedia of Physics, pp. 3-8 (1981); R. G. Herb et al., in Encyclopedia of Applied Physics, Vol. 1, pp. 27-42 (1991); R. G. Herb, IEEE Transactions on Nuclear Science, Vol. NS-30, pp. 1359-1362 (1983); R. G. Herb, Proceedings of the Third International Conference on Electrostatic Accelerator Technology (1981); G. M. Klody et al., Nuclear Instruments and Methods in Physics Research B, Vol. 56-57, pp. 704-707 (1991); G. M. Klody et al., Nuclear Instruments and Methods in Physics Research B, Vol. 240, pp. 463-467 (2005); R. L. Loger, Application of Accelerators in Research and Industry, Proceedings of the Fifteenth International Conference, pp. 640-643 (1999); G. A. Norton et al., Nuclear Instruments and Methods in Physics Research B, Vol. 40-41, pp. 785-789 (1989); G. A. Norton et al., Application of Accelerators in Research and Industry, Proceedings of the Fourteenth International Conference, pp. 1109-1114 (1997); G. Norton et al., Handbook of Accelerator Physics and Engineering, pp. 24-26 (1999); G. A. Norton et al., Symposium of North Eastern Accelerator Personnel, pp. 295-301 (1992); G. Norton, Pramana, Vol. 59, pp. 745-751 (2002); G. A. Norton et al., Nuclear Instruments and Methods in Physics Research B, Vol. 37-38, pp. 403-407 (1989); G. A. Norton, Heavy Ion Accelerator Technology: Eighth International Conference, pp. 3-23 (1999); J. E. Raatz et al., Nuclear Instruments and Methods in Physics Research A, vol. 244, pp. 104-106 (1986); R. D. Rathmell et al., Nuclear Instruments and Methods in Physics Research B, vol. 56-57, pp. 1072-1075 (1991); J. B. Schroeder et al., Nuclear Instruments and Methods in Physics Research B, Vol. 56-57, pp. 1033-1035 (1991); J. B. Schroeder, Nuclear Instruments and Methods in Physics Research B, Vol. 40-41, pp. 535-537 (1989); J. B. Schroeder et al., Radiocarbon, Vol. 46 (2004); J. B. Schroeder et al., Nuclear Instruments and Methods in Physics Research B, Vol. 24-25, pp. 763-766 (1987); P. H. Stelson et al., Nuclear Instruments and Methods in Physics Research A, Vol. 244, pp. 73-74 (1986); M. L. Sundquist et al., Nuclear Instruments and Methods in Physics Research B, Vol. 99, pp. 684-687 (1995); M. L. Sundquist et al., Nuclear Instruments and Methods in Physics Research A, Vol. 287, pp. 87-89 (1990); and M. L. Sundquist, Applications of Accelerators in Research and Industry, Proceedings of the Fifteenth International Conference, pp. 661-664 (1999). All other patents, patent applications, and references cited herein are also incorporated by reference.

Other features and advantages of the invention will be apparent from the following detailed description, and from the claims.

DESCRIPTION OF DRAWINGS

FIG. 7A is a densified fibrous material in pellet form.

FIG. 7B is a transverse cross-section of a hollow pellet in which a center of the hollow is in-line with a center of the pellet.

FIG. 7C is a transverse cross-section of a hollow pellet in which a center of the hollow is out of line with the center of the pellet.

FIG. 7D is a transverse cross-section of a tri-lobal pellet.

FIG. 26 is a block diagram illustrating a dry milling process for corn kernels.

FIG. 27 is a block diagram illustrating a wet milling process for corn kernels.

FIG. 32 is a schematic side view of a sonication apparatus, while

FIGS. 40-1 to 40-4 are infrared spectra of A, A-50e,
S-50e, and S-100e, respectively.

FIGS. 40A-40I are $^1$H-NMR spectra of samples P132,
P132-10, P132-100, P-1e, P-5e, P-10e, P-30e, P-70e, and
P-100e.
FIG. 40J is a comparison of the exchangeable
proton at ~16 ppm from FIGS. 40A-40I.
FIG. 40K is a
$^{13}$C-NMR of sample P-100e.

FIGS. 56A and 56B are schematic diagrams showing ion
beam energy distributions.

FIG. 56C is a schematic diagram showing ion dose
profiles in an exposed sample.

FIG. 57 is a schematic diagram of a scattering element
that includes multiple sub-regions.

DETAILED DESCRIPTION

Figure 1:
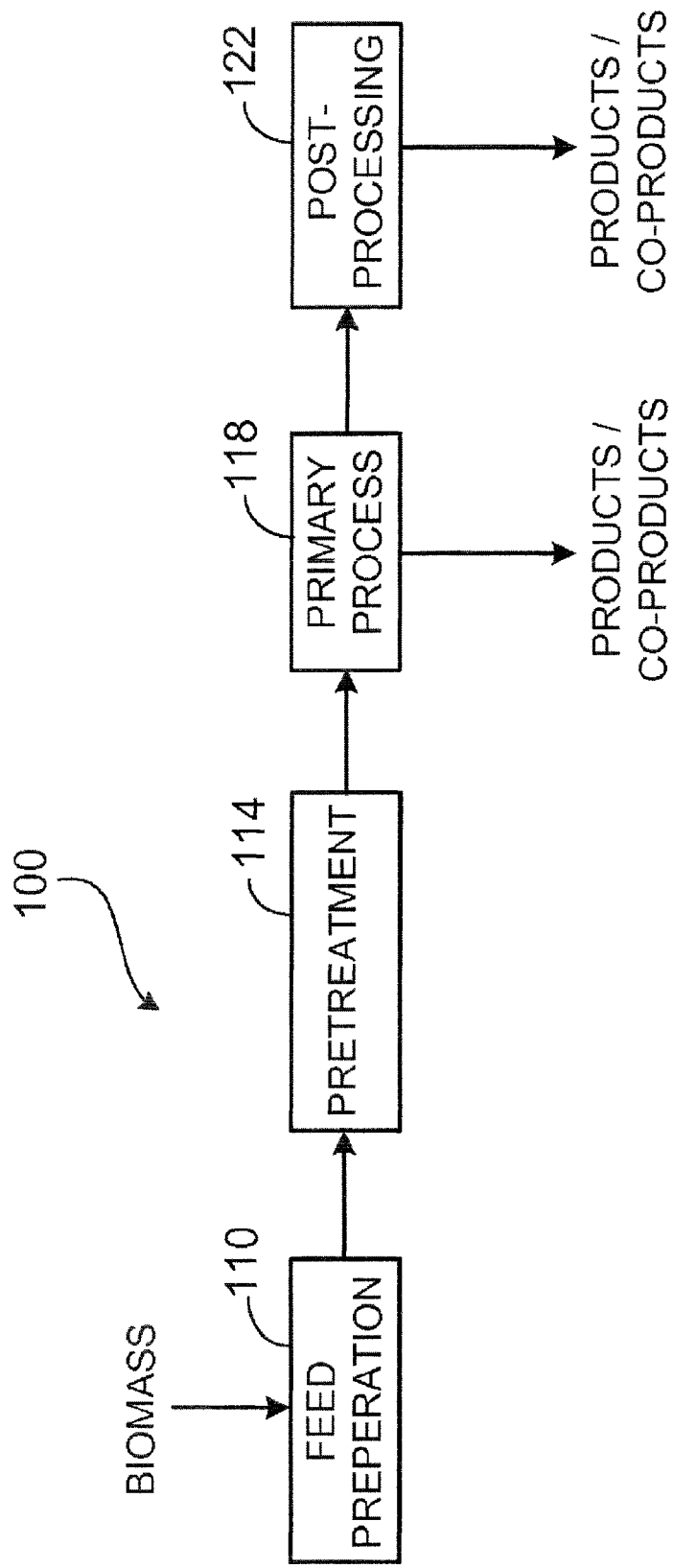
FIG. 1 is a block diagram illustrating conversion of biomass into products and co-products.

Biomass (e.g., plant biomass, such as those that are or that
include one or more low molecular weight sugars, animal
biomass, and municipal waste biomass) can be processed to
produce useful products such as fuels, e.g., fuels for internal
combustion engines, jet engines or feedstocks for fuel cells.
In addition, functionalized materials having desired types
and amounts of functionality, such as carboxylic acid
groups, enol groups, aldehyde groups, ketone groups, nitrile
groups, nitro groups, or nitroso groups, can be prepared
using the methods described herein. Such functionalized
materials can be, e.g., more soluble, easier to utilize by
various microorganisms or can be more stable over the long
term, e.g., less prone to oxidation. Systems and processes are
described herein that can use various biomass materials,
such as cellulosic materials, lignocellulosic materials,
starchy materials or materials that are or that include low
molecular weight sugars, as feedstock materials. Such materials are often readily available, but can be difficult to
process, e.g., by fermentation, or can give sub-optimal
yields at a slow rate, Feedstock materials are first physically
prepared for processing, often by size reduction of raw
feedstock materials. Physically prepared feedstock can be pretreated or processed using one or more of radiation, sonication, oxidation, pyrolysis, and steam explosion. The various pretreatment systems and methods can be used in combinations of two, three, or even four of these technologies.

In some cases, to provide materials that include a carbohydrate, such as cellulose, that can be converted by a microorganism to a number of desirable products, such as a combustible fuels (e.g., ethanol, butanol or hydrogen), feedstocks that include one or more saccharide units can be treated by any one or more of the processes described herein. Other products and co-products that can be produced include, for example, human food, animal feed, pharmaceuticals, and nutriceuticals.

Types of Biomass

Generally, any biomass material that is or includes carbohydrates composed entirely of one or more saccharide units or that include one or more saccharide units can be processed by any of the methods described herein. For example, the biomass material can be cellulosic or lignocellulosic materials, or starchy materials, such as kernels of corn, grains of rice or other foods, or materials that are or that include one or more low molecular weight sugars, such as sucrose or cellobiose.

For example, such materials can include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these. Suitable materials include those listed in the Summary section, above.

Fiber sources include cellulosic fiber sources, including paper and paper products (e.g., polycoated paper and Kraft paper), and lignocellulosic fiber sources, including wood, and wood-related materials, e.g., particle board. Other suitable fiber sources include natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; and synthetic fiber sources, e.g., extruded yarn (oriented yarn or un-oriented yarn). Natural or synthetic fiber sources can be obtained from virgin scrap textile materials, e.g., remnants or they can be post consumer waste, e.g., rags. When paper products are used as fiber sources, they can be virgin materials, e.g., scrap virgin materials, or they can be post-consumer waste. Aside from virgin materials, post-consumer, industrial (e.g., offal), and processing waste (e.g., effluent from paper processing) can also be used as fiber sources. Also, the fiber source can be obtained or derived from human (e.g., sewage), animal or plant wastes. Additional fiber sources have been described in U.S. Pat. Nos. 6,448,307, 6,258,876, 6,207,729, 5,973,035 and 5,952,105.

Examples of biomass include renewable, organic matter, such as plant biomass (defined below), microbial biomass (defined below), animal biomass (e.g., any animal by-product, animal waste, etc.) and municipal waste biomass including any and all combinations of these biomass materials.

Plant biomass and lignocellulosic biomass include organic matter (woody or non-woody) derived from plants, especially matter available on a sustainable basis. Examples include biomass from agricultural or food crops (e.g., sugarcane, sugar beets or corn kernels) or an extract therefrom (e.g., sugar from sugarcane and corn starch from corn), agricultural crop wastes and residues such as corn stover, wheat straw, rice straw, sugar cane bagasse, and the like. Plant biomass further includes, but is not limited to, trees, woody energy crops, wood wastes and residues such as softwood forest thinnings, barky wastes, sawdust, paper and pulp industry waste streams, wood fiber, and the like. Additionally grass crops, such as switchgrass and the like have potential to be produced on a large-scale as another plant biomass source. For urban areas, the plant biomass feedstock includes yard waste (e.g., grass clippings, leaves, tree clippings, and brush) and vegetable processing waste.

Lignocellulosic feedstock can be plant biomass such as, but not limited to, non-woody plant biomass, cultivated crops, such as, but not limited to, grasses, for example, but not limited to, C4 grasses, such as switchgrass, cord grass, rye grass, miscanthus, reed canary grass, or a combination thereof, or sugar processing residues such as bagasse, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. Further, the lignocellulosic feedstock may include cellulosic waste material such as, but not limited to, newsprint, cardboard, sawdust, and the like. Lignocellulosic feedstock may include one species of fiber or alternatively, lignocellulosic feedstock may include a mixture of fibers that originate from different lignocellulosic feedstocks. Furthermore, the lignocellulosic feedstock may comprise fresh lignocellulosic feedstock, partially dried lignocellulosic feedstock, fully dried lignocellulosic feedstock or a combination thereof.

Microbial biomass includes biomass derived from naturally occurring or genetically modified unicellular organisms and/or multicellular organisms, e.g., organisms from the ocean, lakes, bodies of water, e.g., salt water or fresh water, or on land, and that contains a source of carbohydrate (e.g., cellulose). Microbial biomass can include, but is not limited to, for example protists (e.g., animal (e.g., protozoa such as flagellates, amoeboids, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, plankton (e.g., macroplankton, meroplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Animal biomass includes any organic waste material such as animal-derived waste material or excrement or human waste material or excrement (e.g., manure and sewage).

In some embodiments, the carbohydrate is or includes a material having one or more β-1,4-linkages and having a number average molecular weight between about 3,000 and 50,000. Such a carbohydrate is or includes cellulose (I), which is derived from (β-glucose 1) through condensation of β(1→4)-glycosidic bonds. This linkage contrasts itself with that for α(1→4)-glycosidic bonds present in starch and other carbohydrates.

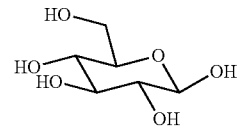

1

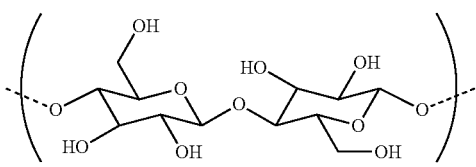

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. In particular embodiments, the starchy material is derived from corn. Various corn starches and derivatives are described in "Corn Starch," Corn Refiners Association (11th Edition, 2006), the contents of which are incorporated herein by reference.

Biomass materials that include low molecular weight sugars can, e.g., include at least about 0.5 percent by weight of the low molecular sugar, e.g., at least about 2, 3, 4, 5, 6, 7, 8, 9, 10, 12.5, 25, 35, 50, 60, 70, 80, 90 or even at least about 95 percent by weight of the low molecular weight sugar. In some instances, the biomass is composed substantially of the low molecular weight sugar, e.g., greater than 95 percent by weight, such as 96, 97, 98, 99 or substantially 100 percent by weight of the low molecular weight sugar.

Biomass materials that include low molecular weight sugars can be agricultural products or food products, such as sugarcane and sugar beets or an extract therefrom, e.g., juice from sugarcane, or juice from sugar beets. Biomass materials that include low molecular weight sugars can be substantially pure extracts, such as raw or crystallized table sugar (sucrose). Low molecular weight sugars include sugar derivatives. For example, the low molecular weight sugars can be oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different.

Specific examples of low molecular weight sugars include cellobiose, lactose, sucrose, glucose and xylose, along with derivatives thereof. In some instances, sugar derivatives are more rapidly dissolved in solution or utilized by microbes to provide a useful material, such as ethanol or butanol. Examples of such sugars and sugar derivatives are shown below.

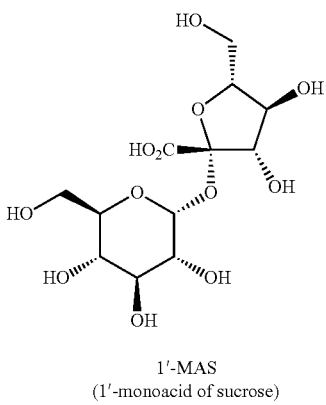

1'-MAS
(1'-monoacid of sucrose)

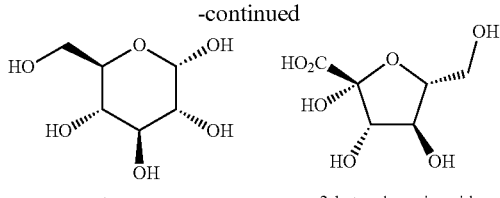

glucose 2-keto-gluconic acid

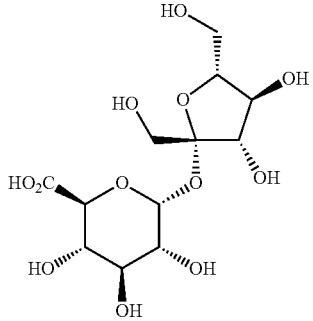

6-MAS
6-monoacid of sucrose

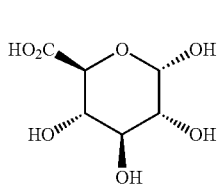

glucuronic acid

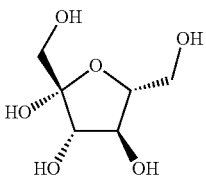

fructose

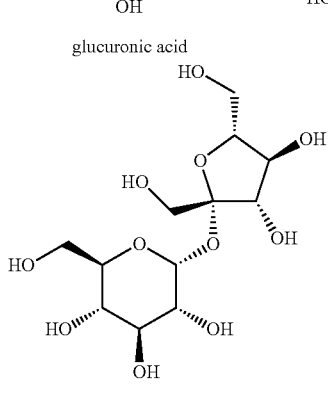

sucrose

Combinations (e.g., by themselves or in combination of any biomass material, component, product, and/or co-product generated using the methods described herein) of any biomass materials described herein can be utilized for making any of the products described herein, such as ethanol. For example, blends of cellulosic materials and starchy materials can be utilized for making any product described herein.

Systems for Treating Biomass

FIG. 1 shows a for converting biomass, particularly biomass with significant cellulosic and lignocellulosic components and/or starchy components, into useful products and co-products. System 100 includes a feed preparation subsystem 110, a pretreatment subsystem 114, a primary process subsystem 118, and a post-processing subsystem 122. Feed preparation subsystem 110 receives biomass in its raw form, physically prepares the biomass for use as feedstock by downstream processes (e.g., reduces the size of and homogenizes the biomass), and stores the biomass both in its raw and feedstock forms.

Biomass feedstock with significant cellulosic and/or lignocellulosic components, or starchy components can have a high average molecular weight and crystallinity that can make processing the feedstock into useful products (e.g., fermenting the feedstock to produce ethanol) difficult. Accordingly it is useful to pretreat biomass feedstock. As described herein, in some embodiments, the pretreatment of biomass feed stock do not use acids, bases and enzymes to process cellulosic, lignocellulosic or starchy feedstocks or only use such treatments in small or catalytic amounts.

Pretreatment subsystem 114 receives feedstock from the feed preparation subsystem 110 and prepares the feedstock for use in primary production processes by, for example, reducing the average molecular weight and crystallinity of the feedstock. Primary process subsystem 118 receives pretreated feedstock from pretreatment subsystem 114 and produces useful products (e.g., ethanol, other alcohols, pharmaceuticals, and/or food products). In some cases, the output of primary process subsystem 118 is directly useful but, in other cases, requires further processing provided by post-processing subsystem 122. Post-processing subsystem 122 provides further processing to product streams from primary process system 118 which require it (e.g., distillation and denaturation of ethanol) as well as treatment for waste streams from the other subsystems. In some cases, the co-products of subsystems 114, 118, 122 can also be directly or indirectly useful as secondary products and/or in increasing the overall efficiency of system 100. For example, post-processing subsystem 122 can produce treated water to be recycled for use as process water in other subsystems and/or can produce burnable waste which can be used as fuel for boilers producing steam and/or electricity.

The optimum size for biomass conversion plants is affected by factors including economies of scale and the type and availability of biomass used as feedstock. Increasing plant size tends to increase economies of scale associated with plant processes. However, increasing plant size also tends to increase the costs (e.g., transportation costs) per unit of feedstock. Studies analyzing these factors suggest that the appropriate size for biomass conversion plants can range from 2000 to 10,000 dried tons of feedstock per day depending at least in part on the type of feedstock used. The type of feedstock can also impact plant storage requirements with plants designed primarily for processing feedstock whose availability varies seasonally (e.g., corn stover) requiring more on- or of-site feedstock storage than plants designed to process feedstock whose availability is relatively steady (e.g., waste paper).

Physical Preparation

In some cases, methods of processing begin with a physical preparation of the feedstock, e.g., size reduction of raw feedstock materials, such as by cutting, grinding, shearing or chopping. In some cases, the material can be reduced into particles using a hammermill, disk-refiner, or flaker. In some cases, loose feedstock (e.g., recycled paper, starchy materials, or switchgrass) is prepared by shearing or shredding. Screens and/or magnets can be used to remove oversized or undesirable objects such as, for example, rocks or nails from the feed stream.

Feed preparation systems can be configured to produce feed streams with specific characteristics such as, for example, specific maximum sizes, specific length-to-width, or specific surface areas ratios. As a part of feed preparation, the bulk density of feedstocks can be controlled (e.g., increased or decreased).

Size Reduction

In some embodiments, the material to be processed is in the form of a fibrous material that includes fibers provided by shearing a fiber source. For example, the shearing can be performed with a rotary knife cutter.

Figure 2:
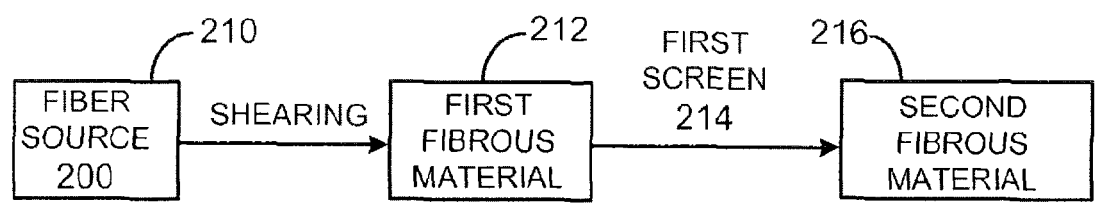
FIG. 2 is block diagram illustrating conversion of a fiber source into a first and second fibrous material.

For example, and by reference to FIG. 2, a fiber source 210 is sheared, e.g., in a rotary knife cutter, to provide a first fibrous material 212. The first fibrous material 212 is passed through a first screen 214 having an average opening size of 1.59 mm or less (1/16 inch, 0.0625 inch) to provide a second fibrous material 216. If desired, fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of fiber source and the passing of the resulting first fibrous material through first screen are performed concurrently. The shearing and the passing can also be performed in a batch-type process.

Figure 3:
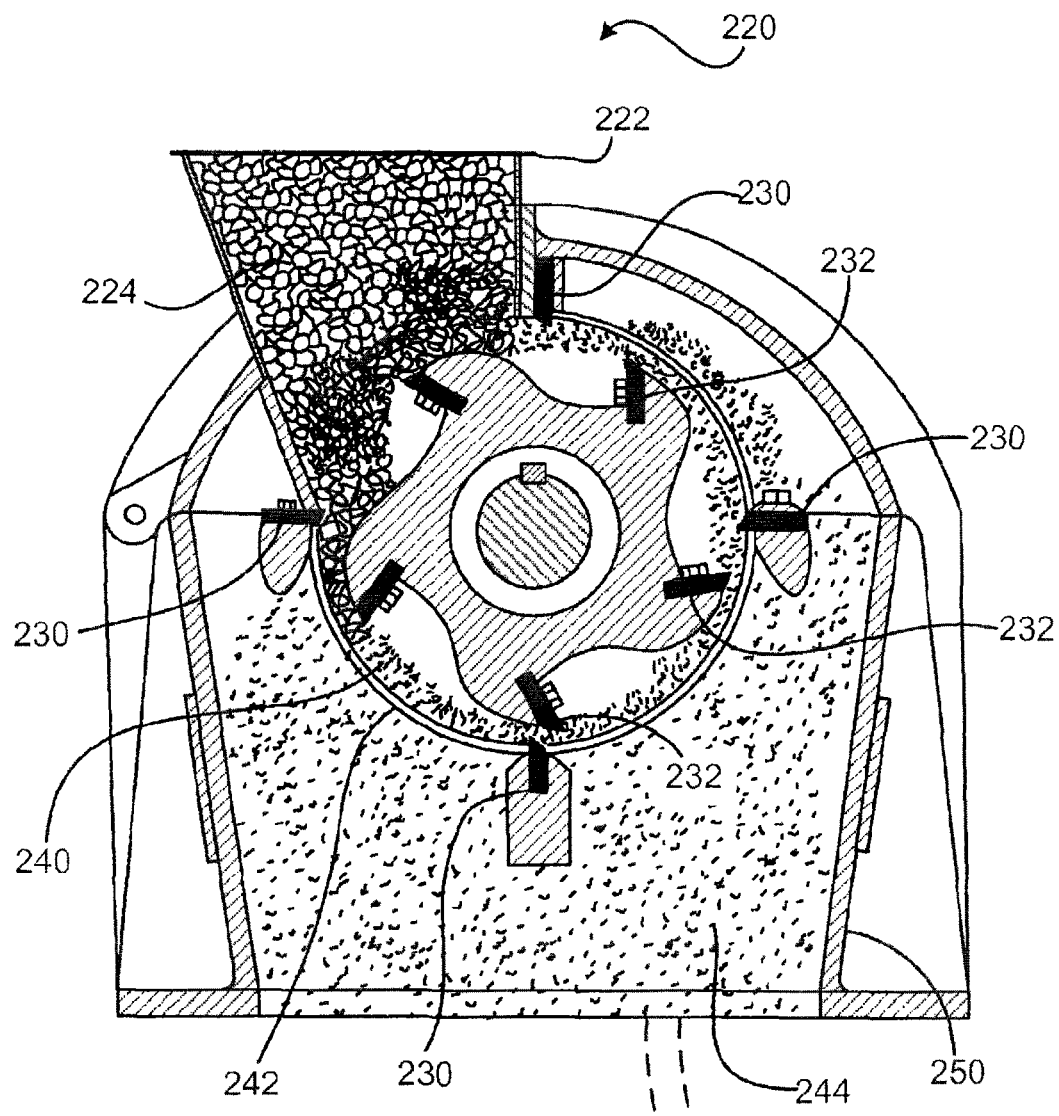
FIG. 3 is a cross-sectional view of a rotary knife cutter.

For example, a rotary knife cutter can be used to concurrently shear the fiber source and screen the first fibrous material. Referring to FIG. 3, a rotary knife cutter 220 includes a hopper 222 that can be loaded with a shredded fiber source 224 prepared by shredding fiber source. Shredded fiber source is sheared between stationary blades 230 and rotating blades 232 to provide a first fibrous material 240. First fibrous material 240 passes through screen 242, and the resulting second fibrous material 244 is captured in bin 250. To aid in the collection of the second fibrous material, the bin can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source 252 is utilized to maintain the bin below nominal atmospheric pressure.

Shearing can be advantageous for "opening up" and "stressing" the fibrous materials, making the cellulose of the materials more susceptible to chain scission and/or reduction of crystallinity. The open materials can also be more susceptible to oxidation when irradiated.

The fiber source can be sheared in a dry state, a hydrated state (e.g., having up to ten percent by weight absorbed water), or in a wet state, e.g., having between about 10 percent and about 75 percent by weight water. The fiber source can even be sheared while partially or fully submerged under a liquid, such as water, ethanol, isopropanol.

The fiber source can also be sheared in under a gas (such as a stream or atmosphere of gas other than air), e.g., oxygen or nitrogen, or steam.

Other methods of making the fibrous materials include, e.g., stone grinding, mechanical ripping or tearing, pin grinding or air attrition milling.

If desired, the fibrous materials can be separated, e.g., continuously or in batches, into fractions according to their length, width, density, material type, or some combination of these attributes. For example, for forming composites, it is often desirable to have a relatively narrow distribution of fiber lengths.

For example, ferrous materials can be separated from any of the fibrous materials by passing a fibrous material that includes a ferrous material past a magnet, e.g., an electromagnet, and then passing the resulting fibrous material through a series of screens, each screen having different sized apertures.

The fibrous materials can also be separated, e.g., by using a high velocity gas, e.g., air. In such an approach, the fibrous materials are separated by drawing off different fractions, which can be characterized photonically, if desired. Such a separation apparatus is discussed in Lindsey et al., U.S. Pat. No. 6,883,667.

The fibrous materials can irradiated immediately following their preparation, or they can may be dried, e.g., at approximately 105° C. for 4-18 hours, so that the moisture content is, e.g., less than about 0.5% before use.

If desired, lignin can be removed from any of the fibrous materials that include lignin. Also, to aid in the breakdown of the materials that include the cellulose, the material can be treated prior to irradiation with heat, a chemical (e.g., mineral acid, base or a strong oxidizer such as sodium hypochlorite) and/or an enzyme.

In some embodiments, the average opening size of the first screen is less than 0.79 mm (1/32 inch, 0.03125 inch), e.g., less than 0.51 mm (1/50 inch, 0.02000 inch), less than 0.40 mm (1/64 inch, 0.015625 inch), less than 0.23 mm (0.009 inch), less than 0.20 mm (1/128 inch, 0.0078125 inch), less than 0.18 mm (0.007 inch), less than 0.13 mm (0.005 inch), or even less than less than 0.10 mm (1/256 inch, 0.00390625 inch). The screen is prepared by interweaving monofilaments having an appropriate diameter to give the desired opening size. For example, the monofilaments can be made of a metal, e.g., stainless steel. As the opening sizes get smaller, structural demands on the monofilaments may become greater. For example, for opening sizes less than 0.40 mm, it can be advantageous to make the screens from monofilaments made from a material other than stainless steel, e.g., titanium, titanium alloys, amorphous metals, nickel, tungsten, rhodium, rhenium, ceramics, or glass. In some embodiments, the screen is made from a plate, e.g. a metal plate, having apertures, e.g., cut into the plate using a laser. In some embodiments, the open area of the mesh is less than 52%, e.g., less than 41%, less than 36%, less than 31%, less than 30%.

In some embodiments, the second fibrous is sheared and passed through the first screen, or a different sized screen. In some embodiments, the second fibrous material is passed through a second screen having an average opening size equal to or less than that of first screen.

Figure 4:
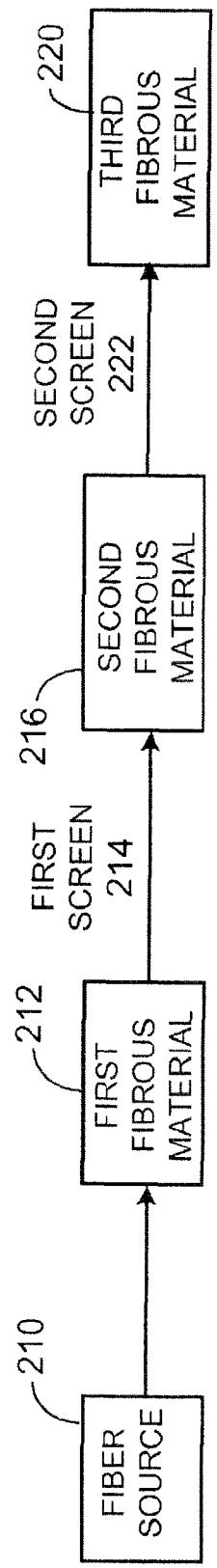
FIG. 4 is block diagram illustrating conversion of a fiber source into a first, second and third fibrous material.

Referring to FIG. 4, a third fibrous material 220 can be prepared from the second fibrous material 216 by shearing the second fibrous material 216 and passing the resulting material through a second screen 222 having an average opening size less than the first screen 214.

Generally, the fibers of the fibrous materials can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (i.e., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

The average length-to-diameter ratio of the second fibrous material 14 can be, e.g. greater than 8/1, e.g., greater than 10/1, greater than 15/1, greater than 20/1, greater than 25/1, or greater than 50/1. An average length of the second fibrous material 14 can be, e.g., between about 0.5 mm and 2.5 mm, e.g., between about 0.75 mm and 1.0 mm, and an average width (i.e., diameter) of the second fibrous material 14 can be, e.g., between about 5 (im and 50 (μm, e.g., between about 10 (μm and 30 μm.

In some embodiments, a standard deviation of the length of the second fibrous material 14 is less than 60 percent of an average length of the second fibrous material 14, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the second fibrous material is greater than 0.1 m$^2$/g, e.g., greater than 0.25 m$^2$/g, greater than 0.5 m$^2$/g, greater than 1.0 m$^2$/g, greater than 1.5 m$^2$/g, greater than 1.75 m$^2$/g, greater than 5.0 m$^2$/g, greater than 10 m$^2$/g, greater than 25 m$^2$/g, greater than 35 m$^2$/g, greater than 50 m$^2$/g, greater than 60 m$^2$/g, greater than 75 m$^2$/g, greater than 100 m$^2$/g, greater than 150 m$^2$/g, greater than 200 m$^2$/g, or even greater than 250 m$^2$/g. A porosity of the second fibrous material 14 can be, e.g., greater than 20 percent, greater than 25 percent, greater than 35 percent, greater than 50 percent, greater than 60 percent, greater than 70 percent, e.g., greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, a ratio of the average length-to-diameter ratio of the first fibrous material to the average length-to-diameter ratio of the second fibrous material is, e.g., less than 1.5, e.g., less than 1.4, less than 1.25, less than 1.1, less than 1.075, less than 1.05, less than 1.025, or even substantially equal to 1.

In particular embodiments, the second fibrous material is sheared again and the resulting fibrous material passed through a second screen having an average opening size less than the first screen to provide a third fibrous material. In such instances, a ratio of the average length-to-diameter ratio of the second fibrous material to the average length to-diameter ratio of the third fibrous material can be, e.g., less than 1.5, e.g., less than 1.4, less than 1.25, or even less than 1.1.

In some embodiments, the third fibrous material is passed through a third screen to produce a fourth fibrous material. The fourth fibrous material can be, e.g., passed through a fourth screen to produce a fifth material. Similar screening processes can be repeated as many times as desired to produce the desired fibrous material having the desired properties.

Densification

Densified materials can be processed by any of the methods described herein, or any material described herein, e.g., any fibrous material described herein, can be processed by any one or more methods described herein, and then densified as described herein.

A material, e.g., a fibrous material, having a low bulk density can be densified to a product having a higher bulk density. For example, a material composition having a bulk density of 0.05 g/cm$^3$ can be densified by sealing the fibrous material in a relatively gas impermeable structure, e.g., a bag made of polyethylene or a bag made of alternating layers of polyethylene and a nylon, and then evacuating the entrapped gas, e.g., air, from the structure. After evacuation of the air from the structure, the fibrous material can have, e.g., a bulk density of greater than 0.3 g/cm³, e.g., 0.5 g/cm³, 0.6 g/cm³, 0.7 g/cm³ or more, e.g., 0.85 g/cm³. After densification, the product can processed by any of the methods described herein, e.g., irradiated, e.g., with gamma radiation. This can be advantageous when it is desirable to transport the material to another location, e.g., a remote manufacturing plant, where the fibrous material composition can be added to a solution, e.g., to produce ethanol. After piercing the substantially gas impermeable structure, the densified fibrous material can revert to nearly its initial bulk density, e.g., greater than 60 percent of its initial bulk density, e.g., 70 percent, 80 percent, 85 percent or more, e.g., 95 percent of its initial bulk density. To reduce static electricity in the fibrous material, an anti-static agent can be added to the material.

In some embodiments, the structure, e.g., bag, is formed of a material that dissolves in a liquid, such as water. For example, the structure can be formed from a polyvinyl alcohol so that it dissolves when in contact with a water-based system. Such embodiments allow densified structures to be added directly to solutions that include a microorganism, without first releasing the contents of the structure, e.g., by cutting.

Figure 5:
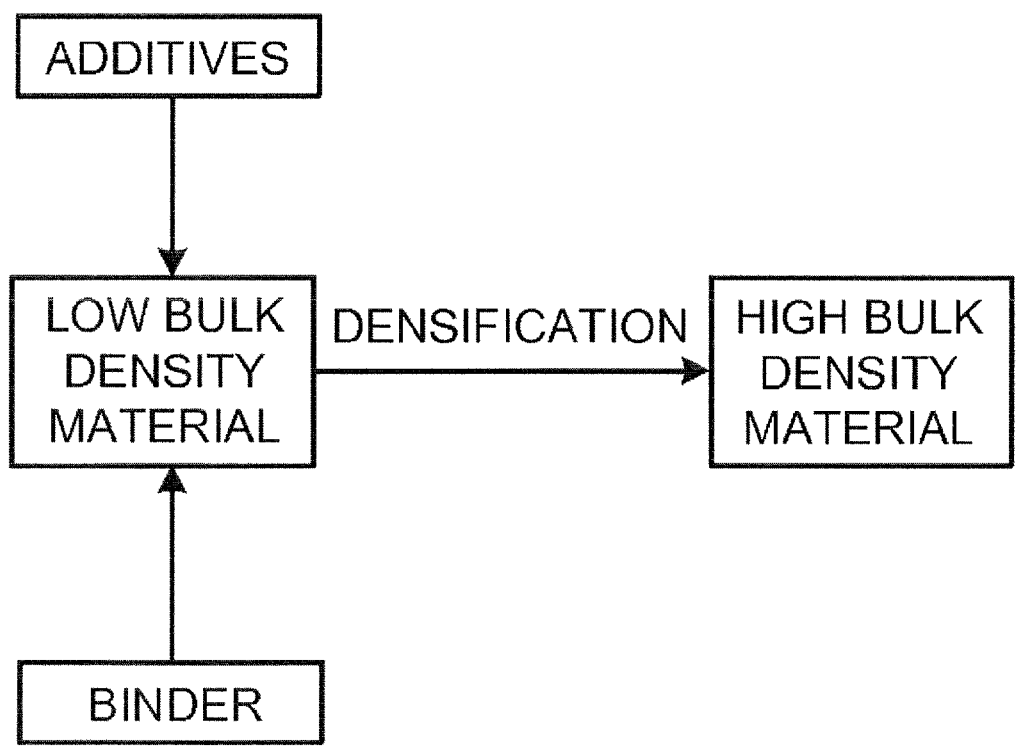
FIG. 5 is block diagram illustrating densification of a material.

Referring to FIG. 5, a biomass material can be combined with any desired additives and a binder, and subsequently densified by application of pressure, e.g., by passing the material through a nip defined between counter-rotating pressure rolls or by passing the material through a pellet mill. During the application of pressure, heat can optionally be applied to aid in the densification of the fibrous material. The densified material can then be irradiated.

In some embodiments, the material prior to densification has a bulk density of less than 0.25 g/cm³, e.g., 0.20 g/cm³, 0.15 g/cm³, 0.10 g/cm³, 0.05 g/cm³ or less, e.g., 0.025 g/cm³. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

The preferred binders include binders that are soluble in water, swollen by water, or that has a glass transition temperature of less 25° C., as determined by differential scanning calorimetry. By water-soluble binders, we mean binders having a solubility of at least about 0.05 weight percent in water. By water swellable binders, we mean binders that increase in volume by more than 0.5 percent upon exposure to water.

In some embodiments, the binders that are soluble or swollen by water include a functional group that is capable of forming a bond, e.g., a hydrogen bond, with the fibers of the fibrous material, e.g., cellulosic fibrous material. For example, the functional group can be a carboxylic acid group, a carboxylate group, a carbonyl group, e.g., of an aldehyde or a ketone, a sulfonic acid group, a sulfonate group, a phosphoric acid group, a phosphate group, an amide group, an amine group, a hydroxyl group, e.g., of an alcohol, and combinations of these groups, e.g., a carboxylic acid group and a hydroxyl group. Specific monomeric examples include glycerin, glyoxal, ascorbic acid, urea, glycine, pentaerythritol, a monosaccharide or a disaccharide, citric acid, and tartaric acid. Suitable saccharides include glucose, sucrose, lactose, ribose, fructose, mannose, arabinose and erythrose. Polymeric examples include polyglycols, polyethylene oxide, polycarboxylic acids, polyamides, polyamines and polysulfonic acids polysulfonates. Specific polymeric examples include polypropylene glycol (PPG), polyethylene glycol (PEG), polyethylene oxide, e.g., POLYOX®, copolymers of ethylene oxide and propylene oxide, polyacrylic acid (PAA), polyacrylamide, polypeptides, polyethylenimine, polyvinylpyridine, poly(sodium-4-styrenesulfonate) and poly(2-acrylamido-methyl-1-propanesulfonic acid). In some embodiments, the binder includes a polymer that has a glass transition temperature less 25° C. Examples of such polymers include thermoplastic elastomers (TPEs). Examples of TPEs include polyether block amides, such as those available under the tradename PEBAX®, polyester elastomers, such as those available under the tradename HYTREL®, and styrenic block copolymers, such as those available under the tradename KRATON®. Other suitable polymers having a glass transition temperature less 25° C. include ethylene vinyl acetate copolymer (EVA), polyolefins, e.g., polyethylene, polypropylene, ethylene-propylene copolymers, and copolymers of ethylene and alpha olefins, e.g., 1-octene, such as those available under the trade name ENGAGE®. In some embodiments, e.g., when the material is a fiberized polycoated paper, the material is densified without the addition of a separate low glass transition temperature polymer.

In a particular embodiment, the binder is a lignin, e.g., a natural or synthetically modified lignin.

A suitable amount of binder added to the material, calculated on a dry weight basis, is, e.g., from about 0.01 percent to about 50 percent, e.g., 0.03 percent, 0.05 percent, 0.1 percent, 0.25 percent, 0.5 percent, 1.0 percent, 5 percent, 10 percent or more, e.g., 25 percent, based on a total weight of the densified material. The binder can be added to the material as a neat, pure liquid, as a liquid having the binder dissolved therein, as a dry powder of the binder, or as pellets of the binder.

Figure 6:
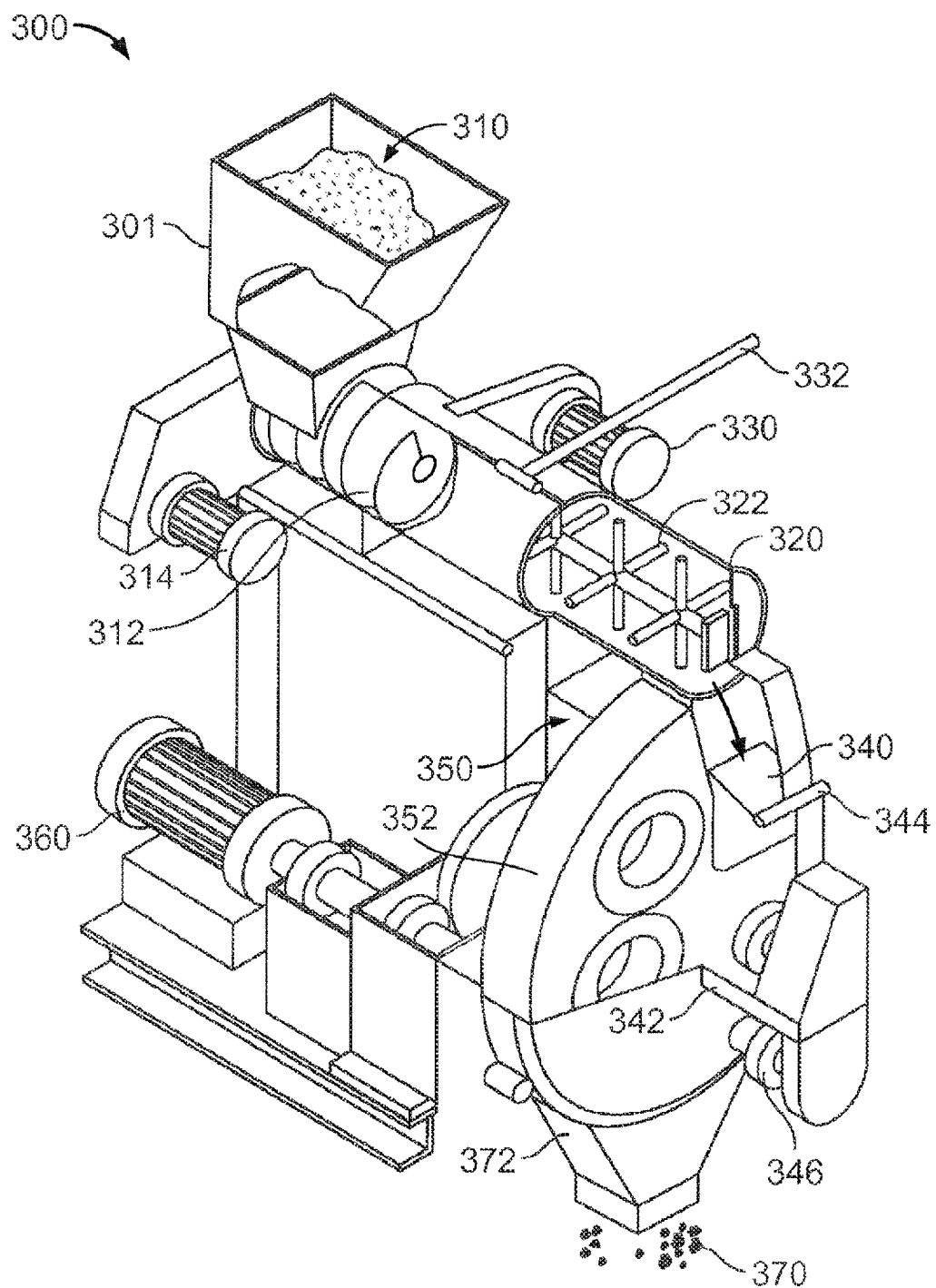
FIG. 6 is a perspective view of a pellet mill.

The densified fibrous material can be made in a pellet mill. Referring to FIG. 6, a pellet mill 300 has a hopper 301 for holding undensified material 310 that includes a carbohydrate-containing materials, such as cellulose. The hopper communicates with an auger 312 that is driven by variable speed motor 314 so that undensified material can be transported to a conditioner 320 that stirs the undensified material with paddles 322 that are rotated by conditioner motor 330. Other ingredients, e.g., any of the additives and/or fillers described herein, can be added at inlet 332. If desired, heat may be added while the fibrous material is in conditioner. After conditioned, the material passes from the conditioner through a dump chute 340, and to another auger 342. The dump chute, as controlled by actuator 344, allows for unobstructed passage of the material from conditioner to auger. Auger is rotated by motor 346, and controls the feeding of the fibrous material into die and roller assembly 350. Specifically, the material is introduced into a hollow, cylindrical die 352, which rotates about a horizontal axis and which has radially extending die holes 250. Die 352 is rotated about the axis by motor 360, which includes a horsepower gauge, indicating total power consumed by the motor. Densified material 370, e.g., in the form of pellets, drops from chute 372 and are captured and processed, such as by irradiation.

The material, after densification, can be conveniently in the form of pellets or chips having a variety of shapes. The pellets can then be irradiated. In some embodiments, the pellets or chips are cylindrical in shape, e.g., having a maximum transverse dimension of, e.g., 1 mm or more, e.g., 2 mm, 3 mm, 5 mm, 8 mm, 10 mm, 15 mm or more, e.g., 25 mm. Another convenient shape for making composites includes pellets or chips that are plate-like in form, e.g., having a thickness of 1 mm or more, e.g., 2 mm, 3 mm, 5 mm, 8 mm, 10 mm or more, e.g., 25 mm; a width of, e.g., 5 mm or more, e.g., 10 mm, 15 mm, 25 mm, 30 mm or more, e.g., 50 mm; and a length of 5 mm or more, e.g., 10 mm, 15 mm, 25 mm, 30 mm or more, e.g., 50 mm.

Referring now FIG. 7A-7D, pellets can be made so that they have a hollow inside. As shown, the hollow can be generally in-line with the center of the pellet (FIG. 7B), or out of line with the center of the pellet (FIG. 7C). Making the pellet hollow inside can increase the rate of dissolution in a liquid after irradiation.

Referring now to FIG. 7D, the pellet can have, e.g., a transverse shape that is multi-lobal, e.g., tri-lobal as shown, or tetra-lobal, penta-lobal, hexa-lobal or deca-lobal. Making the pellets in such transverse shapes can also increase the rate of dissolution in a solution after irradiation.

Alternatively, the densified material can be in any other desired form, e.g., the densified material can be in the form of a mat, roll or bale.

EXAMPLES

In one example, half-gallon juice cartons made of unprinted white Kraft board having a bulk density of 20 lb/ft$^3$ can be used as a feedstock. Cartons can be folded flat and then fed into a shredder to produce a confetti-like material having a width of between 0.1 inch and 0.5 inch, a length of between 0.25 inch and 1 inch and a thickness equivalent to that of the starting material (about 0.075 inch). The confetti-like material can be fed to a rotary knife cutter, which shears the confetti-like pieces, tearing the pieces apart and releasing fibrous material.

In some cases, multiple shredder-shearer trains can be arranged in series with output. In one embodiment, two shredder-shearer trains can be arranged in series with output from the first shearer fed as input to the second shredder. In another embodiment, three shredder-shearer trains can be arranged in series with output from the first shearer fed as input to the second shredder and output from the second shearer fed as input to the third shredder. Multiple passes through shredder-shearer trains are anticipated to increase decrease particle size and increase overall surface area within the feedstream.

In another example, fibrous material produced from shredding and shearing juice cartons can be treated to increase its bulk density. In some cases, the fibrous material can be sprayed with water or a dilute stock solution of POLYOX™ WSR N10 (polyethylene oxide) prepared in water. The wetted fibrous material can then be processed through a pellet mill operating at room temperature. The pellet mill can increase the bulk density of the feedstream by more than an order of magnitude.

Pretreatment

Physically prepared feedstock can be pretreated for use in primary production processes by, for example, reducing the average molecular weight and crystallinity of the feedstock and/or increasing the surface area and/or porosity of the feedstock. Pretreatment processes can include one or more of irradiation, sonication, oxidation, pyrolysis, and steam explosion. The various pretreatment systems and methods can be used in combinations of two, three, or even four of these technologies.

Pretreatment Combinations

In some embodiments, biomass can be processed by applying two or more of any of the processes described herein, such as two or more of radiation, sonication, oxidation, pyrolysis, and steam explosion either with or without prior, intermediate, or subsequent feedstock preparation as described herein. The processes can be applied in any order (or concurrently) to the biomass, e.g., a cellulosic and/or lignocellulosic material and/or a starchy material, such as kernels of corn. In other embodiments, materials that include a carbohydrate are prepared by applying three, four or more of any of the processes described herein (in any order or concurrently). For example, a carbohydrate can be prepared by applying radiation, sonication, oxidation, pyrolysis, and, optionally, steam explosion to a cellulosic and/or lignocellulosic material (in any order or concurrently). The provided carbohydrate-containing material can then be converted by one or more microorganisms, such as bacteria, yeast, or mixtures of yeast and bacteria, to a number of desirable products, as described herein. Multiple processes can provide materials that can be more readily utilized by a variety of microorganisms because of their lower molecular weight, lower crystallinity, and/or enhanced solubility. Multiple processes can provide synergies and can reduce overall energy input required in comparison to any single process.

For example, in some embodiments, feedstocks are provided that include a carbohydrate that is produced by a process that includes irradiating and sonicating (in either order or concurrently) a cellulosic and/or a lignocellulosic material, a process that includes irradiating and oxidizing (in either order or concurrently) a cellulosic and/or a lignocellulosic material, a process that includes irradiating and pyrolyzing (in either order or concurrently) a cellulosic and/or a lignocellulosic material, a process that includes irradiating and pyrolyzing (in either order or concurrently) a cellulosic and/or a lignocellulosic material, or a process that includes irradiating and steam-exploding (in either order or concurrently) a cellulosic and/or a lignocellulosic material. The provided feedstock can then be contacted with a microorganism having the ability to convert at least a portion, e.g., at least about 1 percent by weight, of the feedstock to the product, such as the combustible fuel, as described herein.

In some embodiments, the process does not include hydrolyzing the cellulosic and/or lignocellulosic material, such as with an acid or a base, e.g., a mineral acid, such as hydrochloric or sulfuric acid.

If desired, some or none of the feedstock can include a hydrolyzed material. For example, in some embodiments, at least about seventy percent by weight of the feedstock is an unhydrolyzed material, e.g., at least at 95 percent by weight of the feedstock is an unhydrolyzed material. In some embodiments, substantially all of the feedstock is an unhydrolyzed material.

Any feedstock or any reactor or fermentor charged with a feedstock can include a buffer, such as sodium bicarbonate, ammonium chloride or Tris; an electrolyte, such as potassium chloride, sodium chloride, or calcium chloride; a growth factor, such as biotin and/or a base pair such as uracil or an equivalent thereof; a surfactant, such as Tween® or polyethylene glycol; a mineral, such as such as calcium, chromium, copper, iodine, iron, selenium, or zinc; or a chelating agent, such as ethylene diamine, ethylene diamine tetraacetic acid (EDTA) (or its salt form, e.g., sodium or potassium EDTA), or dimercaprol.

When radiation is utilized, it can be applied to any sample that is dry or wet, or even dispersed in a liquid, such as water. For example, irradiation can be performed on cellulosic and/or lignocellulosic material in which less than about 25 percent by weight of the cellulosic and/or lignocellulosic material has surfaces wetted with a liquid, such as water. In some embodiments, irradiating is performed on cellulosic and/or lignocellulosic material in which substantially none of the cellulosic and/or lignocellulosic material is wetted with a liquid, such as water.

In some embodiments, any processing described herein occurs after the cellulosic and/or lignocellulosic material remains dry as acquired or has been dried, e.g., using heat and/or reduced pressure. For example, in some embodiments, the cellulosic and/or lignocellulosic material has less than about five percent by weight retained water, measured at 25° C. and at fifty percent relative humidity.

If desired, a swelling agent, as defined herein, can be utilized in any process described herein. In some embodiments, when a cellulosic and/or lignocellulosic material is processed using radiation, less than about 25 percent by weight of the cellulosic and/or lignocellulosic material is in a swollen state, the swollen state being characterized as having a volume of more than about 2.5 percent higher than an unswollen state, e.g., more than 5.0, 7.5, 10, or 15 percent higher than the unswollen state. In some embodiments, when radiation is utilized on a cellulosic and/or lignocellulosic material, substantially none of the cellulosic and/or lignocellulosic material is in a swollen state.

In specific embodiments when radiation is utilized, the cellulosic and/or lignocellulosic material includes a swelling agent, and swollen cellulosic and/or lignocellulosic receives a dose of less than about 10 Mrad.

When radiation is utilized in any process, it can be applied while the cellulosic and/or lignocellulosic is exposed to air, oxygen-enriched air, or even oxygen itself, or blanketed by an inert gas such as nitrogen, argon, or helium. When maximum oxidation is desired, an oxidizing environment is utilized, such as air or oxygen and the distance from the radiation source is optimized to maximize reactive gas formation, e.g., ozone and/or oxides of nitrogen.

When radiation is utilized, it may be applied to biomass, such as cellulosic and/or lignocellulosic material, under a pressure of greater than about 2.5 atmospheres, such as greater than 5, 10, 15, 20 or even greater than about 50 atmospheres.

In specific embodiments, the process includes irradiating and sonicating and irradiating precedes sonicating. In other specific embodiments, sonication precedes irradiating, or irradiating and sonicating occur concurrently.

In some embodiments, the process includes irradiating and sonicating (in either order or concurrently) and further includes oxidizing, pyrolyzing or steam exploding.

When the process includes radiation, the irradiating can be performed utilizing an ionizing radiation, such as gamma rays, x-rays, energetic ultraviolet radiation, such as ultraviolet C radiation having a wavelength of from about 100 nm to about 280 nm, a beam of particles, such as a beam of electrons, slow neutrons or alpha particles. In some embodiments, irradiating includes two or more radiation sources, such as gamma rays and a beam of electrons, which can be applied in either order or concurrently.

In specific embodiments, sonicating can performed at a frequency of between about 15 kHz and about 25 kHz, such as between about 18 kHz and 22 kHz utilizing a 1 KW or larger horn, e.g., a 2, 3, 4, 5, or even a 10 KW horn.

In some embodiments, the cellulosic and/or lignocellulosic material includes a first cellulose having a first number average molecular weight and the resulting carbohydrate includes a second cellulose having a second number average molecular weight lower than the first number average molecular weight. For example, the second number average molecular weight is lower than the first number average molecular weight by more than about twenty-five percent, e.g., 2×, 3×, 5×, 7×, 10×, 25×, even 100× reduction.

In some embodiments, the first cellulose has a first crystallinity and the second cellulose has a second crystallinity lower than the first crystallinity, such as lower than about two, three, five, ten, fifteen or twenty-five percent lower.

In some embodiments, the first cellulose has a first level of oxidation and the second cellulose has a second level of oxidation higher than the first level of oxidation, such as two, three, four, five, ten or even twenty-five percent higher.

In one example of the use of radiation with oxidation as a pretreatment, half-gallon juice cartons made of un-printed polycoated white Kraft board having a bulk density of 20 lb/ft$^3$ are used as a feedstock. Cartons are folded flat and then fed into a sequence of three shredder-shearer trains arranged in series with output from the first shearer fed as input to the second shredder, and output from the second shearer fed as input to the third shredder. The fibrous material produced by the can be sprayed with water and processed through a pellet mill operating at room temperature. The densified pellets can be placed in a glass ampoule, which is sealed under an atmosphere of air. The pellets in the ampoule are irradiated with gamma radiation for about 3 hours at a dose rate of about 1 Mrad per hour to provide an irradiated material in which the cellulose has a lower molecular weight than the fibrous Kraft starting material.

Radiation Treatment

One or more irradiation processing sequences can be used to process raw feedstock from a wide variety of different sources to extract useful substances from the feedstock, and to provide partially degraded organic material which functions as input to further processing steps and/or sequences. Irradiation can reduce the molecular weight and/or crystallinity of feedstock. In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock. The doses applied depend on the desired effect and the particular feedstock. For example, high doses of radiation can break chemical bonds within feedstock components and low doses of radiation can increase chemical bonding (e.g., cross-linking) within feedstock components. In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when oxygen-containing functional groups are desired, irradiation in the presence of oxygen or even irradiation with oxygen ions can be performed. For example, when nitrogen-containing functional groups are desirable, irradiation in the presence of nitrogen or even irradiation with nitrogen ions can be performed.

Figure 8:
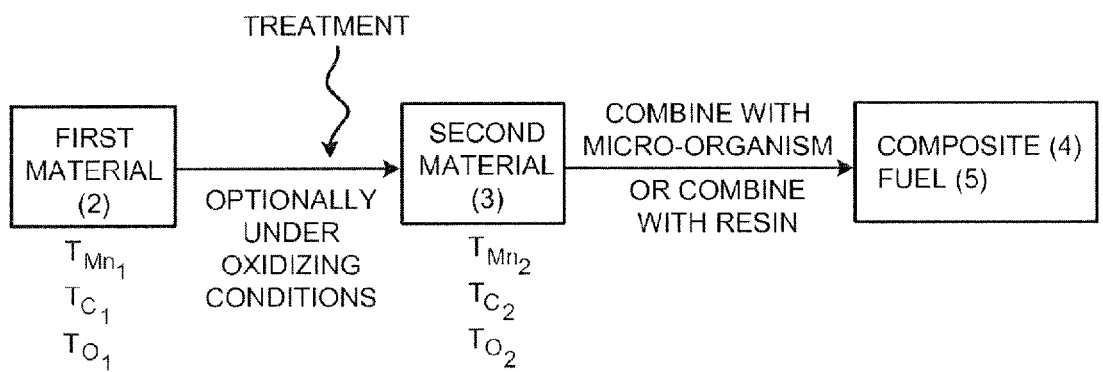
FIG. 8 is a block diagram illustrating a treatment sequence for processing feedstock.

Referring to FIG. 8, in one method, a first material 2 that is or includes cellulose having a first number average molecular weight ($^{T}M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material 3 that includes cellulose having a second number average molecular weight ($^{T}M_{N2}$) lower than the first number average molecular weight. The second material (or the first and second material) can be combined with a microorganism (e.g., a bacterium or a yeast) that can utilize the second and/or first material to produce a fuel 5 that is or includes hydrogen, an alcohol (e.g., ethanol or butanol, such as n-, sec- or t-butanol), an organic acid, a hydrocarbon or mixtures of any of these.

Since the second material 3 has cellulose having a reduced molecular weight relative to the first material, and in some instances, a reduced crystallinity as well, the second material is generally more dispersible, swellable and/or soluble in a solution containing a microorganism. These properties make the second material 3 more susceptible to chemical, enzymatic and/or biological attack relative to the first material 2, which can greatly improve the production rate and/or production level of a desired product, e.g., ethanol. Radiation can also sterilize the materials.

In some embodiments, the second number average molecular weight ($M_{N2}$) is lower than the first number average molecular weight ($^{T}M_{N1}$) by more than about 10 percent, e.g., 15, 20, 25, 30, 35, 40, 50 percent, 60 percent, or even more than about 75 percent.

In some instances, the second material has cellulose that has as crystallinity ($^{T}C_{2}$) that is lower than the crystallinity ($^{T}C_{1}$) of the cellulose of the first material. For example, ($^{T}C_{2}$) can be lower than ($^{T}C_{1}$) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($^{T}O_{2}$) that is higher than the level of oxidation ($^{T}O_{1}$) of the first material. A higher level of oxidation of the material can aid in its dispersibility, swellability and/or solubility, further enhancing the materials susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the biomass via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part, due to their acidic nature. When particles are utilized, the particles can have the mass of a resting electron, or greater, e.g., 500, 1000, 1500, or 2000 or more, e.g., 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodotron® system, while DC type accelerators are available from RDI, now IBA Industrial, such as the Dynamitron®. Exemplary ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy", Columbus-Ohio, ICRU-IAEA Meeting, 18-20 Mar. 2006, Iwata, Y. et al., "Alternating-Phase-Focused IH-DTL for Heavy-Ion Medical Accelerators", Proceedings of EPAC 2006, Edinburgh, Scotland, and Leitner, C. M. et al., "Status of the Superconducting ECR Ion Source Venus", Proceedings of EPAC 2000, Vienna, Austria.

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission.

Electromagnetic radiation interacts via three processes: photoelectric absorption, Compton scattering, and pair production. The dominating interaction is determined by the energy of the incident radiation and the atomic number of the material. The summation of interactions contributing to the absorbed radiation in cellulosic material can be expressed by the mass absorption coefficient (see "Ionization Radiation" in PCT/US2007/022719).

Electromagnetic radiation can be subclassified as gamma rays, x rays, ultraviolet rays, infrared rays, microwaves, or radio waves, depending on wavelength.

Figure 9:
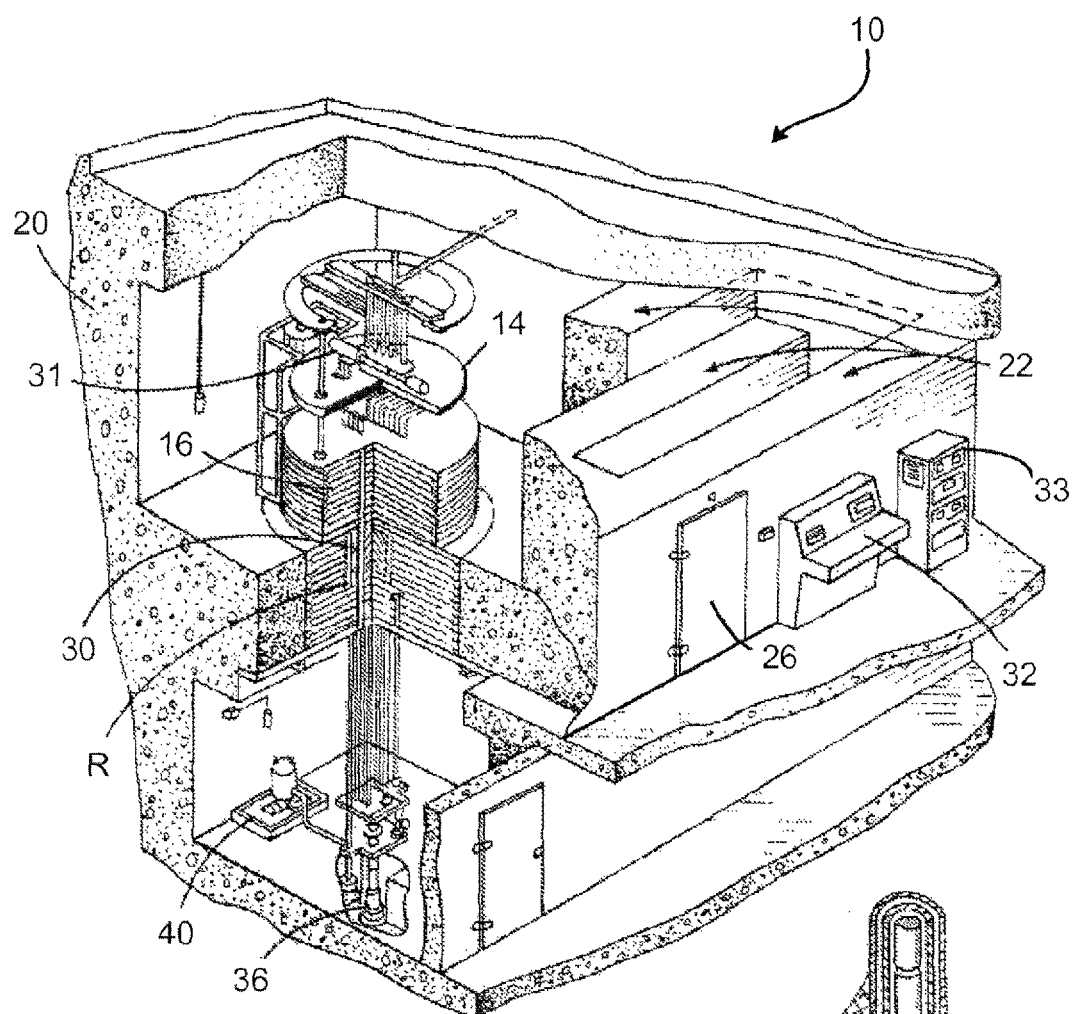
FIG. 9 is a perspective, cut-away view of a gamma irradiator housed in a concrete vault.
Figure 10:
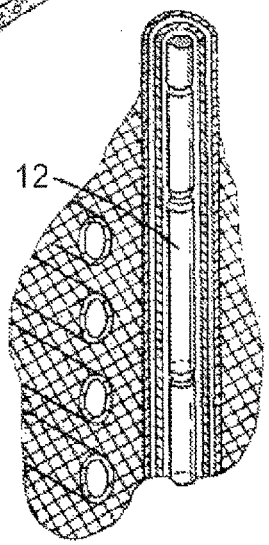
FIG. 10 is an enlarged perspective view of region R of FIG. 9.

For example, gamma radiation can be employed to irradiate the materials. Referring to FIGS. 9 and 10 (an enlarged view of region R), a gamma irradiator 10 includes gamma radiation sources 408, e.g., $^{60}$Co pellets, a working table 14 for holding the materials to be irradiated and storage 16, e.g., made of a plurality of iron plates, all of which are housed in a concrete containment chamber (vault) 20 that includes a maze entranceway 22 beyond a lead-lined door 26. Storage 16 includes a plurality of channels 30, e.g., sixteen or more channels, allowing the gamma radiation sources to pass through storage on their way proximate the working table.

In operation, the sample to be irradiated is placed on a working table. The irradiator is configured to deliver the desired dose rate and monitoring equipment is connected to an experimental block 31. The operator then leaves the containment chamber, passing through the maze entranceway and through the lead-lined door. The operator mans a control panel 32, instructing a computer 33 to lift the radiation sources 12 into working position using cylinder 36 attached to a hydraulic pump 40.

Gamma radiation has the advantage of a significant penetration depth into a variety of material in the sample. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Electron Beam

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

In some embodiments, electrons used to treat biomass material can have average energies of 0.05 c or more (e.g., 0.10 c or more, 0.2 c or more, 0.3 c or more, 0.4 c or more, 0.5 c or more, 0.6 c or more, 0.7 c or more, 0.8 c or more, 0.9 c or more, 0.99 c or more, 0.9999 c or more), where c corresponds to the vacuum velocity of light.

Figure 11A:
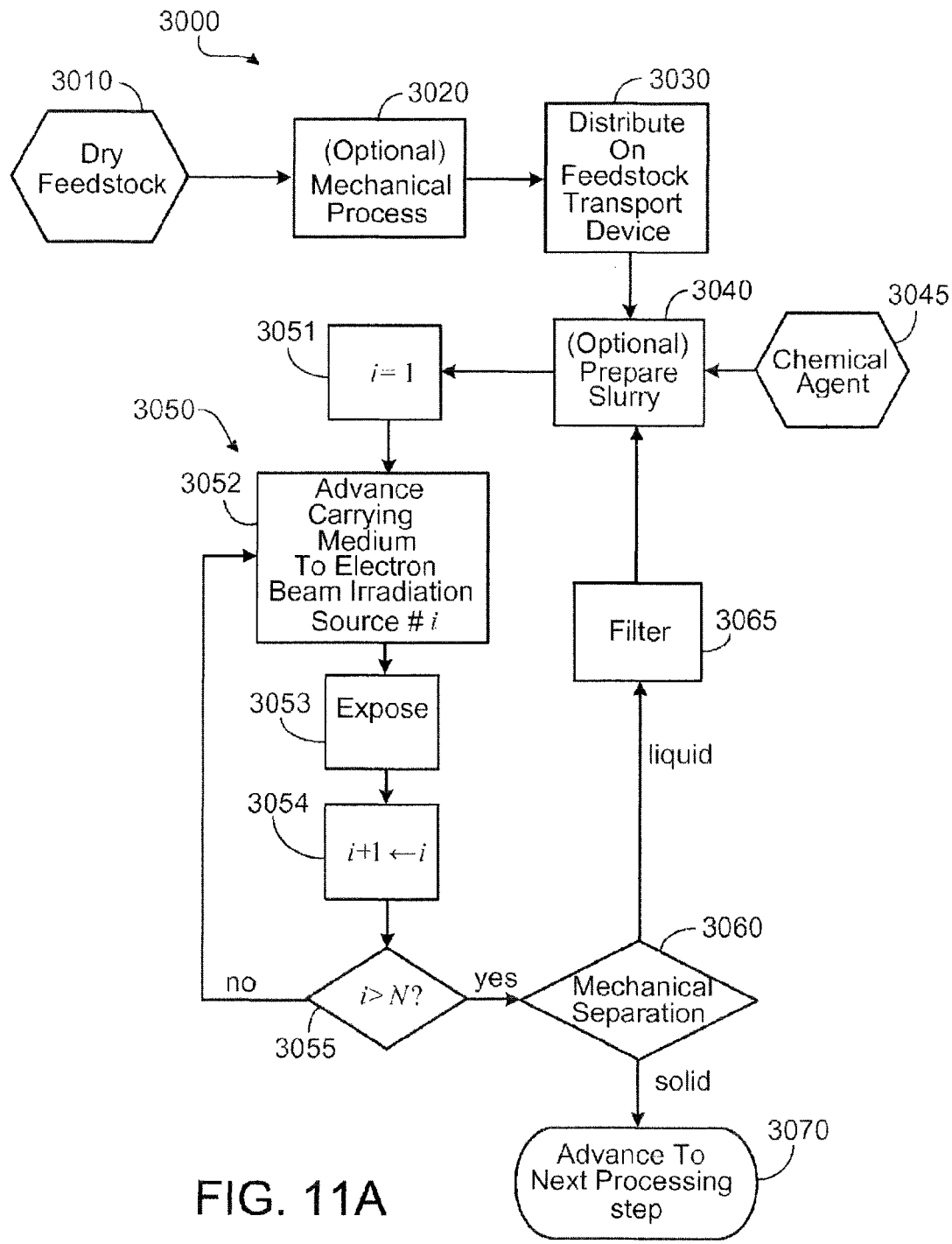
FIG. 11A is a block diagram illustrating an electron beam irradiation feedstock pretreatment sequence.

FIG. 11A shows a process flow diagram 3000 that includes various steps in an electron beam irradiation feedstock pretreatment sequence. In first step 3010, a supply of dry feedstock is received from a feed source. As discussed above, the dry feedstock from the feed source may be pre-processed prior to delivery to the electron beam irradiation devices. For example, if the feedstock is derived from plant sources, certain portions of the plant material may be removed prior to collection of the plant material and/or before the plant material is delivered by the feedstock transport device. Alternatively, or in addition, as expressed in optional step 3020, the biomass feedstock can be subjected to mechanical processing (e.g., to reduce the average length of fibers in the feedstock) prior to delivery to the electron beam irradiation devices.

In step 3030, the dry feedstock is transferred to a feedstock transport device (e.g., a conveyor belt) and is distributed over the cross-sectional width of the feedstock transport device approximately uniformly by volume. This can be accomplished, for example, manually or by inducing a localized vibration motion at some point in the feedstock transport device prior to the electron beam irradiation processing.

In some embodiments, a mixing system introduces a chemical agent 3045 into the feedstock in an optional process 3040 that produces a slurry. Combining water with the processed feedstock in mixing step 3040 creates an aqueous feedstock slurry that may be transported through, for example, piping rather than using, for example, a conveyor belt.

The next step 3050 is a loop that encompasses exposing the feedstock (in dry or slurry form) to electron beam radiation via one or more (say, N) electron beam irradiation devices. The feedstock slurry is moved through each of the N "showers" of electron beams at step 3052. The movement may either be at a continuous speed through and between the showers, or there may be a pause through each shower, followed by a sudden movement to the next shower. A small slice of the feedstock slurry is exposed to each shower for some predetermined exposure time at step 3053.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. Effectiveness of depolymerization of the feedstock slurry depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, irradiation devices are housed in a vault, e.g., of lead or concrete.

Tradeoffs in considering electron energies include energy costs; a lower electron energy may be advantageous in encouraging depolymerization of certain feedstock slurry (see, for example, Bouchard, et al., Cellulose (2006) 13: 601-610).

It may be advantageous to provide a double-pass of electron beam irradiation in order to provide a more effective depolymerization process. For example, the feedstock transport device could direct the feedstock (in dry or slurry form) underneath and in a reverse direction to its initial transport direction. Double-pass systems can allow thicker feedstock slurries to be processed and can provide a more uniform depolymerization through the thickness of the feedstock slurry.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available.

Once a portion of feedstock slurry has been transported through the N electron beam irradiation devices, it may be necessary in some embodiments, as in step 3060, to mechanically separate the liquid and solid components of the feedstock slurry. In these embodiments, a liquid portion of the feedstock slurry is filtered for residual solid particles and recycled back to the slurry preparation step 3040. A solid portion of the feedstock slurry is then advanced on to the next processing step 3070 via the feedstock transport device. In other embodiments, the feedstock is maintained in slurry form for further processing.

Ion Particle Beams

Particles heavier than electrons can be utilized to irradiate carbohydrates or materials that include carbohydrates, e.g., cellulosic materials, lignocellulosic materials, starchy materials, or mixtures of any of these and others described herein. For example, protons, helium nuclei, argon ions, silicon ions, neon ions carbon ions, phoshorus ions, oxygen ions or nitrogen ions can be utilized. In some embodiments, particles heavier than electrons can induce higher amounts of chain scission. In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

The types and properties of particles that can be used to irradiate various types of biomass materials are disclosed in further detail below. Further, systems and methods for producing beams of such particles are disclosed.

1. Types of Ions

In general, many different types of ions can be used to irradiate biomass materials. For example, in some embodiments, ion beams can include relatively light ions, such as protons and/or helium ions. In certain embodiments, the ion beams can include moderately heavier ions, such as carbon ions, nitrogen ions, oxygen ions, and/or neon ions. In some embodiments, ion beams can include still heavier ions, such as argon ions, silicon ions, phosphorus ions, sodium ions, calcium ions, and/or iron ions.

In certain embodiments, ion beams used to irradiate biomass materials can include more than one different type of ions. For example, ion beams can include mixtures of two or more (e.g., three, or four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam, where each of the different types of ions has different effectiveness in irradiating different types of biomass materials.

In some embodiments, ion beams for irradiating biomass materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to biomass materials, initiating and sustaining cationic ring-opening chain scission reactions in an oxidative environment.

In certain embodiments, ion beams for irradiating biomass materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to biomass materials, causing anionic ring-opening chain scission reactions in a reducing environment.

In some embodiments, beams for irradiating biomass materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

The preceding discussion has focused on ion beams that include mononuclear ions and/or neutral particles (e.g., atomic ions and neutral atoms). Typically, such particles are the easiest—in energetic terms—to generate, and parent particles from which these species are generated may be available in abundant supply. However, in some embodiments, beams for irradiating biomass materials can include one or more types of ions or neutral particles that are polynuclear, e.g., including two or more different types of nuclei. For example, ion beams can include positive and/or negative ions and/or neutral particles formed from species such as $N_2$, $O_2$, $H_2$, $CH_4$, and other molecular species. Ion beams can also include ions and/or neutral particles formed from heavier species that include even more nuclei, such as various hydrocarbon-based species and/or various inorganic species, including coordination compounds of various metals.

In certain embodiments, ion beams used to irradiate biomass materials include singly-charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^-$, $Ca^+$, and $Fe^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions, by virtue of the electronic structures of the ions.

2. Ion Generation

In this section, various methods for the generation of ions suitable for ion beams are discussed. After the ions have been generated, they are typically accelerated in one or more of various types of accelerators, and then directed to impinge on biomass materials. Accelerators and the structures thereof will be discussed in more detail in the next section.

(i) Hydrogen Ions

Hydrogen ions can be generated using a variety of different methods in an ion source. Typically, hydrogen ions are introduced into an ionizing chamber of an ion source, and ions are produced by supplying energy to gas molecules. During operation, such chambers can produce large ion currents suitable for seeding a downstream ion accelerator.

Figure 43:
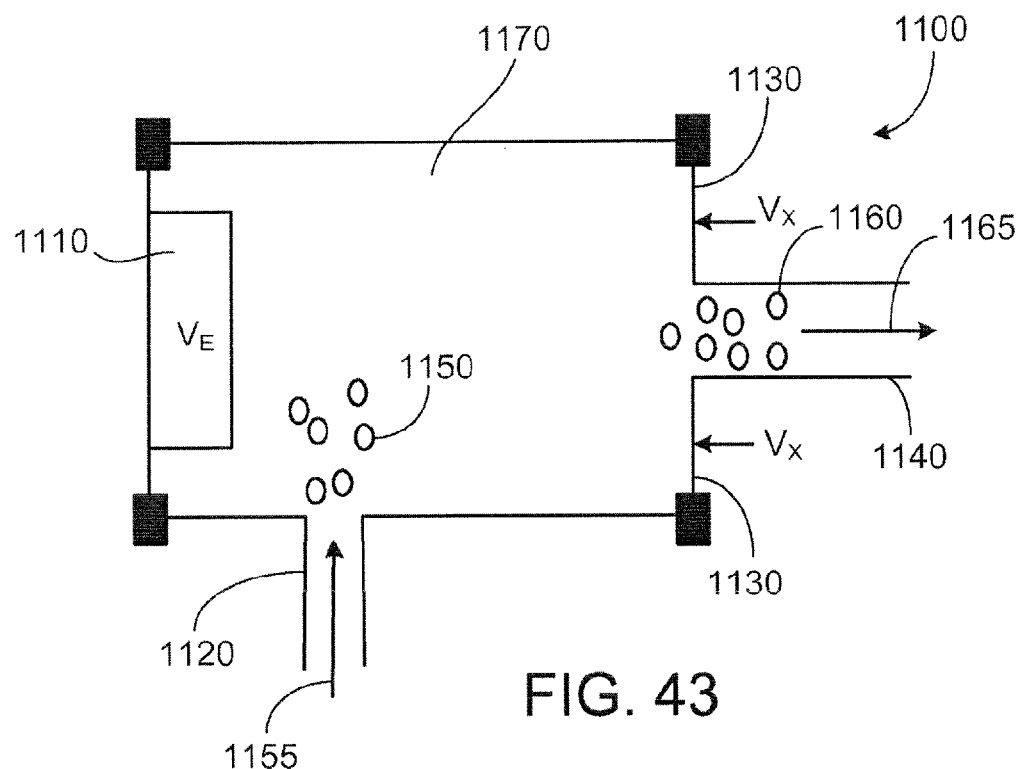
FIG. 43 is a schematic diagram of a field ionization
source.

In some embodiments, hydrogen ions are produced via field ionization of hydrogen gas. A schematic diagram of a field ionization source is shown in FIG. 43. Field ionization source 1100 includes a chamber 1170 where ionization of gas molecules (e.g., hydrogen gas molecules) occurs. Gas molecules 1150 enter chamber 1170 by flowing along direction 1155 in supply tube 1120. Field ionization source 1100 includes an ionization electrode 1110. During operation, a large potential $V_E$ (relative to a common system ground potential) is applied to electrode 1110. Molecules 1150 that circulate within a region adjacent to electrode 1110 are ionized by the electric field that results from potential $V_E$. Also during operation, an extraction potential $V_X$ is applied to extractors 1130. The newly-formed ions migrate towards extractors 1130 under the influence of the electric fields of potentials $V_E$ and $V_X$. In effect, the newly-formed ions experience repulsive forces relative to ionization electrode 1110, and attractive forces relative to extractors 1130. As a result, certain of the newly-formed ions enter discharge tube 1140, and propagate along direction 1165 under the influence of potentials $V_E$ and $V_X$.

Depending upon the sign of potential $V_E$ (relative to the common ground potential), both positively and negatively charged ions can be formed. For example, in some embodiments, a positive potential can be applied to electrode 1110 and a negative potential can be applied to extractors 1130. Positively charged hydrogen ions (e.g., protons $H^+$) that are generated in chamber 1170 are repelled away from electrode 1110 and toward extractors 1130. As a result, discharged particle stream 1160 includes positively charged hydrogen ions that are transported to an injector system.

In certain embodiments, a negative potential can be applied to electrode 1110 and a positive potential can be applied to extractors 1130. Negatively charged hydrogen ions (e.g., hydride ions $H^-$) that are generated in chamber 1170 are repelled away from electrode 1110 and toward extractors 1130. Discharged particle stream 1160 includes negatively charged hydrogen ions, which are then transported to an injector system.

In some embodiments, both positive and negative hydrogen ions can be produced via direct thermal heating of hydrogen gas. For example, hydrogen gas can be directed to enter a heating chamber that is evacuated to remove residual oxygen and other gases. The hydrogen gas can then be heated via a heating element to produce ionic species. Suitable heating elements include, for example, arc discharge electrodes, heating filaments, heating coils, and a variety of other thermal transfer elements.

Figure 44:
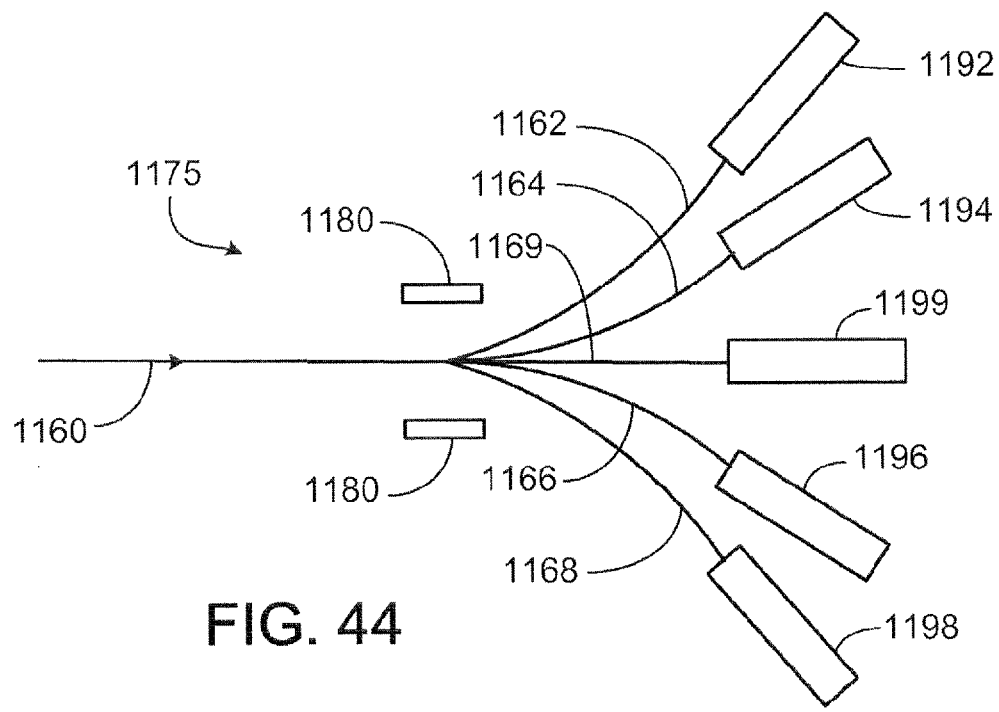
FIG. 44 is a schematic diagram of an electrostatic ion
separator.

In certain embodiments, when hydrogen ions are produced via either field emission or thermal heating, various hydrogen ion species can be produced, including both positively and negatively charged ion species, and singly- and multiply-charged ion species. The various ion species can be separated from one another via one or more electrostatic and/or magnetic separators. FIG. 44 shows a schematic diagram of an electrostatic separator 1175 that is configured to separate a plurality of hydrogen ion species from one another. Electrostatic separator 1175 includes a pair of parallel electrodes 1180 to which a potential $V_s$ is applied by a voltage source (not shown). Particle stream 1160, propagating in the direction indicated by the arrow, includes a variety of positively- and negatively-charged, and singly- and multiply-charged, ion species. As the various ion species pass through electrodes 1180, the electric field between the electrodes deflects the ion trajectories according to the magnitude and sign of the ion species. In FIG. 44, for example, the electric field points from the lower electrode toward the upper electrode in the region between electrodes 1180. As a result, positively-charged ions are deflected along an upward trajectory in FIG. 44, and negatively-charged ions are deflected along a downward trajectory. Ion beams 1162 and 1164 each correspond to positively-charged ion species, with the ion species in ion beam 1162 having a larger positive charge than the ion species is beam 1164 (e.g., due to the larger positive charge of the ions in beam 1162, the beam is deflected to a greater extent).

Similarly, ion beams 1166 and 1168 each correspond to negatively-charged ion species, with the ion species in ion beam 1168 having a larger negative charge than the ion species in ion beam 1166 (and thereby being deflected to a larger extent by the electric field between electrodes 1180). Beam 1169 includes neutral particles originally present in particle stream 1160; the neutral particles are largely unaffected by the electric field between electrodes 1180, and therefore pass undeflected through the electrodes. Each of the separated particle streams enters one of delivery tubes 1192, 1194, 1196, 1198, and 1199, and can be delivered to an injector system for subsequent acceleration of the particles, or steered to be incident directly on the biomass material. Alternatively, or in addition, any or all of the separated particle streams can be blocked to prevent ion and/or atomic species from reaching biomass material. As yet another alternative, certain particle streams can be combined and then directed to an injector system and/or steered to be incident directly on the biomass material using known techniques.

In general, particle beam separators can also use magnetic fields in addition to, or rather than, electric fields for deflecting charged particles. In some embodiments, particle beam separators include multiple pairs of electrodes, where each pair of electrodes generates an electric field that deflects particles passing therethrough. Alternatively, or in addition, particle beam separators can include one or more magnetic deflectors that are configured to deflect charged particles according to magnitude and sign of the particle charges.

(ii) Noble Gas Ions

Figure 45:
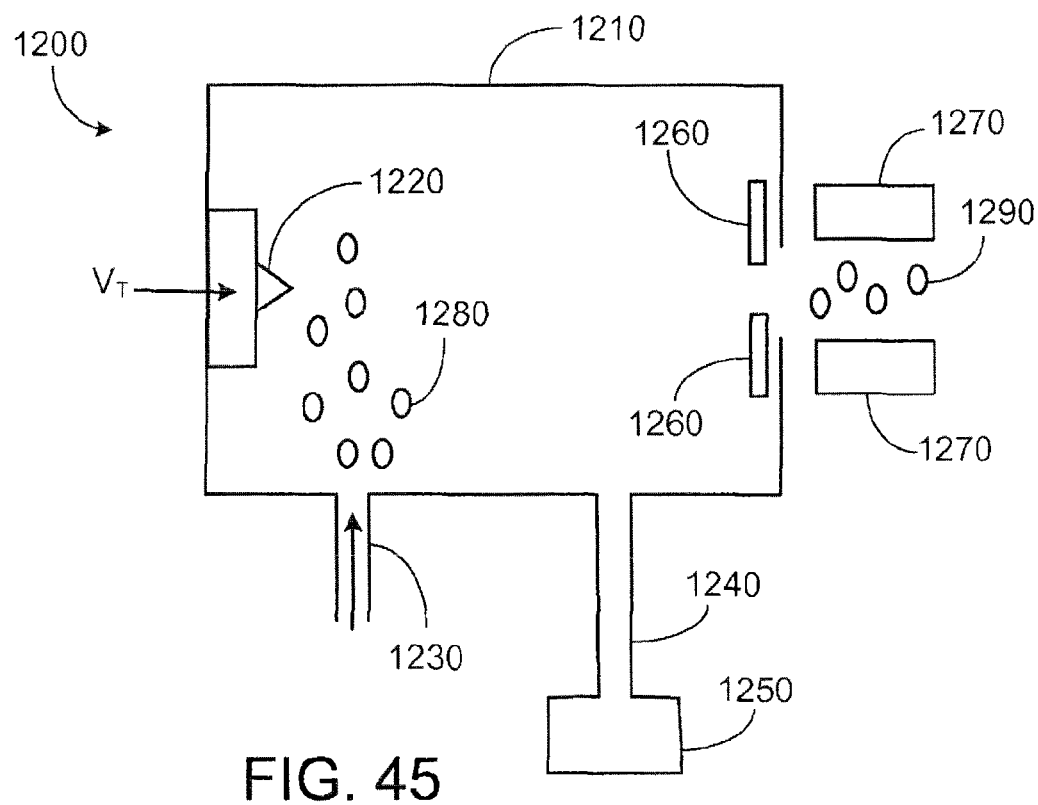
FIG. 45 is a schematic diagram of a field ionization
generator.

Noble gas atoms (e.g., helium atoms, neon atoms, argon atoms) form positively-charged ions when acted upon by relatively strong electric fields. Methods for generating noble gas ions therefore typically include generating a high-intensity electric field, and then introducing noble gas atoms into the field region to cause field ionization of the gas atoms. A schematic diagram of a field ionization generator for noble gas ions (and also for other types of ions) is shown in FIG. 45. Field ionization generator 1200 includes a tapered electrode 1220 positioned within a chamber 1210. A vacuum pump 1250 is in fluid communication with the interior of chamber 1210 via inlet 1240, and reduces the pressure of background gases within chamber 1210 during operation. One or more noble gas atoms 1280 are admitted to chamber 1210 via inlet tube 1230.

During operation, a relatively high positive potential $V_T$ (e.g., positive relative to a common external ground) is applied to tapered electrode 1220. Noble gas atoms 1280 that enter a region of space surrounding the tip of electrode 1220 are ionized by the strong electric field extending from the tip; the gas atoms lose an electron to the tip, and form positively charged noble gas ions.

The positively charged noble gas ions are accelerated away from the tip, and a certain fraction of the gas ions 1290 pass through extractor 1260 and exit chamber 1210, into an ion optical column that includes lens 1270, which further deflects and/or focuses the ions.

Electrode 1220 is tapered to increase the magnitude of the local electric field in the region near the apex of the tip. Depending upon the sharpness of the taper and the magnitude of potential $V_T$, the region of space in chamber 1210 within which ionization of noble gas atoms occurs can be relatively tightly controlled. As a result, a relatively well collimated beam of noble gas ions 1290 can be obtained following extractor 1260.

As discussed above in connection with hydrogen ions, the resulting beam of noble gas ions 1290 can be transported through a charged particle optical column that includes various particle optical elements for deflecting and/or focusing the noble gas ion beam. The noble gas ion beam can also pass through an electrostatic and/or magnetic separator, as discussed above in connection with FIG. 44.

Noble gas ions that can be produced in field ionization generator 1200 include helium ions, neon ions, argon ions, and krypton ions. In addition, field ionization generator 1200 can be used to generate ions of other gaseous chemical species, including hydrogen, nitrogen, and oxygen.

Noble gas ions may have particular advantages relative to other ion species when treating biomass. For example, while noble gas ions can react with biomass materials, neutralized noble gas ions (e.g., noble gas atoms) that are produced from such reactions are generally inert, and do not further react with the biomass. Moreover, neutral noble gas atoms do not remain embedded in the biomass material, but instead diffuse out of the material. Noble gases are non-toxic and can be used in large quantities without adverse consequences to either human health or the environment.

(iii) Carbon, Oxygen, and Nitrogen Ions

Ions of carbon, oxygen, and nitrogen can typically be produced by field ionization in a system such as field ionization source 1100 or field ionization generator 1200. For example, oxygen gas molecules and/or oxygen atoms (e.g., produced by heating oxygen gas) can be introduced into a chamber, where the oxygen molecules and/or atoms are field ionized to produce oxygen ions. Depending upon the sign of the potential applied to the field ionization electrode, positively- and/or negatively-charged oxygen ions can be produced. The desired ion species can be preferentially selected from among various ion species and neutral atoms and molecules by an electrostatic and/or magnetic particle selector, as shown in FIG. 44.

As another example, nitrogen gas molecules can be introduced into the chamber of either field ionization source 1100 or field ionization generator 1200, and ionized to form positively- and/or negatively-charged nitrogen ions by the relatively strong electric field within the chamber. The desired ion species can then be separated from other ionic and neutral species via an electrostatic and/or magnetic separator, as shown in FIG. 44.

To form carbon ions, carbon atoms can be supplied to the chamber of either field ionization source 1100 or field ionization generator 1200, wherein the carbon atoms can be ionized to form either positively- and/or negatively-charged carbon ions. The desired ion species can then be separated from other ionic and neutral species via an electrostatic and/or magnetic separator, as shown in FIG. 44. The carbon atoms that are supplied to the chamber of either field ionization source 1100 or field ionization generator 1200 can be produced by heating a carbon-based target (e.g., a graphite target) to cause thermal emission of carbon atoms from the target. The target can be placed in relatively close proximity to the chamber, so that emitted carbon atoms enter the chamber directly following emission.

(iv) Heavier Ions

Ions of heavier atoms such as sodium and iron can be produced via a number of methods. For example, in some embodiments, heavy ions such as sodium and/or iron ions are produced via thermionic emission from a target material that includes sodium and/or iron, respectively. Suitable target materials include materials such as sodium silicates and/or iron silicates. The target materials typically include other inert materials such as beta-alumina. Some target materials are zeolite materials, and include channels formed therein to permit escape of ions from the target material.

Figure 46:
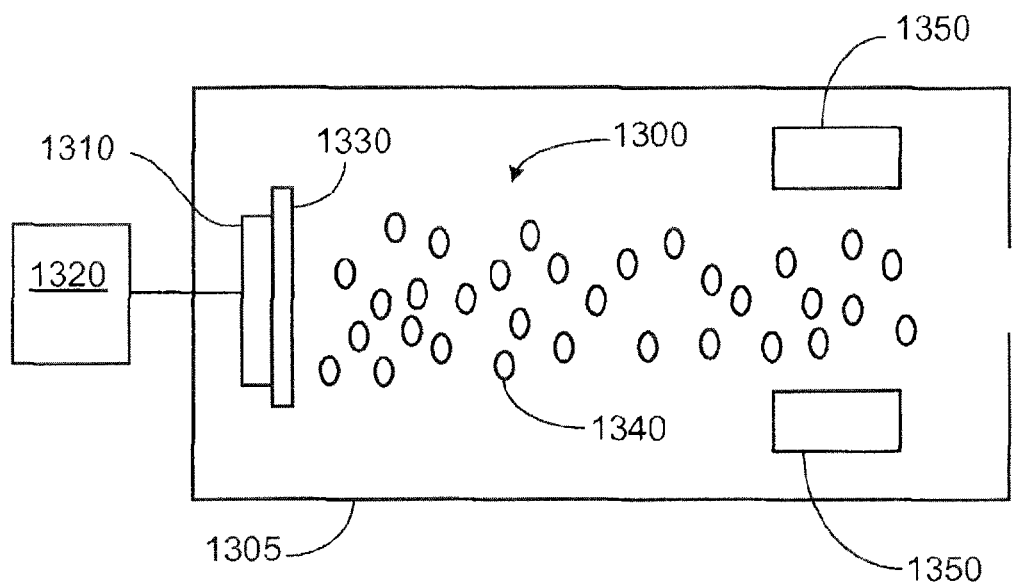
FIG. 46 is a schematic diagram of a thermionic emission
source.

FIG. 46 shows a thermionic emission source 1300 that includes a heating element 1310 that contacts a target material 1330, both of which are positioned inside an evacuated chamber 1305. Heating element 1310 is controlled by controller 1320, which regulates the temperature of heating element 1310 to control the ion current generated from target material 1330. When sufficient heat is supplied to target material 1330, thermionic emission from the target material generates a stream of ions 1340. Ions 1340 can include positively-charged ions of materials such as sodium, iron, and other relatively heavy atomic species (e.g., other metal ions). Ions 1340 can then be collimated, focused, and/or otherwise deflected by electrostatic and/or magnetic electrodes 1350, which can also deliver ions 1340 to an injector.

Thermionic emission to form ions of relatively heavy atomic species is also discussed, for example, in U.S. Pat. No. 4,928,033, entitled "Thermionic Ionization Source," the entire contents of which are incorporated herein by reference.

Figure 47:
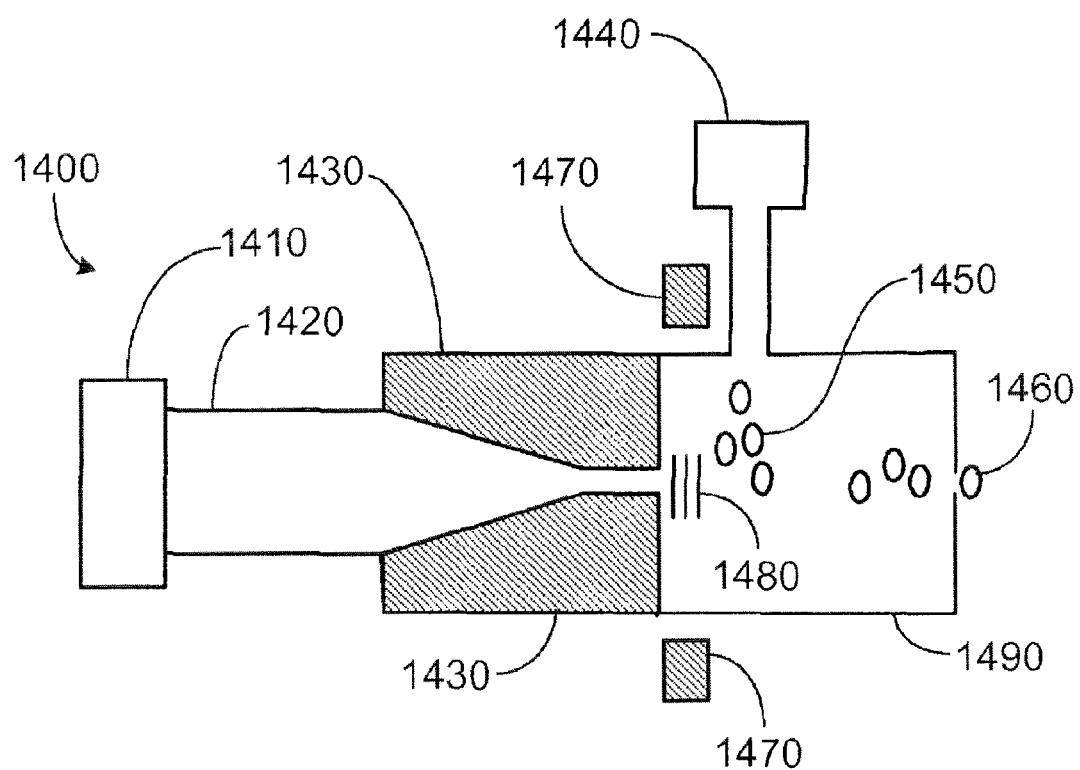
FIG. 47 is a schematic diagram of a microwave discharge
ion source.

In certain embodiments, relatively heavy ions such as sodium ions and/or iron ions can be produced by microwave discharge. FIG. 47 shows a schematic diagram of a microwave discharge source 1400 that produces ions from relatively heavy atoms such as sodium and iron. Discharge source 1400 includes a microwave field generator 1410, a waveguide tube 1420, a field concentrator 1430, and an ionization chamber 1490. During operation, field generator 1410 produces a microwave field which propagates through waveguide 1420 and concentrator 1430; concentrator 1430 increases the field strength by spatially confining the field, as shown in FIG. 47. The microwave field enters ionization chamber 1490. In a first region inside chamber 1490, a solenoid 1470 produces a strong magnetic field 1480 in a region of space that also includes the microwave field. Source 1440 delivers atoms 1450 to this region of space. The concentrated microwave field ionizes atoms 1450, and the magnetic field 1480 generated by solenoid 1470 confines the ionized atoms to form a localized plasma. A portion of the plasma exits chamber 1490 as ions 1460. Ions 1460 can then be deflected and/or focused by one or more electrostatic and/or magnetic elements, and delivered to an injector.

Atoms 1450 of materials such as sodium and/or iron can be generated by thermal emission from a target material, for example. Suitable target materials include materials such as silicates and other stable salts, including zeolite-based materials. Suitable target materials can also include metals (e.g., iron), which can be coated on an inert base material such as a glass material.

Microwave discharge sources are also discussed, for example, in the following U.S. patents: U.S. Pat. No. 4,409,520, entitled "Microwave Discharge Ion Source," and U.S. Pat. No. 6,396,211, entitled "Microwave Discharge Type Electrostatic Accelerator Having Upstream and Downstream Acceleration Electrodes." The entire contents of each of the foregoing patents are incorporated herein by reference.

3. Particle Beam Sources

Particle beam sources that generate beams for use in irradiating biomass material typically include three component groups: an injector, which generates or receives ions and introduces the ions into an accelerator; an accelerator, which receives ions from the injector and increases the kinetic energy of the ions; and output coupling elements, which manipulate the beam of accelerated ions.

(i) Injectors

Injectors can include, for example, any of the ion sources discussed in the preceding sections above, which supply a stream of ions for subsequent acceleration. Injectors can also include various types of electrostatic and/or magnetic particle optical elements, including lenses, deflectors, collimators, filters, and other such elements. These elements can be used to condition the ion beam prior to entering the accelerator; that is, these elements can be used to control the propagation characteristics of the ions that enter the accelerator. Injectors can also include pre-accelerating electrostatic and/or magnetic elements that accelerate charged particles to a selected energy threshold prior to entering the accelerator. An example of an injector is shown in Iwata, Y. et al., Alternating-Phase-Focused IH-DTL for Heavy-Ion Medical Accelerators", Proceedings of EPAC 2006, Edinburgh, Scotland.

(ii) Accelerators

Figure 48:
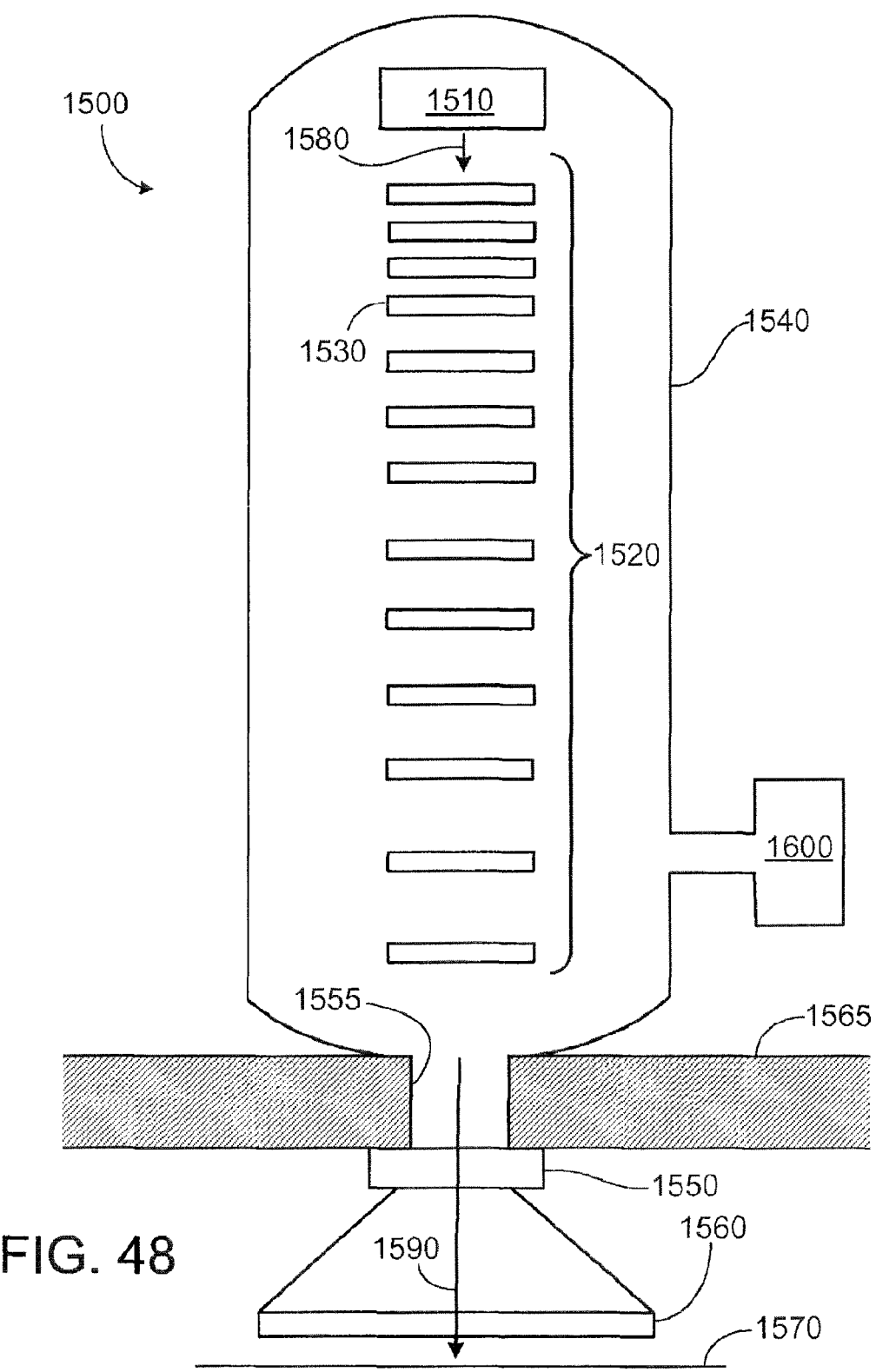
FIG. 48 is a schematic diagram of a DC accelerator.

One type of accelerator that can be used to accelerate ions produced using the sources discussed above is a Dynamitron® (available, for example, from Radiation Dynamics Inc., now a unit of IBA, Louvain-la-Neuve, Belgium). A schematic diagram of a Dynamitron® accelerator 1500 is shown in FIG. 48. Accelerator 1500 includes an injector 1510 (which includes an ion source), and an accelerating column 1520 that includes a plurality of annular electrodes 1530. Injector 1510 and column 1520 are housed within an enclosure 1540 that is evacuated by a vacuum pump 1600.

Injector 1510 produces a beam of ions 1580, and introduces beam 1580 into accelerating column 1520. The annular electrodes 1530 are maintained at different electric potentials, so that ions are accelerated as they pass through gaps between the electrodes (e.g., the ions are accelerated in the gaps, but not within the electrodes, where the electric potentials are uniform). As the ions travel from the top of column 1520 toward the bottom in FIG. 48, the average speed of the ions increases. The spacing between subsequent annular electrodes 1530 typically increases, therefore, to accommodate the higher average ion speed.

After the accelerated ions have traversed the length of column 1520, the accelerated ion beam 1590 is coupled out of enclosure 1540 through delivery tube 1555. The length of delivery tube 1555 is selected to permit adequate shielding (e.g., concrete shielding) to be positioned adjacent to column 1520 to isolate the column. After passing through tube 1555, ion beam 1590 passes through scan magnet 1550. Scan magnet 1550, which is controlled by an external logic unit (not shown), can sweep accelerated ion beam 1590 in controlled fashion across a two-dimensional plane oriented perpendicular to a central axis of column 1520. As shown in FIG. 48, ion beam 1590 passes through window 1560 (e.g., a metal foil window or screen) and then is directed to impinge on selected regions of a sample 1570 by scan magnet 1550.

In some embodiments, the electric potentials applied to electrodes 1530 are static potentials generated, for example, by DC potential sources. In certain embodiments, some or all of the electric potentials applied to electrodes 1530 are variable potentials generated by variable potential sources. Suitable variable sources of large electric potentials include amplified field sources such as klystrons, for example. Accordingly, depending upon the nature of the potentials applied to electrodes 1530, accelerator 1500 can operate in either pulsed or continuous mode.

To achieve a selected accelerated ion energy at the output end of column 1520, the length of column 1520 and the potentials applied to electrodes 1530 are chosen based on considerations that are well-known in the art. However, it is notable that to reduce the length of column 1520, multiply-charged ions can be used in place of singly-charged ions. That is, the accelerating effect of a selected electric potential difference between two electrodes is greater for an ion bearing a charge of magnitude 2 or more than for an ion bearing a charge of magnitude 1. Thus, an arbitrary ion $X^{2+}$ can be accelerated to a final energy E over a shorter length than a corresponding arbitrary ion $X^+$. Triply- and quadruply-charged ions (e.g., $X^{3+}$ and $X^{4+}$) can be accelerated to final energy E over even shorter distances. Therefore, the length of column 1520 can be significantly reduced when ion beam 1580 includes primarily multiply-charged ion species.

To accelerate positively-charged ions, the potential differences between electrodes 1530 of column 1520 are selected so that the direction of increasing field strength in FIG. 48 is downward (e.g., toward the bottom of column 1520). Conversely, when accelerator 1500 is used to accelerate negatively-charged ions, the electric potential differences between electrodes 1530 are reversed in column 1520, and the direction of increasing field strength in FIG. 48 is upward (e.g., toward the top of column 1520). Reconfiguring the electric potentials applied to electrodes 1530 is a straightforward procedure, so that accelerator 1500 can be converted relatively rapidly from accelerating positive ions to accelerating negative ions, or vice versa. Similarly, accelerator 1500 can be converted rapidly from accelerating singly-charged ions to accelerating multiply-charged ions, and vice versa.

Another type of accelerator that can be used to accelerate ions for treatment of biomass-based material is a Rhodotron® accelerator (available, for example, from IBA, Louvain-la-Neuve, Belgium). In general, Rhodotron-type accelerators include a single recirculating cavity through which ions that are being accelerated make multiple passes. As a result, Rhodotron® accelerators can be operated in continuous mode at relatively high continuous ion currents.

Figure 49:
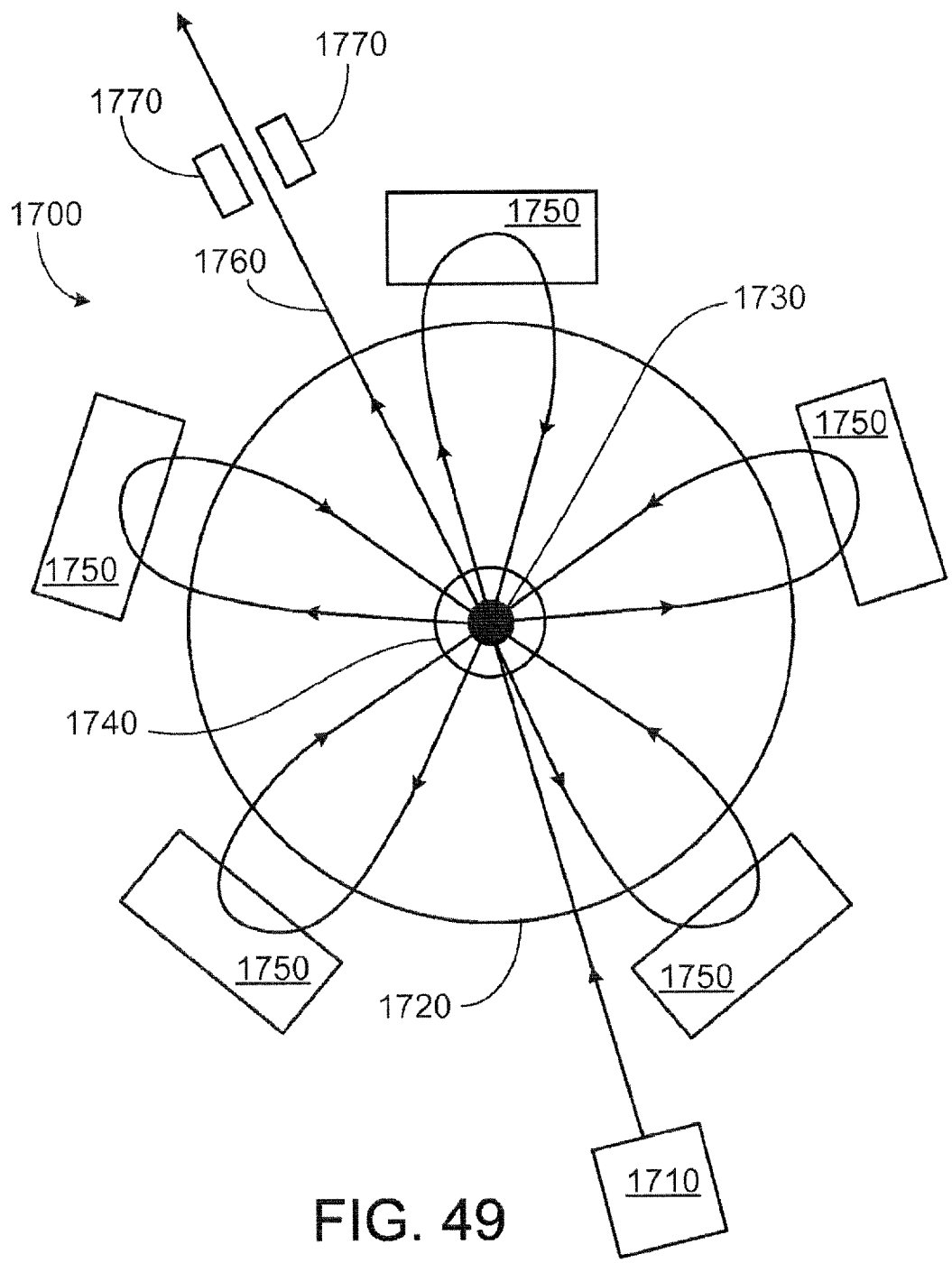
FIG. 49 is a schematic diagram of a recirculating accelerator.

FIG. 49 shows a schematic diagram of a Rhodotron® accelerator 1700. Accelerator 1700 includes an injector 1710, which introduces accelerated ions into recirculating cavity 1720. An electric field source 1730 is positioned within an inner chamber 1740 of cavity 1720, and generates an oscillating radial electric field. The oscillation frequency of the radial field is selected to match the transit time of injected ions across one pass of recirculating cavity 1720. For example, a positively-charged ion is injected into cavity 1720 by injector 1710 when the radial electric field in the cavity has zero amplitude. As the ion propagates toward chamber 1740, the amplitude of the radial field in chamber 1740 increases to a maximum value, and then decreases again. The radial field points inward toward chamber 1740, and the ion is accelerated by the radial field. The ion passes through a hole in the wall of inner chamber 1740, crosses the geometrical center of cavity 1720, and passes out through another hole in the wall of inner chamber 1740. When the ion is positioned at the enter of cavity 1720, the electric field amplitude inside cavity 1720 has been reduced to zero (or nearly zero). As the ion emerges from inner chamber 1740, the electric field amplitude in cavity 1720 begins to increase again, but the field is now oriented radially outward. The field magnitude during the second half of the ion's pass through cavity 1720 again reaches a maximum and then begins to diminish. As a result, the positive ion is again accelerated by the electric field as the ion completes the second half of a first pass through cavity 1720.

Upon reaching the wall of cavity 1720, the magnitude of the electric field in cavity 1720 is zero (or nearly zero) and the ion passes through an aperture in the wall and encounters one of beam deflection magnets 1750. The beam deflection magnets essentially reverse the trajectory of the ion, as shown in FIG. 49, directing the ion to re-enter cavity 1720 through another aperture in the wall of the chamber. When the ion re-enters cavity 1720, the electric field therein begins to increase in amplitude again, but is now once more oriented radially inward. The second and subsequent passes of the ion through cavity 1720 follow a similar pattern, so that the orientation of the electric field always matches the direction of motion of the ion, and the ion is accelerated on every pass (and every half-pass) through cavity 1720.

As shown in FIG. 49, after six passes through cavity 1720, the accelerated ion is coupled out of cavity 1720 as a portion of accelerated ion beam 1760. The accelerated ion beam passes through one or more electrostatic and/or magnetic particle optical elements 1770, which can include lenses, collimators, beam deflectors, filters, and other optical elements. For example, under control of an external logic unit, elements 1770 can include an electrostatic and/or magnetic deflector that sweeps accelerated beam 1760 across a two-dimensional planar region oriented perpendicular to the direction of propagation of beam 1760.

Ions that are injected into cavity 1720 are accelerated on each pass through cavity 1720. In general, therefore, to obtain accelerated beams having different average ion energies, accelerator 1700 can include more than one output coupling. For example, in some embodiments, one or more of deflection magnets 1750 can be modified to allow a portion of the ions reaching the magnets to be coupled out of accelerator 1700, and a portion of the ions to be returned to chamber 1720. Multiple accelerated output beams can therefore be obtained from accelerator 1700, each beam corresponding to an average ion energy that is related to the number of passes through cavity 1720 for the ions in the beam.

Accelerator 1700 includes 5 deflection magnets 1750, and ions injected into cavity 1720 make 6 passes through the cavity. In general, however, accelerator 1700 can include any number of deflection magnets, and ions injected into cavity 1720 can make any corresponding number of passes through the cavity. For example, in some embodiments, accelerator 1700 can include at least 6 deflection magnets and ions can make at least 7 passes through the cavity (e.g., at least 7 deflection magnets and 8 passes through the cavity, at least 8 deflection magnets and 9 passes through the cavity, at least 9 deflection magnets and 10 passes through the cavity, at least 10 deflection magnets and 11 passes through the cavity).

Typically, the electric field generated by field source 1730 provides a single-cavity-pass gain of about 1 MeV to an injected ion. In general, however, higher single-pass gains are possible by providing a higher-amplitude electric field within cavity 1720. In some embodiments, for example, the single-cavity-pass gain is about 1.2 MeV or more (e.g., 1.3 MeV or more, 1.4 MeV or more, 1.5 MeV or more, 1.6 MeV or more, 1.8 MeV or more, 2.0 MeV or more, 2.5 MeV or more).

The single-cavity-pass gain also depends upon the magnitude of the charge carried by the injected ion. For example, ions bearing multiple charges will experience higher single-pass-cavity gain than ions bearing single charges, for the same electric field within cavity. As a result, the single-pass-cavity gain of accelerator 1700 can be further increased by injecting ions having multiple charges.

In the foregoing description of accelerator 1700, a positively-charged ion was injected into cavity 1720. Accelerator 1700 can also accelerate negatively charged ions. To do so, the negatively charged ions are injected so that the direction of their trajectories is out of phase with the radial electric field direction. That is, the negatively charged ions are injected so that on each half pass through cavity 1720, the direction of the trajectory of each ion is opposite to the direction of the radial electric field. Achieving this involves simply adjusting the time at which negatively-charged ions are injected into cavity 1720. Accordingly, accelerator 1700 is capable of simultaneously accelerating ions having the same approximate mass, but opposite charges. More generally, accelerator 1700 is capable of simultaneously accelerating different types of both positively- and negatively-charged (and both singly- and multiply-charged) ions, provided that the transit times of the ions across cavity 1720 are relatively similar. In some embodiments, accelerator 1700 can include multiple output couplings, providing different types of accelerated ion beams having similar or different energies.

Other types of accelerators can also be used to accelerate ions for irradiation of biomass material. For example, in some embodiments, ions can be accelerated to relatively high average energies in cyclotron- and/or synchrotron-based accelerators. The construction and operation of such accelerators is well-known in the art. As another example, in some embodiments, Penning-type ion sources can be used to generate and/or accelerate ions for treating biomass-based material. The design of Penning-type sources is discussed in section 7.2.1 of Prelec (Krsto Prelec, FIZIKA B 6 (1997) 4, 177-206).

Figure 50:
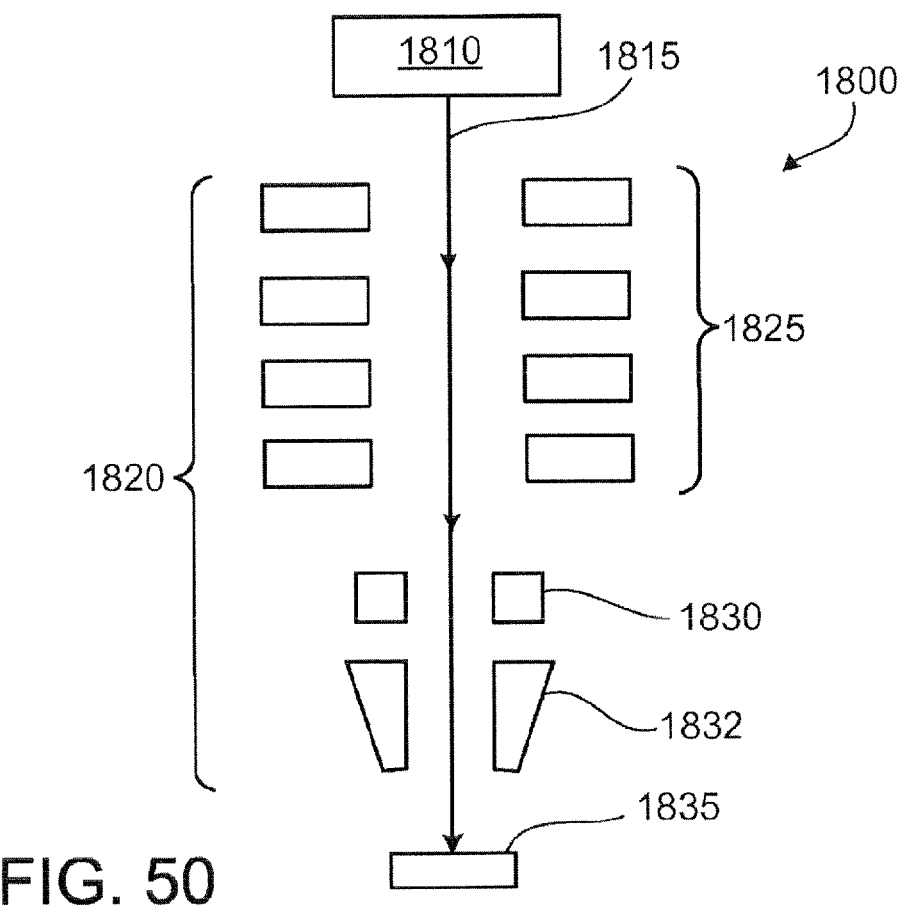
FIG. 50 is a schematic diagram of a static accelerator.

Static and/or dynamic accelerators of various types can also generally be used to accelerate ions. Static accelerators typically include a plurality of electrostatic lenses that are maintained at different DC voltages. By selecting appropriate values of the voltages applied to each of the lens elements, ions introduced into the accelerator can be accelerated to a selected final energy. FIG. 50 shows a simplified schematic diagram of a static accelerator 1800 that is configured to accelerate ions to treat biomass material 1835. Accelerator 1800 includes an ion source 1810 that produces ions and introduces the ions into an ion column 1820. Ion column 1820 includes a plurality of electrostatic lenses 1825 that accelerate the ions generated by ion source 1810 to produce an ion beam 1815. DC voltages are applied to lenses 1825; the potentials of the lenses remain approximately constant during operation. Generally, the electrical potential within each lens is constant, and the ions of ion beam 1815 are accelerated in the gaps between the various lenses 1825. Ion column 1820 also includes a deflection lens 1830 and a collimation lens 1832. These two lenses operate to direct ion beam 1815 to a selected position on biomass material 1835, and to focus ion beam 1815 onto the biomass material.

Although FIG. 50 shows a particular embodiment of a static accelerator, many other variations are possible and suitable for treating biomass material. In some embodiments, for example, the relative positions of deflection lens 1830 and collimation lens 1832 along ion column 1820 can be exchanged. Additional electrostatic lenses can also be present in ion column 1820, and ion column 1820 can further include magnetostatic optical elements. In certain embodiments, a wide variety of additional elements can be present in ion column 1820, including deflectors (e.g., quadrupole, hexapole, and/or octopole deflectors), filtering elements such as apertures to remove undesired species (e.g., neutrals and/or certain ionic species) from ion beam 1815, extractors (e.g., to establish a spatial profile for ion beam 1815), and other electrostatic and/or magnetostatic elements.

Dynamic linear accelerators—often referred to as LFNACs—can also be used to generate an ion beam that can be used to treat biomass. Typically, dynamic linear accelerators include an ion column with a linear series of radiofrequency cavities, each of which produces an intense, oscillating radiofrequency (RF) field that is timed to coincide with injection and propagation of ions into the ion column. As an example, devices such as klystrons can be used to generated the RF fields in the cavities. By matching the field oscillations to the injection times of ions, the RF cavities can accelerate ions to high energies without having to maintain peak potentials for long periods of time. As a result, LFNACs typically do not have the same shielding requirements as DC accelerators, and are typically shorter in length. LFNACs typically operate at frequencies of 3 GHz (S-band, typically limited to relatively low power) and 1 GHz (L-band, capable of significantly higher power operation). Typical LINACs have an overall length of 2-4 meters.

Figure 51:
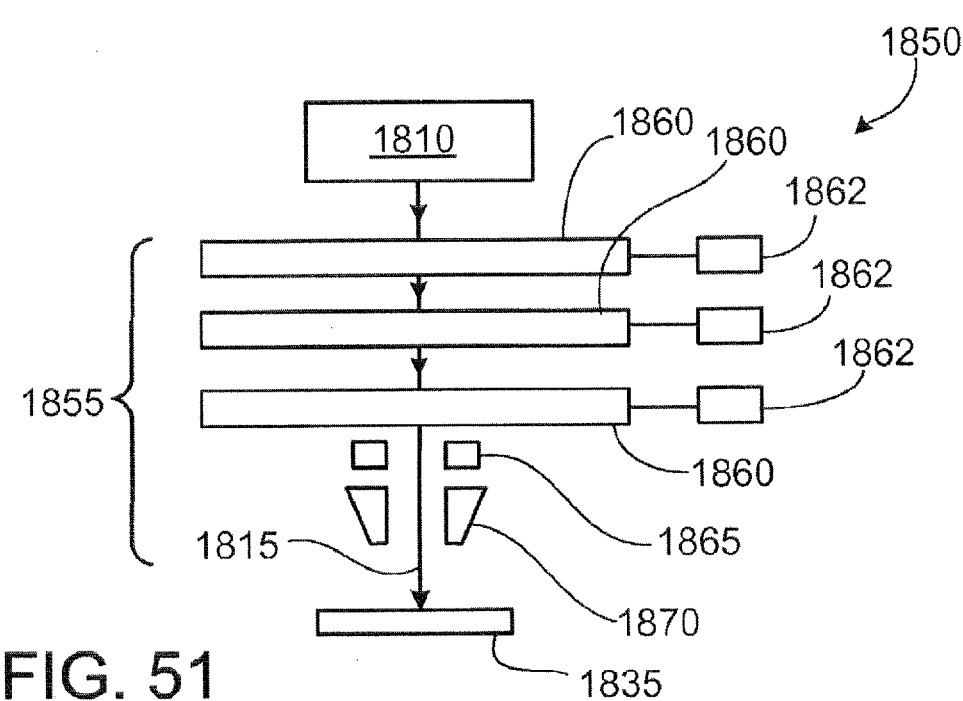
FIG. 51 is a schematic diagram of a dynamic linear
accelerator.

A schematic diagram of a dynamic linear accelerator 1850 (e.g., a LINAC) is shown in FIG. 51. LINAC 1850 includes an ion source 1810 and an ion column 1855 that includes three acceleration cavities 1860, a deflector 1865, and a focusing lens 1870. Deflector 1865 and focusing lens 1870 function to steer and focus ion beam 1815 onto biomass material 1835 following acceleration, as discussed above. Acceleration cavities 1860 are formed of a conductive material such as copper, and function as a waveguide for the accelerated ions. Klystrons 1862, connected to each of cavities 1860, generate the dynamic RF fields that accelerate the ions within the cavities. Klystrons 1862 are individually configured to produce RF fields that, together, accelerate the ions in ion beam 1815 to a final, selected energy prior to being incident on biomass material 1835.

As discussed above in connection with static accelerators, many variations of dynamic accelerator 1850 are possible and can be used to produce an ion beam for treating biomass material. For example, in some embodiments, additional electrostatic lenses can also be present in ion column 1855, and ion column 1855 can further include magnetostatic optical elements. In certain embodiments, a wide variety of additional elements can be present in ion column 1855, including deflectors (e.g., quadrupole, hexapole, and/or octopole deflectors), filtering elements such as apertures to remove undesired species (e.g., neutrals and/or certain ionic species) from ion beam 1815, extractors (e.g., to establish a spatial profile for ion beam 1815), and other electrostatic and/or magnetostatic elements. In addition to the specific static and dynamic accelerators discussed above, other suitable accelerator systems include, for example: DC insulated core transformer (ICT) type systems, available from Nissin High Voltage, Japan; S-band LFNACs, available from L3-PSD (USA), Linac Systems (France), Mevex (Canada), and Mitsubishi Heavy Industries (Japan); L-band LINACs, available from Iotron Industries (Canada); and ILU-based accelerators, available from Budker Laboratories (Russia).

Figure 52:
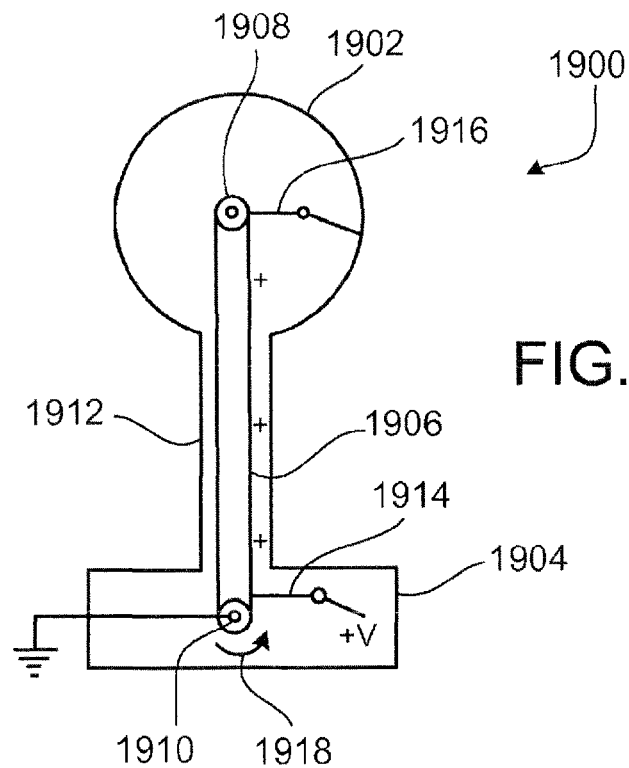
FIG. 52 is a schematic diagram of a van de Graaff
accelerator.

In some embodiments, van de Graaff-based accelerators can be used to produce and/or accelerate ions for subsequent treatment of biomass. FIG. 52 shows an embodiment of a van de Graaff accelerator 1900 that includes a spherical shell electrode 1902 and an insulating belt 1906 that recirculates between electrode 1902 and a base 1904 of accelerator 1900. During operation, insulating belt 1906 travels over pulleys 1910 and 1908 in the direction shown by arrow 1918, and carries charge into electrode 1902. Charge is removed from belt 1906 and transferred to electrode 1902, so that the magnitude of the electrical potential on electrode 1902 increases until electrode 1902 is discharged by a spark (or, alternatively, until the charging current is balanced by a load current).

Pulley 1910 is grounded, as shown in FIG. 52. A corona discharge is maintained between a series of points or a fine wire on one side of belt 1906. Wire 1914 is configured to maintain the corona discharge in accelerator 1900. Wire 1914 is maintained at a positive potential, so that belt 1906 intercepts positive ions moving from wire 1914 to pulley 1910. As belt 1906 moves in the direction of arrow 1918, the intercepted charges are carried into electrode 1902, where they are removed from belt 1906 by a needle point 1916 and transferred to electrode 1902. As a result, positive charges accumulate on the surface of electrode 1902; these charges can be discharged from the surface of electrode 1902 and used to treat biomass material. In some embodiments, accelerator 1900 can be configured to provide negatively charged ions by operating wire 1914 and needle point 1916 at a negative potential with respect to grounded pulley 1910.

In general, accelerator 1900 can be configured to provide a wide variety of different types of positive and negative charges for treating biomass. Exemplary types of charges include electrons, protons, hydrogen ions, carbon ions, oxygen ions, halogen ions, metal ions, and other types of ions.

Figure 53:
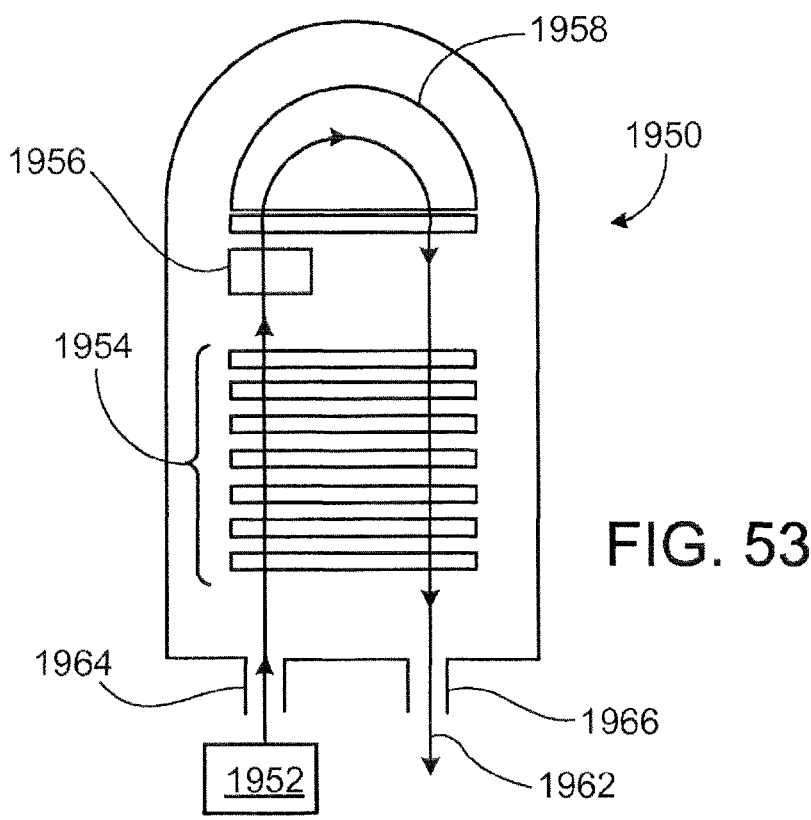
FIG. 53 is a schematic diagram of a folded tandem
accelerator.

In certain embodiments, tandem accelerators (including folded tandem accelerators) can be used to generate ion beams for treatment of biomass material. An example of a folded tandem accelerator 1950 is shown in FIG. 53. Accelerator 1950 includes an accelerating column 1954, a charge stripper 1956, a beam deflector 1958, and an ion source 1952.

During operation, ion source 1952 produces a beam 1960 of negatively charged ions, which is directed to enter accelerator 1950 through input port 1964. In general, ion source 1952 can be any type of ion source that produces negatively charged ions. For example, suitable ion sources include a source of negative ions by cesium sputtering (SNICS) source, a RF-charge exchange ion source, or a toroidal volume ion source (TORVIS). Each of the foregoing exemplary ion sources is available, for example, from National Electrostatics Corporation (Middleton, Wis.).

Once inside accelerator 1950, the negative ions in beam 1960 are accelerated by accelerating column 1954. Typically, accelerating column 1954 includes a plurality of accelerating elements such as electrostatic lenses. The potential difference applied in column 1954 to accelerate the negative ions can be generated using various types of devices. For example, in some embodiments, (e.g., Pelletron® accelerators), the potential is generated using a Pelletron® charging device. Pelletron® devices include a charge-carrying belt that is formed from a plurality of metal (e.g., steel) chain links or pellets that are bridged by insulating connectors (e.g., formed from a material such as nylon). During operation, the belt recirculates between a pair of pulleys, one of which is maintained at ground potential. As the belt moves between the grounded pulley and the opposite pulley (e.g., the terminal pulley), the metal pellets are positively charged by induction. Upon reaching the terminal pulley, the positive charge that has accumulated on the belt is removed, and the pellets are negatively charged as they leave the terminal pulley and return to the ground pulley.

The Pelletron® device generates a large positive potential within column 1954 that is used to accelerate the negative ions of beam 1960. After undergoing acceleration in column 1954, beam 1960 passes through charge stripper 1956. Charge stripper 1956 can be implemented as a thin metal foil and/or a tube containing a gas that strips electrons from the negative ions, for example. The negatively charged ions are thereby converted to positively charged ions, which emerge from charge stripper 1956. The trajectories of the emerging positively charged ions are altered so that the positively charged ions travel back through accelerating column 1954, undergoing a second acceleration in the column before emerging as positively charged ion beam 1962 from output port 1966. Positively charged ion beam 1962 can then be used to treat biomass material according to the various methods disclosed herein.

Due to the folded geometry of accelerator 1950, ions are accelerated to a kinetic energy that corresponds to twice the potential difference generated by the Pelletron® charging device. For example, in a 2 MV Pelletron® accelerator, hydride ions that are introduced by ion source 1952 will be accelerated to an intermediate energy of 2 MeV during the first pass through column 1954, converted to positive ions (e.g., protons), and accelerated to a final energy of 4 MeV during the second pass through column 1954.

In certain embodiments, column 1954 can include elements in addition to, or as alternatives to, the Pelletron® charging device. For example, column 1954 can include static accelerating elements (e.g., DC electrodes) and/or dynamic acceleration cavities (e.g., LINAC-type cavities with pulse RF field generators for particle acceleration). Potentials applied to the various accelerating devices are selected to accelerate the negatively charged ions of beam 1960.

Exemplary tandem accelerators, including both folded and non-folded accelerators, are available from National Electrostatics Corporation (Middleton, Wis.), for example.

In some embodiments, combinations of two or more of the various types of accelerators can be used to produce ion beams that are suitable for treating biomass. For example, a folded tandem accelerator can be used in combination with a linear accelerator, a Rhodotron® accelerator, a Dynamitron®, a static accelerator, or any other type of accelerator to produce ion beams. Accelerators can be used in series, with the output ion beam from one type of accelerator directed to enter another type of accelerator for additional acceleration. Alternatively, multiple accelerators can be used in parallel to generate multiple ion beams for biomass treatment. In certain embodiments, multiple accelerators of the same type can be used in parallel and/or in series to generate accelerated ion beams.

In some embodiments, multiple similar and/or different accelerators can be used to generate ion beams having different compositions. For example, a first accelerator can be used to generate one type of ion beam, while a second accelerator can be used to generate a second type of ion beam. The two ion beams can then each be further accelerated in another accelerator, or can be used to treat biomass.

Further, in certain embodiments, a single accelerator can be used to generate multiple ion beams for treating biomass. For example, any of the accelerators discussed herein (and other types of accelerators as well) can be modified to produce multiple output ion beams by sub-dividing an initial ion current introduced into the accelerator from an ion source. Alternatively, or in addition, any one ion beam produced by any of the accelerators disclosed herein can include only a single type of ion, or multiple different types of ions.

In general, where multiple different accelerators are used to produce one or more ion beams for treatment of biomass, the multiple different accelerators can be positioned in any order with respect to one another. This provides for great flexibility in producing one or more ion beams, each of which has carefully selected properties for treating biomass (e.g., for treating different components in biomass).

The ion accelerators disclosed herein can also be used in combination with any of the other biomass treatment steps disclosed herein. For example, in some embodiments, electrons and ions can be used in combination to treat biomass. The electrons and ions can be produced and/or accelerated separately, and used to treat biomass sequentially (in any order) and/or simultaneously. In certain embodiments, electron and ion beams can be produced in a common accelerator and used to treat biomass. For example, many of the ion accelerators disclosed herein can be configured to produce electron beams as an alternative to, or in addition to, ion beams. For example, Dynamitron® accelerators, Rhodotron® accelerators, and LFNACs can be configured to produce electron beams for treatment of biomass.

Moreover, treatment of biomass with ion beams can be combined with other techniques such as sonication. In general, sonication-based treatment can occur before, during, or after ion-based biomass treatment. Other treatments such as electron beam treatment can also occur in any combination and/or order with ultrasonic treatment and ion beam treatment.

(iii) Output Coupling Elements and Other Components

In general, any of the sources disclosed herein can include various types of output coupling elements to control the propagation and characteristics of accelerated ion beams. For example, sources can include one or more ion lenses, deflectors, filters, collimators, or other electrode-based elements, to which both static and variable potentials can be applied. These elements can be electrostatic, magnetic, or both electrostatic and magnetic.

Sources can include one or more electric and/or magnetic field sources, including static field sources and/or variable field sources. Variable field sources can produce fields having frequencies ranging from 1 Hz to $10^{15}$ Hz.

In some embodiments, ozone is produced when accelerated ions interact with atmospheric oxygen gas. Production of excess ozone gas may represent a potential health hazard to system operators working in the vicinity of the sources disclosed herein. Accordingly, the sources can include an ozone removal system, which typically includes one or more outlet vents connected to vacuum pumps to actively remove ozone and other gases. In certain embodiments, sources can include a shield than encloses a volume of space through which the accelerated ions travel, to assist in confining ozone gas to the enclosed volume. The enclosed volume can be pumped by an evacuation system.

In some embodiments, accelerated ions are used to directly treat biomass material. However, due to the relatively sharp Bragg peak in the dose distribution for many types of ions, providing uniform treatment of thick materials can be challenging. Accordingly, in some embodiments, when relatively thick biomass material is treated with an accelerated ion beam, the energy of the ion beam is changed during exposure of the material (for example, by changing certain accelerating potentials in an accelerator). The effect of changing the energy of the ion beam is to "sweep" the Bragg peak of the dose distribution through the thickness of the material. The sweeping of the Bragg peak can be performed in a manner such that the ion dose received throughout the thickness of the material is nominally uniform.

In certain embodiments, a similar effect can be achieved by spreading out the Bragg peak of the ion beam. For example, a dispersive element can be placed in the path of the accelerated ions to cause broadening of the energy spectrum of the accelerated ions, as shown in FIG. 2 of Chu (2006). As a result of the energy broadening, the Bragg peak can be significantly broadened, resulting in more uniform dosing of an exposed biomass material.

In certain embodiments, charged particles used to expose biomass materials can include antiparticles. For example, in some embodiments, antiparticles such as positrons and/or antiprotons can be used to expose materials. Moreover, in certain embodiments, various different isotopes of ions can be used to expose biomass materials. For example, deuterium ions and/or ions derived from various isotopes of carbon, nitrogen, oxygen, and various metals, can be used. In particular, in some embodiments, an ion beam that exposes biomass materials can include at least some ions that are positron emitters, such as ions of $^{10}C$, $^{11}C$, and $^{15}O$. When these ions interact with material such as biomass material, the ions emit positrons in a region of the material close to the position of the Bragg peak. By monitoring positron emission, the position of the Bragg peak can therefore be located in the material. This technique can be particularly useful when the Bragg peak is swept through the material by changing the ion energy, as discussed above.

In some embodiments, combinations of different ions can be used to treat biomass material. For example, material can be treated with a combination of protons and carbon ions. In general, any combination of two or more ions can be used to treat material; the ions have the same or different charge signs and magnitudes, and the same or different masses. Different ions can, in certain embodiments, be accelerated in the same accelerator. Alternatively, or in addition, different ions can be accelerated in different accelerators, and biomass treatment facility can include multiple ion accelerators configured to produce ion beams.

4. Operating Parameters

In general, when a condensed medium is exposed to a charged particle beam, the charged particles penetrate the medium and deposit within the medium at a distribution of depths below the surface upon which the particles are incident. It has generally been observed (see, for example, FIG. 1 in Prelec (infra, 1997)) that the dose distribution for ions includes a significantly sharper maximum (the Bragg peak), and that ions exhibit significantly less lateral scattering, than other particles such as electrons and neutrons and other forms of electromagnetic radiation such as x-rays. Accordingly, due to the relatively well-controlled dosing profile of accelerated ions, they operate relatively efficiently to alter the structure of biomass material. Furthermore, as is apparent from FIG. 6 of Prelec (infra, 1997), heavier ions (such as carbon ions) have even sharper dosing profiles than lighter ions such as protons, and so the relative effectiveness of these heavier ions at treating biomass material is even greater than for lighter ions.

In some embodiments, the average energy of the accelerated ions that are incident on biomass material is 1 MeV/u or more (e.g., 2, 3, 4, 5, 6, 7, 8, 9, 10, 12, 15, 20, 30, 50, 100, 300, 500, 600, 800, or even 1000 MeV/u or more).

In certain embodiments, the average energy of the accelerated ions is 10 MeV or more (e.g., 20, 30, 50, 100, 200, 300, 400, 500, 600, 800, 1000, 2000, 3000, 4000, or even 5000 MeV or more).

In certain embodiments, an average velocity of the accelerated ions is 0.0005 c or more (e.g., 0.005 c or more, 0.05 c or more, 0.1 c or more, 0.2 c or more, 0.3 c or more, 0.4 c or more, 0.5 c or more, 0.6 c or more, 0.7 c or more, 0.8 c or more, 0.9 c or more). In general, for a given accelerating potential, lighter ions are accelerated to higher velocities than heavier ions. For example, for a given accelerating potential, a maximum velocity of a hydrogen ion may be about 0.05 c, while a maximum velocity of a carbon ion may be about 0.0005 c. These values are only exemplary; the velocity of the accelerated ions depends on the accelerating potential applied, the mode of operation of the accelerator, the number of passes through the accelerating field, and other such parameters.

In some embodiments, an average ion current of the accelerated ions is $10^5$ particles/s or more (e.g., $10^6$, $10^7$, $10^8$, $10^9$, $10^{10}$, $10^{11}$, $10^{12}$, $10^{13}$, $10^{14}$, $10^{15}$, or even $10^{16}$ particles/s or more).

In some embodiments, a radiation dose delivered to biomass material from an ion beam is 5 Mrad or more (e.g., 10, 15, 20, 30, 40, 50, 60, 80, or even 100 Mrad or more).

5. Ion Beam Exposure Conditions

Figure 54:
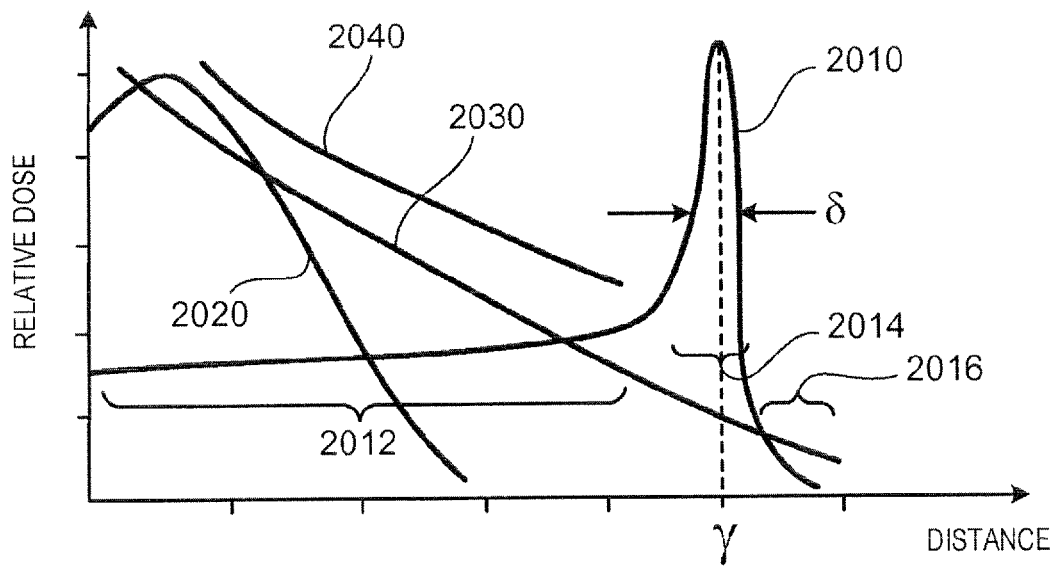
FIG. 54 is a schematic diagram showing dose profiles for
ions, electrons, and photons in a condensed-phase material.

When a sample is exposed to an ion beam, energy is deposited in the sample according to an ion dose profile (also sometimes referred to as a depth-dose distribution). FIG. 54 shows a schematic diagram of a representative ion dose profile 2010 for a condensed-phase sample. The vertical axis of ion dose profile 2010 in FIG. 54 shows the relative ion dose, plotted as a function of depth below a surface of the sample that is exposed to the ion beam, on the horizontal axis. FIG. 54 also includes, for comparative purposes, an electron dose profile 2020, a gamma radiation dose profile 2030, and an x-ray dose profile 2040.

As shown in FIG. 54, both gamma radiation and x-ray radiation (and further, other types of electromagnetic radiation) are absorbed strongly in a region adjacent to the surface of the sample, leading to the highest energy doses being deposited near the sample surface. Gamma and x-ray radiation dose profiles 2030 and 2040 decrease approximately exponentially from the surface of the sample, as progressively fewer photons are able to penetrate deeper into the sample to be absorbed.

Electron dose profile 2020 shows a build-up effect whereby, due to the penetrating ability of Compton electrons, the deposited energy dose increases in the vicinity of the exposed surface of the sample to a maximum deposited dose at a penetration depth of, typically, about 3-4 cm in condensed media. Thereafter, the relative dose of deposited energy decreases relatively rapidly with increasing distance beneath the sample surface.

Ion beams, in contrast, typically have dose profiles that are sometimes described as being inverse with respect to the dose profiles of electrons and photons. As shown in FIG. 54, ion dose profile 2010 includes a region 2012 in which a relatively constant energy dose is applied to the sample.

Thereafter, ion dose profile 2010 includes a region 2014 referred to as the Bragg peak, which corresponds to a portion of the sample into which a comparatively larger fraction of the ion beam's energy is deposited, followed by a region 2016 in which a much smaller energy dose is deposited. The Bragg peak, which has a full width at half maximum (FWHM) of δ, ensures that the dose profile for ions differs significantly from the dose profiles for electrons and photons of various wavelengths. As a result, exposing materials such as biomass materials to ion beams can yield effects that are different from the effects produced by photons and electron beams.

Typically, the width δ of Bragg peak 2014 depends upon a number of factors, including the nature of the sample, the type of ions, and the average ion energy. One important factor that influences the width δ of Bragg peak 2014 is the distribution of energies in the incident ion beam. In general, the narrower the distribution of energies in the incident ion beam, the narrower the width δ of Bragg peak 2014. As an example, Bragg peak 2014 typically has a width of about 3 mm or less for a distribution of ion energies that has a FWHM of 1 keV or less. The width δ of Bragg peak 2014 can be much less than 3 mm under these conditions as well, e.g., 2.5 mm or less, 2.0 mm or less, 1.5 mm or less, 1.0 mm or less.

The position of Bragg peak 2014, indicated by γ in FIG. 54, depends upon a number of factors including the average energy of the incident ion beam. In general, for larger average ion beam energies, Bragg peak 2014 will shift to larger depths in FIG. 54, because higher-energy ions have the ability to penetrate more deeply into a material before most of the ions' kinetic energy is lost via scattering events.

Figure 55:
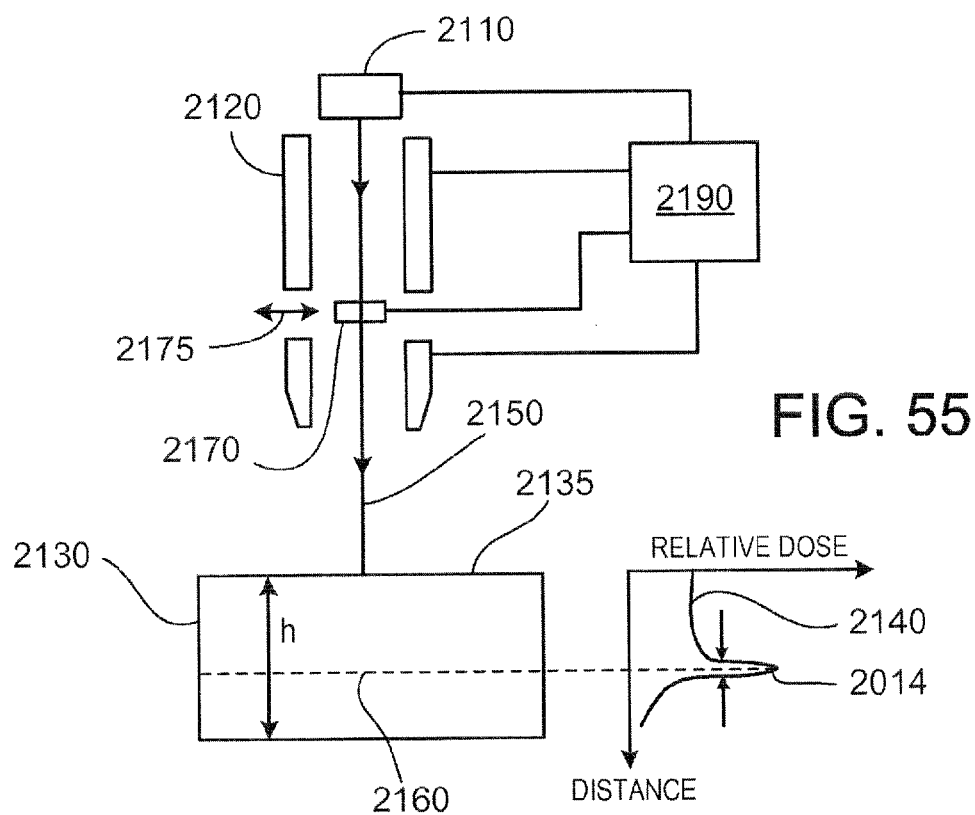
FIG. 55 is a schematic diagram of an ion beam exposure
system.

Various properties of one or more incident ion beams can be adjusted to expose samples (e.g., biomass materials) to ion beam radiation, which can lead to de-polymerization and other chain-scission reactions in the samples, reducing the molecular weight of the samples in a predictable and controlled manner. FIG. 55 shows a schematic diagram of an ion beam exposure system 2100. System 2100 includes an ion source 2110 that generates an ion beam 2150. Optical elements 2120 (including, for example, lenses, apertures, deflectors, and/or other electrostatic and/or magnetic elements for adjusting ion beam 2150) direct ion beam 2150 to be incident on sample 2130, which has a thickness h in a direction normal to surface 2135 of sample 2130. In addition to directing ion beam 2150, optical elements 2120 can be used to control various properties of ion beam 2150, including collimation and focusing of ion beam 2150. Sample 2130 typically includes, for example, one or more of the various types of biomass materials that are discussed herein. System 2100 also includes an electronic controller 2190 in electrical communication with the various components of the system (and with other components not shown in FIG. 55). Electronic controller 2190 can control and/or adjust any of the system parameters disclosed herein, either fully automatically or in response to input from a human operator.

FIG. 55 also shows the ion dose profile that results from exposure of sample 2130 to ion beam 2150. The position 2160 of the Bragg peak within sample 2130 depends upon the average energy of ion beam 2150, the nature of the ions in ion beam 2150, the material from which sample 2130 is formed, and other factors.

In many applications of ion beams, such as ion therapy for tumor eradication, the relatively small width δ of Bragg peak 2014 is advantageous, because it allows reasonably fine targeting of particular tissues within a patient undergoing therapy, and helps to reduce damage due to exposure of nearby benign tissues.

However, when exposing biomass materials such as sample 2130 to ion beam 2150, the relatively small width δ of Bragg peak 2014 can restrict throughput. Typically, for example, the thickness h of sample 2130 is larger than the width δ of Bragg peak 2014. In some embodiments, h can be substantially larger than δ (e.g., larger by a factor of 5 or more, or 10 or more, or 20 or more, or 50 or more, or 100 or more, or even more).

To increase a thickness of sample 2130 in which a selected dose can be delivered in a particular time interval, the energy distribution of ion beam 2150 can be adjusted. Various methods can be used to adjust the energy distribution of ion beam 2150. One such method is to employ one or more removable scattering elements 2170 positioned in the patch of ion beam 2150, as shown in FIG. 55. Scattering element 2170 can be, for example, a thin membrane formed of a metal material such as tungsten, tantalum, copper, and/or a polymer-based material such as Lucite®.

Prior to passing through scattering element 2170, ion beam 2150 has an energy distribution of width w, shown in FIG. 56A. When ion beam 2150 passes through element(s) 2170, at least some of the ions in ion beam 2150 undergo scattering events with atoms in element(s) 2170, transferring a portion of their kinetic energy to the atoms of element(s) 2170. As a result, the energy distribution of ion beam 2150 is broadened to a width b larger than w, as shown in FIG. 56B. In particular, the energy distribution of ion beam 2150 acquires a broader low-energy tail as a result of scattering in element(s) 2170.

FIG. 56C shows the effect of broadening the ion energy distribution of ion beam 2150 on the ion dose profiles in sample 2130. Ion dose profile 2140a is produced by exposing sample 2130 to ion beam 2150 having the ion energy distribution shown in FIG. 56A. Ion dose profile 2140a includes a relatively narrow Bragg peak. As a result, the region of sample 2130 in which a relatively high dose is deposited is small. In contrast, by broadening the ion energy distribution of ion beam 2150 to yield the distribution shown in FIG. 56B, ion dose profile 2140b is obtained in sample 2130 after exposing the sample to the broadened distribution of ion energies. As dose profile 2140b shows, by broadening the ion energy distribution, the region of sample 2130 in which a relatively high dose is deposited is increased relative to ion dose profile 2140a. By increasing the region of sample 2130 exposed to a relatively high dose, the throughput of the exposure process can be improved.

In certain embodiments, the width b of the broadened energy distribution can be larger than w by a factor of 1.1 or more (e.g., 1.2, 1.3, 1.4, 1.5, 1.7, 2.0, 2.5, 3.0, 3.5, 4.0, 5.0, or even 10.0 or more).

Typically, the ion dose profile in sample 2130 produced by exposure of the sample to the broadened ion energy distribution shown in FIG. 56B has a Bragg peak having a full width at half maximum (FWHM) of c. As a result of broadening the ion energy distribution, c can be larger than c by a factor of 1.1 or more (e.g., 1.2 or more, 1.3 or more, 1.5 or more, 1.7 or more, 2.0 or more, 2.5 or more, 3.0 or more, 4.0 or more, 5.0 or more, 6.0 or more, 7.0 or more, 10.0 or more).

For sample 2130 of thickness h, after broadening the ion energy distribution of ion beam 2150 and exposing the sample to the ion beam, a ratio of ϵ/h can be $1 \times 10^{-6}$ or more (e.g., $1 \times 10^{-5}$, $5 \times 10^{-5}$, $1 \times 10^{-4}$, $5 \times 10^{-4}$, $1 \times 10^{-3}$, $5 \times 10^{-3}$, 0.01, 0.05, 0.08, 0.1, or even 0.5 or more).

In certain embodiments, sample 2130 includes a plurality of particles (e.g., approximately spherical particles, and/or fibers, and/or filaments, and/or other particle types). In general, the particles have a distribution of different sizes, with an average particle size r. The ion energy distribution of ion beam 2150 can be adjusted (e.g., via broadening) based on the average particle size r of sample 2130 to improve the efficiency of ion-based treatment of sample 2130. For example, ion beam 2150 can be adjusted to that a ratio of 8/r is 0.001 or more (e.g., 0.005 or more, 0.01 or more, 0.05 or more, 0.1 or more, 0.5 or more, 1.0 or more, 1.5 or more, 2.0 or more, 2.5 or more, 3.0 or more, 3.5 or more, 4.0 or more, 5.0 or more, 6.0 or more, 8.0 or more, 10 or more, 50 or more, 100 or more, 500 or more, 1000 or more, or even more).

In some embodiments, a scattering element 2170 can include multiple different scattering sub-elements that are configured to broaden the distribution of ion energies in ion beam 2150 by different amounts. For example, FIG. 57 shows a multi-sub-element scattering element 2170 that includes sub-elements 2170a-e. Each of sub-elements 2170a-e broadens the distribution of ion energies in ion beam 2150 to a different extent.

During operation of system 2100, electronic controller 2190 can be configured to select an appropriate sub-element of scattering element 2170 based on information such as the thickness h of sample 2130, the type of ions in ion beam 2150, and the average ion energy in ion beam 2150. The selection of an appropriate sub-element can be made in fully automated fashion, or based at least in part on input from a human operator. Selection of an appropriate sub-element is made by translating scattering element 2170 in the direction shown by arrow 2175 to position a selected sub-element in the path of ion beam 2150.

In certain embodiments, other devices can be used in addition to, or as an alternative to, scattering element(s) 2170. For example, in some embodiments, combinations of electric and or magnetic fields, produced by ion optical elements, can be used to broaden the ion energy distribution of ion beam 2150. Ion beam 2150 can pass through a first field configured to spatially disperse ions in the ion beam. Then the spatially dispersed ions can pass through a second field that is well-localized spatially, and which selectively retards only a portion of the spatially dispersed ions. The ions then pass through a third field that spatially re-assembles all of the ions into a collimated beam, which is then directed onto the surface of sample 2130. Typically, the ion optical elements used to generate the fields that adjust the ion energy distribution are controlled by electronic controller 2190. By applying spatially localized fields selectively, a high degree of control over the modified ion energy distribution is possible, including the generation of ion energy distributions having complicated profiles (e.g., multiple lobes). For example, in some embodiments, by applying a localized field that accelerates a portion of the spatially dispersed ion distribution, the ion energy distribution shown in FIG. 56A can be broadened on the high-energy side of the distribution maximum.

The information used by electronic controller 2190 to adjust the ion energy distribution of ion beam 2150 can include the thickness h of sample 2130, as discussed above. In some embodiments, electronic controller 2190 can use information about the expected ion dose profile in sample 2130 to adjust the ion energy distribution of ion beam 2150. Information about the expected ion dose profile can be obtained from a database, for example, that includes measurements of ion dose profiles acquired from literature sources and/or from calibration experiments performed on representative samples of the material from which sample 2130 is formed. Alternatively, or in addition, information about the expected ion dose profile can be determined from a mathematical model of ion interactions in sample 2130 (e.g., an ion scattering model).

In certain embodiments, the information about the expected ion dose profile can include information about the FWHM of the Bragg peak in the expected ion dose profile. The FWHM of the Bragg peak can be determined from measurements of ion dose profiles and/or from one or more mathematical models of ion scattering in the sample. Adjustments of the ion energy distribution of ion beam 2150 can be performed to reduce a difference between the thickness h of sample 2130 and the FWHM of the Bragg peak. In some embodiments, for example, a difference between h and the full width at half maximum of the Bragg peak is 20 cm or less (e.g., 18, 16, 14, 12, 10, 8, 6 cm, 5, 4, 3, 2, 1, 0.5, 0.1, 0.05, 0.01, or even 0.001 cm or less).

Figure 58:
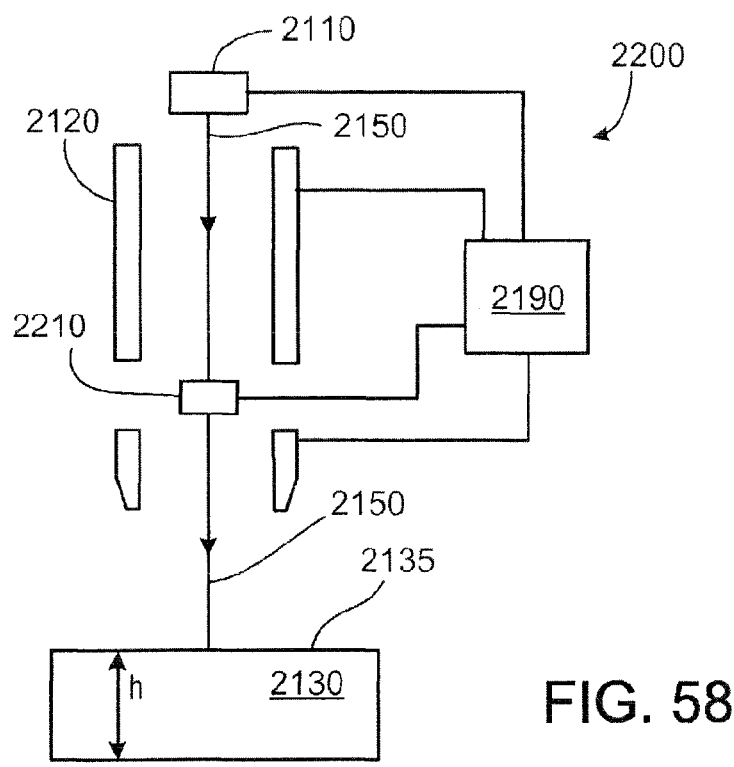
FIG. 58 is a schematic diagram of an ion beam exposure
system that includes an ion filter.

In some embodiments, the ion beam exposure system can adjust the distribution of ion energies in ion beam 2150 in other ways. For example, the ion beam exposure system can be configured to filter the ion beam by removing ions from ion beam 2150 that have energies below a selected energy threshold and/or above a selected energy threshold. FIG. 58 shows an ion beam exposure system 2200 that includes an ion filter 2210 discussed in more detail below. The other components of system 2200 are similar to the components of system 2100, and will not be further discussed.

Figure 59A:
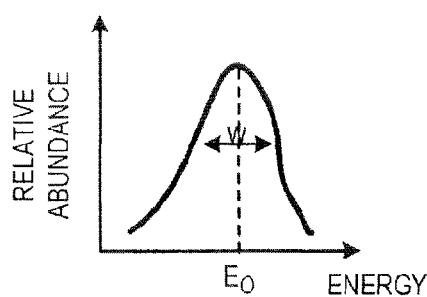
FIGS. 59A-C are schematic diagrams showing energy
distributions for unfiltered and filtered ion beams.
Figure 59B:
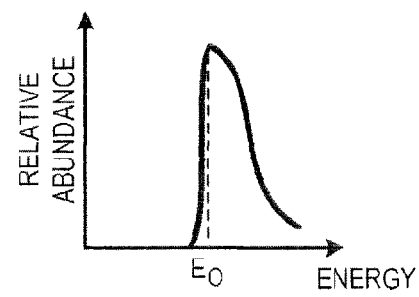

FIG. 59A shows an ion energy distribution corresponding to ion beam 2150 produced by ion source 2110. Ion beam 2150, with an energy distribution as shown in FIG. 59A, enters ion filter 2210 where the energy distribution of ion beam 2150 is adjusted by filtering out certain ions from the ion beam. For example, in some embodiments, ion filter 2210 can be configured to remove ions from ion beam 2150 that have an energy smaller than a selected energy threshold. In FIG. 59A, the selected energy threshold is the position $E_O$ of the peak in the ion energy distribution, although more generally, any energy threshold can be selected. By filtering out all (or even just a large fraction of) ions having an energy less than $E_O$, the ion energy distribution for ion beam 2150 is as shown in FIG. 59B.

Figure 59C:
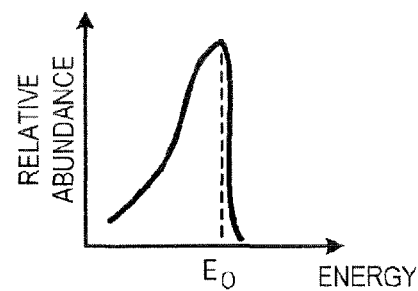

In contrast, in some embodiments, ion filter 2210 can be configured to remove ions from ion beam 2150 that have an energy larger than a selected energy threshold (e.g., when ion filter 2210 is implemented as a hemispherical analyzer). For example, the selected energy threshold can correspond to the position $E_0$ of the peak in the ion energy distribution, although more generally, any energy threshold can be selected. By removing all (or even a large fraction of) ions from ion beam 2150 having an energy more than $E_0$, the ion energy distribution for ion beam 2150 is as shown in FIG. 59C.

In certain embodiments, sample 2130 can be exposed directly to a filtered ion beam 2150. By filtering the ion beam to achieve a narrower ion energy distribution, for example, the ion dose profile in sample 2130 is sharper following sample exposure than it would otherwise have been without filtering ion beam 2150. As a result, the width of the Bragg peak in sample 2130 is smaller relative to the Bragg peak width for an unfiltered ion beam. By exposing sample 2130 to a narrower distribution of incident ion energies, more refined control over the position of ion beam 2150 can be achieved; this level of ion exposure control can be useful when exposing various types of delicate sample materials.

Alternatively, the filtered ion beam can then be passed through one or more scattering elements and/or other devices to increase the width of the distribution of ion energies. This two-step approach to modifying the ion energy distribution—a first filtering step, followed by a second broadening step—can be used to produce ion energy distributions that are tailored for specific applications (e.g., specific to certain ion types, certain materials, and/or certain pre-processing conditions) that may not be achievable using a simpler one-step energy distribution broadening procedure.

As an example, by first filtering ion beam 2150, and then passing the filtered ion beam through one or more scattering elements 2170, the shape of the ion energy distribution can be made more Gaussian than would otherwise be possible using only a scattering step instead of the two-step procedure.

Ion filter 2210 can include one or more of a variety of different devices for removing ions from ion beam 2150. For example, in some embodiments, ion filter 2210 includes a hemispherical analyzer and aperture filter. The hemispherical analyzer includes a magnetic field source that disperses the ions of ion beam 2150 according to their kinetic energies. The aperture filter is then positioned in the path of the dispersed ion beam 2150 to permit only ions having a particular range of energies to pass through the aperture.

In certain embodiments, other devices can be used to filter ion beam 2150. For example, absorbing elements (e.g., elements configured to absorb incident ions having energies smaller than a selected energy threshold can be used to filter ion beam 2150. Suitable absorbing elements include metal foils, for example.

In some embodiments, ion beam 2150 (and in particular, the Bragg peak in an expected ion dose profile produced following exposure of sample 2130 to ion beam 2150) can be swept through sample 2130 to deliver selected radiation doses to various portions of the sample. In general, the position of the Bragg peak in sample 2130 can be selected by adjusting the average energy of ion beam 2150 (the average energy of ion beam 2150 typically corresponds to the maximum in the ion energy distribution). Ion source 2110, under the control of electronic controller 2190, can adjust the average energy of ion beam 2150 by changing an extraction voltage applied to accelerate ions in the ion source.

Figure 60:
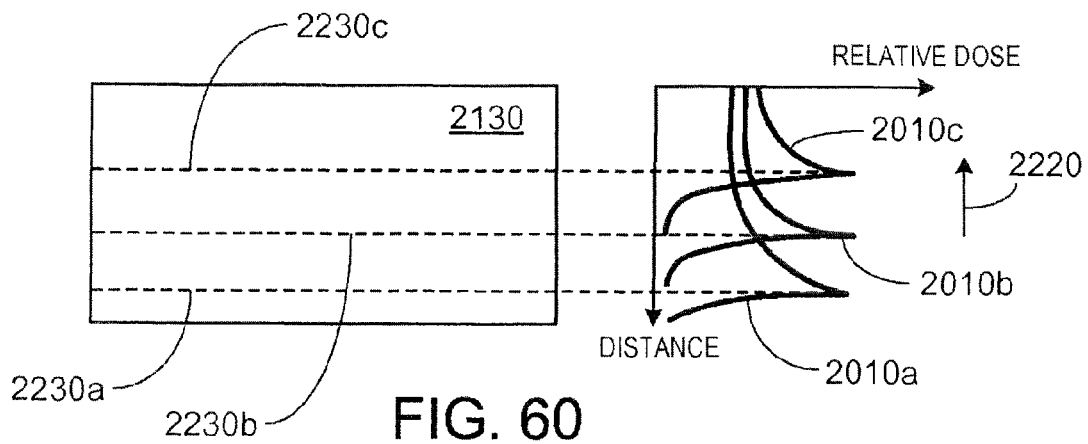
FIG. 60 is a schematic diagram showing three ion dose
profiles corresponding to exposure of a sample to ion beams
having different average energies.

FIG. 60 is a schematic diagram that shows how the Bragg peak of an ion dose profile in sample 2130 can be swept through the sample. As a first step, ion exposure system 2100 is configured to produce a first ion beam with a selected average ion energy corresponding to a particular extraction voltage applied in ion source 2110. When sample 2130 is exposed to the first ion beam, ion dose profile 2010a results in the sample, with the Bragg peak at position 2230a. Following exposure, the extraction voltage in ion source 2110 is adjusted to produce a second ion beam with a different average ion energy. When sample 2130 is exposed to the second ion beam, ion dose profile 2010b results in the sample. By further repeating the adjusting of the extraction voltage in ion source 2110 to produce additional beams with different average ion energies, and exposing sample 2130 to the additional beams, the Bragg peak of the ion dose profile can be swept through sample 2130 in the direction shown by arrow 2220, for example. More generally, however, by changing the extraction voltage in ion source 2110, the position of the Bragg peak in sample 2130 can be selected as desired, permitting delivery of large doses to selected regions of sample 2130 in any sequence.

In general, other properties of ion beam 2150 can also be adjusted in addition to, or as an alternative to, adjusting the average ion energy of the ion beam. For example, in some embodiments, the divergence angle of ion beam 2150 at the surface of sample 2130 can be adjusted to control the ion dose profile in sample 2130. Generally, by increasing the divergence angle of ion beam 2150 at the surface of sample 2130, the full width at half maximum of the Bragg peak in sample 2130 can be increased. Thus, in certain embodiments, the average energy of the ion beam can be maintained, but the ion dose profile in the material—including the position of the Bragg peak—can be changed by adjusting the ion beam's divergence angle.

The divergence angle can be adjusted automatically or by operator control by electronic controller 2190. Typically optical elements 2120 include one or more ion beam steering elements such as quadrupole and/or octopole deflectors. By adjusting potentials applied to the various electrodes of such deflectors, the divergence angle (and the angle of incidence) of ion beam 2150 at the surface of sample 2130 can be adjusted.

In some embodiments—unlike in other applications of ion beams such as surgical intervention—it can be advantageous to use ion beams with relatively large divergence angles, to ensure that the Bragg peak positioned in sample 2130 covers a suitable fraction of the thickness of sample 2130. For example, in certain embodiments, sample 2130 can be exposed to an ion beam having a divergence angle of 2 degrees or more (e.g., 5, 10, 15, 20, 30, 40, or even 50 degrees or more).

Figure 61A:
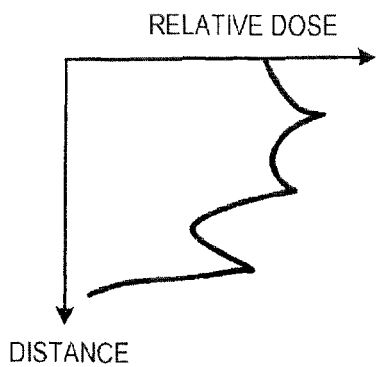
FIG. 61A is a schematic diagram showing a net ion dose
profile for an exposed sample based on the three ion dose
profiles of FIG. 60.

In some embodiments, both an ion beam current of ion beam 2150 and the average ion energy of ion beam 2150 can be adjusted to deliver a relatively constant dose as a function of thickness h of sample 2130. For example, if sample 2130 is exposed according to the sequential ion dose profiles 2010a, 2010b, and 2010c in FIG. 60, the net ion dose profile in sample 2130 corresponds to the sum of profiles 2010a-c, which is shown in FIG. 61A. Based on the net ion dose profile of FIG. 61A, it is evident that certain regions of sample 2130 receive larger net doses than other regions of sample 2130.

Figure 61B:
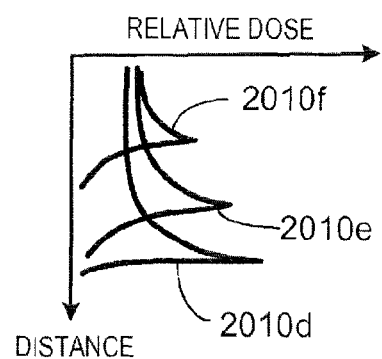
FIG. 61B is a schematic diagram showing three different
ion dose profiles corresponding to ion beams of different
average energy and ion current.
Figure 61C:
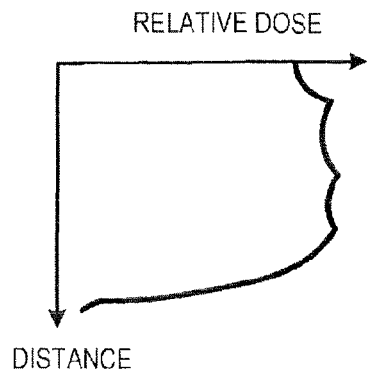
FIG. 61C is a schematic diagram showing a net ion dose
profile based on the three ion dose profiles of FIG. 61.

The differences in net dose can be reduced by adjusting the ion beam current of ion beam 2150 together with adjustments of the average ion energy. The ion beam current can be adjusted in ion source 2110 under the control of electronic controller 2190. For example, to reduce the difference in the net dose delivered to sample 2130 when the Bragg peak is swept through sample 2130 in the direction indicated by arrow 2220 in FIG. 60, the ion beam current can be successively reduced for each successive reduction in ion beam energy. Three ion dose profiles, each corresponding to successive decreases in both average ion energy and ion current in ion beam 2150, are shown as profiles 2010d-f, respectively, in FIG. 61B. The net ion dose profile in sample 2130 that results from these three sequential exposures is shown in FIG. 61C. The net ion dose profile shows significantly reduced variation as a function of position in sample 2130 relative to the net ion dose profile of FIG. 61A.

By carefully controlling the average energy and ion current of ion beam 2150, variations in net relative ion dose through the thickness of sample 2130 following exposure of the sample to ion beam 2150 can be relatively small. For example, a difference between a maximum net relative ion dose and a minimum net relative ion dose in sample 2130 following multiple exposures to ion beam 2150 can be 0.2 or less (e.g., 0.15, 0.1, 0.05, 0.04, 0.03, 0.02, 0.01 or even 0.005 or less).

By controlling the average energy and ion current of ion beam 2150, each portion of the exposed sample can receive a net dose of between 0.001 Mrad and 100 Mrad following multiple exposures to the ion beam (e.g., between 0.005 Mrad and 50 Mrad, between 0.01 Mrad and 50 Mrad, between 0.05 Mrad and 30 Mrad, between 0.1 Mrad and 20 Mrad, between 0.5 Mrad and 20 Mrad, between 1 Mrad and 10 Mrad).

Figure 62A:
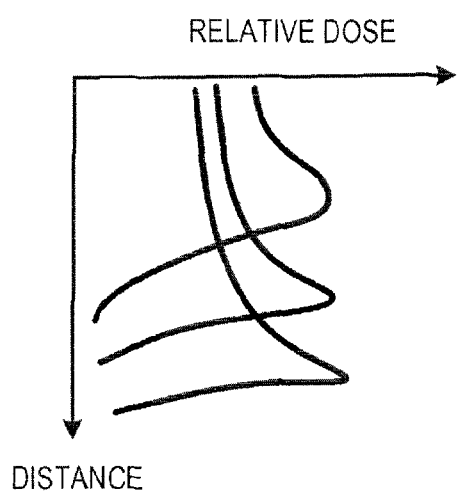
FIG. 62A is a schematic diagram showing three different
ion dose profiles corresponding to exposure of a sample to
beams of three different types of ions.
Figure 62B:
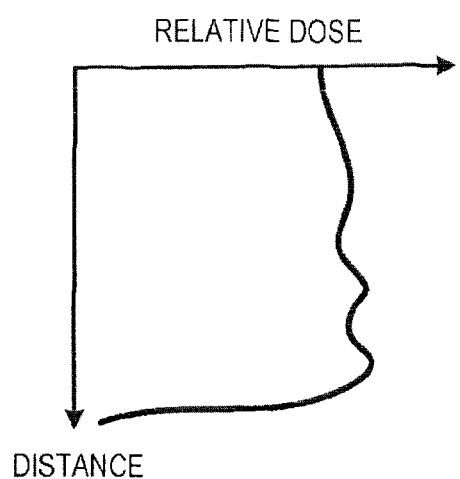
FIG. 62B is a schematic diagram showing a net ion dose
profile based on the three ion dose profiles of FIG. 62A.

In some embodiments, sample 2130 can be exposed to different types of ions. Sample 2130 can be sequentially exposed to only one type of ion at a time, or the exposure of sample 2130 can include exposing sample 2130 to one or more ion beams that include two or more different types of ions. Different types of ions produce different ion dose profiles in an exposed material, and by exposing a sample to different types of ions, a particular net ion dose profile in the sample can be realized. FIG. 62A shows a schematic diagram of three different ion dose profiles 2010*g-i* that result from exposing a sample 2130 to three different types of ions. Ion dose profiles 2010*g-i* can be produced via sequential exposure of the sample to each one of the different types of ions, or via concurrent exposure of the sample to two or even all three of the different types of ions. The net ion dose profile in sample 2130 that results from exposure to the three different types of ions is shown in FIG. 62B. Variations in the net ion dose profile as a function of thickness of the sample are reduced relative to any one of the individual ion dose profiles shown in FIG. 62A.

In some embodiments, the different types of ions can include ions of different atomic composition. For example, the different types of ions can include protons, carbon ions, oxygen ions, hydride ions, nitrogen ions, chlorine ions, fluorine ions, argon ions, neon ions, krypton ions, and various types of metal ions such as sodium ions, calcium ions, and lithium ions. Generally, any of these different types of ions can be used to treat sample 2130, and each will produce a different ion dose profile in a sample. In certain embodiments, ions can be generated from commonly available gases such as air. When air is used as a source gas, many different types of ions can be generated. The various different types of ions can be separated from one another prior to exposing sample 2130, or sample 2130 can be exposed to multiple different types of ions generated from a source gas such as air.

In some embodiments, the different types of ions can include ions having different charges. For example, the different types of ions can include various positive and/or negative ions. Further, the different types of ions can include ions having single and/or multiple charges. In general, positive and negative ions of the same chemical species can produce different ion dose profiles in a particular sample, and ions of the same chemical species that have different charge magnitudes (e.g., singly-charged, doubly-charged, triply-charged) can produce different ion dose profiles in a particular sample. By exposing a sample to multiple different types of ions, sample breakdown (e.g., depolymerization, chain scission, and/or molecular weight reduction) can be carefully and selectively controlled.

In some embodiments, the ion beam exposure system can adjust the composition of the ion beam based on the sample material. For example, certain types of sample, such as cellulosic biomass, include a large concentration of hydroxyl groups. Accordingly, the effective penetration depth of certain types of ions—particularly protons—in such materials can be considerably larger than would other wise be expected based on ion energy alone. Site-to-site proton hopping and other similar atomic excursions can significantly increase the mobility of such ions in the sample, effectively increasing the penetration depth of the incident ions. Further, the increased mobility of the ions in the sample can lead to a broadening of the Bragg peak. The ion beam exposure system can be configured to select particular types of ions for exposure of certain samples, accounting for the chemical and structural features of the sample. Further, the ion beam exposure system can be configured to take into account the expected interactions between the ion beam and the material when determining how to modify other parameters of the ion beam such as the distribution of ion energies therein.

The various techniques disclosed herein that are based on ion beam exposure of a biomass material can be used cooperatively with other disclosed techniques such as sonication, electron beam irradiation, chemical methods, and biological methods. The ion beam techniques provide significant advantages, including the ability to perform ion beam exposure of dry samples, to deliver large radiation doses to samples in short periods of time for high throughput applications, and to exercise relatively precise control over exposure conditions.

6. Ion-Beam Treatment of Biomass

A wide variety of different methods and systems can be used to produce ion beams for treating biomass. In addition, ion beams produced using the systems and methods disclosed herein can be used alone to treat biomass, or the ion beams can be used in combination with other treatment methods (e.g., electron beams, sonication, biological agents, chemical treatments) to process biomass material.

An important aspect of the ion beam systems and methods disclosed herein is that the disclosed systems and methods enable exposure of biomass to ions in the presence of one or more additional fluids (e.g., gases and/or liquids). Typically, for example, when a material is exposed to an ion beam, the exposure occurs in a reduced pressure environment such as a vacuum chamber. The reduced pressure environment is used to reduce or prevent contamination of the exposed material, and also to reduce or prevent scattering of the ion beam by gas molecules. Unfortunately, ion beam exposure of materials in closed environments such as a vacuum chamber greatly restricts potential throughput for high volume material processing, however.

In the systems and methods disclosed herein, it has been recognized that exposure of biomass to an ion beam in the presence of one or more additional fluids can increase the efficiency of the biomass treatment. Additionally, exposure of biomass to an ion beam in an open environment (e.g., in air at normal atmospheric pressure) provides for much higher throughput than would otherwise be possible in a reduced pressure environment.

As discussed above, in some embodiments, biomass is exposed to an ion beam in the presence of a fluid such as air. Ions accelerated in any one or more of the types of accelerators disclosed herein (or another type of accelerator) are coupled out of the accelerator via an output port (e.g., a thin membrane such as a metal foil), pass through a volume of space occupied by the fluid, and are then incident on the biomass material. In addition to directly treating the biomass, some of the ions generate additional chemical species by interacting with fluid particles (e.g., ions and/or radicals generated from various constituents of air). These generated chemical species can also interact with the biomass, and can act as initiators for a variety of different chemical bond-breaking reactions in the biomass (e.g., depolymerization reactions).

In certain embodiments, additional fluids can be selectively introduced into the path of an ion beam before the ion beam is incident on the biomass. As discussed above, reactions between the ions and the particles of the introduced fluids can generate additional chemical species which react with the biomass and can assist in reducing the molecular weight of the biomass, and/or otherwise selectively altering certain properties of the biomass. The one or more additional fluids can be directed into the path of the ion beam from a supply tube, for example. The direction and flow rate of the fluid(s) that is/are introduced can be selected according to a desired exposure rate and/or direction to control the efficiency of the overall biomass treatment, including effects that result from both ion-based treatment and effects that are due to the interaction of dynamically generated species from the introduced fluid with the biomass. In addition to air, exemplary fluids that can be introduced into the ion beam include oxygen, nitrogen, one or more noble gases, one or more halogens, and hydrogen.

In some embodiments, ion beams that include more that one different type of ions can be used to treat biomass. Beams that include multiple different types of ions can be generated by combining two or more different beams, each formed of one type of ion. Alternatively, or in addition, in certain embodiments, ion beams that include multiple different types of ions can be generated by introducing a multicomponent supply gas into and ion source and/or accelerator. For example, a multicomponent gas such as air can be used to generate an ion beam having different types of ions, including nitrogen ions, oxygen ions, argon ions, carbon ions, and other types of ions. Other multicomponent materials (e.g., gases, liquids, and solids) can be used to generate ion beams having different compositions. Filtering elements (e.g., hemispherical electrostatic filters) can be used to filter out certain ionic constituents and/or neutral species to selectively produce an ion beam having a particular composition, which can then be used to treat biomass. By using air as a source for producing ion beams for biomass treatment, the operating costs of a treatment system can be reduced relative to systems that rely on pure materials, for example.

Certain types of biomass materials may be particularly amenable to treatment with multiple different types of ions and/or multiple different processing methods. For example, cellulosic materials typically include crystalline polymeric cellulose chains which are cross-linked by amorphous hemicellulose fraction. The cellulose and hemicellulose is embedded within an amorphous lignin matrix. Separation of the cellulose fraction from the lignin and the hemicellulose using conventional methods is difficult and can be energy-intensive.

However, cellulosic biomass can be treated with multiple different types of ions to break down and separate the various components therein for further processing. In particular, the chemical properties of various types of ionic species can be used to process cellulosic biomass (and other types of biomass) to selectively degrade and separate the components thereof. For example, positively charged ions—and in particular, protons—act as acids when exposed to biomass material. Conversely, negatively charged ions, particularly hydride ions, act as bases when exposed to biomass material. As a result, the chemical properties of these species can be used to target specific components of treated biomass.

When treating lignocellulosic biomass, for example, the lignin matrix typically decomposes in the presence of basic reagents. Accordingly, by first treating cellulosic biomass with basic ions such as hydride ions (or electrons) from an ion (electron) beam, the lignin fraction can be preferentially degraded and separated from the cellulose and hemicellulose fractions. Cellulose is relatively unaffected by such an ion treatment, as cellulose is typically stable in the presence of basic agents.

In addition to negative ion treatment (or as an alternative to negative ion treatment), the lignocellulosic biomass can be treated with one or more basic agents in solution to assist in separating the lignin. For example, treatment of the lignocellulosic biomass with a sodium bicarbonate solution can degrade and/or solubilize the lignin, enabling separation of the solvated and/or suspended lignin from the cellulose and hemicellulose fractions.

Negative ion treatment with an ion beam may also assist in separating hemicellulose, which is also chemically sensitive to basic reagents. Depending upon the particular structure of the cellulosic biomass, more than treatment with negative ions may be used (and/or may be necessary) to effectively separate the hemicellulose fraction from the cellulose fraction. In addition, more that one type of ion can be used to separate the hemicellulose. For example, a relatively less basic ion beam such as an oxygen ion beam can be used to treat cellulosic biomass to degrade and/or remove the lignin fraction. Then, a stronger basic ion beam such as a hydride ion beam can be used to degrade and separate the hemicellulose from the cellulose. The cellulosic fraction remains largely unchanged as a result of exposure to two different types of basic ions.

However, the cellulose fraction decomposes in the presence of acidic agents. Accordingly, a further processing step can include exposing the cellulose fraction to one or more acidic ions such as protons from an ion beam, to assist in depolymerizing and/or degrading the cellulose fraction.

Each of the above ion treatments can be used in combination with other processing steps. For example, separation steps (including introducing a solvent such as water) can be used to wash away particular fractions of the cellulosic biomass as they are degraded. Additional chemical agents can be added to assist in separating the various components. For example, it has been observed that lignin that is separated from the cellulose and hemicellulose fractions can be suspended in a washing solution. However, the lignin can readily re-deposit from the solution onto the cellulose and hemicellulose fractions. To avoid re-deposition of the lignin, the suspension can be gently heated to ensure that the lignin remains below its glass transition temperature, and therefore remains fluid. By maintaining the lignin below its glass transition temperature, the lignin can be more readily washed out of cellulosic biomass. In general, heating of the suspension is carefully controlled to avoid thermal degradation of the sugars in the cellulosic fraction.

In addition, other treatment steps can be used to remove lignin from cellulose and hemicellulose. For example, in certain embodiments, lignocellulosic biomass can first be treated with relatively heavy ions (e.g., carbon ions, oxygen ions) to degrade lignin, and the cellulose and hemicellulose can then be treated with relatively light ions (e.g., protons, helium ions) and/or electrons to cause degradation of the cellulose and/or hemicellulose.

In some embodiments, one or more functionalizing agents can be added to the suspension containing the lignin to enhance the solubility of lignin in solution, thereby discouraging re-deposition on the cellulose and hemicellulose fractions. For example, agents such as ammonia gas and/or various types of alcohols can be used (to introduce amino and hydroxyl/alkoxy groups, respectively) to functionalize the lignin.

In certain embodiments, structural agents can be added to the lignin suspension to prevent re-deposition of the lignin onto the cellulose and hemicellulose fractions. Typically, when lignin forms a matrix surrounding cellulose and/or hemicellulose, the lignin adopts a heavily folded structure, which permits relatively extensive van der Waals interactions with cellulose and hemicellulose. In contrast, when lignin is separated from cellulose and hemicellulose, the lignin adopts a more open, unfolded structure. By adding one or more agents that assist in preventing lignin re-folding to the lignin suspension, re-association of the lignin with cellulose and hemicellulose can be discouraged, and the lignin can be more effectively removed via washing, for example.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ Hz, greater than $10^{17}$ Hz, $10^{18}$, $10^{19}$, $10^{20}$, or even greater than $10^{21}$ Hz. In some embodiments, the electromagnetic radiation has a frequency of between $10^{18}$ and $10^{22}$ Hz, e.g., between $10^{19}$ to $10^{21}$ Hz.

Doses

In some embodiments, the irradiating (with any radiation source or a combination of sources) is performed until the material receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad.

In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

In some embodiments, relatively low doses of radiation can crosslink, graft, or otherwise increase the molecular weight of a carbohydrate-containing material, such as a cellulosic or lignocellulosic material (e.g., cellulose). Such a material having increased molecular weight can be useful, e.g., in making a composite, e.g., having improved mechanical properties, such as abrasion resistance, compression strength, fracture resistance, impact strength, bending strength, tensile modulus, flexural modulus and elongation at break. Such a material having increased molecular weight can be useful in making a composition.

For example, a fibrous material that includes a first cellulosic and/or lignocellulosic material having a first molecular weight can be irradiated in such a manner as to provide a second cellulosic and/or lignocellulosic material having a second molecular weight higher than the first molecular weight. For example, if gamma radiation is utilized as the radiation source, a dose of from about 1 Mrad to about 10 Mrad, e.g., from about 1.5 Mrad to about 7.5 Mrad or from about 2.0 Mrad to about 5.0 Mrad, can be applied. After the low dose of radiation, the second cellulosic and/or lignocellulosic material can be combined with a resin and formed into a composite, e.g., by compression molding, injection moldings or extrusion. Forming composites is described in WO 2006/102543, and in U.S. Provisional Patent Application Ser. No. 60/664,832, filed on Mar. 24, 2005, 60/688,002, filed on Jun. 7, 2005, 60/711,057, filed on Aug. 24, 2005, 60/715,822, filed on Sep. 9, 2005, 60/725,674, filed on Oct. 12, 2005, 60/726,102, filed on Oct. 12, 2005, and 60/750,205, filed on Dec. 13, 2005.

Alternatively, a material, e.g., a fibrous material that includes a first cellulosic and/or lignocellulosic material having a first molecular weight can be combined with a resin to provide a composite, and then the composite can be irradiated with a relatively low dose of radiation so as to provide a second cellulosic and/or lignocellulosic material having a second molecular weight higher than the first molecular weight. For example, if gamma radiation is utilized as the radiation source, a dose of from about 1 Mrad to about 10 Mrad can be applied. Using this approach increases the molecular weight of the material while it is within a resin matrix. In some embodiments, the resin is a cross-linkable resin and as such it crosslinks as the carbohydrate-containing material increases in molecular weight, which can provide a synergistic effect to provide advantageous mechanical properties to the composite. For example, such composites can have excellent low temperature performance, e.g., having a reduced tendency to break and/or crack at low temperatures, e.g., temperatures below 0° C., e.g., below −10° C., −20° C., −40° C., −50° C., −60° C. or even below −100° C., and/or excellent performance at high temperatures, e.g., capable of maintaining their advantageous mechanical properties at relatively high temperature, e.g., at temperatures above 100° C., e.g., above 125° C., 150° C., 200° C., 250° C., 300° C., 400° C., or even above 500° C. In addition, such composites can have excellent chemical resistance, e.g., resistance to swelling in a solvent, e.g., a hydrocarbon solvent, resistance to chemical attack, e.g., by strong acids, strong bases, strong oxidants (e.g., chlorine or bleach) or reducing agents (e.g., active metals such as sodium and potassium).

Alternatively, in another example, a fibrous material that includes a cellulosic and/or lignocellulosic material is irradiated and, optionally, treated with acoustic energy, e.g., ultrasound.

In one example of the use of radiation as a pretreatment, half-gallon juice cartons made of un-printed polycoated white Kraft board having a bulk density of 20 lb/ft$^3$ are used as a feedstock. Cartons are folded flat and then fed into a sequence of three shredder-shearer trains arranged in series with output from the first shearer fed as input to the second shredder, and output from the second shearer fed as input to the third shredder. The fibrous material produced by the can be sprayed with water and processed through a pellet mill operating at room temperature. The densified pellets can be placed in a glass ampoule which is evacuated under high vacuum and then back-filled with argon gas. The ampoule is sealed under argon. The pellets in the ampoule are irradiated with gamma radiation for about 3 hours at a dose rate of about 1 Mrad per hour to provide an irradiated material in which the cellulose has a lower molecular weight than the starting material.

Quenching and Controlled Functionalization of Biomass

After treatment with one or more ionizing radiations, such as photonic radiation (e.g., X-rays or gamma-rays), e-beam radiation or particles heavier than electrons that are positively or negatively charged (e.g., protons or carbon ions), any of the carbohydrate-containing materials or mixtures described herein become ionized; that is, they include radicals at levels that are detectable with an electron spin resonance spectrometer. The current practical limit of detection of the radicals is about $10^{14}$ spins at room temperature. After ionization, any biomass material that has been ionized can be to reduce the level of radicals in the ionized biomass, e.g., such that the radicals are no longer detectable with the electron spin resonance spectrometer. For example, the radicals can be quenched by the application of a sufficient pressure to the biomass and/or utilizing a fluid in contact with the ionized biomass, such as a gas or liquid, that reacts with (quenches) the radicals. The use of a gas or liquid to at least aid in the quenching of the radicals also allows the operator to control functionalization of the ionized biomass with a desired amount and kinds of functional groups, such as carboxylic acid groups, enol groups, aldehyde groups, nitro groups, nitrile groups, amino groups, alkyl amino groups, alkyl groups, chloroalkyl groups or chlorofluoroalkyl groups. In some instances, such quenching can improve the stability of some of the ionized biomass materials. For example, quenching can improve the biomass's resistance to oxidation. Functionalization by quenching can also improve the solubility of any biomass described herein, can improve its thermal stability, which can be important in the manufacture of composites and boards described herein, and can improve material utilization by various microorganisms. For example, the functional groups imparted to the biomass material by quenching can act as receptor sites for attachment by microorganisms, e.g., to enhance cellulose hydrolysis by various microorganisms.

Figure 11B:
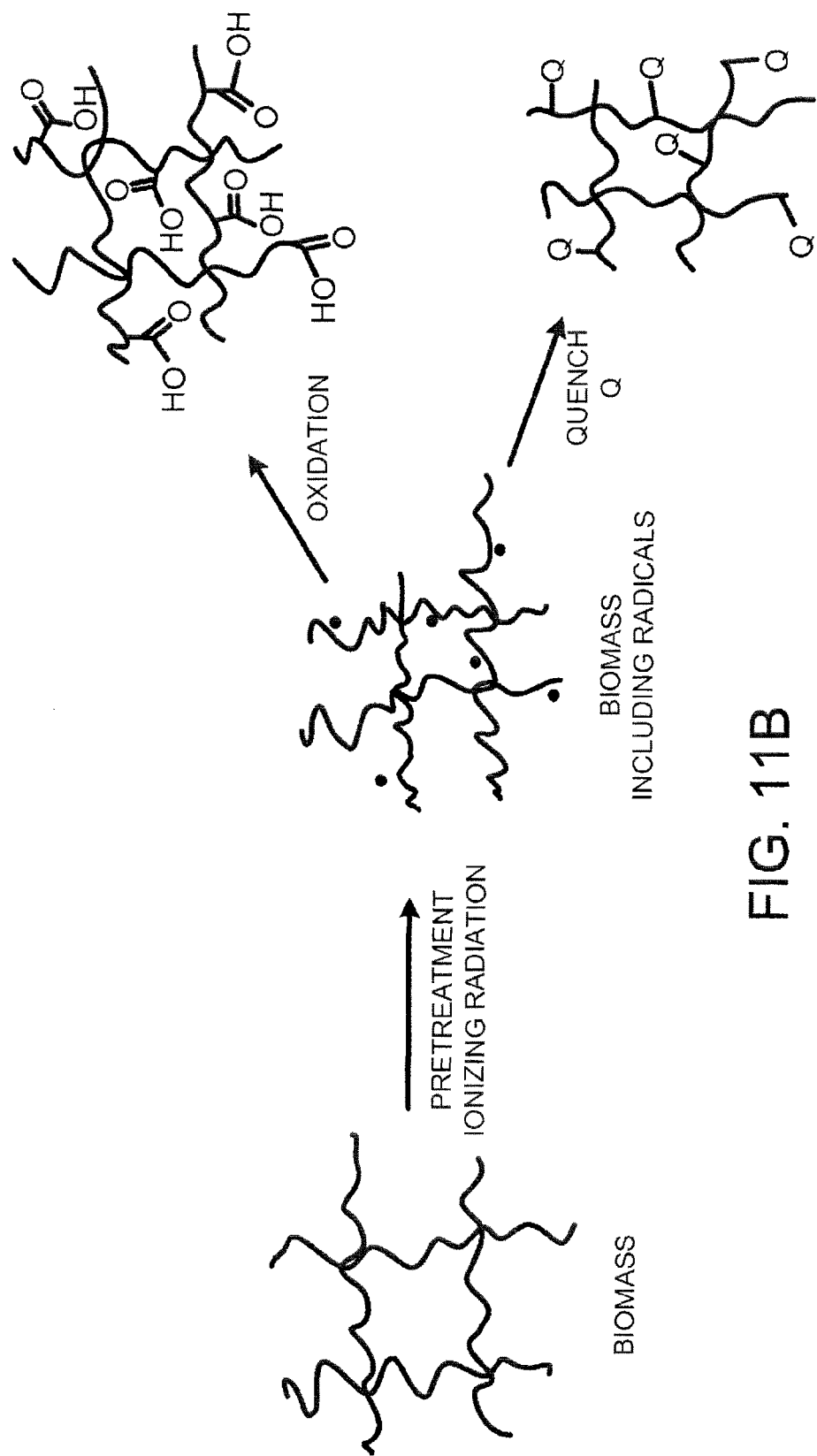
FIG. 11B is a schematic representation of biomass being ionized, and then oxidized or quenched.

FIG. 11B illustrates changing a molecular and/or a supramolecular structure of a biomass feedstock by pretreating the biomass feedstock with ionizing radiation, such as with electrons or ions of sufficient energy to ionize the biomass feedstock, to provide a first level of radicals. As shown in FIG. 11B, if the ionized biomass remains in the atmosphere, it will be oxidized, such as to an extent that carboxylic acid groups are generated by reacting with the atmospheric oxygen. In some instances with some materials, such oxidation is desired because it can aid in the further breakdown in molecular weight of the carbohydrate-containing biomass, and the oxidation groups, e.g., carboxylic acid groups can be helpful for solubility and microorganism utilization in some instances. However, since the radicals can "live" for some time after irradiation, e.g., longer than 1 day, 5 days, 30 days, 3 months, 6 months or even longer than 1 year, material properties can continue to change over time, which in some instances, can be undesirable. Detecting radicals in irradiated samples by electron spin resonance spectroscopy and radical lifetimes in such samples is discussed in Bartolotta et al., Physics in Medicine and Biology, 46 (2001), 461-471 and in Bartolotta et al., Radiation Protection Dosimetry, Vol. 84, Nos. 1-4, pp. 293-296 (1999), the contents of each of which are incorporated herein by reference. As shown in FIG. 11B, the ionized biomass can be quenched to functionalize and/or to stabilize the ionized biomass. At any point, e.g., when the material is "alive", "partially alive" or fully quenched, the pretreated biomass can be converted into a product, e.g., a fuel, a food, or a composite.

In some embodiments, the quenching includes an application of pressure to the biomass, such as by mechanically deforming the biomass, e.g., directly mechanically compressing the biomass in one, two, or three dimensions, or applying pressure to a fluid in which the biomass is immersed, e.g., isostatic pressing. In such instances, the deformation of the material itself brings radicals, which are often trapped in crystalline domains, in sufficient proximity so that the radicals can recombine, or react with another group. In some instances, the pressure is applied together with the application of heat, such as a sufficient quantity of heat to elevate the temperature of the biomass to above a melting point or softening point of a component of the biomass, such as lignin, cellulose or hemicellulose. Heat can improve molecular mobility in the polymeric material, which can aid in the quenching of the radicals. When pressure is utilized to quench, the pressure can be greater than about 1000 psi, such as greater than about 1250 psi, 1450 psi, 3625 psi, 5075 psi, 7250 psi, 10000 psi or even greater than 15000 psi.

In some embodiments, quenching includes contacting the biomass with a fluid, such as a liquid or gas, e.g., a gas capable of reacting with the radicals, such as acetylene or a mixture of acetylene in nitrogen, ethylene, chlorinated ethylenes or chlorofluoroethylenes, propylene or mixtures of these gases. In other particular embodiments, quenching includes contacting the biomass with a liquid, e.g., a liquid soluble in, or at least capable of penetrating into the biomass and reacting with the radicals, such as a diene, such as 1,5-cyclooctadiene. In some specific embodiments, the quenching includes contacting the biomass with an antioxidant, such as Vitamin E. If desired, the biomass feedstock can include an antioxidant dispersed therein, and the quenching can come from contacting the antioxidant dispersed in the biomass feedstock with the radicals.

Other methods for quenching are possible. For example, any method for quenching radicals in polymeric materials described in Muratoglu et al., U.S. Patent Application Publication No. 2008/0067724 and Muratoglu et al., U.S. Pat. No. 7,166,650, the contents of each of which are incorporated herein by reference, can be utilized for quenching any ionized biomass material described herein. Furthermore any quenching agent (described as a "sensitizing agent" in the above-noted Muratoglu disclosures) and/or any antioxidant described in either Muratoglu reference can be utilized to quench any ionized biomass material.

Functionalization can be enhanced by utilizing heavy charged ions, such as any of the heavier ions described herein. For example, if it is desired to enhance oxidation, charged oxygen ions can be utilized for the irradiation. If nitrogen functional groups are desired, nitrogen ions or an ions that includes nitrogen can be utilized. Likewise, if sulfur or phosphorus groups are desired, sulfur or phosphorus ions can be used in the irradiation.

In some embodiments, after quenching any of the quenched materials described herein can be further treated with one or more of radiation, such as ionizing or non-ionizing radiation, sonication, pyrolysis, and oxidation for additional molecular and/or supramolecular structure change.

In particular embodiments, functionalized materials described herein are treated with an acid, base, nucleophile or Lewis acid for additional molecular and/or supramolecular structure change, such as additional molecular weight breakdown. Examples of acids include organic acids, such as acetic acid and mineral acids, such as hydrochloric, sulfuric and/or nitric acid. Examples of bases include strong mineral bases, such as a source of hydroxide ion, basic ions, such as fluoride ion, or weaker organic bases, such as amines. Even water and sodium bicarbonate, e.g., when dissolved in water, can effect molecular and/or supramolecular structure change, such as additional molecular weight breakdown.

Sonication

One or more sonication processing sequences can be used to process raw feedstock from a wide variety of different sources to extract useful substances from the feedstock, and to provide partially degraded organic material which functions as input to further processing steps and/or sequences. Sonication can reduce the molecular weight and/or crystallinity of feedstock and biomass, e.g., one or more carbohydrate sources, such as cellulosic or lignocellulosic materials, or starchy materials.

Referring again to FIG. 8, in one method, a first material 2 that includes cellulose having a first number average molecular weight ($^T M_{N1}$) is dispersed in a medium, such as water, and sonicated and/or otherwise cavitated, to provide a second material 3 that includes cellulose having a second number average molecular weight ($^T M N_2$) lower than the first number average molecular weight. The second material (or the first and second material in certain embodiments) can be combined with a microorganism (e.g., a bacterium or a yeast) that can utilize the second and/or first material to produce a fuel 5 that is or includes hydrogen, an alcohol, an organic acid, a hydrocarbon, or mixtures of any of these.

Since the second material has cellulose having a reduced molecular weight relative to the first material, and in some instances, a reduced crystallinity as well, the second material is generally more dispersible, swellable, and/or soluble in a solution containing the microorganism, e.g., at a concentration of greater than $10^6$ microorganisms/mL. These properties make the second material 3 more susceptible to chemical, enzymatic, and/or microbial attack relative to the first material 2, which can greatly improve the production rate and/or production level of a desired product, e.g., ethanol. Sonication can also sterilize the materials, but should not be used while the microorganisms are supposed to be alive.

In some embodiments, the second number average molecular weight ($^T M_{N2}$) is lower than the first number average molecular weight ($^t M_{N1}$) by more than about 10 percent, e.g., 15, 20, 25, 30, 35, 40, 50 percent, 60 percent, or even more than about 75 percent.

In some instances, the second material has cellulose that has as crystallinity ($^T C_2$) that is lower than the crystallinity ($^T C_1$) of the cellulose of the first material. For example, ($^T C_2$) can be lower than ($^T C_1$) by more than about 10 percent, e.g., 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($^T O_2$) that is higher than the level of oxidation ($^T O_1$) of the first material. A higher level of oxidation of the material can aid in its dispersibility, swellability, and/or solubility, further enhancing the materials susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Without wishing to be bound by any particular theory, it is believed that sonication breaks bonds in the cellulose by creating bubbles in the medium containing the cellulose, which grow and then violently collapse. During the collapse of the bubble, which can take place in less than a nanosecond, the implosive force raises the local temperature within the bubble to about 5100 K (even higher in some instance; see, e.g., Suslick et al., Nature 434, 52-55, 2005) and generates pressures of from a few hundred atmospheres to over 1000 atmospheres or more. It is these high temperatures and pressures that break the bonds. In addition, without wishing to be bound by any particular theory, it is believed that reduced crystallinity arises, at least in part, from the extremely high cooling rates during collapse of the bubbles, which can be greater than about $10^{11}$K/second. The high cooling rates generally do not allow the cellulose to organize and crystallize, resulting in materials that have reduced crystallinity. Ultrasonic systems and sonochemistry are discussed in, e.g., Olli et al., U.S. Pat. No. 5,766,764; Roberts, U.S. Pat. No. 5,828,156; Mason, Chemistry with Ultrasound, Elsevier, Oxford, (1990); Suslick (editor), Ultrasound: its Chemical, Physical and Biological Effects, VCH, Weinheim, (1988); Price, "Current Trends in Sonochemistry" Royal Society of Chemistry, Cambridge, (1992); Suslick et al., Ann. Rev. Mater. Sci. 29, 295, (1999); Suslick et al., Nature 353, 414 (1991); Hiller et al., Phys. Rev. Lett. 69, 1182 (1992); Barber et al., Nature, 352, 414 (1991); Suslick et al., J. Am. Chem. Soc, 108, 5641 (1986); Tang et al., Chem. Comm., 2119 (2000); Wang et al., Advanced Mater., 12, 1137 (2000); Landau et al., J. of Catalysis, 201, 22 (2001); Perkas et al., Chem. Comm., 988 (2001); Nikitenko et al., Angew. Chem. Inter. Ed. (December 2001); Shafi et al., J. Phys. Chem B 103, 3358 (1999); Avivi et al., J. Amer. Chem. Soc. 121, 4196 (1999); and Avivi et al., J. Amer. Chem. Soc. 122, 4331 (2000).

Sonication Systems

Figure 12:
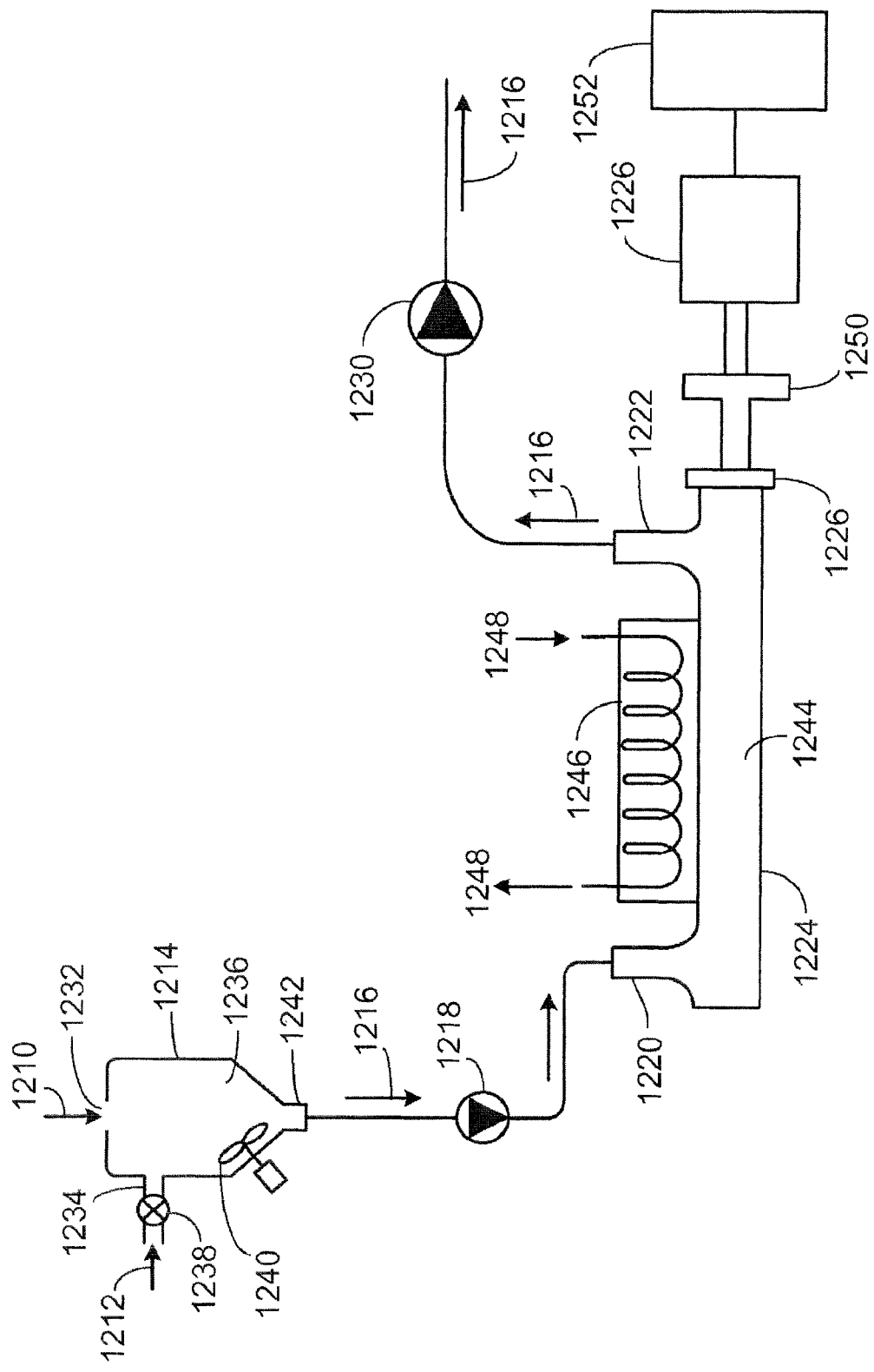
FIG. 12 is a schematic view of a system for sonicating a process stream of cellulosic material in a liquid medium.

FIG. 12 shows a general system in which a cellulosic material stream 1210 is mixed with a water stream 1212 in a reservoir 1214 to form a process stream 1216. A first pump 1218 draws process stream 1216 from reservoir 1214 and toward a flow cell 1224. Ultrasonic transducer 1226 transmits ultrasonic energy into process stream 1216 as the process stream flows through flow cell 1224. A second pump 1230 draws process stream 1216 from flow cell 1224 and toward subsequent processing.

Reservoir 1214 includes a first intake 1232 and a second intake 1234 in fluid communication with a volume 1236. A conveyor (not shown) delivers cellulosic material stream 1210 to reservoir 1214 through first intake 1232. Water stream 1212 enters reservoir 1214 through second intake 1234. In some embodiments, water stream 1212 enters volume 1236 along a tangent establishing a swirling flow within volume 1236. In certain embodiments, cellulosic material stream 1210 and water stream 1212 are introduced into volume 1236 along opposing axes to enhance mixing within the volume.

Valve 1238 controls the flow of water stream 1212 through second intake 1232 to produce a desired ratio of cellulosic material to water (e.g., approximately 10% cellulosic material, weight by volume). For example, 2000 tons/day of cellulosic material can be combined with 1 million to 1.5 million gallons/day, e.g., 1.25 million gallons/day, of water.

Mixing of cellulosic material and water in reservoir 1214 is controlled by the size of volume 1236 and the flow rates of cellulosic material and water into the volume. In some embodiments, volume 1236 is sized to create a minimum mixing residence time for the cellulosic material and water. For example, when 2000 tons/day of cellulosic material and 1.25 million gallons/day of water are flowing through reservoir 1214, volume 1236 can be about 32,000 gallons to produce a minimum mixing residence time of about 15 minutes.

Reservoir 1214 includes a mixer 1240 in fluid communication with volume 1236. Mixer 1240 agitates the contents of volume 1236 to disperse cellulosic material throughout the water in the volume. For example, mixer 1240 can be a rotating vane disposed in reservoir 1214. In some embodiments, mixer 1240 disperses the cellulosic material substantially uniformly throughout the water.

Reservoir 1214 further includes an exit 1242 in fluid communication with volume 1236 and process stream 1216. The mixture of cellulosic material and water in volume 1236 flows out of reservoir 1214 via exit 1242. Exit 1242 is arranged near the bottom of reservoir 1214 to allow gravity to pull the mixture of cellulosic material and water out of reservoir 1214 and into process stream 1216.

First pump 1218 (e.g., any of several recessed impeller vortex pumps made by Essco Pumps & Controls, Los Angeles, Calif.) moves the contents of process stream 1216 toward flow cell 1224. In some embodiments, first pump 1218 agitates the contents of process stream 1216 such that the mixture of cellulosic material and water is substantially uniform at inlet 1220 of flow cell 1224. For example, first pump 1218 agitates process stream 1216 to create a turbulent flow that persists along the process stream between the first pump and inlet 1220 of flow cell 1224.

Flow cell 1224 includes a reactor volume 1244 in fluid communication with inlet 1220 and outlet 1222. In some embodiments, reactor volume 1244 is a stainless steel tube capable of withstanding elevated pressures (e.g., 10 bars). In addition or in the alternative, reactor volume 1244 includes a rectangular cross section.

Flow cell 1224 further includes a heat exchanger 1246 in thermal communication with at least a portion of reactor volume 1244. Cooling fluid 1248 (e.g., water) flows into heat exchanger 1246 and absorbs heat generated when process stream 1216 is sonicated in reactor volume 1244. In some embodiments, the flow rate of cooling fluid 1248 into heat exchanger 1246 is controlled to maintain an approximately constant temperature in reactor volume 1244. In addition or in the alternative, the temperature of cooling fluid 1248 flowing into heat exchanger 1246 is controlled to maintain an approximately constant temperature in reactor volume 1244. In some embodiments, the temperature of reactor volume 1244 is maintained at 20 to 50° C., e.g., 25, 30, 35, 40, or 45° C. Additionally or alternatively, heat transferred to cooling fluid 1248 from reactor volume 1244 can be used in other parts of the overall process.

An adapter section 1226 creates fluid communication between reactor volume 1244 and a booster 1250 coupled (e.g., mechanically coupled using a flange) to ultrasonic transducer 1226. For example, adapter section 1226 can include a flange and O-ring assembly arranged to create a leak tight connection between reactor volume 1244 and booster 1250. In some embodiments, ultrasonic transducer 1226 is a high-powered ultrasonic transducer made by Hielscher Ultrasonics of Teltow, Germany.

In operation, a generator 1252 delivers electricity to ultrasonic transducer 1252. Ultrasonic transducer 1226 includes a piezoelectric element that converts the electrical energy into sound in the ultrasonic range. In some embodiments, the materials are sonicated using sound having a frequency of from about 16 kHz to about 110 kHz, e.g., from about 18 kHz to about 75 kHz or from about 20 kHz to about 40 kHz. (e.g., sound having a frequency of 20 kHz to 40 kHz).

The ultrasonic energy is then delivered to the working medium through booster 1248.

The ultrasonic energy traveling through booster 1248 in reactor volume 1244 creates a series of compressions and rarefactions in process stream 1216 with an intensity sufficient to create cavitation in process stream 1216. Cavitation disaggregates the cellulosic material dispersed in process stream 1216. Cavitation also produces free radicals in the water of process stream 1216. These free radicals act to further break down the cellulosic material in process stream 1216.

In general, 5 to 4000 MJ/m$^3$, e.g., 10, 25, 50, 100, 250, 500, 750, 1000, 2000, or 3000 MJ/m$^3$, of ultrasonic energy is applied to process stream 16 flowing at a rate of about 0.2 m$^3$/s (about 3200 gallons/min). After exposure to ultrasonic energy in reactor volume 1244, process stream 1216 exits flow cell 1224 through outlet 1222. Second pump 1230 moves process stream 1216 to subsequent processing (e.g., any of several recessed impeller vortex pumps made by Essco Pumps & Controls, Los Angeles, Calif.).

While certain embodiments have been described, other embodiments are possible.

As an example, while process stream 1216 has been described as a single flow path, other arrangements are possible. In some embodiments for example, process stream 1216 includes multiple parallel flow paths (e.g., flowing at a rate of 10 gallon/min). In addition or in the alternative, the multiple parallel flow paths of process stream 1216 flow into separate flow cells and are sonicated in parallel (e.g., using a plurality of 16 kW ultrasonic transducers).

As another example, while a single ultrasonic transducer 1226 has been described as being coupled to flow cell 1224, other arrangements are possible. In some embodiments, a plurality of ultrasonic transducers 1226 are arranged in flow cell 1224 (e.g., ten ultrasonic transducers can be arranged in a flow cell 1224). In some embodiments, the sound waves generated by each of the plurality of ultrasonic transducers 1226 are timed (e.g., synchronized out of phase with one another) to enhance the cavitation acting upon process stream 1216.

As another example, while a single flow cell 1224 has been described, other arrangements are possible. In some embodiments, second pump 1230 moves process stream to a second flow cell where a second booster and ultrasonic transducer further sonicate process stream 1216.

As still another example, while reactor volume 1244 has been described as a closed volume, reactor volume 1244 is open to ambient conditions in certain embodiments. In such embodiments, sonication pretreatment can be performed substantially simultaneously with other pretreatment techniques. For example, ultrasonic energy can be applied to process stream 1216 in reactor volume 1244 while electron beams are simultaneously introduced into process stream 1216.

As another example, while a flow through process has been described, other arrangements are possible. In some embodiments, sonication can be performed in a batch process. For example, a volume can be filled with a 10% (weight by volume) mixture of cellulosic material in water and exposed to sound with intensity from about 50 W/cm$^2$ to about 600 W/cm$^2$, e.g., from about 75 W/cm$^2$ to about 300 W/cm$^2$ or from about 95 W/cm$^2$ to about 200 W/cm$^2$. Additionally or alternatively, the mixture in the volume can be sonicated from about 1 hour to about 24 hours, e.g., from about 1.5 hours to about 12 hours, or from about 2 hours to about 10 hours. In certain embodiments, the material is sonicated for a pre-determined time, and then allowed to stand for a second pre-determined time before sonicating again.

Figure 13:
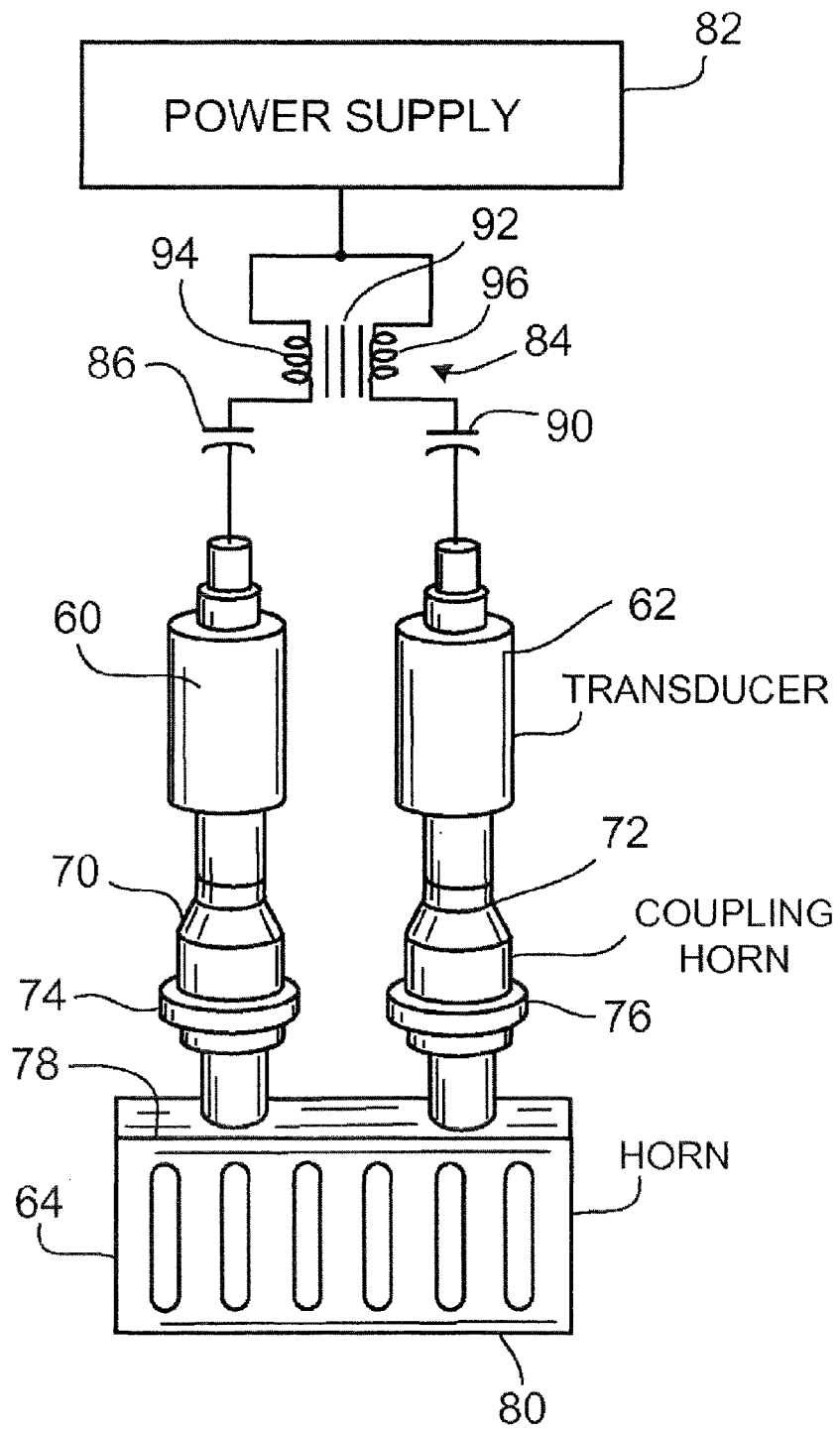
FIG. 13 is a schematic view of a sonicator having two transducers coupled to a single horn.

Referring now to FIG. 13, in some embodiments, two electro-acoustic transducers are mechanically coupled to a single horn. As shown, a pair of piezoelectric transducers 60 and 62 is coupled to a slotted bar horn 64 by respective intermediate coupling horns 70 and 72, the latter also being known as booster horns. The mechanical vibrations provided by the transducers, responsive to high frequency electrical energy applied thereto, are transmitted to the respective coupling horns, which may be constructed to provide a mechanical gain, such as a ratio of 1 to 1.2. The horns are provided with a respective mounting flange 74 and 76 for supporting the transducer and horn assembly in a stationary housing.

The vibrations transmitted from the transducers through the coupling or booster horns are coupled to the input surface 78 of the horn and are transmitted through the horn to the oppositely disposed output surface 80, which, during operation, is in forced engagement with a workpiece (not shown) to which the vibrations are applied.

The high frequency electrical energy provided by the power supply 82 is fed to each of the transducers, electrically connected in parallel, via a balancing transformer 84 and a respective series connected capacitor 86 and 90, one capacitor connected in series with the electrical connection to each of the transducers. The balancing transformer is known also as "balun" standing for "balancing unit." The balancing transformer includes a magnetic core 92 and a pair of identical windings 94 and 96, also termed the primary winding and secondary winding, respectively.

In some embodiments, the transducers include commercially available piezoelectric transducers, such as Branson Ultrasonics Corporation models 105 or 502, each designed for operation at 20 kHz and a maximum power rating of 3 kW. The energizing voltage for providing maximum motional excursion at the output surface of the transducer is 930 volt rms. The current flow through a transducer may vary between zero and 3.5 ampere depending on the load impedance. At 930 volt rms the output motion is approximately 20 microns. The maximum difference in terminal voltage for the same motional amplitude, therefore, can be 186 volt. Such a voltage difference can give rise to large circulating currents flowing between the transducers. The balancing unit 430 assures a balanced condition by providing equal current flow through the transducers, hence eliminating the possibility of circulating currents. The wire size of the windings must be selected for the full load current noted above and the maximum voltage appearing across a winding input is 93 volt.

As an alternative to using ultrasonic energy, high-frequency, rotor-stator devices can be utilized. This type of device produces high-shear, microcavitation forces which can disintegrate biomass in contact with such forces. Two commercially available high-frequency, rotor-stator dispersion devices are the Supraton™ devices manufactured by Krupp Industrietechnik GmbH and marketed by Don-Oliver Deutschland GmbH of Connecticut, and the Dispax™ devices manufactured and marketed by Ika-Works, Inc. of Cincinnati, Ohio. Operation of such a microcavitation device is discussed in Stuart, U.S. Pat. No. 5,370,999.

While ultrasonic transducer 1226 has been described as including one or more piezoelectric active elements to create ultrasonic energy, other arrangements are possible. In some embodiments, ultrasonic transducer 1226 includes active elements made of other types of magnetostrictive materials (e.g., ferrous metals). Design and operation of such a high-powered ultrasonic transducer is discussed in Hansen et al., U.S. Pat. No. 6,624,539. In some embodiments, ultrasonic energy is transferred to process stream 16 through an electro-hydraulic system.

While ultrasonic transducer 1226 has been described as using the electromagnetic response of magnetorestrictive materials to produce ultrasonic energy, other arrangements are possible. In some embodiments, acoustic energy in the form of an intense shock wave can be applied directly to process stream 16 using an underwater spark. In some embodiments, ultrasonic energy is transferred to process stream 16 through a thermo-hydraulic system. For example, acoustic waves of high energy density can be produced by applying power across an enclosed volume of electrolyte, thereby heating the enclosed volume and producing a pressure rise that is subsequently transmitted through a sound propagation medium (e.g., process stream 1216). Design and operation of such a thermo-hydraulic transducer is discussed in Hartmann et al., U.S. Pat. No. 6,383,152.

Pyrolysis

One or more pyrolysis processing sequences can be used to process raw feedstock from a wide variety of different sources to extract useful substances from the feedstock, and to provide partially degraded organic material which functions as input to further processing steps and/or sequences.

Referring again to the general schematic in FIG. 8, a first material 2 that includes cellulose having a first number average molecular weight ($^{T}M_{N1}$) is pyrolyzed, e.g., by heating the first material in a tube furnace, to provide a second material 3 that includes cellulose having a second number average molecular weight ($^{T}M_{N2}$) lower than the first number average molecular weight. The second material (or the first and second material in certain embodiments) is/are combined with a microorganism (e.g., a bacterium or a yeast) that can utilize the second and/or first material to produce a fuel 5 that is or includes hydrogen, an alcohol (e.g., ethanol or butanol, such as n-, sec or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing the microorganism, e.g., at a concentration of greater than $10^6$ microorganisms/mL. These properties make the second material 3 more susceptible to chemical, enzymatic and/or microbial attack relative to the first material 2, which can greatly improve the production rate and/or production level of a desired product, e.g., ethanol. Pyrolysis can also sterilize the first and second materials.

In some embodiments, the second number average molecular weight ($^TM_{N2}$) is lower than the first number average molecular weight ($^TM_{N1}$) by more than about 10 percent, e.g., 15, 20, 25, 30, 35, 40, 50 percent, 60 percent, or even more than about 75 percent.

In some instances, the second material has cellulose that has as crystallinity ($^TC_2$) that is lower than the crystallinity ($^TC_1$) of the cellulose of the first material. For example, ($^TC_2$) can be lower than ($^TC_1$) by more than about 10 percent, e.g., 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($^TO_2$) that is higher than the level of oxidation ($^TO_1$) of the first material. A higher level of oxidation of the material can aid in its dispersibility, swellability and/or solubility, further enhancing the materials susceptibility to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, which can increase its hydrophilicity.

In some embodiments, the pyrolysis of the materials is continuous. In other embodiments, the material is pyrolyzed for a pre-determined time, and then allowed to cool for a second pre-determined time before pyrolyzing again.

Pyrolysis Systems

Figure 14:
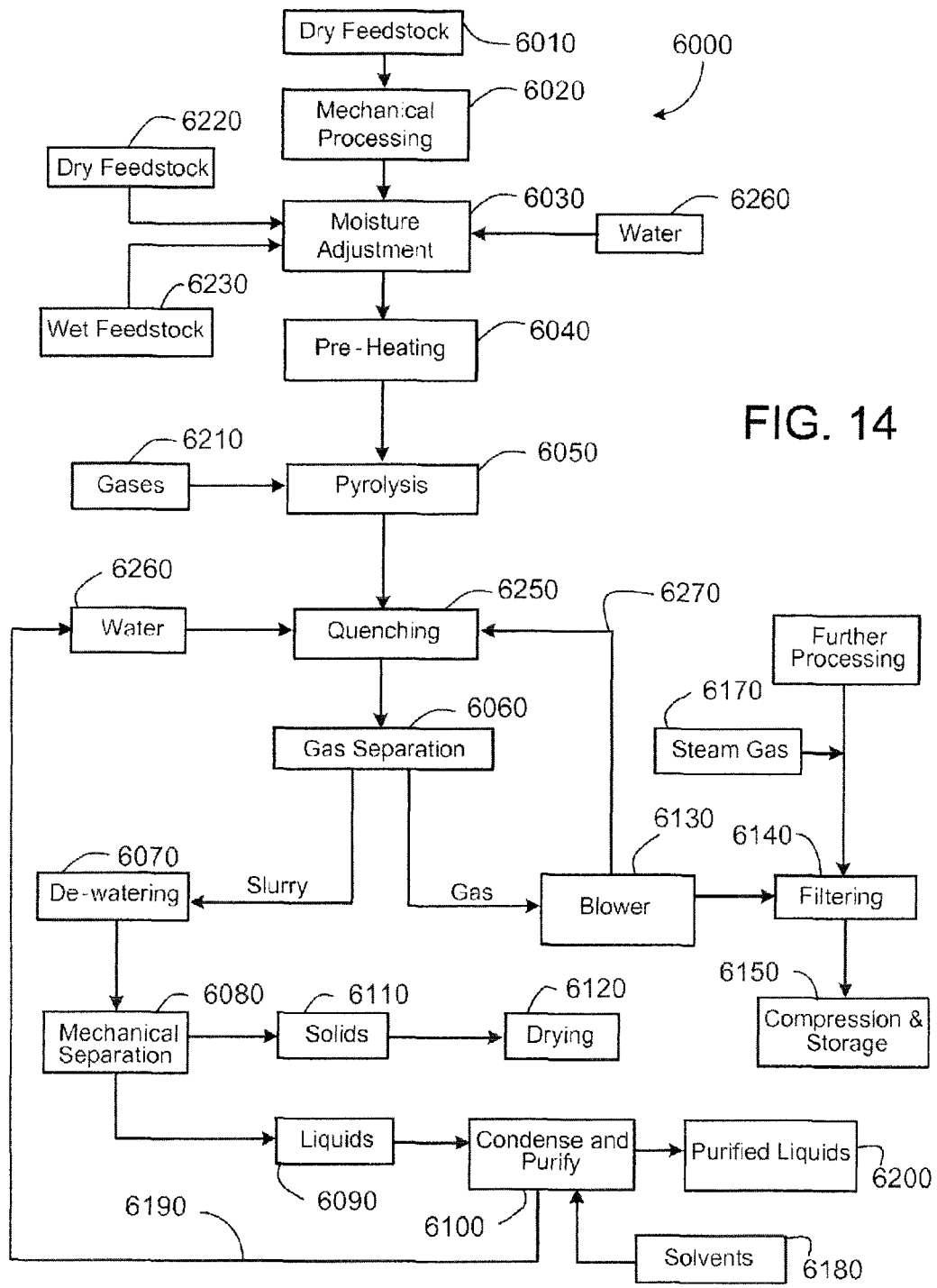
FIG. 14 is a block diagram illustrating a pyrolytic feedstock pretreatment system.

FIG. 14 shows a process flow diagram 6000 that includes various steps in a pyrolytic feedstock pretreatment system. In first step 6010, a supply of dry feedstock is received from a feed source.

As described above, the dry feedstock from the feed source may be pre-processed prior to delivery to the pyrolysis chamber. For example, if the feedstock is derived from plant sources, certain portions of the plant material may be removed prior to collection of the plant material and/or before the plant material is delivered by the feedstock transport device. Alternatively, or in addition, the biomass feedstock can be subjected to mechanical processing 6020 (e.g., to reduce the average length of fibers in the feedstock) prior to delivery to the pyrolysis chamber.

Following mechanical processing, the feedstock undergoes a moisture adjustment step 6030. The nature of the moisture adjustment step depends upon the moisture content of the mechanically processed feedstock. Typically, pyrolysis of feedstock occurs most efficiently when the moisture content of the feedstock is between about 10% and about 30% (e.g., between 15% and 25%) by weight of the feedstock. If the moisture content of the feedstock is larger than about 40% by weight, the extra thermal load presented by the water content of the feedstock increases the energy consumption of subsequent pyrolysis steps.

In some embodiments, if the feedstock has a moisture content which is larger than about 30% by weight, drier feedstock material 6220 which has a low moisture content can be blended in, creating a feedstock mixture in step 6030 with an average moisture content that is within the limits discussed above. In certain embodiments, feedstock with a high moisture content can simply be dried by dispersing the feedstock material on a moving conveyor that cycles the feedstock through an in-line heating unit. The heating unit evaporates a portion of the water present in the feedstock.

In some embodiments, if the feedstock from step 6020 has a moisture content which is too low (e.g., lower than about 10% by weight), the mechanically processed feedstock can be combined with wetter feedstock material 6230 with a higher moisture content, such as sewage sludge. Alternatively, or in addition, water 6240 can be added to the dry feedstock from step 6020 to increase its moisture content.

In step 6040, the feedstock—now with its moisture content adjusted to fall within suitable limits—can be preheated in an optional preheating step 6040. Preheating step 6040 can be used to increase the temperature of the feedstock to between 75° C. and 150° C. in preparation for subsequent pyrolysis of the feedstock. Depending upon the nature of the feedstock and the particular design of the pyrolysis chamber, preheating the feedstock can ensure that heat distribution within the feedstock remains more uniform during pyrolysis, and can reduce the thermal load on the pyrolysis chamber.

The feedstock is then transported to a pyrolysis chamber to undergo pyrolysis in step 6050. In some embodiments, transport of the feedstock is assisted by adding one or more pressurized gases 6210 to the feedstock stream. The gases create a pressure gradient in a feedstock transport conduit, propelling the feedstock into the pyrolysis chamber (and even through the pyrolysis chamber). In certain embodiments, transport of the feedstock occurs mechanically; that is, a transport system that includes a conveyor such as an auger transports the feedstock to the pyrolysis chamber.

Other gases 6210 can also be added to the feedstock prior to the pyrolysis chamber. In some embodiments, for example, one or more catalyst gases can be added to the feedstock to assist decomposition of the feedstock during pyrolysis. In certain embodiments, one or more scavenging agents can be added to the feedstock to trap volatile materials released during pyrolysis. For example, various sulfur-based compounds such as sulfides can be liberated during pyrolysis, and an agent such as hydrogen gas can be added to the feedstock to cause desulfurization of the pyrolysis products. Hydrogen combines with sulfides to form hydrogen sulfide gas, which can be removed from the pyrolyzed feedstock.

Pyrolysis of the feedstock within the chamber can include heating the feedstock to relatively high temperatures to cause partial decomposition of the feedstock. Typically, the feedstock is heated to a temperature in a range from 150° C. to 1100° C. The temperature to which the feedstock is heated depends upon a number of factors, including the composition of the feedstock, the feedstock average particle size, the moisture content, and the desired pyrolysis products. For many types of biomass feedstock, for example, pyrolysis temperatures between 300° C. and 550° C. are used.

The residence time of the feedstock within the pyrolysis chamber generally depends upon a number of factors, including the pyrolysis temperature, the composition of the feedstock, the feedstock average particle size, the moisture content, and the desired pyrolysis products. In some embodiments, feedstock materials are pyrolyzed at a temperature just above the decomposition temperature for the material in an inert atmosphere, e.g., from about 2° C. above to about 10° C. above the decomposition temperature or from about 3° C. above to about 7° C. above the decomposition temperature. In such embodiments, the material is generally kept at this temperature for greater than 0.5 hour, e.g., greater than 1.0 hour or greater than about 2.0 hours. In other embodiments, the materials are pyrolyzed at a temperature well above the decomposition temperature for the material in an inert atmosphere, e.g., from about 75° C. above to about 175° C. above the decomposition temperature or from about 85° C. above to about 150° C. above the decomposition temperature. In such embodiments, the material is generally kept at this temperature for less than 0.5 hour, e.g., less 20 minutes, less than 10 minutes, less than 5 minutes or less than 2 minutes. In still other embodiments, the materials are pyrolyzed at an extreme temperature, e.g., from about 200° C. above to about 500° C. above the decomposition temperature of the material in an inert environment or from about 250° C. above to about 400° C. above the decomposition temperature. In such embodiments, the material us generally kept at this temperature for less than 1 minute, e.g., less than 30 seconds, less than 15 seconds, less than 10 seconds, less than 5 seconds, less than 1 second or less than 500 ms. Such embodiments are typically referred to as flash pyrolysis.

In some embodiments, the feedstock is heated relatively rapidly to the selected pyrolysis temperature within the chamber. For example, the chamber can be designed to heat the feedstock at a rate of between 500° C./s and 11,000° C./s. Typical heating rates for biomass-derived feedstock material are from 500° C./s to 1000° C./s, for example.

A turbulent flow of feedstock material within the pyrolysis chamber is usually advantageous, as it ensures relatively efficient heat transfer to the feedstock material from the heating sub-system. Turbulent flow can be achieved by blowing the feedstock material through the chamber using one or more injected carrier gases 6210, for example. In general, the carrier gases are relatively inert towards the feedstock material, even at the high temperatures in the pyrolysis chamber. Exemplary carrier gases include, for example, nitrogen, argon, methane, carbon monoxide, and carbon dioxide. Alternatively, or in addition, mechanical transport systems such as augers can transport and circulate the feedstock within the pyrolysis chamber to create a turbulent feedstock flow.

In some embodiments, pyrolysis of the feedstock occurs substantially in the absence of oxygen and other reactive gases. Oxygen can be removed from the pyrolysis chamber by periodic purging of the chamber with high pressure nitrogen (e.g., at nitrogen pressures of 2 bar or more). Following purging of the chamber, a gas mixture present in the pyrolysis chamber (e.g., during pyrolysis of the feedstock) can include less than 4 mole % oxygen (e.g., less than 1 mole % oxygen, and even less than 0.5 mole % oxygen). The absence of oxygen ensures that ignition of the feedstock does not occur at the elevated pyrolysis temperatures.

In certain embodiments, relatively small amounts of oxygen can be introduced into the feedstock and are present during pyrolysis. This technique is referred to as oxidative pyrolysis. Typically, oxidative pyrolysis occurs in multiple heating stages. For example, in a first heating stage, the feedstock is heated in the presence of oxygen to cause partial oxidation of the feedstock. This stage consumes the available oxygen in the pyrolysis chamber. Then, in subsequent heating stages, the feedstock temperature is further elevated. With all of the oxygen in the chamber consumed, however, feedstock combustion does not occur, and combustion-free pyrolytic decomposition of the feedstock (e.g., to generate hydrocarbon products) occurs. In general, the process of heating feedstock in the pyrolysis chamber to initiate decomposition is endothermic. However, in oxidative pyrolysis, formation of carbon dioxide by oxidation of the feedstock is an exothermic process. The heat released from carbon dioxide formation can assist further pyrolysis heating stages, thereby lessening the thermal load presented by the feedstock.

In some embodiments, pyrolysis occurs in an inert environment, such as while feedstock materials are bathed in argon or nitrogen gas. In certain embodiments, pyrolysis can occur in an oxidizing environment, such as in air or argon enriched in air. In some embodiments, pyrolysis can take place in a reducing environment, such as while feedstock materials are bathed in hydrogen gas. To aid pyrolysis, various chemical agents, such as oxidants, reductants, acids or bases can be added to the material prior to or during pyrolysis. For example, sulfuric acid can be added, or a peroxide (e.g., benzoyl peroxide) can be added.

As discussed above, a variety of different processing conditions can be used, depending upon factors such as the feedstock composition and the desired pyrolysis products. For example, for cellulose-containing feedstock material, relatively mild pyrolysis conditions can be employed, including flash pyrolysis temperatures between 375° C. and 450° C., and residence times of less than 1 second. As another example, for organic solid waste material such as sewage sludge, flash pyrolysis temperatures between 500° C. and 650° C. are typically used, with residence times of between 0.5 and 3 seconds. In general, many of the pyrolysis process parameters, including residence time, pyrolysis temperature, feedstock turbulence, moisture content, feedstock composition, pyrolysis product composition, and additive gas composition can be regulated automatically by a system of regulators and an automated control system.

Following pyrolysis step 6050, the pyrolysis products undergo a quenching step 6250 to reduce the temperature of the products prior to further processing. Typically, quenching step 6250 includes spraying the pyrolysis products with streams of cooling water 6260. The cooling water also forms a slurry that includes solid, undissolved product material and various dissolved products. Also present in the product stream is a mixture that includes various gases, including product gases, carrier gases, and other types of process gases.

The product stream is transported via in-line piping to a gas separator that performs a gas separation step 6060, in which product gases and other gases are separated from the slurry formed by quenching the pyrolysis products. The separated gas mixture is optionally directed to a blower 6130, which increases the gas pressure by blowing air into the mixture. The gas mixture can be subjected to a filtration step 6140, in which the gas mixture passes through one or more filters (e.g., activated charcoal filters) to remove particulates and other impurities. In a subsequent step 6150, the filtered gas can be compressed and stored for further use. Alternatively, the filtered gas can be subjected to further processing steps 6160. For example, in some embodiments, the filtered gas can be condensed to separate different gaseous compounds within the gas mixture. The different compounds can include, for example, various hydrocarbon products (e.g., alcohols, alkanes, alkenes, alkynes, ethers) produced during pyrolysis. In certain embodiments, the filtered gas containing a mixture of hydrocarbon components can be combined with steam gas 6170 (e.g., a mixture of water vapor and oxygen) and subjected to a cracking process to reduce molecular weights of the hydrocarbon components.

In some embodiments, the pyrolysis chamber includes heat sources that burn hydrocarbon gases such as methane, propane, and/or butane to heat the feedstock. A portion 6270 of the separated gases can be recirculated into the pyrolysis chamber for combustion, to generate process heat to sustain the pyrolysis process.

In certain embodiments, the pyrolysis chamber can receive process heat that can be used to increase the temperature of feedstock materials. For example, irradiating feedstock with radiation (e.g., gamma radiation, electron beam radiation, or other types of radiation) can heat the feedstock materials to relatively high temperatures. The heated feedstock materials can be cooled by a heat exchange system that removes some of the excess heat from the irradiated feedstock. The heat exchange system can be configured to transport some of the heat energy to the pyrolysis chamber to heat (or pre-heat) feedstock material, thereby reducing energy cost for the pyrolysis process.

The slurry containing liquid and solid pyrolysis products can undergo an optional de-watering step 6070, in which excess water can be removed from the slurry via processes such as mechanical pressing and evaporation. The excess water 6280 can be filtered and then recirculated for further use in quenching the pyrolysis decomposition products in step 6250.

The de-watered slurry then undergoes a mechanical separation step 6080, in which solid product material 6110 is separated from liquid product material 6090 by a series of increasingly-fine filters. In step 6100, the liquid product material 6090 can then be condensed (e.g., via evaporation) to remove waste water 6190, and purified by processes such as extraction. Extraction can include the addition of one or more organic solvents 6180, for example, to separate products such as oils from products such as alcohols. Suitable organic solvents include, for example, various hydrocarbons and halo-hydrocarbons. The purified liquid products 6200 can then be subjected to further processing steps. Waste water 6190 can be filtered if necessary, and recirculated for further use in quenching the pyrolysis decomposition products in step 6250.

After separation in step 6080, the solid product material 6110 is optionally subjected to a drying step 6120 that can include evaporation of water. Solid material 6110 can then be stored for later use, or subjected to further processing steps, as appropriate.

The pyrolysis process parameters discussed above are exemplary. In general, values of these parameters can vary widely according to the nature of the feedstock and the desired products. Moreover, a wide variety of different pyrolysis techniques, including using heat sources such as hydrocarbon flames and/or furnaces, infrared lasers, microwave heaters, induction heaters, resistive heaters, and other heating devices and configurations can be used.

A wide variety of different pyrolysis chambers can be used to decompose the feedstock. In some embodiments, for example, pyrolyzing feedstock can include heating the material using a resistive heating member, such as a metal filament or metal ribbon. The heating can occur by direct contact between the resistive heating member and the material.

In certain embodiments, pyrolyzing can include heating the material by induction, such as by using a Currie-Point pyrolyzer. In some embodiments, pyrolyzing can include heating the material by the application of radiation, such as infrared radiation. The radiation can be generated by a laser, such as an infrared laser.

In certain embodiments, pyrolyzing can include heating the material with a convective heat. The convective heat can be generated by a flowing stream of heated gas. The heated gas can be maintained at a temperature of less than about 1200° C., such as less than 1000° C., less than 750° C., less than 600° C., less than 400° C. or even less than 300° C. The heated gas can be maintained at a temperature of greater than about 250° C. The convective heat can be generated by a hot body surrounding the first material, such as in a furnace.

In some embodiments, pyrolyzing can include heating the material with steam at a temperature above about 250° C.

Figure 15:
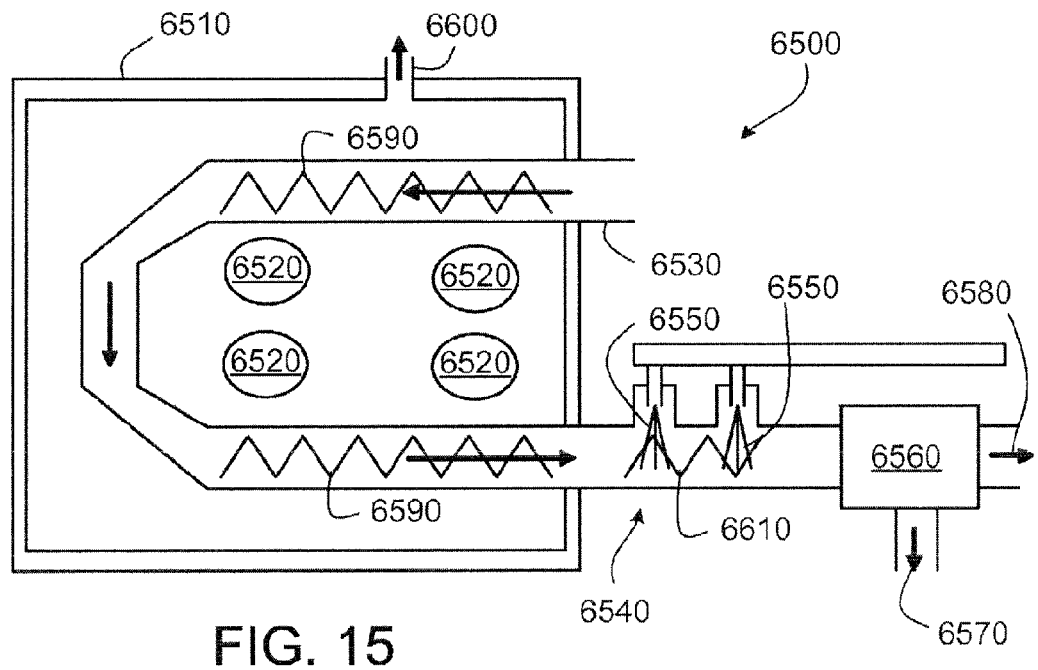
FIG. 15 is a cross-sectional side view of a pyrolysis chamber.

An embodiment of a pyrolysis chamber is shown in FIG. 15. Chamber 6500 includes an insulated chamber wall 6510 with a vent 6600 for exhaust gases, a plurality of burners 6520 that generate heat for the pyrolysis process, a transport duct 6530 for transporting the feedstock through chamber 6500, augers 6590 for moving the feedstock through duct 6530 in a turbulent flow, and a quenching system 6540 that includes an auger 6610 for moving the pyrolysis products, water jets 6550 for spraying the pyrolysis products with cooling water, and a gas separator for separating gaseous products 6580 from a slurry 6570 containing solid and liquid products.

Figure 16:
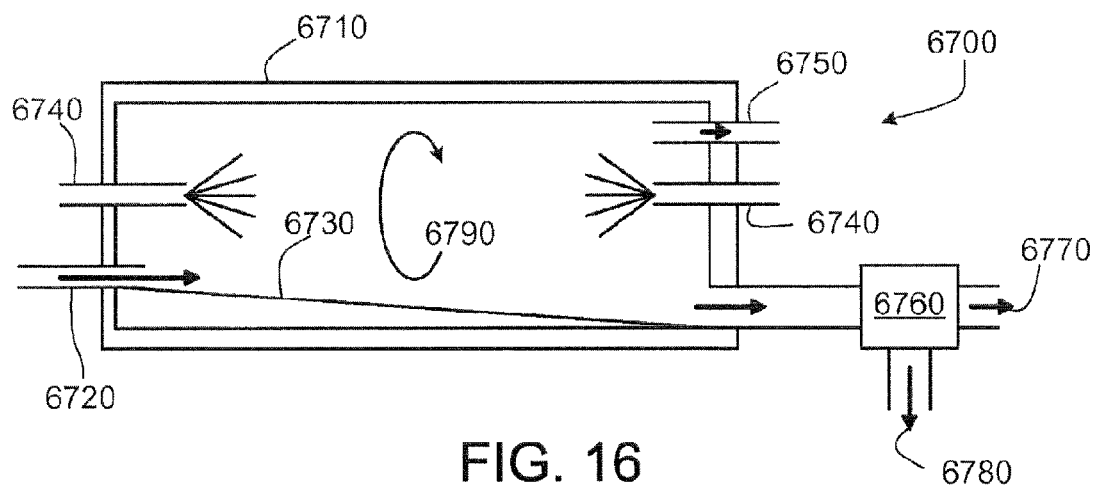
FIG. 16 is a cross-sectional side view of a pyrolysis chamber.

Another embodiment of a pyrolysis chamber is shown in FIG. 16. Chamber 6700 includes an insulated chamber wall 6710, a feedstock supply duct 6720, a sloped inner chamber wall 6730, burners 6740 that generate heat for the pyrolysis process, a vent 6750 for exhaust gases, and a gas separator 6760 for separating gaseous products 6770 from liquid and solid products 6780. Chamber 6700 is configured to rotate in the direction shown by arrow 6790 to ensure adequate mixing and turbulent flow of the feedstock within the chamber.

Figure 17:
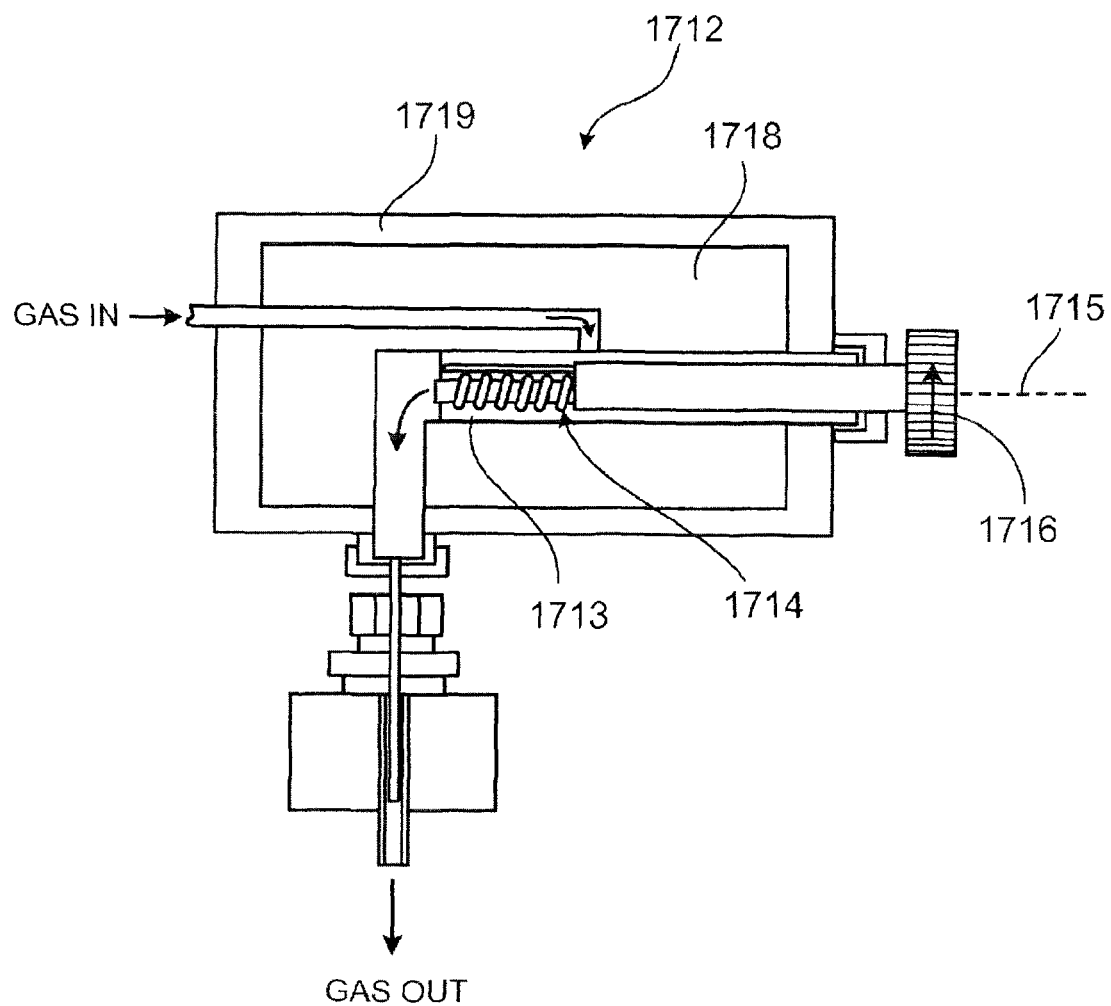
FIG. 17 is a cross-sectional side view of a pyrolyzer that includes a heated filament.

A further embodiment of a pyrolysis chamber is shown in FIG. 17. Filament pyrolyzer 1712 includes a sample holder 1713 with resistive heating element 1714 in the form of a wire winding through the open space defined by the sample holder 1713. Optionally, the heated element can be spun about axis 1715 (as indicated by arrow 1716) to tumble the material that includes the cellulosic material in sample holder 1713. The space 1718 defined by enclosure 1719 is maintained at a temperature above room temperature, e.g., 200 to 250° C. In a typical usage, a carrier gas, e.g., an inert gas, or an oxidizing or reducing gas, traverses through the sample holder 1713 while the resistive heating element is rotated and heated to a desired temperature, e.g., 325° C. After an appropriate time, e.g., 5 to 10 minutes, the pyrolyzed material is emptied from the sample holder. The system shown in FIG. 17 can be scaled and made continuous. For example, rather than a wire as the heating member, the heating member can be an auger screw. Material can continuously fall into the sample holder, striking a heated screw that pyrolizes the material. At the same time, the screw can push the pyrolyzed material out of the sample holder to allow for the entry of fresh, unpyrolyzed material.

Figure 18:
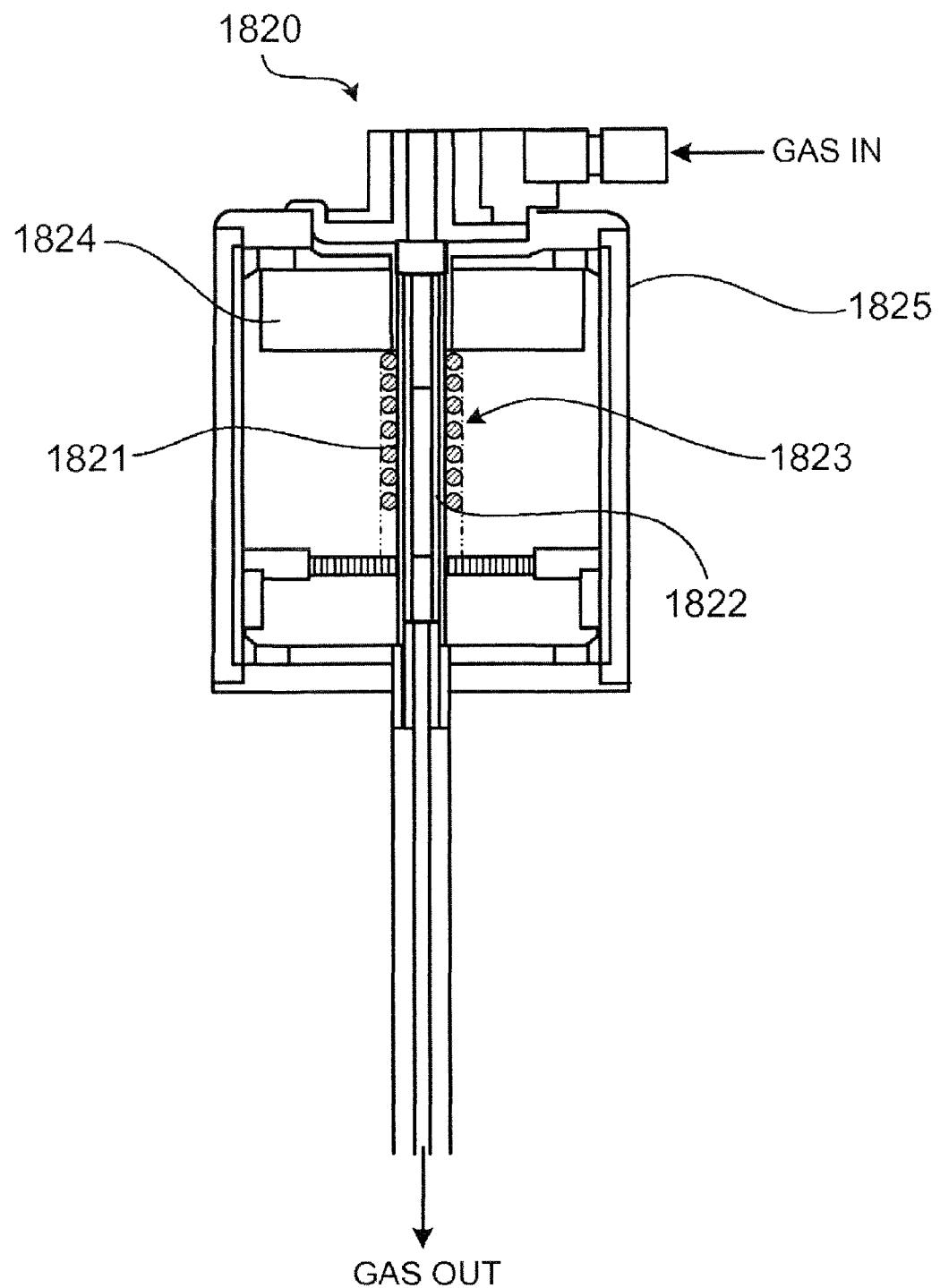
FIG. 18 is a schematic cross-sectional side view of a Curie-Point pyrolyzer.

Another embodiment of a pyrolysis chamber is shown in FIG. 18, which features a Curie-Point pyrolyzer 1820 that includes a sample chamber 1821 housing a ferromagnetic foil 1822. Surrounding the sample chamber 1821 is an RF coil 1823. The space 1824 defined by enclosure 1825 is maintained at a temperature above room temperature, e.g., 200 to 250° C. In a typical usage, a carrier gas traverses through the sample chamber 1821 while the foil 1822 is inductively heated by an applied RF field to pyrolize the material at a desired temperature.

Figure 19:
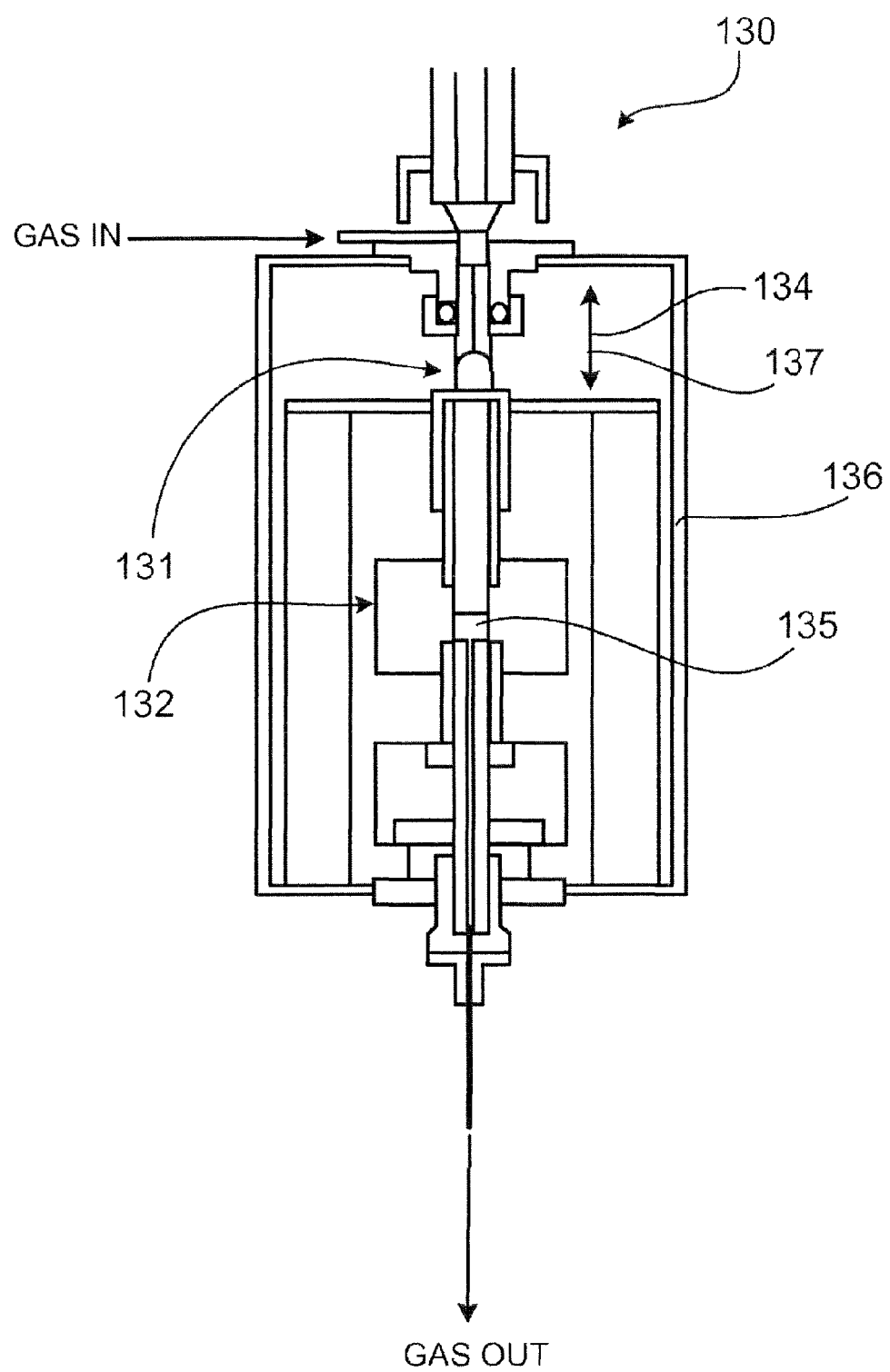
FIG. 19 is a schematic cross-sectional side view of a furnace pyrolyzer.

Yet another embodiment of a pyrolysis chamber is shown in FIG. 19. Furnace pyrolyzer 130 includes a movable sample holder 131 and a furnace 132. In a typical usage, the sample is lowered (as indicated by arrow 137) into a hot zone 135 of furnace 132, while a carrier gas fills the housing 136 and traverses through the sample holder 131. The sample is heated to the desired temperature for a desired time to provide a pyrolyzed product. The pyrolyzed product is removed from the pyrolyzer by raising the sample holder (as indicated by arrow 134).

Figure 20:
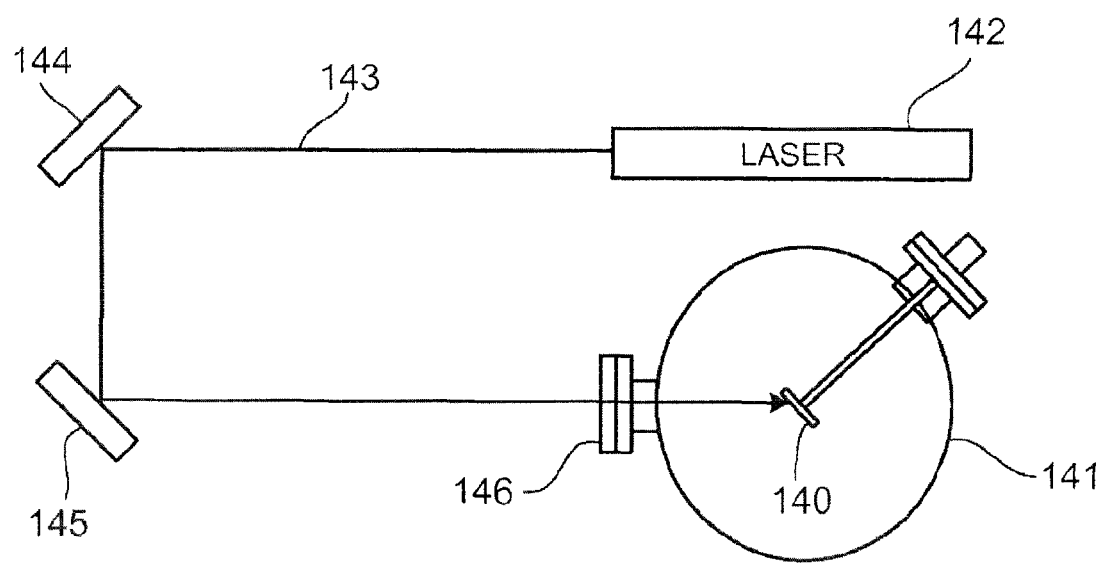
FIG. 20 is a schematic cross-sectional top view of a laser pyrolysis apparatus.

In certain embodiments, as shown in FIG. 20, a cellulosic target 140 can be pyrolyzed by treating the target, which is housed in a vacuum chamber 141, with laser light, e.g., light having a wavelength of from about 225 nm to about 1500 nm. For example, the target can be ablated at 266 nm, using the fourth harmonic of a Nd-YAG laser (Spectra Physics, GCR170, San Jose, Calif.). The optical configuration shown allows the nearly monochromatic light 143 generated by the laser 142 to be directed using mirrors 144 and 145 onto the target after passing though a lens 146 in the vacuum chamber 141. Typically, the pressure in the vacuum chamber is maintained at less than about $10^{-6}$ mm Hg. In some embodiments, infrared radiation is used, e.g., 1.06 micron radiation from a Nd-YAG laser. In such embodiments, a infrared sensitive dye can be combined with the cellulosic material to produce a cellulosic target. The infrared dye can enhance the heating of the cellulosic material. Laser ablation is described by Blanchet-Fincher et al. in U.S. Pat. No. 5,942,649.

Figure 21:
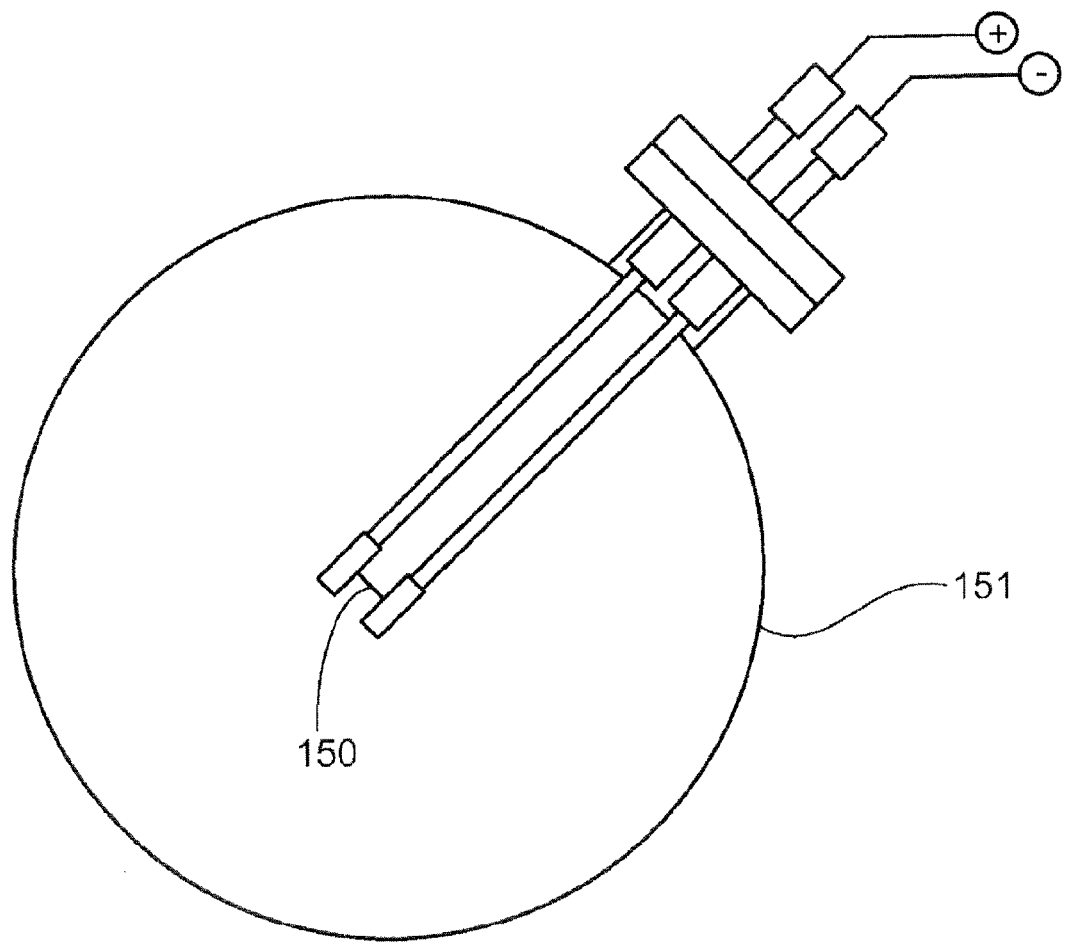
FIG. 21 is a schematic cross-sectional top view of a tungsten filament flash pyrolyzer.

Referring to FIG. 21, in some embodiments, a cellulosic material can be flash pyrolyzed by coating a tungsten filament 150, such as a 5 to 25 mil tungsten filament, with the desired cellulosic material while the material is housed in a vacuum chamber 151. To affect pyrolysis, current is passed through the filament, which causes a rapid heating of the filament for a desired time. Typically, the heating is continued for seconds before allowing the filament to cool. In some embodiments, the heating is performed a number of times to effect the desired amount of pyrolysis.

In certain embodiments, carbohydrate-containing biomass material can be heated in an absence of oxygen in a fluidized bed reactor. If desired, the carbohydrate containing biomass can have relatively thin cross-sections, and can include any of the fibrous materials described herein, for efficient heat transfer. The material can be heated by thermal transfer from a hot metal or ceramic, such as glass beads or sand in the reactor, and the resulting pyrolysis liquid or oil can be transported to a central refinery for making combustible fuels or other useful products.

Oxidation

One or more oxidative processing sequences can be used to process raw feedstock from a wide variety of different sources to extract useful substances from the feedstock, and to provide partially degraded organic material which functions as input to further processing steps and/or sequences.

Referring again to FIG. 8, a first material 2 that includes cellulose having a first number average molecular weight ($^TM_{N1}$) and having a first oxygen content ($^TO_1$) is oxidized, e.g., by heating the first material in a tube furnace in stream of air or oxygen-enriched air, to provide a second material 3 that includes cellulose having a second number average molecular weight ($^TM_{N2}$) and having a second oxygen content ($^TO_2$) higher than the first oxygen content ($^TO_1$). The second material (or the first and second material in certain embodiments) can be, e.g., combined with a resin, such as a molten thermoplastic resin or a microorganism, to provide a composite 4 having desirable mechanical properties, or a fuel 5. Providing a higher level of oxidation can improve dispersibility of the oxidized material in a resin and can also improve the interfacial bond between the oxidized material and the resin. Improved dispersibility and/or interfacial bonding (in some instances in combination with maintaining molecular weight) can provide composites with exceptional mechanical properties, such as improved abrasion resistance, compression strength, fracture resistance, impact strength, bending strength, tensile modulus, flexural modulus and elongation at break.

Such materials can also be combined with a solid and/or a liquid. For example, the liquid can be in the form of a solution and the solid can be particulate in form. The liquid and/or solid can include a microorganism, e.g., a bacterium, and/or an enzyme. For example, the bacterium and/or enzyme can work on the cellulosic or lignocellulosic material to produce a fuel, such as ethanol, or a coproduct, such as a protein. Exemplary fuels and coproducts are described in FIBROUS MATERIALS AND COMPOSITES," U.S. Ser. No. 11/453,951, filed Jun. 15, 2006.

In some embodiments, the second number average molecular weight is not more 97 percent lower than the first number average molecular weight, e.g., not more than 95 percent, 90, 85, 80, 75, 70, 65, 60, 55, 50, 45, 40, 30, 20, 12.5, 10.0, 7.5, 5.0, 4.0, 3.0, 2.5, 2.0 or not more than 1.0 percent lower than the first number average molecular weight. The amount of reduction of molecular weight will depend upon the application. For example, in some preferred embodiments that provide composites, the second number average molecular weight is substantially the same as the first number average molecular weight. In other applications, such as making ethanol or another fuel or coproduct, a higher amount of molecular weight reduction is generally preferred.

For example, in some embodiments that provide a composite, the starting number average molecular weight (prior to oxidation) is from about 200,000 to about 3,200,000, e.g., from about 250,000 to about 1,000,000 or from about 250,000 to about 700,000, and the number average molecular weight after oxidation is from about 175,000 to about 3,000,000, e.g., from about 200,000 to about 750,000 or from about 225,000 to about 600,000.

Resins utilized can be thermosets or thermoplastics. Examples of thermoplastic resins include rigid and elastomeric thermoplastics. Rigid thermoplastics include polyolefins (e.g., polyethylene, polypropylene, or polyolefin copolymers), polyesters (e.g., polyethylene terephthalate), polyamides (e.g., nylon 6, 6/12 or 6/10), and polyethyleneimines. Examples of elastomeric thermoplastic resins include elastomeric styrenic copolymers (e.g., styrene-ethylene-butylene-styrene copolymers), polyamide elastomers (e.g., polyether-polyamide copolymers) and ethylene-vinyl acetate copolymer.

In particular embodiments, lignin is utilized, e.g., any lignin that is generated in any process described herein.

In some embodiments, the thermoplastic resin has a melt flow rate of between 10 g/10 minutes to 60 g/10 minutes, e.g., between 20 g/10 minutes to 50 g/10 minutes, or between 30 g/10 minutes to 45 g/10 minutes, as measured using ASTM 1238. In certain embodiments, compatible blends of any of the above thermoplastic resins can be used.

In some embodiments, the thermoplastic resin has a polydispersity index (PDI), i.e., a ratio of the weight average molecular weight to the number average molecular weight, of greater than 1.5, e.g., greater than 2.0, greater than 2.5, greater than 5.0, greater than 7.5, or even greater than 10.0.

In specific embodiments, polyolefins or blends of polyolefins are utilized as the thermoplastic resin.

Examples of thermosetting resins include natural rubber, butadiene-rubber and polyurethanes.

In some embodiments in which the materials are used to make a fuel or a coproduct, the starting number average molecular weight (prior to oxidation) is from about 200,000 to about 3,200,000, e.g., from about 250,000 to about 1,000,000 or from about 250,000 to about 700,000, and the number average molecular weight after oxidation is from about 50,000 to about 200,000, e.g., from about 60,000 to about 150,000 or from about 70,000 to about 125,000. However, in some embodiments, e.g., after extensive oxidation, it is possible to have a number average molecular weight of less than about 10,000 or even less than about 5,000.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the oxygen content of the first material. Oxygen content is measured by elemental analysis by pyrolyzing a sample in a furnace operating 1300° C. or higher. A suitable elemental analyzer is the LECO CHNS-932 analyzer with a VTF-900 high temperature pyrolysis furnace.

In some embodiments, oxidation of first material 200 does not result in a substantial change in the crystallinity of the cellulose. However, in some instances, e.g., after extreme oxidation, the second material has cellulose that has as crystallinity ($^T C_2$) that is lower than the crystallinity ($^T C_1$) of the cellulose of the first material. For example, ($^T C_2$) can be lower than ($^T C_1$) by more than about 5 percent, e.g., 10, 15, 20, or even 25 percent. This can be desirable when optimizing the flexural fatigue properties of the composite is a goal. For example, reducing the crystallinity can improve the elongation at break or can enhance the impact resistance of a composite. This can also be desirable to enhance solubility of the materials in a liquid, such as a liquid that includes a bacterium and/or an enzyme.

In some embodiments, the starting crystallinity index (prior to oxidation) is from about 40 to about 87.5 percent, e.g., from about 50 to about 75 percent or from about 60 to about 70 percent, and the crystallinity index after oxidation is from about 30 to about 75.0 percent, e.g., from about 35.0 to about 70.0 percent or from about 37.5 to about 65.0 percent. However, in certain embodiments, e.g., after extensive oxidation, it is possible to have a crystallinity index of lower than 5 percent. In some embodiments, the material after oxidation is substantially amorphous.

Without wishing to be bound by any particular theory, it is believed that oxidation increases the number of hydrogen-bonding groups on the cellulose, such as hydroxyl groups, aldehyde groups, ketone groups carboxylic acid groups or anhydride groups, which can increase its dispersibility and/or its solubility (e.g., in a liquid). To further improve dispersibility in a resin, the resin can include a component that includes hydrogen-bonding groups, such as one or more anhydride groups, carboxylic acid groups, hydroxyl groups, amide groups, amine groups or mixtures of any of these groups. In some preferred embodiments, the component includes a polymer copolymerized with and/or grafted with maleic anhydride. Such materials are available from DuPont under the trade name FUSABOND®.

Generally, oxidation of first material 200 occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Oxidation Systems

Figure 22:
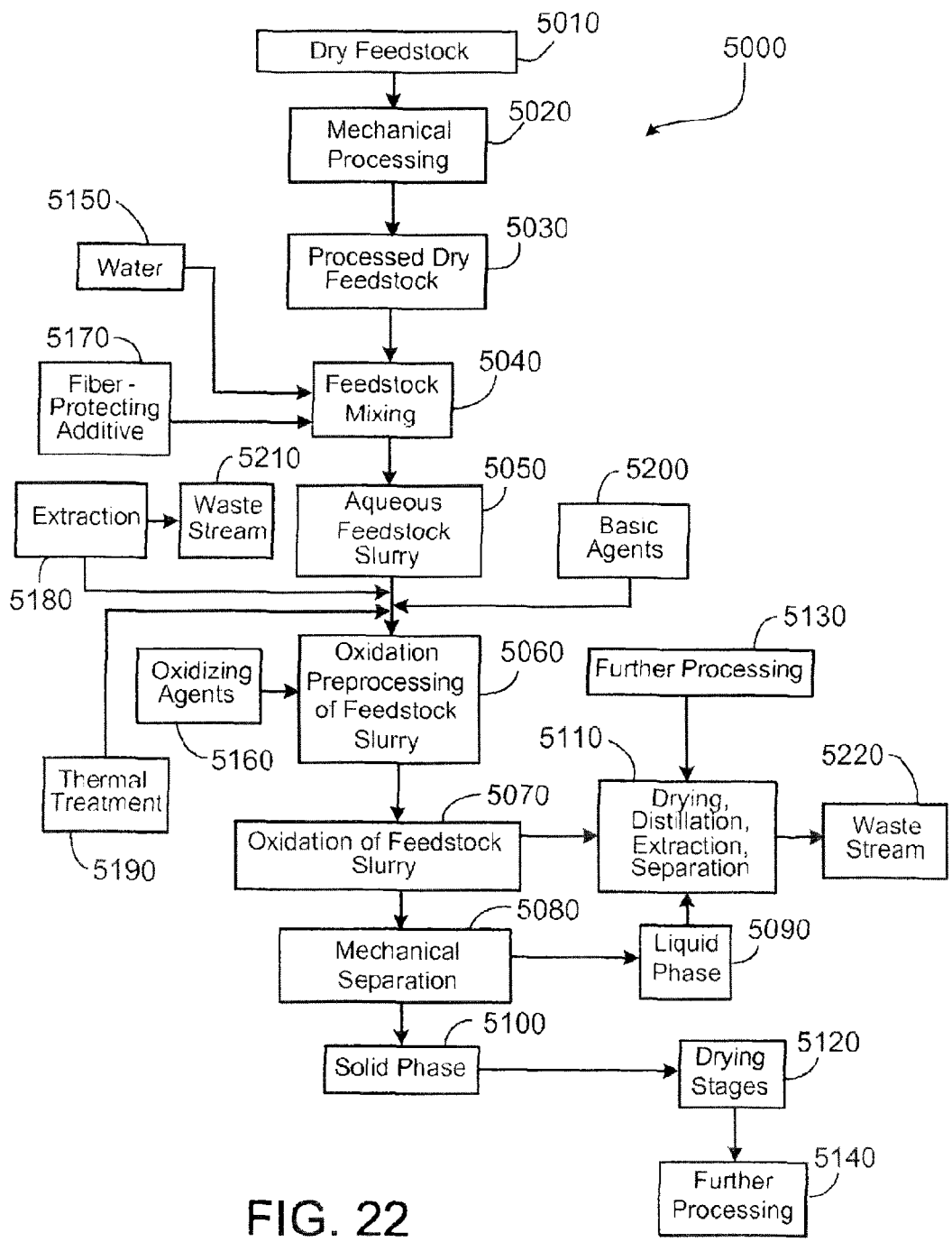
FIG. 22 is a block diagram illustrating an oxidative feedstock pretreatment system.

FIG. 22 shows a process flow diagram 5000 that includes various steps in an oxidative feedstock pretreatment system. In first step 5010, a supply of dry feedstock is received from a feed source. The feed source can include, for example, a storage bed or container that is connected to an in-line oxidation reactor via a conveyor belt or another feedstock transport device.

As described above, the dry feedstock from the feed source may be pre-processed prior to delivery to the oxidation reactor. For example, if the feedstock is derived from plant sources, certain portions of the plant material may be removed prior to collection of the plant material and/or before the plant material is delivered by the feedstock transport device. Alternatively, or in addition, the biomass feedstock can be subjected to mechanical processing (e.g., to reduce the average length of fibers in the feedstock) prior to delivery to the oxidation reactor.

Following mechanical processing 5020, feedstock 5030 is transported to a mixing system which introduces water 5150 into the feedstock in a mechanical mixing process. Combining water with the processed feedstock in mixing step 5040 creates an aqueous feedstock slurry 5050, which can then be treated with one or more oxidizing agents.

Typically, one liter of water is added to the mixture for every 0.02 kg to 1.0 kg of dry feedstock. The ratio of feedstock to water in the mixture depends upon the source of the feedstock and the specific oxidizing agents used further downstream in the overall process. For example, in typical industrial processing sequences for lignocellulosic biomass, aqueous feedstock slurry 5050 includes from about 0.5 kg to about 1.0 kg of dry biomass per liter of water.

In some embodiments, one or more fiber-protecting additives 5170 can also be added to the feedstock slurry in feedstock mixing step 5040. Fiber-protecting additives help to reduce degradation of certain types of biomass fibers (e.g., cellulose fibers) during oxidation of the feedstock. Fiber-protecting additives can be used, for example, if a desired product from processing a lignocellulosic feedstock includes cellulose fibers. Exemplary fiber-protecting additives include magnesium compounds such as magnesium hydroxide. Concentrations of fiber-protecting additives in feedstock slurry 5050 can be from 0.1% to 0.4% of the dry weight of the biomass feedstock, for example.

In certain embodiments, aqueous feedstock slurry 5050 can be subjected to an optional extraction 5180 with an organic solvent to remove water-insoluble substances from the slurry. For example, extraction of slurry 5050 with one or more organic solvents yields a purified slurry and an organic waste stream 5210 that includes water-insoluble materials such as fats, oils, and other non-polar, hydrocarbon-based substances. Suitable solvents for performing extraction of slurry 5050 include various alcohols, hydrocarbons, and halo-hydrocarbons, for example.

In some embodiments, aqueous feedstock slurry 5050 can be subjected to an optional thermal treatment 5190 to further prepare the feedstock for oxidation. An example of a thermal treatment includes heating the feedstock slurry in the presence of pressurized steam. In fibrous biomass feedstock, the pressurized steam swells the fibers, exposing a larger fraction of fiber surfaces to the aqueous solvent and to oxidizing agents that are introduced in subsequent processing steps.

In certain embodiments, aqueous feedstock slurry 5050 can be subjected to an optional treatment with basic agents 5200. Treatment with one or more basic agents can help to separate lignin from cellulose in lignocellulosic biomass feedstock, thereby improving subsequent oxidation of the feedstock. Exemplary basic agents include alkali and alkaline earth hydroxides such as sodium hydroxide, potassium hydroxide, and calcium hydroxide. In general, a variety of basic agents can be used, typically in concentrations from about 0.01% to about 0.5% of the dry weight of the feedstock.

Aqueous feedstock slurry 5050 is transported (e.g., by an in-line piping system) to a chamber, which can be an oxidation preprocessing chamber or an oxidation reactor. In oxidation preprocessing step 5060, one or more oxidizing agents 5160 are added to feedstock slurry 5050 to form an oxidizing medium. In some embodiments, for example, oxidizing agents 5160 can include hydrogen peroxide. Hydrogen peroxide can be added to slurry 5050 as an aqueous solution, and in proportions ranging from 3% to between 30% and 35% by weight of slurry 5050. Hydrogen peroxide has a number of advantages as an oxidizing agent. For example, aqueous hydrogen peroxide solution is relatively inexpensive, is relatively chemically stable, and is not particularly hazardous relative to other oxidizing agents (and therefore does not require burdensome handling procedures and expensive safety equipment). Moreover, hydrogen peroxide decomposes to form water during oxidation of feedstock, so that waste stream cleanup is relatively straightforward and inexpensive.

In certain embodiments, oxidizing agents 5160 can include oxygen (e.g., oxygen gas) either alone, or in combination with hydrogen peroxide. Oxygen gas can be bubbled into slurry 5050 in proportions ranging from 0.5% to 10% by weight of slurry 5050. Alternatively, or in addition, oxygen gas can also be introduced into a gaseous phase in equilibrium with slurry 5050 (e.g., a vapor head above slurry 5050). The oxygen gas can be introduced into either an oxidation preprocessing chamber or into an oxidation reactor (or into both), depending upon the configuration of the oxidative processing system. Typically, for example, the partial pressure of oxygen in the vapor above slurry 5050 is larger than the ambient pressure of oxygen, and ranges from 0.5 bar to 35 bar, depending upon the nature of the feedstock.

The oxygen gas can be introduced in pure form, or can be mixed with one or more carrier gases. For example, in some embodiments, high-pressure air provides the oxygen in the vapor. In certain embodiments, oxygen gas can be supplied continuously to the vapor phase to ensure that a concentration of oxygen in the vapor remains within certain predetermined limits during processing of the feedstock. In some embodiments, oxygen gas can be introduced initially in sufficient concentration to oxidize the feedstock, and then the feedstock can be transported to a closed, pressurized vessel (e.g., an oxidation reactor) for processing.

In certain embodiments, oxidizing agents 5160 can include nascent oxygen (e.g., oxygen radicals). Typically, nascent oxygen is produced as needed in an oxidation reactor or in a chamber in fluid communication with an oxidation reactor by one or more decomposition reactions. For example, in some embodiments, nascent oxygen can be produced from a reaction between NO and $O_2$ in a gas mixture or in solution. In certain embodiments, nascent oxygen can be produced from decomposition of HOCl in solution. Other methods by which nascent oxygen can be produced include via electrochemical generation in electrolyte solution, for example.

In general, nascent oxygen is an efficient oxidizing agent due to the relatively high reactivity of the oxygen radical. However, nascent oxygen can also be a relatively selective oxidizing agent. For example, when lignocellulosic feedstock is treated with nascent oxygen, selective oxidation of lignin occurs in preference to the other components of the feedstock such as cellulose. As a result, oxidation of feedstock with nascent oxygen provides a method for selective removal of the lignin fraction in certain feedstocks. Typically, nascent oxygen concentrations of between about 0.5% and 5% of the dry weight of the feedstock are used to effect efficient oxidation.

Without wishing to be bound by theory, it is believed that nascent oxygen reacts with lignocellulosic feedstock according to at least two different mechanisms. In a first mechanism, nascent oxygen undergoes an addition reaction with the lignin, resulting in partial oxidation of the lignin, which solubilizes the lignin in aqueous solution. As a result, the solubilized lignin can be removed from the rest of the feedstock via washing. In a second mechanism, nascent oxygen disrupts butane cross-links and/or opens aromatic rings that are connected via the butane cross-links. As a result, solubility of the lignin in aqueous solution increases, and the lignin fraction can be separated from the remainder of the feedstock via washing.

In some embodiments, oxidizing agents 5160 include ozone ($O_3$). The use of ozone can introduce several chemical handling considerations in the oxidation processing sequence. If heated too vigorously, an aqueous solution of ozone can decompose violently, with potentially adverse consequences for both human system operators and system equipment. Accordingly, ozone is typically generated in a thermally isolated, thick-walled vessel separate from the vessel that contains the feedstock slurry, and transported thereto at the appropriate process stage.

Without wishing to be bound by theory, it is believed that ozone decomposes into oxygen and oxygen radicals, and that the oxygen radicals (e.g., nascent oxygen) are responsible for the oxidizing properties of ozone in the manner discussed above. Ozone typically preferentially oxidizes the lignin fraction in lignocellulosic materials, leaving the cellulose fraction relatively undisturbed.

Conditions for ozone-based oxidation of biomass feedstock generally depend upon the nature of the biomass. For example, for cellulosic and/or lignocellulosic feedstocks, ozone concentrations of from 0.1 $g/m^3$ to 20 $g/m^3$ of dry feedstock provide for efficient feedstock oxidation. Typically, the water content in slurry 5050 is between 10% by weight and 80% by weight (e.g., between 40% by weight and 60% by weight). During ozone-based oxidation, the temperature of slurry 5050 can be maintained between 0° C. and 100° C. to avoid violent decomposition of the ozone.

In some embodiments, feedstock slurry 5050 can be treated with an aqueous, alkaline solution that includes one or more alkali and alkaline earth hydroxides such as sodium hydroxide, potassium hydroxide, and calcium hydroxide, and then treated thereafter with an ozone-containing gas in an oxidation reactor. This process has been observed to significantly increase decomposition of the biomass in slurry 5050. Typically, for example, a concentration of hydroxide ions in the alkaline solution is between 0.001% and 10% by weight of slurry 5050. After the feedstock has been wetted via contact with the alkaline solution, the ozone-containing gas is introduced into the oxidation reactor, where it contacts and oxidizes the feedstock.

Oxidizing agents 5160 can also include other substances. In some embodiments, for example, halogen-based oxidizing agents such as chlorine and oxychlorine agents (e.g., hypochlorite) can be introduced into slurry 5050. In certain embodiments, nitrogen-containing oxidizing substances can be introduced into slurry 5050. Exemplary nitrogen-containing oxidizing substances include NO and $NO_2$, for example. Nitrogen-containing agents can also be combined with oxygen in slurry 5050 to create additional oxidizing agents. For example, NO and $NO_2$ both combine with oxygen in slurry 5050 to form nitrate compounds, which are effective oxidizing agents for biomass feedstock. Halogen- and nitrogen-based oxidizing agents can, in some embodiments, cause bleaching of the biomass feedstock, depending upon the nature of the feedstock. The bleaching may be desirable for certain biomass-derived products that are extracted in subsequent processing steps.

Other oxidizing agents can include, for example, various peroxyacids, peroxyacetic acids, persulfates, percarbonates, permanganates, osmium tetroxide, and chromium oxides.

Following oxidation preprocessing step 5060, feedstock slurry 5050 is oxidized in step 5070. If oxidizing agents 5160 were added to slurry 5050 in an oxidation reactor, then oxidation proceeds in the same reactor. Alternatively, if oxidizing agents 5160 were added to slurry 5050 in a preprocessing chamber, then slurry 5050 is transported to an oxidation reactor via an in-line piping system. Once inside the oxidation reactor, oxidation of the biomass feedstock proceeds under a controlled set of environmental conditions. Typically, for example, the oxidation reactor is a cylindrical vessel that is closed to the external environment and pressurized. Both batch and continuous operation is possible, although environmental conditions are typically easier to control in in-line batch processing operations.

Oxidation of feedstock slurry 5050 typically occurs at elevated temperatures in the oxidation reactor. For example, the temperature of slurry 5050 in the oxidation reactor is typically maintained above 100° C., in a range from 120° C. to 240° C. For many types of biomass feedstock, oxidation is particularly efficient if the temperature of slurry 5050 is maintained between 150° C. and 220° C. Slurry 5050 can be heating using a variety of thermal transfer devices. For example, in some embodiments, the oxidation reactor contacts a heating bath that includes oil or molten salts. In certain embodiments, a series of heat exchange pipes surround and contact the oxidation reactor, and circulation of hot fluid within the pipes heats slurry 5050 in the reactor. Other heating devices that can be used to heat slurry 5050 include resistive heating elements, induction heaters, and microwave sources, for example.

The residence time of feedstock slurry 5050 in the oxidation reactor can be varied as desired to process the feedstock. Typically, slurry 5050 spends from 1 minute to 60 minutes undergoing oxidation in the reactor. For relatively soft biomass material such as lignocellulosic matter, the residence time in the oxidation reactor can be from 5 minutes to 30 minutes, for example, at an oxygen pressure of between 3 and 12 bars in the reactor, and at a slurry temperature of between 160° C. and 210° C. For other types of feedstock, however, residence times in the oxidation reactor can be longer, e.g., as long 48 hours. To determine appropriate residence times for slurry 5050 in the oxidation reactor, aliquots of the slurry can be extracted from the reactor at specific intervals and analyzed to determine concentrations of particular products of interest such as complex saccharides. Information about the increase in concentrations of certain products in slurry 5050 as a function of time can be used to determine residence times for particular classes of feedstock material.

In some embodiments, during oxidation of feedstock slurry 5050, adjustment of the slurry pH may be performed by introducing one or more chemical agents into the oxidation reactor. For example, in certain embodiments, oxidation occurs most efficiently in a pH range of about 9-11. To maintain a pH in this range, agents such as alkali and alkaline earth hydroxides, carbonates, ammonia, and alkaline buffer solutions can be introduced into the oxidation reactor.

Circulation of slurry 5050 during oxidation can be important to ensure sufficient contact between oxidizing agents 5160 and the feedstock. Circulation of the slurry can be achieved using a variety of techniques. For example, in some embodiments, a mechanical stirring apparatus that includes impeller blades or a paddle wheel can be implemented in the oxidation reactor. In certain embodiments, the oxidation reactor can be a loop reactor, in which the aqueous solvent in which the feedstock is suspended is simultaneously drained from the bottom of the reactor and recirculated into the top of the reactor via pumping, thereby ensuring that the slurry is continually re-mixed and does not stagnate within the reactor.

After oxidation of the feedstock is complete, the slurry is transported to a separation apparatus where a mechanical separation step 5080 occurs. Typically, mechanical separation step 5080 includes one or more stages of increasingly-fine filtering of the slurry to mechanically separate the solid and liquid constituents.

Liquid phase 5090 is separated from solid phase 5100, and the two phases are processed independently thereafter. Solid phase 5100 can optionally undergo a drying step 5120 in a drying apparatus, for example. Drying step 5120 can include, for example, mechanically dispersing the solid material onto a drying surface, and evaporating water from solid phase 5100 by gentle heating of the solid material. Following drying step 5120 (or, alternatively, without undergoing drying step 5120), solid phase 5100 is transported for further processing steps 5140.

Liquid phase 5090 can optionally undergo a drying step 5110 to reduce the concentration of water in the liquid phase. In some embodiments, for example, drying step 5110 can include evaporation and/or distillation and/or extraction of water from liquid phase 5090 by gentle heating of the liquid. Alternatively, or in addition, one or more chemical drying agents can be used to remove water from liquid phase 5090. Following drying step 5110 (or alternatively, without undergoing drying step 5110), liquid phase 5090 is transported for further processing steps 5130, which can include a variety of chemical and biological treatment steps such as chemical and/or enzymatic hydrolysis.

Drying step 5110 creates waste stream 5220, an aqueous solution that can include dissolved chemical agents such as acids and bases in relatively low concentrations. Treatment of waste stream 5220 can include, for example, pH neutralization with one or more mineral acids or bases. Depending upon the concentration of dissolved salts in waste stream 5220, the solution may be partially de-ionized (e.g., by passing the waste stream through an ion exchange system). Then, the waste stream—which includes primarily water—can be re-circulated into the overall process (e.g., as water 5150), diverted to another process, or discharged.

Typically, for lignocellulosic biomass feedstocks following separation step 5070, liquid phase 5090 includes a variety of soluble poly- and oligosaccharides, which can then be separated and/or reduced to smaller-chain saccharides via further processing steps. Solid phase 5100 typically includes primarily cellulose, for example, with smaller amounts of hemicellulose- and lignin-derived products.

In some embodiments, oxidation can be carried out at elevated temperature in a reactor such as a pyrolysis chamber. For example, referring again to FIG. 17, feedstock materials can be oxidized in filament pyrolyzer 1712. In a typical usage, an oxidizing carrier gas, e.g., air or an air/argon blend, traverses through the sample holder 1713 while the resistive heating element is rotated and heated to a desired temperature, e.g., 325° C. After an appropriate time, e.g., 5 to 10 minutes, the oxidized material is emptied from the sample holder. The system shown in FIG. 2 can be scaled and made continuous. For example, rather than a wire as the heating member, the heating member can be an auger screw. Material can continuously fall into the sample holder, striking a heated screw that pyrolizes the material. At the same time, the screw can push the oxidized material out of the sample holder to allow for the entry of fresh, unoxidized material.

Referring again to FIG. 18, feedstock materials can be oxidized in a Curie-Point pyrolyzer 1820. In a typical usage, an oxidizing carrier gas traverses through the sample chamber 1821 while the foil 1822 is inductively heated by an applied RF field to oxidize the material at a desired temperature.

Referring again to FIG. 19, feedstock materials can be oxidized in a furnace pyrolyzer 130. In a typical usage, the sample is lowered (as indicated by arrow 137) into a hot zone 135 of furnace 132, while an oxidizing carrier gas fills the housing 136 and traverses through the sample holder 131. The sample is heated to the desired temperature for a desired time to provide an oxidized product. The oxidized product is removed from the pyrolyzer by raising the sample holder (as indicated by arrow 134).

Referring again to FIG. 20, feedstock materials can be oxidized by forming a cellulosic target 140, along with an oxidant, such as a peroxide, and treating the target, which is housed in a vacuum chamber 141, with laser light, e.g., light having a wavelength of from about 225 nm to about 1600 nm. The optical configuration shown allows the monochromatic light 143 generated by the laser 142 to be directed using mirrors 144 and 145 onto the target after passing though a lens 146 in the vacuum chamber 141. Typically, the pressure in the vacuum chamber is maintained at less than about $10^{-6}$ mm Hg. In some embodiments, infrared radiation is used, e.g., 1.06 micron radiation from a Nd-YAG laser. In such embodiments, a infrared sensitive dye can be combined with the cellulosic material to produce a cellulosic target. The infrared dye can enhance the heating of the cellulosic material. Laser treatment of polymers is described by Blanchet-Fincher et al. in U.S. Pat. No. 5,942,649.

Referring again to FIG. 21, feedstock materials can be rapidly oxidized by coating a tungsten filament 150, together with an oxidant, such as a peroxide, with the desired cellulosic material while the material is housed in a vacuum chamber 151. To affect oxidation, current is passed through the filament, which causes a rapid heating of the filament for a desired time. Typically, the heating is continued for seconds before allowing the filament to cool. In some embodiments, the heating is performed a number of times to effect the desired amount of oxidation.

Referring again to FIG. 12, in some embodiments, feedstock materials can be oxidized with the aid of sound and/or cavitation. Generally, to effect oxidation, the materials are sonicated in an oxidizing environment, such as water saturated with oxygen or another chemical oxidant, such as hydrogen peroxide.

Referring again to FIGS. 9 and 10, in certain embodiments, ionizing radiation is used to aid in the oxidation of feedstock materials. Generally, to effect oxidation, the materials are irradiated in an oxidizing environment, such as air or oxygen. For example, gamma radiation and/or electron beam radiation can be employed to irradiate the materials.

Other Processes

Steam explosion can be used alone without any of the processes described herein, or in combination with any of the processes described herein.

Figure 23:
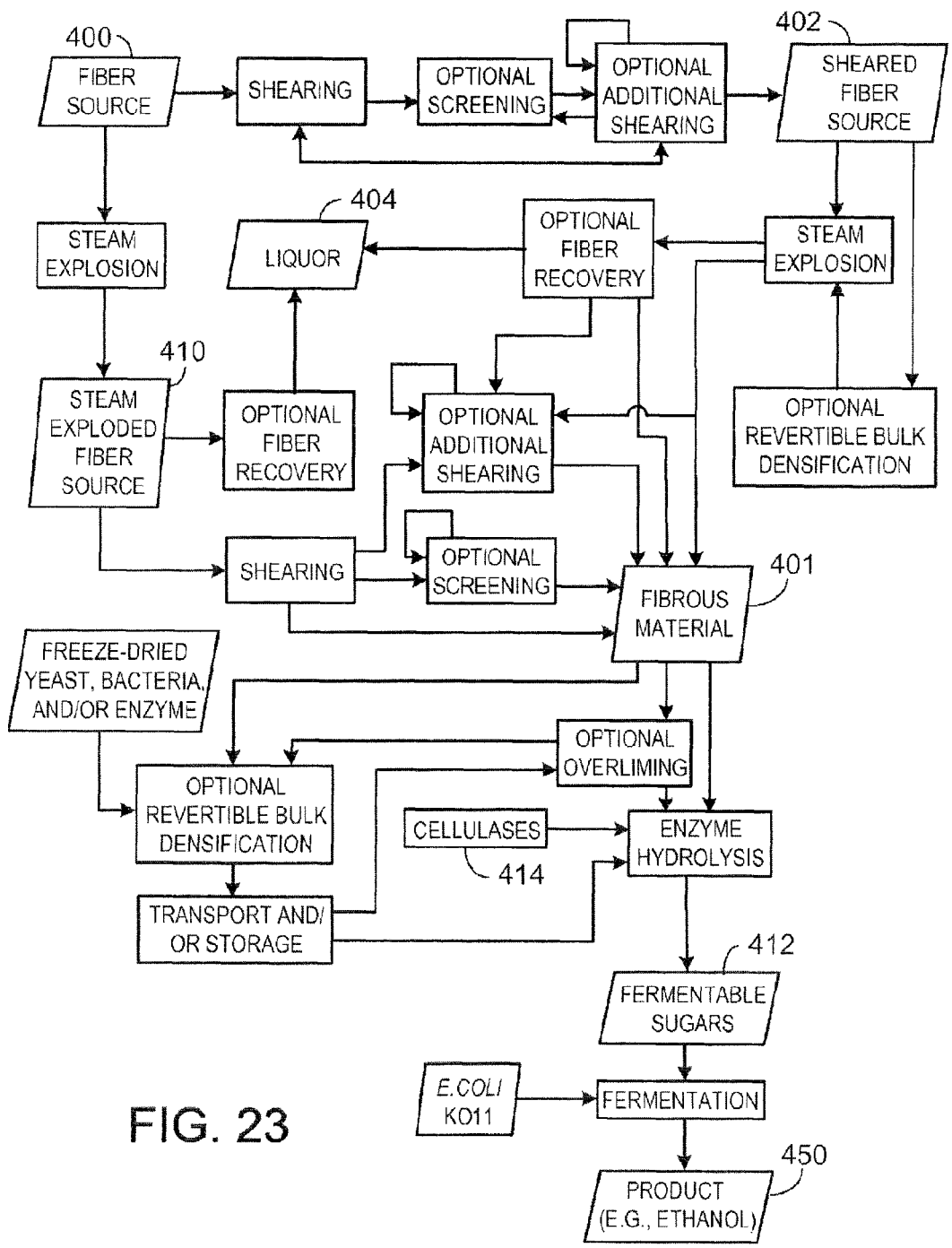
FIG. 23 is block diagram illustrating a general overview of the process of converting a fiber source into a product, e.g., ethanol.

FIG. 23 shows an overview of the entire process of converting a fiber source 400 into a product 450, such as ethanol, by a process that includes shearing and steam explosion to produce a fibrous material 401, which is then hydrolyzed and converted, e.g., fermented, to produce the product. The fiber source can be transformed into the fibrous material 401 through a number of possible methods, including at least one shearing process and at least one steam explosion process.

For example, one option includes shearing the fiber source, followed by optional screening step(s) and optional additional shearing step(s) to produce a sheared fiber source 402, which can then be steam exploded to produce the fibrous material 401. The steam explosion process is optionally followed by a fiber recovery process to remove liquids or the "liquor" 404, resulting from the steam exploding process. The material resulting from steam exploding the sheared fiber source may be further sheared by optional additional shearing step(s) and/or optional screening step(s).

In another method, the fibrous material 401 is first steam exploded to produce a steam exploded fiber source 410. The resulting steam exploded fiber source is then subjected to an optional fiber recovery process to remove liquids, or the liquor. The resulting steam exploded fiber source can then be sheared to produce the fibrous material. The steam exploded fiber source can also be subject to one or more optional screening steps and/or one or more optional additional shearing steps. The process of shearing and steam exploding the fiber source to produce the sheared and steam exploded fibrous material will be further discussed below.

The fiber source can be cut into pieces or strips of confetti material prior to shearing or steam explosion. The shearing processes can take place in a dry (e.g., having less than 0.25 percent by weight absorbed water), hydrated, or even while the material is partially or fully submerged in a liquid, such as water or isopropanol. The process can also optimally include steps of drying the output after steam exploding or shearing to allow for additional steps of dry shearing or steam exploding. The steps of shearing, screening, and steam explosion can take place with or without the presence of various chemical solutions.

In a steam explosion process, the fiber source or the sheared fiber source is contacted with steam under high pressure, and the steam diffuses into the structures of the fiber source (e.g., the lignocellulosic structures). The steam then condenses under high pressure thereby "wetting" the fiber source. The moisture in the fiber source can hydrolyze any acetyl groups in the fiber source (e.g., the acetyl groups in the hemicellulose fractions), forming organic acids such as acetic and uronic acids. The acids, in turn, can catalyze the depolymerization of hemicellulose, releasing xylan and limited amounts of glucan. The "wet" fiber source (or sheared fiber source, etc.) is then "exploded" when the pressure is released. The condensed moisture instantaneously evaporates due to the sudden decrease in pressure and the expansion of the water vapor exerts a shear force upon the fiber source (or sheared fiber source, etc.). A sufficient shear force will cause the mechanical breakdown of the internal structures (e.g., the lignocellulosic structures) of the fiber source.

The sheared and steam exploded fibrous material is then converted into a useful product, such as ethanol. In some embodiments, the fibrous material is converted into a fuel. One method of converting the fibrous material into a fuel is by hydrolysis to produce fermentable sugars, 412, which are then fermented to produce the product. Other known and unknown methods of converting fibrous materials into fuels may also be used.

In some embodiments, prior to combining the microorganism, the sheared and steam exploded fibrous material 401 is sterilized to kill any competing microorganisms that may be on the fibrous material. For example, the fibrous material can be sterilized by exposing the fibrous material to radiation, such as infrared radiation, ultraviolet radiation, or an ionizing radiation, such as gamma radiation. The microorganisms can also be killed using chemical sterilants, such as bleach (e.g., sodium hypochlorite), chlorhexidine, or ethylene oxide.

One method to hydrolyze the sheared and steam exploded fibrous material is by the use of cellulases. Cellulases are a group of enzymes that act synergistically to hydrolyze cellulose. Commercially available Accellerase® 1000 enzyme complex, which contains a complex of enzymes that reduces lignocellulosic biomass into fermentable sugars can also be used.

According to current understanding, the components of cellulase include endoglucanases, exoglucanases (cellobiohydrolases), and b-glucosidases (cellobiases). Synergism between the cellulase components exists when hydrolysis by a combination of two or more components exceeds the sum of the activities expressed by the individual components. The generally accepted mechanism of a cellulase system (particularly of $T.$ $longibrachiatum$) on crystalline cellulose is: endoglucanase hydrolyzes internal β-1,4-glycosidic bonds of the amorphous regions, thereby increasing the number of exposed non-reducing ends. Exoglucanases then cleave off cellobiose units from the nonreducing ends, which in turn are hydrolyzed to individual glucose units by β-glucosidases. There are several configurations of both endo- and exo-glucanases differing in stereospecificities. In general, the synergistic action of the components in various configurations is required for optimum cellulose hydrolysis. Cellulases, however, are more inclined to hydrolyze the amorphous regions of cellulose. A linear relationship between crystallinity and hydrolysis rates exists whereby higher crystallinity indices correspond to slower enzyme hydrolysis rates. Amorphous regions of cellulose hydrolyze at twice the rate of crystalline regions. The hydrolysis of the sheared and steam exploded fibrous material may be performed by any hydrolyzing biomass process.

Steam explosion of biomass sometimes causes the formation of by-products, e.g., toxicants, that are inhibitory to microbial and enzymatic activities. The process of converting the sheared and steam exploded fibrous material into a fuel can therefore optionally include an overliming step prior to fermentation to precipitate some of the toxicants. For example, the pH of the sheared and steam exploded fibrous material may be raised to exceed the pH of 10 by adding calcium hydroxide ($Ca(OH)_2$) followed by a step of lowering the pH to about 5 by adding $H_2SO_4$. The overlimed fibrous material may then be used as is without the removal of precipitates. As shown in FIG. 23, the optional overliming step occurs just prior to the step of hydrolysis of the sheared and steam exploded fibrous material, but it is also contemplated to perform the overliming step after the hydrolysis step and prior to the fermenting step.

Figure 24:
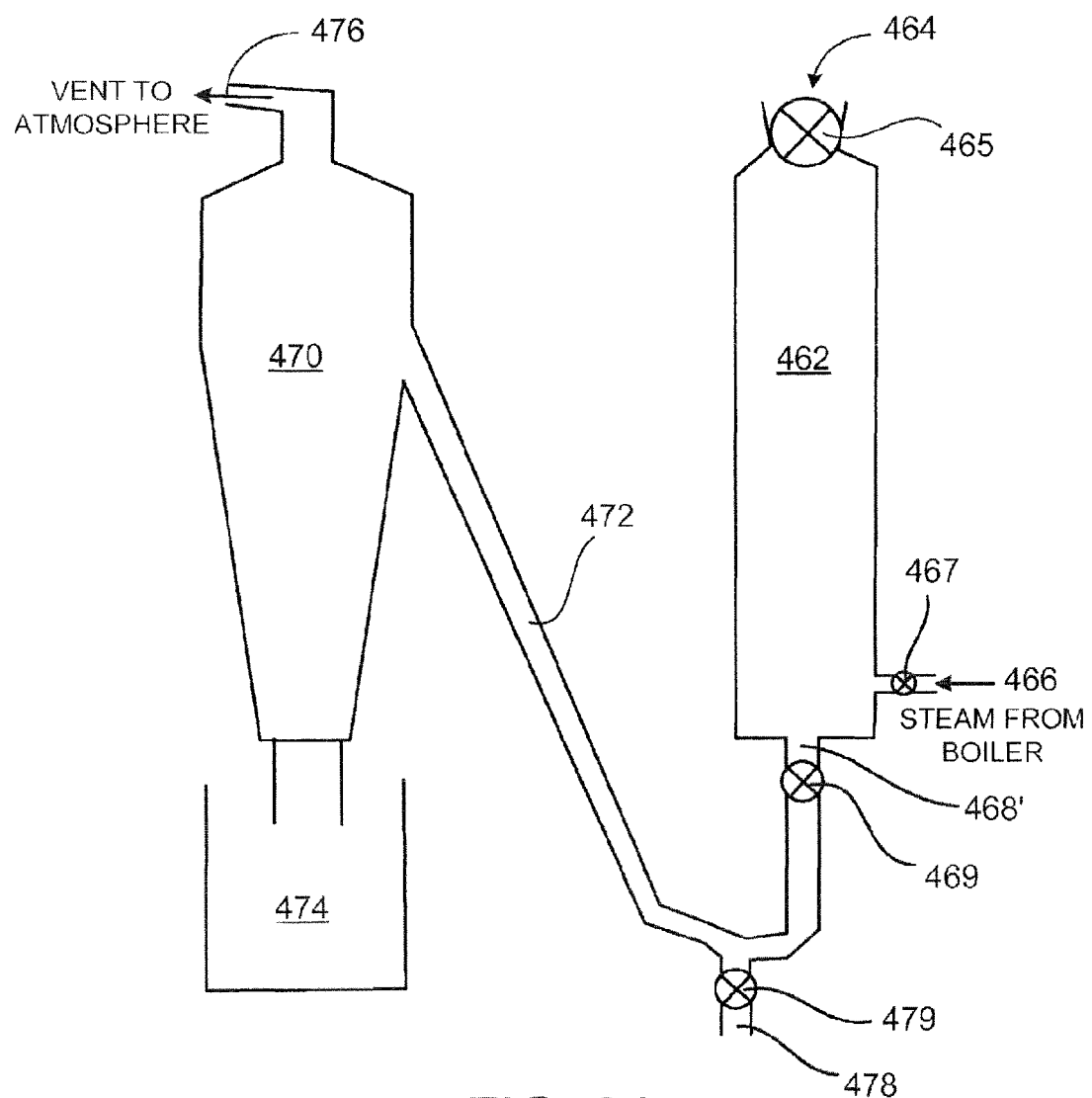
FIG. 24 is a cross-sectional view of a steam explosion apparatus.

FIG. 24 depicts an example of a steam explosion apparatus 460. The steam explosion apparatus 460 includes a reaction chamber 462, in which the fiber source and/or the fibrous material placed through a fiber source inlet 464. The reaction chamber is sealed by closing fiber source inlet valve 465. The reaction chamber further includes a pressurized steam inlet 466 that includes a steam valve 467. The reaction chamber further includes an explosive depressurization outlet 468 that includes an outlet valve 469 in communication with the cyclone 470 through the connecting pipe 472. Once the reaction chamber includes the fiber source and/or sheared fiber source and is sealed by closing valves 465, 467 and 469, steam is delivered into the reaction chamber 462 by opening the steam inlet valve 467 allowing steam to travel through steam inlet 466. Once the reaction chamber reaches target temperature, which can take about 20-60 seconds, the holding time begins. The reaction temperature is held at the target temperature for the desired holding time, which typically lasts from about 10 seconds to 5 minutes. At the end of the holding time period, outlet valve is open to allow for explosive depressurization to occur. The process of explosive depressurization propels the contents of the reaction chamber 462 out of the explosive depressurization outlet 468, through the connecting pipe 472, and into the cyclone 470. The steam exploded fiber source or fibrous material then exits the cyclone in a sludge form into the collection bin 474 as much of the remaining steam exits the cyclone into the atmosphere through vent 476. The steam explosion apparatus further includes wash outlet 478 with wash outlet valve 479 in communication with connecting pipe 472. The wash outlet valve 479 is closed during the use of the steam explosion apparatus 460 for steam explosion, but opened during the washing of the reaction chamber 462. The target temperature of the reaction chamber 462 is preferably between 180 and 240 degrees Celsius or between 200 and 220 degrees Celsius. The holding time is preferably between 10 seconds and 30 minutes, or between 30 seconds and 10 minutes, or between 1 minute and 5 minutes.

Because the steam explosion process results in a sludge of steam exploded fibrous material, the steam exploded fibrous material may optionally include a fiber recovery process where the "liquor" is separated from the steam exploded fibrous material. This fiber recovery step is helpful in that it enables further shearing and/or screening processes and can allow for the conversion of the fibrous material into fuel. The fiber recovery process occurs through the use of a mesh cloth to separate the fibers from the liquor. Further drying processes can also be included to prepare the fibrous material or steam exploded fiber source for subsequent processing.

Any processing technique described herein can be used at pressure above or below normal, earth-bound atmospheric pressure. For example, any process that utilizes radiation, sonication, oxidation, pyrolysis, steam explosion, or combinations of any of these processes to provide materials that include a carbohydrate can be performed under high pressure, which, can increase reaction rates. For example, any process or combination of processes can be performed at a pressure greater than about greater than 25 MPa, e.g., greater than 50 MPa, 75 MPa, 100 MPa, 150 MPa, 200 MPa, 250 MPa, 350 MPa, 500 MPa, 750 MPa, 1,000 MPa, or greater than 1,500 MPa.

Combinations of Irradiating, Sonicating, and Oxidizing Devices

In some embodiments, it may be advantageous to combine two or more separate irradiation, sonication, pyrolization, and/or oxidation devices into a single hybrid machine. For such a hybrid machine, multiple processes may be performed in close juxtaposition or even simultaneously, with the benefit of increasing pretreatment throughput and potential cost savings.

For example, consider the electron beam irradiation and sonication processes. Each separate process is effective in lowering the mean molecular weight of cellulosic material by an order of magnitude or more, and by several orders of magnitude when performed serially.

Figure 25:
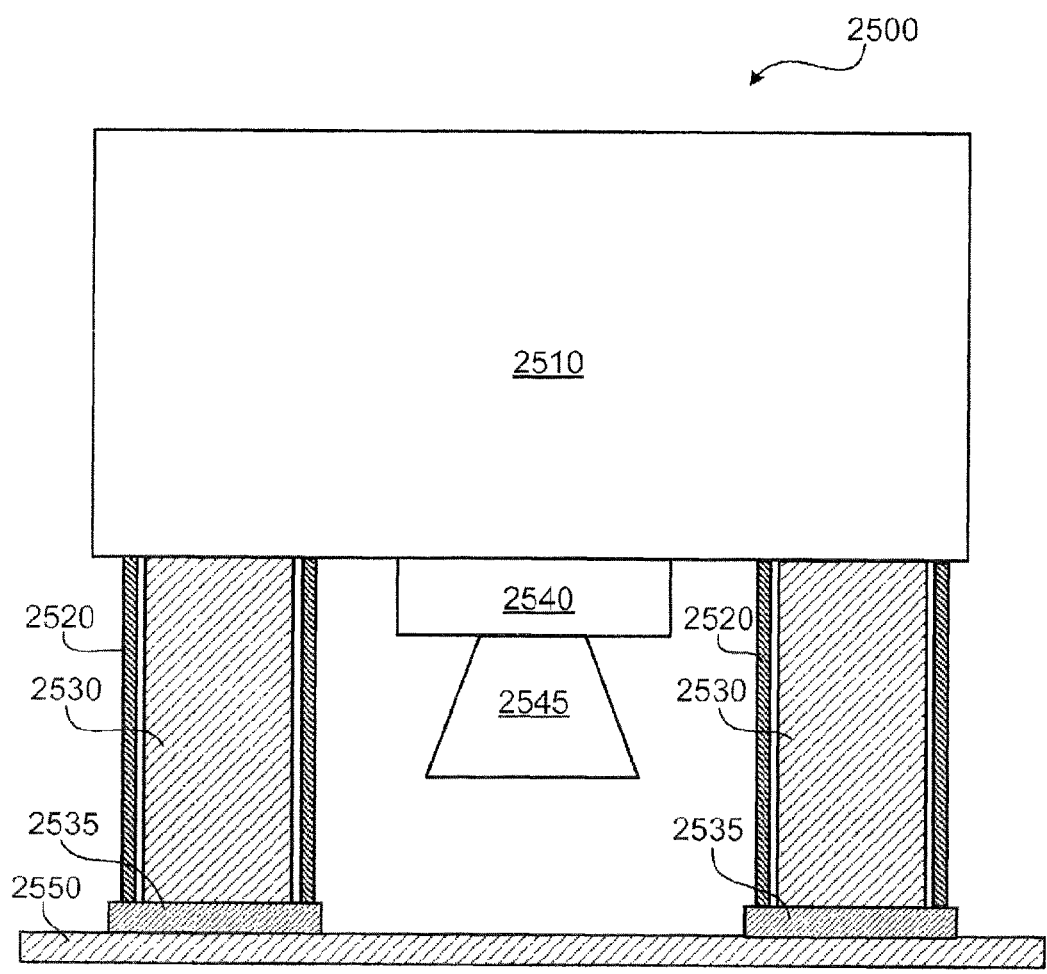
FIG. 25 is a schematic cross-sectional side view of a hybrid electron beam/sonication device.
Figure 28:
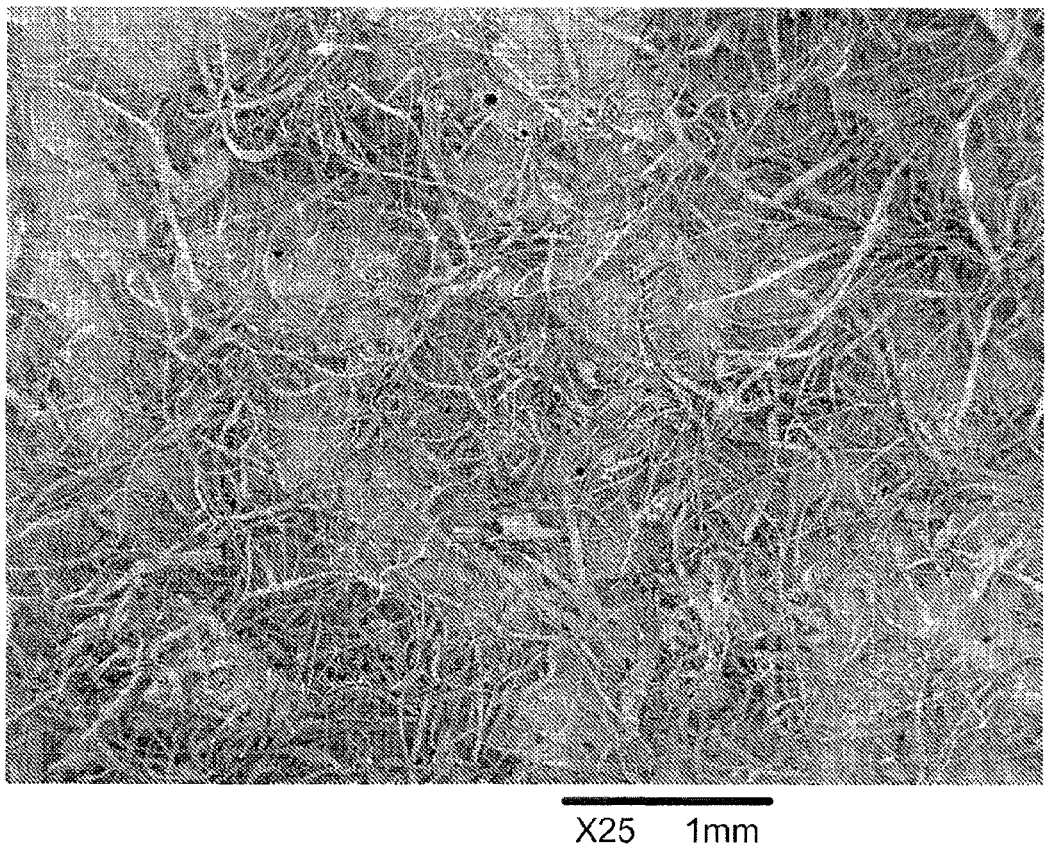
FIG. 28 is a scanning electron micrograph of a fibrous material produced from polycoated paper at 25× magnification. The fibrous material was produced on a rotary knife cutter utilizing a screen with ⅛ inch openings.

Both irradiation and sonication processes can be applied using a hybrid electron beam/sonication device as is illustrated in FIG. 25. Hybrid electron beam/sonication device 2500 is pictured above a shallow pool (depth~3-5 cm) of a slurry of cellulosic material 2550 dispersed in an aqueous, oxidant medium, such as hydrogen peroxide or carbamide peroxide. Hybrid device 2500 has an energy source 2510, which powers both electron beam emitter 2540 and sonication horns 2530.

Electron beam emitter 2540 generates electron beams which pass though an electron beam aiming device 2545 to impact the slurry 2550 containing cellulosic material. The electron beam aiming device can be a scanner that sweeps a beam over a range of up to about 6 feet in a direction approximately parallel to the surface of the slurry 2550.

On either side of the electron beam emitter 2540 are sonication horns 2530, which deliver ultrasonic wave energy to the slurry 2550. The sonication horns 2530 end in a detachable endpiece 2535 that is in contact with the slurry 2550.

The sonication horns 2530 are at risk of damage from long-term residual exposure to the electron beam radiation. Thus, the horns can be protected with a standard shield 2520, e.g., made of lead or a heavy-metal-containing alloy such as Lipowitz metal, which is impervious to electron beam radiation. Precautions must be taken, however, to ensure that the ultrasonic energy is not affected by the presence of the shield. The detachable endpieces 2535, are constructed of the same material and attached to the horns 2530, are used to be in contact with the cellulosic material 2550 and are expected to be damaged. Accordingly, the detachable endpieces 2535 are constructed to be easily replaceable.

A further benefit of such a simultaneous electron beam and ultrasound process is that the two processes have complementary results. With electron beam irradiation alone, an insufficient dose may result in cross-linking of some of the polymers in the cellulosic material, which lowers the efficiency of the overall depolymerization process. Lower doses of electron beam irradiation and/or ultrasound radiation may also be used to achieve a similar degree of depolymerization as that achieved using electron beam irradiation and sonication separately.

An electron beam device can also be combined with one or more of high-frequency, rotor-stator devices, which can be used as an alternative to ultrasonic energy devices, and performs a similar function.

Further combinations of devices are also possible. For example, an ionizing radiation device that produces gamma radiation emitted from, e.g., $^{60}$Co pellets, can be combined with an electron beam source and/or an ultrasonic wave source. Shielding requirements may be more stringent in this case.

The radiation devices for pretreating biomass discussed above can also be combined with one or more devices that perform one or more pyrolysis processing sequences. Such a combination may again have the advantage of higher throughput. Nevertheless, caution must be observed, as there may be conflicting requirements between some radiation processes and pyrolysis. For example, ultrasonic radiation devices may require the feedstock be immersed in a liquid oxidizing medium. On the other hand, as discussed previously, it may be advantageous for a sample of feedstock undergoing pyrolysis to be of a particular moisture content. In this case, the new systems automatically measure and monitor for a particular moisture content and regulate the same Further, some or all of the above devices, especially the pyrolysis device, can be combined with an oxidation device as discussed previously.

Primary Processes

Fermentation

Generally, various microorganisms can produce a number of useful products, such as a fuel, by operating on, e.g., fermenting the pretreated biomass materials. For example, Natural Force™ Chemistry methods can be used to prepare biomass materials for use in fermentation. Alcohols, organic acids, hydrocarbons, hydrogen, proteins or mixtures of any of these materials, for example, can be produced by fermentation or other processes.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

To aid in the breakdown of the materials that include the cellulose, one or more enzymes, e.g., a cellulolytic enzyme can be utilized. In some embodiments, the materials that include the cellulose are first treated with the enzyme, e.g., by combining the material and the enzyme in an aqueous solution. This material can then be combined with the microorganism. In other embodiments, the materials that include the cellulose, the one or more enzymes and the microorganism are combined at the concurrently, e.g., by combining in an aqueous solution.

Also, to aid in the breakdown of the materials that include the cellulose, the materials can be treated post irradiation with heat, a chemical (e.g., mineral acid, base or a strong oxidizer such as sodium hypochlorite), and/or an enzyme.

During the fermentation, sugars released from cellulolytic hydrolysis or the saccharification step, are fermented to, e.g., ethanol, by a fermenting microorganism such as yeast. Suitable fermenting microorganisms have the ability to convert carbohydrates, such as glucose, xylose, arabinose, mannose, galactose, oligosaccharides or polysaccharides into fermentation products. Fermenting microorganisms include strains of the genus Saccharomyces spp. e.g., Saccharomyces cerevisiae (baker's yeast), Saccharomyces distaticus, Saccharomyces uvarum; the genus Kluyveromyces, e.g., species Kluyveromyces marxianus, Kluyveromyces fragilis; the genus Candida, e.g., Candida pseudotropicalis, and Candida brassicae, Pichia stipitis (a relative of Candida shehatae, the genus Clavispora, e.g., species Clavispora lusitaniae and Clavispora opuntiae the genus Pachysolen, e.g., species Pachysolen tannophilus, the genus Bretannomyces, e.g., species Bretannomyces clausenii (Philippidis, G. P., 1996, Cellulose bioconversion technology, in Handbook on Bioethanol: Production and Utilization, Wyman, C. E., ed., Taylor & Francis, Washington, D.C., 179-212).

Commercially available yeast include, for example, Red Star®/Lesaffre Ethanol Red (available from Red Star/Lesaffre, USA) FALI® (available from Fleischmann's Yeast, a division of Burns Philip Food Inc., USA), SUPERSTART® (available from Alltech, now Lallemand), GERT STRAND® (available from Gert Strand AB, Sweden) and FERMOL® (available from DSM Specialties).

Bacteria that can ferment bimoss to ethanol and other products include, e.g., Zymomonas mobilis and Clostridium thermocellum (Philippidis, 1996, supra). Leschine et al. (International Journal of Systematic and Evolutionary Microbiology 2002, 52, 1155-1160) isolated an anaerobic, mesophilic, cellulolytic bacterium from forest soil, Clostridium phytofermentans sp. nov., which converts cellulose to ethanol.

Fermentation of biomass to ethanol and other products may be carried out using certain types of thermophilic or genetically engineered microorganisms, such Thermoanaerobacter species, including T. mathranii, and yeast species such as Pichia species. An example of a strain of T. mathranii is A3M4 described in Sonne-Hansen et al. (Applied Microbiology and Biotechnology 1993, 38, 537-541) or Ahring et al. (Arch. Microbiol. 1997, 168, 114-119).

Yeast and Zymomonas bacteria can be used for fermentation or conversion. The optimum pH for yeast is from about pH 4 to 5, while the optimum pH for Zymomonas is from about pH 5 to 6. Typical fermentation times are about 24 to 96 hours with temperatures in the range of 26° C. to 40° C., however thermophilic microorganisms prefer higher temperatures.

Enzymes which break down biomass, such as cellulose, to lower molecular weight carbohydrate-containing materials, such as glucose, during saccharification are referred to as cellulolytic enzymes or cellulase. These enzymes may be a complex of enzymes that act synergistically to degrade crystalline cellulose. Examples of cellulolytic enzymes include: endoglucanases, cellobiohydrolases, and cellobiases (β-glucosidases). A cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble β-1,4-linked dimer of glucose. Finally cellobiase cleaves cellobiose to yield glucose.

A cellulase is capable of degrading biomass and may be of fungal or bacterial origin. Suitable enzymes include cellulases from the genera Bacillus, Pseudomonas, Humicola, Fusarium, Thielavia, Acremonium, Chrysosporium and Trichoderma, and include species of Humicola, Coprinus, Thielavia, Fusarium, Myceliophthora, Acremonium, Cephalosporium, Scytalidium, Penicillium or Aspergillus (see, e.g., EP 458162), especially those produced by a strain selected from the species Humicola insolens (reclassified as Scytalidium thermophilum, see, e.g., U.S. Pat. No. 4,435,307), Coprinus cinereus, Fusarium oxysporum, Myceliophthora thermophila, Meripilus giganteus, Thielavia terrestris, Acremonium sp., Acremonium persicinum, Acremonium acremonium, Acremonium brachypenium, Acremonium dichromosporum, Acremonium obclavatum, Acremonium pinkertoniae, Acremonium roseogriseum, Acremonium incoloratum, and Acremonium furatum; preferably from the species Humicola insolens DSM 1800, Fusarium oxysporum DSM 2672, Myceliophthora thermophila CBS 117.65, Cephalosporium sp. RYM-202, Acremonium sp. CBS 478.94, Acremonium sp. CBS 265.95, Acremonium persicinum CBS 169.65, Acremonium acremonium AHU 9519, Cephalosporium sp. CBS 535.71, Acremonium brachypenium CBS 866.73, Acremonium dichromosporum CBS 683.73, Acremonium obclavatum CBS 311.74, Acremonium pinkertoniae CBS 157.70, Acremonium roseogriseum CBS 134.56, Acremonium incoloratum CBS 146.62, and Acremonium furatum CBS 299.70H. Cellulolytic enzymes may also be obtained from Chrysosporium, preferably a strain of Chrysosporium lucknowense. Additionally, Trichoderma (particularly Trichoderma viride, Trichoderma reesei, and Trichoderma koningii), alkalophilic Bacillus (see, for example, U.S. Pat. No. 3,844,890 and EP 458162), and Streptomyces (see, e.g., EP 458162) may be used. The bacterium, Saccharophagus degradans, produces a mixture of enzymes capable of degrading a range of cellulosic materials and may also be used in this process.

Anaerobic cellulolytic bacteria have also been isolated from soil, e.g., a novel cellulolytic species of Clostridium, Clostridium phytofermentans sp. nov. (see Leschine et. al, International Journal of Systematic and Evolutionary Microbiology (2002), 52, 1155-1160).

Cellulolytic enzymes using recombinant technology can also be used (see, e.g., WO 2007/071818 and WO 2006/110891).

The cellulolytic enzymes used can be produced by fermentation of the above-noted microbial strains on a nutrient medium containing suitable carbon and nitrogen sources and inorganic salts, using procedures known in the art (see, e.g., Bennett, J. W. and LaSure, L. (eds.), More Gene Manipulations in Fungi, Academic Press, CA 1991). Suitable media are available from commercial suppliers or may be prepared according to published compositions (e.g., in catalogues of the American Type Culture Collection). Temperature ranges and other conditions suitable for growth and cellulase production are known in the art (see, e.g., Bailey, J. E., and Ollis, D. F., Biochemical Engineering Fundamentals, McGraw-Hill Book Company, NY, 1986).

Treatment of cellulose with cellulase is usually carried out at temperatures between 30° C. and 65° C. Cellulases are active over a range of pH of about 3 to 7. A saccharification step may last up to 120 hours. The cellulase enzyme dosage achieves a sufficiently high level of cellulose conversion. For example, an appropriate cellulase dosage is typically between 5.0 and 50 Filter Paper Units (FPU or IU) per gram of cellulose. The FPU is a standard measurement and is defined and measured according to Ghose (1987, Pure and Appl. Chem. 59:257-268).

Mobile fermentors can be utilized, as described in U.S. Provisional Patent Application Ser. 60/832,735, now Published International Application No. WO 2008/011598.

Gasification

In addition to using pyrolysis for pre-treatment of feedstock, pyrolysis can also be used to process pre-treated feedstock to extract useful materials. In particular, a form of pyrolysis known as gasification can be employed to generate fuel gases along with various other gaseous, liquid, and solid products. To perform gasification, the pre-treated feedstock is introduced into a pyrolysis chamber and heated to a high temperature, typically 700° C. or more. The temperature used depends upon a number of factors, including the nature of the feedstock and the desired products.

Quantities of oxygen (e.g., as pure oxygen gas and/or as air) and steam (e.g., superheated steam) are also added to the pyrolysis chamber to facilitate gasification. These compounds react with carbon-containing feedstock material in a multiple-step reaction to generate a gas mixture called synthesis gas (or "syngas"). Essentially, during gasification, a limited amount of oxygen is introduced into the pyrolysis chamber to allow some feedstock material to combust to form carbon monoxide and generate process heat. The process heat can then be used to promote a second reaction that converts additional feedstock material to hydrogen and carbon monoxide.

In a first step of the overall reaction, heating the feedstock material produces a char that can include a wide variety of different hydrocarbon-based species. Certain volatile materials can be produced (e.g., certain gaseous hydrocarbon materials), resulting in a reduction of the overall weight of the feedstock material. Then, in a second step of the reaction, some of the volatile material that is produced in the first step reacts with oxygen in a combustion reaction to produce both carbon monoxide and carbon dioxide. The combustion reaction releases heat, which promotes the third step of the reaction. In the third step, carbon dioxide and steam (e.g., water) react with the char generated in the first step to form carbon monoxide and hydrogen gas. Carbon monoxide can also react with steam, in a water gas shift reaction, to form carbon dioxide and further hydrogen gas.

Gasification can be used as a primary process to generate products directly from pre-treated feedstock for subsequent transport and/or sale, for example. Alternatively, or in addition, gasification can be used as an auxiliary process for generating fuel for an overall processing system. The hydrogen-rich syngas that is generated via the gasification process can be burned, for example, to generate electricity and/or process heat that can be directed for use at other locations in the processing system. As a result, the overall processing system can be at least partially self-sustaining. A number of other products, including pyrolysis oils and gaseous hydrocarbon-based substances, can also be obtained during and/or following gasification; these can be separated and stored or transported as desired.

A variety of different pyrolysis chambers are suitable for gasification of pre-treated feedstock, including the pyrolysis chambers disclosed herein. In particular, fluidized bed reactor systems, in which the pre-treated feedstock is fluidized in steam and oxygen/air, provide relatively high throughput and straightforward recovery of products. Solid char that remains following gasification in a fluidized bed system (or in other pyrolysis chambers) can be burned to generate additional process heat to promote subsequent gasification reactions.

Post-Processing

Distillation

After fermentation, the resulting fluids can be distilled using, for example, a "beer column" to separate ethanol and other alcohols from the majority of water and residual solids. The vapor exiting the beer column can be 35% by weight ethanol and fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Waste Water Treatment

Wastewater treatment is used to minimize makeup water requirements of the plant by treating process water for reuse within the plant. Wastewater treatment can also produce fuel (e.g., sludge and biogas) that can be used to improve the overall efficiency of the ethanol production process. For example, as described in further detail below, sludge and biogas can be used to create steam and electricity that can be used in various plant processes.

Wastewater is initially pumped through a screen (e.g., a bar screen) to remove large particles, which are collected in a hopper. In some embodiments, the large particles are sent to a landfill. Additionally or alternatively, the large particles are burned to create steam and/or electricity as described in further detail below. In general, the spacing on the bar screen is between ¼ inch to 1 inch spacing (e.g., ½ inch spacing).

The wastewater then flows to an equalization tank, where the organic concentration of the wastewater is equalized during a retention time. In general, the retention time is between 8 hours and 36 hours (e.g., 24 hours). A mixer is disposed within the tank to stir the contents of the tank. In some embodiments, a plurality of mixers disposed throughout the tank are used to stir the contents of the tank. In certain embodiments, the mixer substantially mixes the contents of the equalization tank such that conditions (e.g., wastewater concentration and temperature) throughout the tank are uniform.

A first pump moves water from the equalization tank through a liquid-to-liquid heat exchanger. The heat exchanger is controlled (e.g., by controlling the flow rate of fluid through the heat exchanger) such that wastewater exiting the heat exchanger is at a desired temperature for anaerobic treatment. For example, the desired temperature for anaerobic treatment can be between 40° C. to 60° C.

After exiting the heat exchanger, the wastewater enters one or more anaerobic reactors. In some embodiments, the concentration of sludge in each anaerobic reactor is the same as the overall concentration of sludge in the wastewater. In other embodiments, the anaerobic reactor has a higher concentration of sludge than the overall concentration of sludge in the wastewater.

A nutrient solution containing nitrogen and phosphorus is metered into each anaerobic reactor containing wastewater. The nutrient solution reacts with the sludge in the anaerobic reactor to produce biogas which can contain 50% methane and have a heating value of approximately 12,000 British thermal units, or Btu, per pound). The biogas exits each anaerobic reactor through a vent and flows into a manifold, where a plurality of biogas streams are combined into a single stream. A compressor moves the stream of biogas to a boiler or a combustion engine as described in further detail below. In some embodiments, the compressor also moves the single stream of biogas through a desulphurization catalyst. Additionally or alternatively, the compressor can move the single stream of biogas through a sediment trap.

A second pump moves anaerobic effluent from the anaerobic reactors to one or more aerobic reactors (e.g., activated sludge reactors). An aerator is disposed within each aerobic reactor to mix the anaerobic effluent, sludge, and oxygen (e.g., oxygen contained in air). Within each aerobic reactor, oxidation of cellular material in the anaerobic effluent produces carbon dioxide, water, and ammonia.

Aerobic effluent moves (e.g., via gravity) to a separator, where sludge is separated from treated water. Some of the sludge is returned to the one or more aerobic reactors to create an elevated sludge concentration in the aerobic reactors, thereby facilitating the aerobic breakdown of cellular material in the wastewater. A conveyor removes excess sludge from the separator. As described in further detail below, the excess sludge is used as fuel to create steam and/or electricity.

The treated water is pumped from the separator to a settling tank. Solids dispersed throughout the treated water settle to the bottom of the settling tank and are subsequently removed. After a settling period, treated water is pumped from the settling tank through a fine filter to remove any additional solids remaining in the water. In some embodiments, chlorine is added to the treated water to kill pathogenic bacteria. In some embodiments, one or more physical-chemical separation techniques are used to further purify the treated water. For example, treated water can be pumped through a carbon adsorption reactor. As another example, treated water can pumped through a reverse osmosis reactor.

Waste Combustion

The production of alcohol from biomass can result in the production of various by-product streams useful for generating steam and electricity to be used in other parts of the plant. For example, steam generated from burning by-product streams can be used in the distillation process. As another example, electricity generated from burning by-product streams can be used to power electron beam generators and ultrasonic transducers used in pretreatment.

The by-products used to generate steam and electricity are derived from a number of sources throughout the process. For example, anaerobic digestion of wastewater produces a biogas high in methane and a small amount of waste biomass (sludge). As another example, post-distillate solids (e.g., unconverted lignin, cellulose, and hemicellulose remaining from the pretreatment and primary processes) can be used as a fuel.

The biogas is diverted to a combustion engine connected to an electric generator to produce electricity. For example, the biogas can be used as a fuel source for a spark-ignited natural gas engine. As another example, the biogas can be used as a fuel source for a direct-injection natural gas engine. As another example, the biogas can be used as a fuel source for a combustion turbine. Additionally or alternatively, the combustion engine can be configured in a cogeneration configuration. For example, waste heat from the combustion engines can be used to provide hot water or steam throughout the plant.

The sludge, and post-distillate solids are burned to heat water flowing through a heat exchanger. In some embodiments, the water flowing through the heat exchanger is evaporated and superheated to steam. In certain embodiments, the steam is used in the pretreatment rector and in heat exchange in the distillation and evaporation processes. Additionally or alternatively, the steam expands to power a multi-stage steam turbine connected to an electric generator. Steam exiting the steam turbine is condensed with cooling water and returned to the heat exchanger for reheating to steam. In some embodiments, the flow rate of water through the heat exchanger is controlled to obtain a target electricity output from the steam turbine connected to an electric generator. For example, water can be added to the heat exchanger to ensure that the steam turbine is operating above a threshold condition (e.g., the turbine is spinning fast enough to turn the electric generator).

While certain embodiments have been described, other embodiments are possible.

As an example, while the biogas is described as being diverted to a combustion engine connected to an electric generator, in certain embodiments, the biogas can be passed through a fuel reformer to produce hydrogen. The hydrogen is then converted to electricity through a fuel cell.

As another example, while the biogas is described as being burned apart from the sludge and post-distillate solids, in certain embodiments, all of the waste by-products can be burned together to produce steam.

Products/Co-Products

Alcohols

The alcohol produced can be a monohydroxy alcohol, e.g., ethanol, or a polyhydroxy alcohol, e.g., ethylene glycol or glycerin. Examples of alcohols that can be produced include methanol, ethanol, propanol, isopropanol, butanol, e.g., n-, sec- or t-butanol, ethylene glycol, propylene glycol, 1, 4-butane diol, glycerin or mixtures of these alcohols.

Each of the alcohols produced by the plant have commercial value as industrial feedstock. For example, ethanol can be used in the manufacture of varnishes and perfume. As another example, methanol can be used as a solvent used as a component in windshield wiper fluid. As still another example, butanol can be used in plasticizers, resins, lacquers, and brake fluids.

Bioethanol produced by the plant is valuable as an ingredient used in the food and beverage industry. For example, the ethanol produced by the plant can be purified to food grade alcohol and used as a primary ingredient in the alcoholic beverages.

Bioethanol produced by the plant also has commercial value as a transportation fuel. The use of ethanol as a transportation fuel can be implemented with relatively little capital investment from spark ignition engine manufacturers and owners (e.g., changes to injection timing, fuel-to-air ratio, and components of the fuel injection system). Many automotive manufacturers currently offer flex-fuel vehicles capable of operation on ethanol/gasoline blends up to 85% ethanol by volume (e.g., standard equipment on a Chevy Tahoe 4×4).

Fuels and other products (e.g., ethanol, bioethanol, other alcohols, and other combustible hydrocarbons) produced via the methods disclosed herein can be blended with other hydrocarbon-containing species. For example, ethanol produced using any of the methods disclosed herein can be blended with gasoline to produce "gasohol," which can be used as combustible fuel in a wide variety of applications, including automobile engines.

Bioethanol produced by this plant can be used as an engine fuel to improve environmental and economic conditions beyond the location of the plant. For example, ethanol produced by this plant and used as a fuel can reduce greenhouse gas emissions from manmade sources (e.g., transportation sources). As another example, ethanol produced by this plant and used as an engine fuel can also displace consumption of gasoline refined from oil.

Bioethanol has a greater octane number than conventional gasoline and, thus, can be used to improve the performance (e.g., allow for higher compression ratios) of spark ignition engines. For example, small amounts (e.g., 10% by volume) of ethanol can be blended with gasoline to act as an octane enhancer for fuels used in spark ignition engines. As another example, larger amounts (e.g., 85% by volume) of ethanol can be blended with gasoline to further increase the fuel octane number and displace larger volumes of gasoline.

Bioethanol strategies are discussed, e.g., by DiPardo in *Journal of Outlook for Biomass Ethanol Production and Demand (EIA Forecasts)*, 2002; Sheehan in *Biotechnology Progress*, 15:8179, 1999; Martin in *Enzyme Microbes Technology*, 31:274, 2002; Greer in *BioCycle*, 61-65, April 2005; Lynd in *Microbiology and Molecular Biology Reviews*, 66:3, 506-577, 2002; Ljungdahl et al. in U.S. Pat. No. 4,292,406; and Bellamy in U.S. Pat. No. 4,094,742.

Organic Acids

The organic acids produced can include monocarboxylic acids or a polycarboxylic acids. Examples of organic acids include formic acid, acetic acid, propionic acid, butyric acid, valeric acid, caproic, palmitic acid, stearic acid, oxalic acid, malonic acid, succinic acid, glutaric acid, oleic acid, linoleic acid, glycolic acid, lactic acid, γ-hydroxybutyric acid or mixtures of these acids.

Food Products

In some embodiments, all or a portion of the fermentation process can be interrupted before the cellulosic material is completely converted to ethanol. The intermediate fermentation products include high concentrations of sugar and carbohydrates. These intermediate fermentation products can be used in preparation of food for human or animal consumption or for use in agriculture or aquaculture. In some embodiments, irradiation pretreatment of the cellulosic material will render the intermediate fermentation products sterile (e.g., fit for human consumption or for use in agriculture or aquaculture). In some embodiments, the intermediate fermentation products will require post-processing prior to use as food. For example, a dryer can be used to remove moisture from the intermediate fermentation products to facilitate storage, handling, and shelf-life. Additionally or alternatively, the intermediate fermentation products can be ground to a fine particle size in a stainless-steel laboratory mill to produce a flour-like substance.

Animal Feed

Distillers grains and solubles can be converted into a valuable byproduct of the distillation-dehydration process. After the distillation-dehydration process, distillers grains and solubles can be dried to improve the ability to store and handle the material. The resulting dried distillers grains and solubles (DDGS) is low in starch, high in fat, high in protein, high in fiber, and high in phosphorous. Thus, for example, DDGS can be valuable as a source of animal feed (e.g., as a feed source for dairy cattle). DDGS can be subsequently combined with nutritional additives to meet specific dietary requirements of specific categories of animals (e.g., balancing digestible lysine and phosphorus for swine diets).

Pharmaceuticals

The pretreatment processes discussed above can be applied to plants with medicinal properties. In some embodiments, sonication can stimulate bioactivity and/or bioavailabilty of the medicinal components of plants with medicinal properties. Additionally or alternatively, irradiation stimulates bioactivity and/or bioavailabilty of the medicinal components of plants with medicinal properties. For example, sonication and irradiation can be combined in the pretreatment of willow bark to stimulate the production of salicin.

Nutriceuticals

In some embodiments, intermediate fermentation products (e.g., products that include high concentrations of sugar and carbohydrates) can be supplemented to create a nutriceutical. For example, intermediate fermentation products can be supplemented with calcium to create a nutriceutical that provides energy and helps improve or maintain bone strength.

Co-Products

Lignin Residue

As described above, lignin-containing residues from primary and pretreatment processes has value as a high/medium energy fuel and can be used to generate power and steam for use in plant processes. However, such lignin residues are a new type of solids fuel and there is little demand for it outside of the plant boundaries, and the costs of drying it for transportation only subtract from its potential value. In some cases, gasification of the lignin residues can convert the residues to a higher-value product with lower cost.

Other Co-Products

Cell matter, furfural, and acetic acid have been identified as potential co-products of biomass-to-fuel processing facilities. Interstitial cell matter could be valuable, but might require significant purification. Markets for furfural and acetic acid are in place, although it is unlikely that they are large enough to consume the output of a fully commercialized lignocellulose-to-ethanol industry.

Conversion of Starchy Materials

FIGS. 26 and 27 show block diagrams for a dry and wet milling process, respectively, and illustrate the conversion, e.g., fermentation, of corn kernels to ethanol and other valuable co-products.

Referring particularly now to FIG. 26, in some implementations, a dry milling process for the conversion of corn kernels to ethanol, e.g., anhydrous ethanol, that can be utilized as a fuel, e.g., automobile or aviation fuel, can begin with pretreating the dried corn kernels with any one or more pretreatments described herein, such as radiation, e.g., any one or more types of radiation described herein (e.g., a beam of electrons in which each electron has an energy of about 5 MeV or a beam of protons in which the energy of each proton is about 3-100 MeV). After pre-treatment, the corn kernels can be ground and/or sheared into a powder. Although any one or more pretreatments described herein can be applied after grinding and/or at any time during the dry milling process outlined in FIG. 26, pretreating prior to grinding and/or shearing can be advantageous in that the kernels are generally more brittle after pretreatment and, as a result, are easier and can require less energy to grind and/or shear. In some embodiments, a selected pretreatment can be applied more than once during conversion, e.g., prior to milling and then after milling.

After grinding and/or shearing, the milled, dry kernels can be optionally hydrated by adding the milled material to a vessel containing water and, optionally, hydrating agents, such as surfactants. Optionally, this reaction vessel can also include one or more enzymes, such as amylase, to aid in further breakdown of starchy biomass, or the reaction vessel may contain one or more acids, such as a mineral acid, e.g., dilute sulfuric acid. If a hydration vessel is utilized, its contents are emptied into a conversion vessel, e.g., a fermentation vessel, that includes one or more conversion microbes, such as one or more yeasts, bacteria or mixtures of yeasts and/or bacteria. If a hydration vessel is not utilized, the milled material can be directly charged to the conversion vessel, e.g., for fermentation.

After conversion, the remaining solids are removed and dried to give distillers dry grains (DDG), while the ethanol is distilled off. In some embodiments, a thermophilic microbe is utilized for the conversion and the ethanol is continuously removed by evaporation as it is produced. If desired, the distilled ethanol can be fully dehydrated, such as by passing the wet ethanol through a zeolite bed, or distilling with benzene.

Referring particularly now to FIG. 27, in some implementations, the wet milling process for the conversion of corn kernels to anhydrous ethanol begins with pretreating the dried corn kernels with any one or more pretreatments described herein, such as radiation, e.g., any one or more types of radiation described herein (e.g., a beam of electrons in which each electron has an energy of about 5 MeV). After pre-treatment, the corn kernels are steeped in dilute sulfuric acid and gently stirred to break the corn kernels into its constituents. After steeping, the fiber, oil and germ portions are fractionated and dried, and then combined with any solids remaining after distillation to give corn gluten feed (CGF). After removing germ and fiber, in some embodiments, the gluten is separated to give corn gluten meal (CGM). The remaining starch can be pretreated again (or for the first time) by any pretreatment described herein, e.g., to reduce its molecular weight and/or to functionalize the starch so that it is more soluble. In some embodiments, the starch is then charged to a reaction vessel containing water and, optionally, hydrating agents, such as surfactants. Optionally, this reaction vessel can also include one or more enzymes, such as amylase, to aid in further breakdown of starch, or the reaction vessel may contain one or more acids, such as a mineral acid, e.g., dilute sulfuric acid. As shown, saccharification can occur in several vessels and then the contents of the final vessel can be emptied into a conversion vessel, e.g., a fermentation vessel, that includes one or more conversion microbes, such as one or more yeasts or bacteria.

After conversion, the ethanol is distilled off. In some embodiments, a thermophilic microbe is utilized for the conversion and the ethanol is continuously removed by evaporation as it is produced. If desired, the distilled ethanol can be fully dehydrated, such as by passing the wet ethanol through a zeolite bed.

EXAMPLES

The following Examples are intended to illustrate, and do not limit the teachings of this disclosure.

Example 1

Preparation of Fibrous Material from Polycoated Paper

A 1500 pound skid of virgin, half-gallon juice cartons made of un-printed polycoated white Kraft board having a bulk density of 20 lb/ft$^3$ was obtained from International Paper. Each carton was folded flat, and then fed into a 3 hp Flinch Baugh shredder at a rate of approximately 15 to 20 pounds per hour. The shredder was equipped with two 12 inch rotary blades, two fixed blades and a 0.30 inch dis-charge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch).

The confetti-like material was fed to a Munson rotary knife cutter, Model SC30. Model SC30 is equipped with four rotary blades, four fixed blades, and a discharge screen having ⅛ inch openings. The gap between the rotary and fixed blades was set to approximately 0.020 inch. The rotary knife cutter sheared the confetti-like pieces across the knife-edges, tearing the pieces apart and releasing a fibrous material at a rate of about one pound per hour. The fibrous material had a BET surface area of 0.9748 m$^2$/g+/−0.0167 m$^2$/g, a porosity of 89.0437 percent and a bulk density (@0.53 psia) of 0.1260 g/mL. An average length of the fibers was 1.141 mm and an average width of the fibers was 0.027 mm, giving an average L/D of 42:1. A scanning electron micrograph of the fibrous material is shown in FIG. 26 at 25× magnification.

Example 2

Preparation of Fibrous Material from Bleached Kraft Board

Figure 29:
FIG. 29 is a scanning electron micrograph of a fibrous material produced from bleached Kraft board paper at 25× magnification. The fibrous material was produced on a rotary knife cutter utilizing a screen with ⅛ inch openings.

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch). The confetti-like material was fed to a Munson rotary knife cutter, Model SC30. The discharge screen had ⅛ inch openings. The gap between the rotary and fixed blades was set to approximately 0.020 inch. The rotary knife cutter sheared the confetti-like pieces, releasing a fibrous material at a rate of about one pound per hour. The fibrous material had a BET surface area of 1.1316 m$^2$/g+/− 0.0103 m$^2$/g, a porosity of 88.3285 percent and a bulk density (@0.53 psia) of 0.1497 g/mL. An average length of the fibers was 1.063 mm and an average width of the fibers was 0.0245 mm, giving an average L/D of 43:1. A scanning electron micrographs of the fibrous material is shown in FIG. 29 at 25× magnification.

Example 3

Preparation of Twice Sheared Fibrous Material from Bleached Kraft Board

Figure 30:
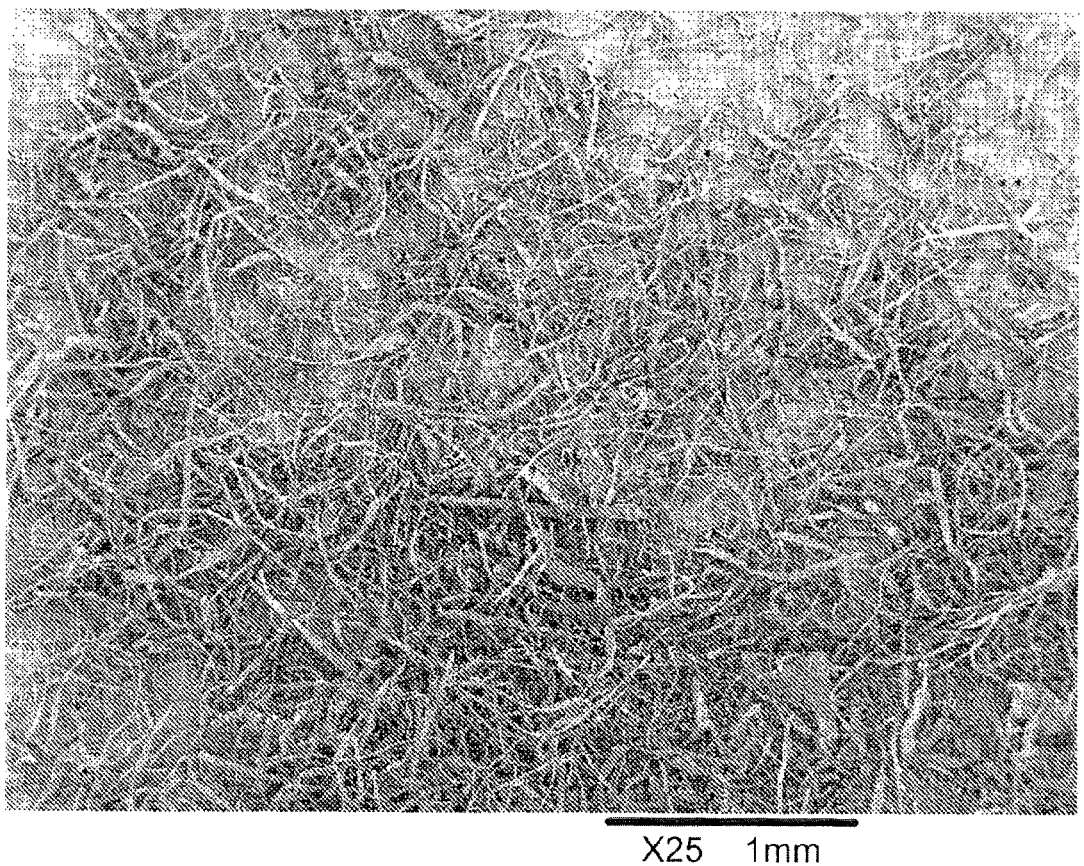
FIG. 30 is a scanning electron micrograph of a fibrous material produced from bleached Kraft board paper at 25× magnification. The fibrous material was twice sheared on a rotary knife cutter utilizing a screen with 1/16 inch openings during each shearing.

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had 1/16 inch openings. The gap between the rotary and fixed blades was set to approximately 0.020 inch. The rotary knife cutter the confetti-like pieces, releasing a fibrous material at a rate of about one pound per hour. The material resulting from the first shearing was fed back into the same setup described above and sheared again. The resulting fibrous material had a BET surface area of 1.4408 m$^2$/g+/−0.0156 m$^2$/g, a porosity of 90.8998 percent and a bulk density (@0.53 psia) of 0.1298 g/mL. An average length of the fibers was 0.891 mm and an average width of the fibers was 0.026 mm, giving an average L/D of 34:1. A scanning electron micrograph of the fibrous material is shown in FIG. 30 at 25× magnification.

Example 4

Preparation of Thrice Sheared Fibrous Material from Bleached Kraft Board

Figure 31:
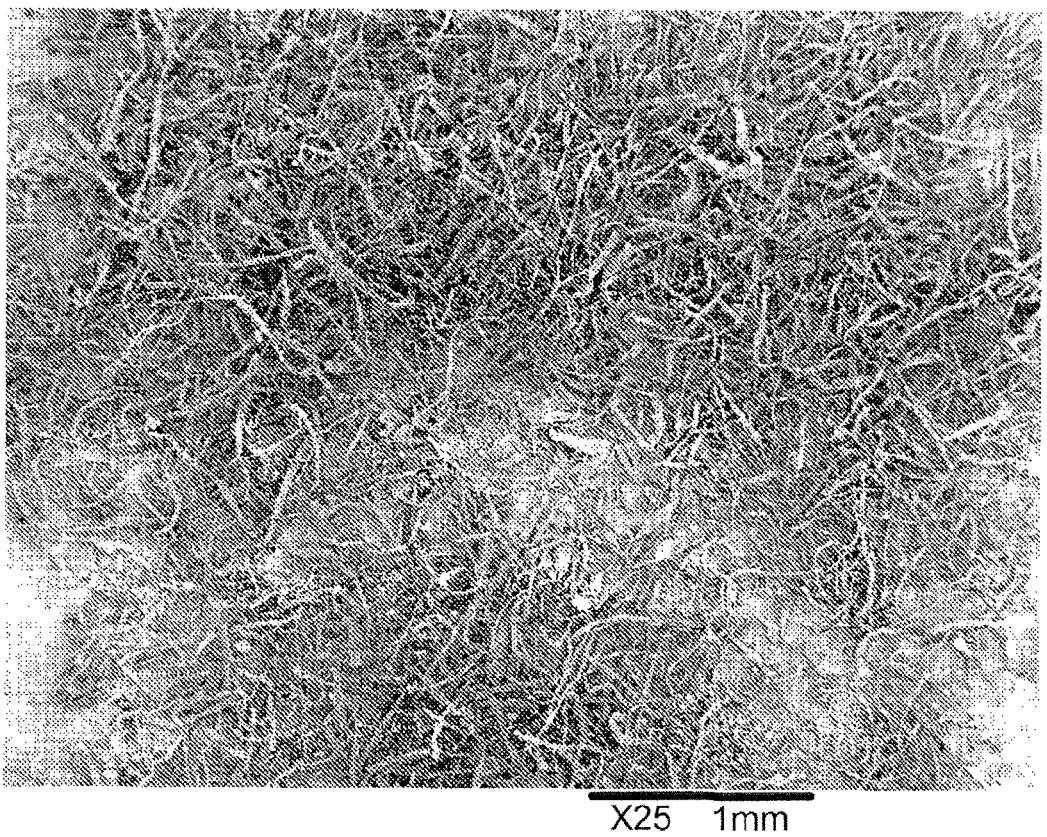
FIG. 31 is a scanning electron micrograph of a fibrous material produced from bleached Kraft board paper at 25× magnification. The fibrous material was thrice sheared on a rotary knife cutter. During the first shearing, a ⅛ inch screen was used; during the second shearing, a 1/16 inch screen was used, and during the third shearing a 1/32 inch screen was used.
Figure 31A:
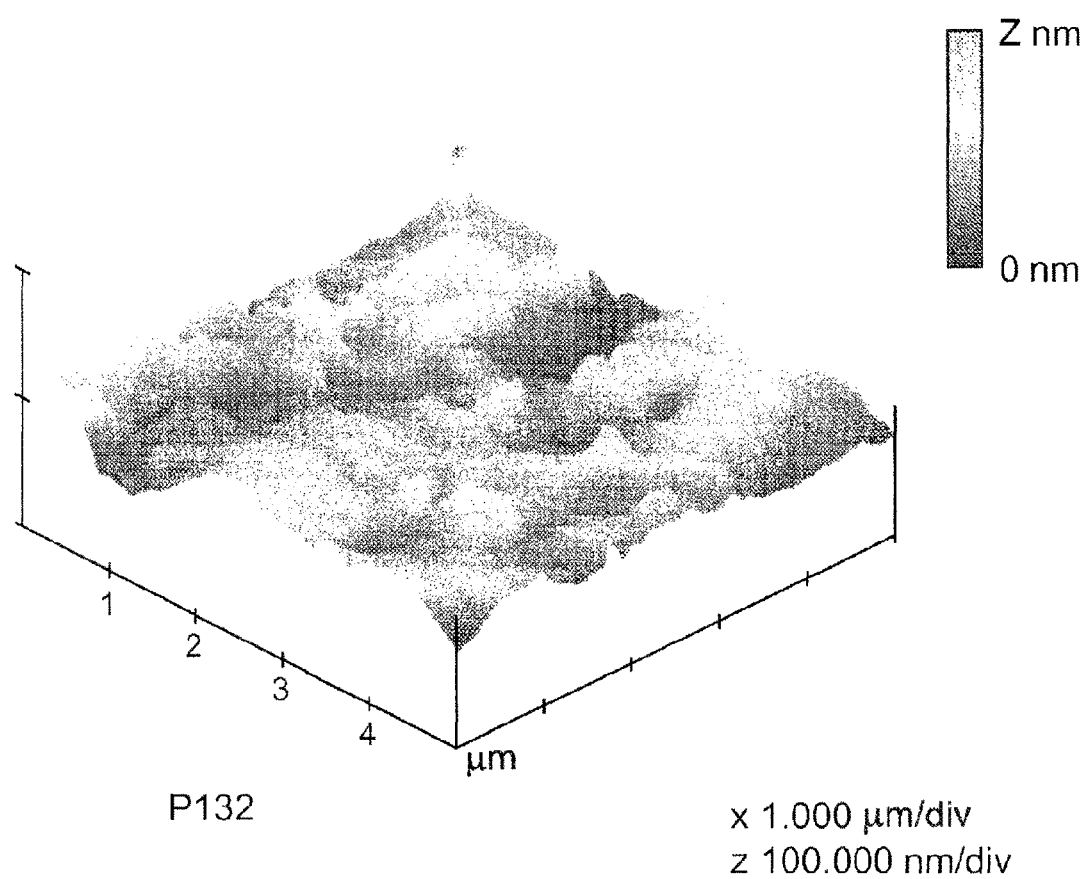
FIGS. 31A-31F are 3D AFM micrographs from the surface of fibers from samples P132, P132-10, P132-100, P-1e, P-30e, and P-100e, respectively.
Figure 31B:
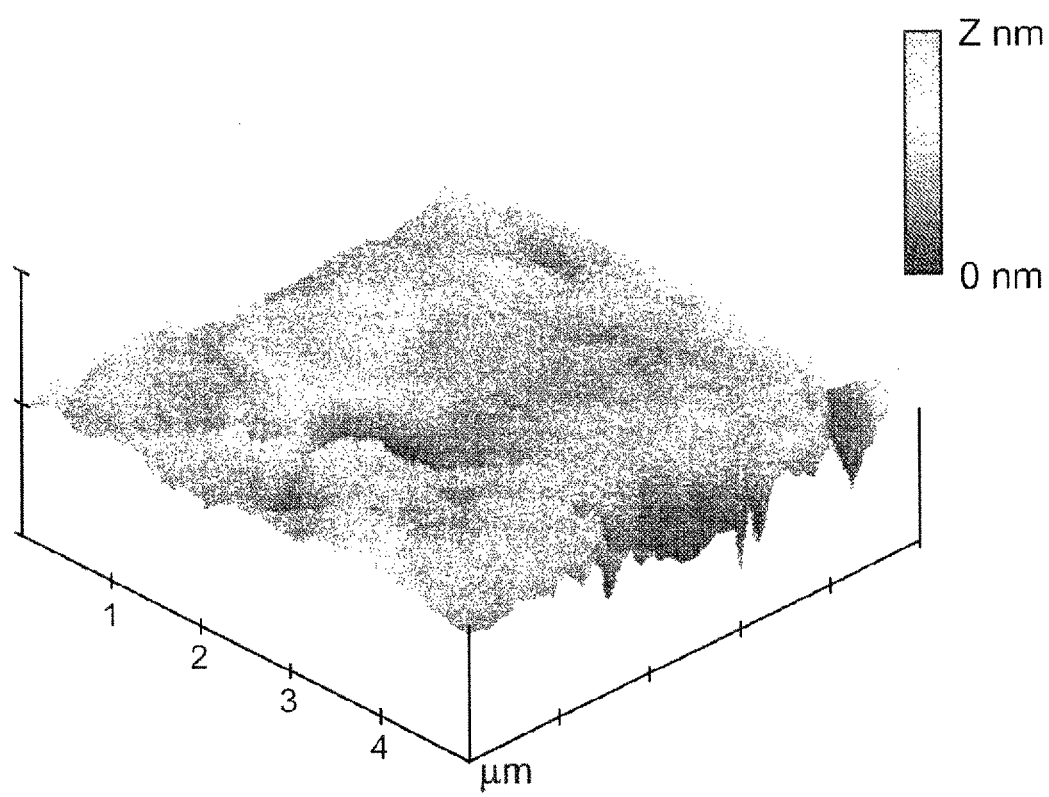
Figure 31C:
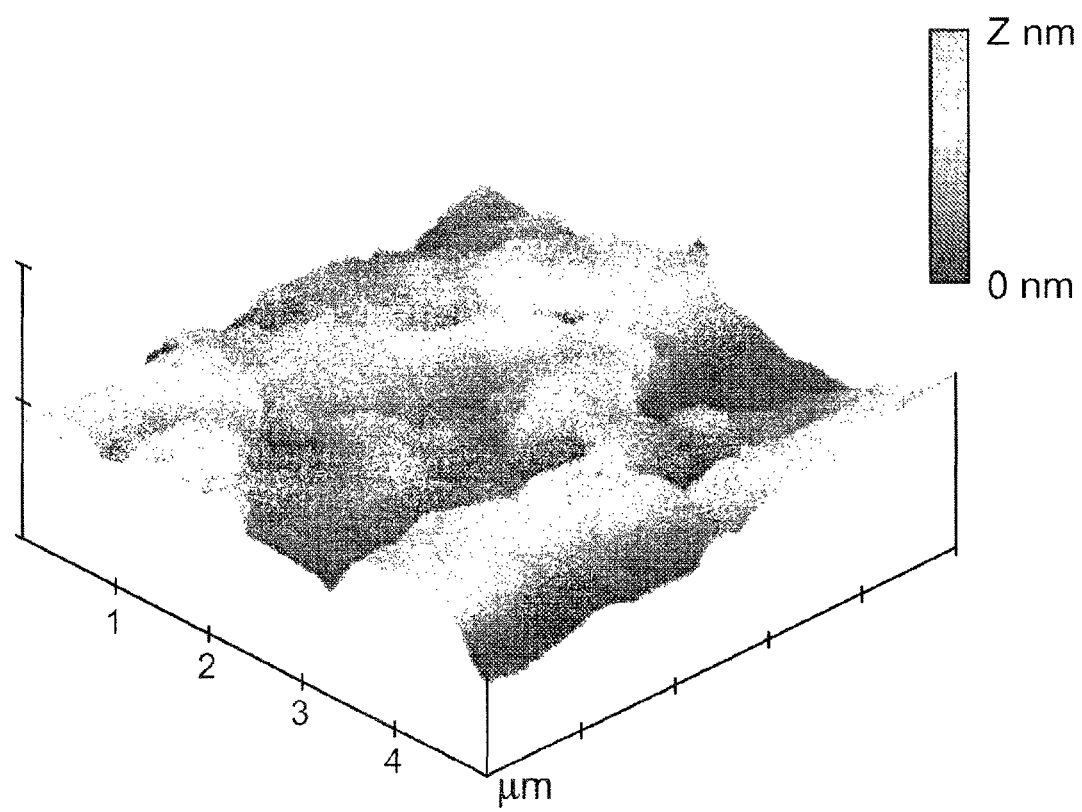
Figure 31D:
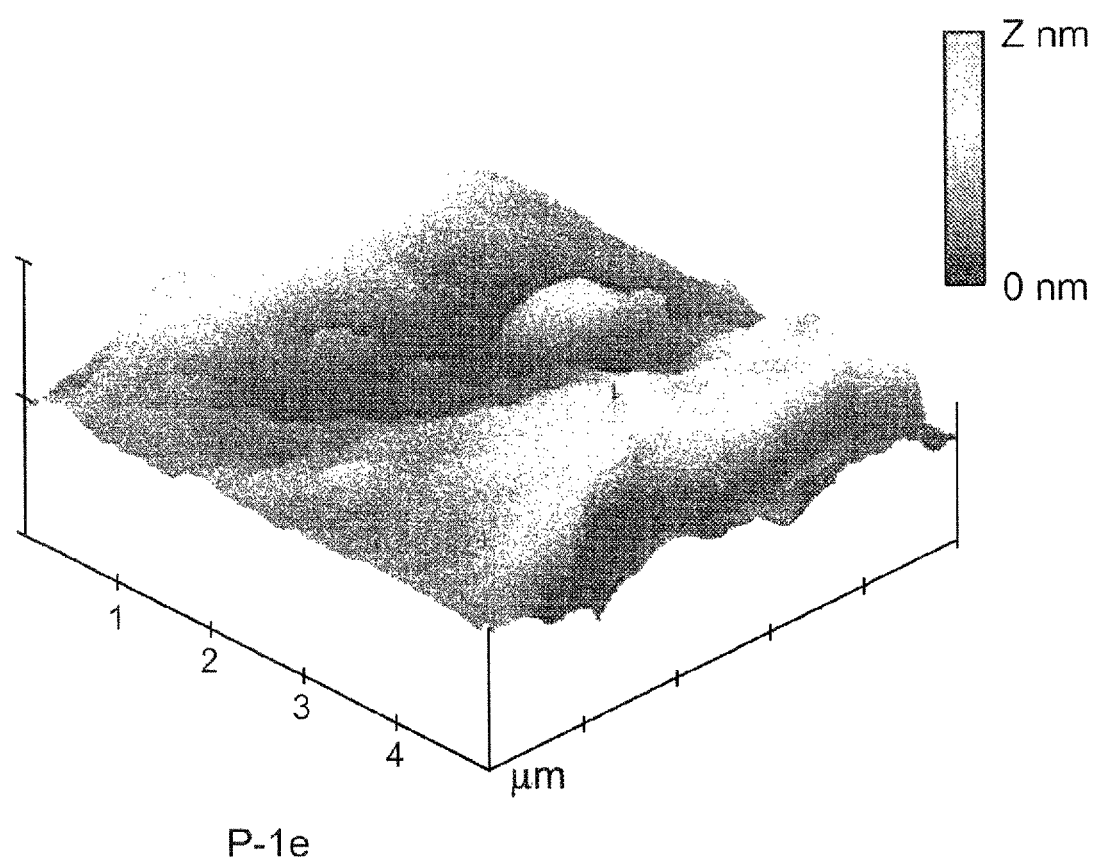
Figure 31E:
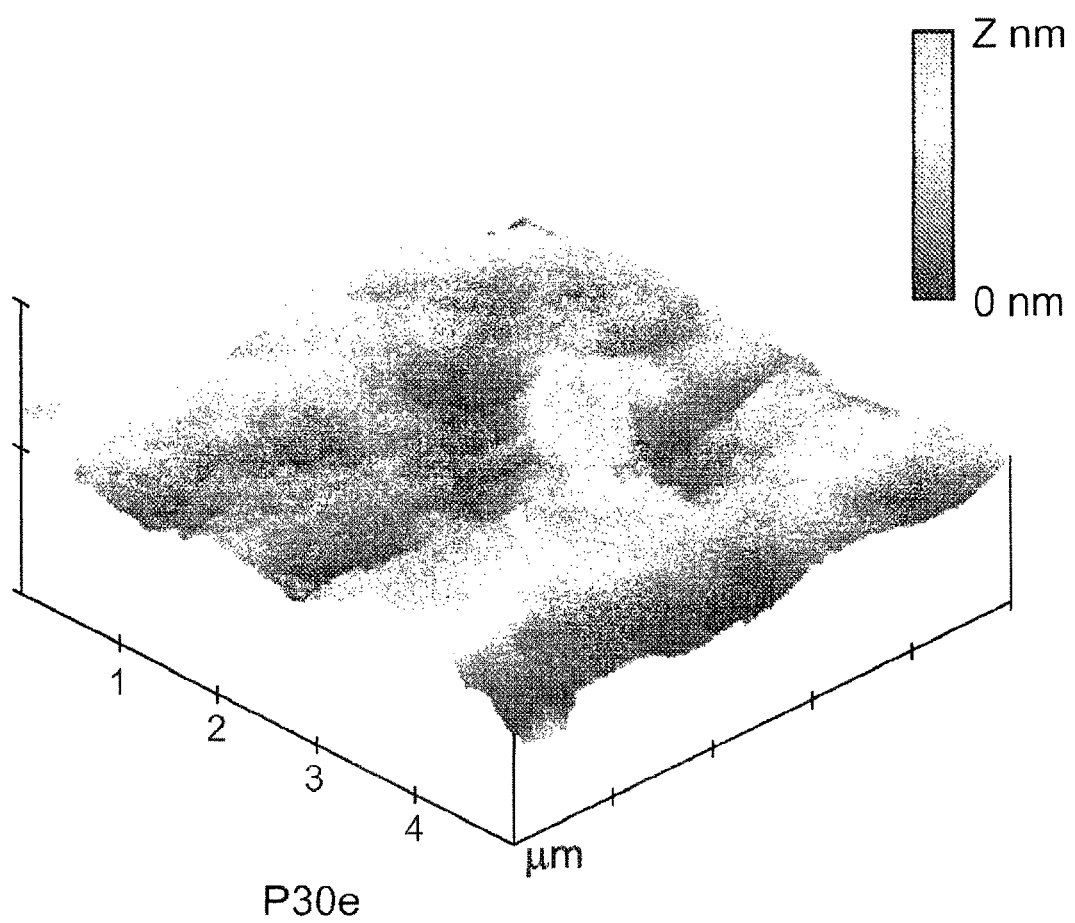
Figure 31F:
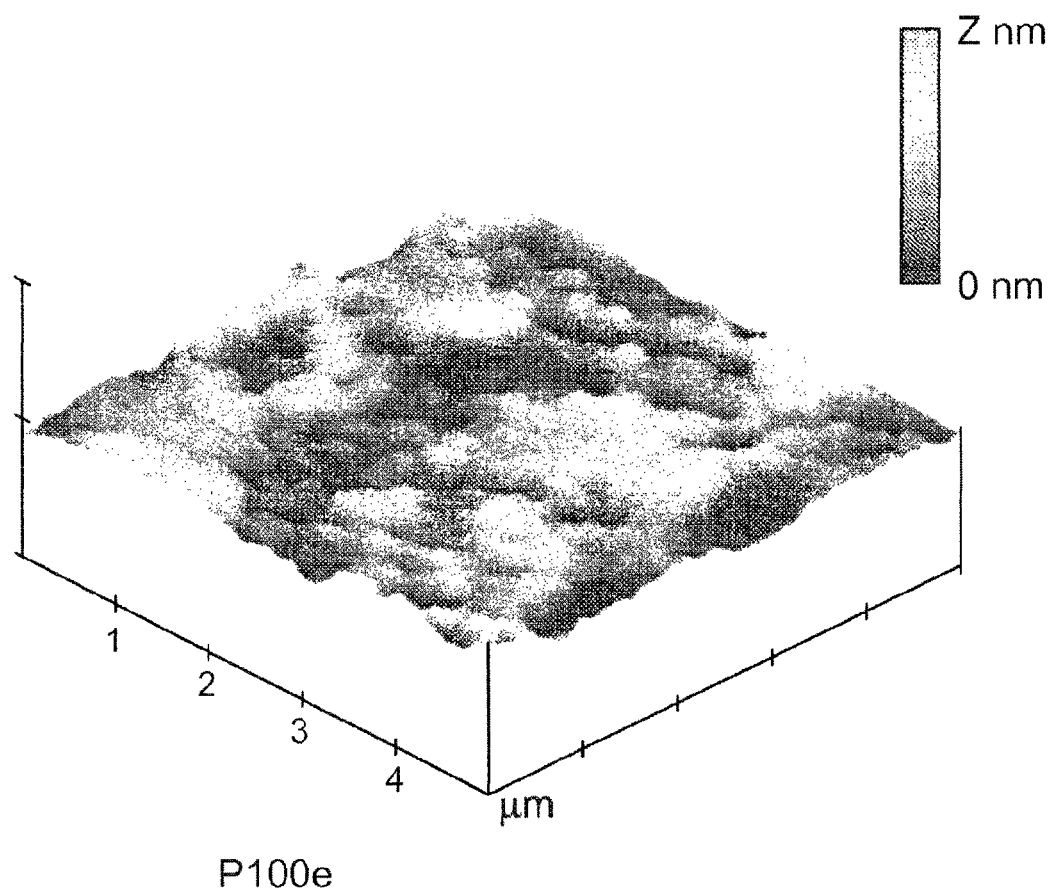

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had ⅛ inch openings. The gap between the rotary and fixed blades was set to approximately 0.020 inch. The rotary knife cutter sheared the confetti-like pieces across the knife-edges. The material resulting from the first shearing was fed back into the same setup and the screen was replaced with a 1/16 inch screen. This material was sheared. The material resulting from the second shearing was fed back into the same setup and the screen was replaced with a 1/32 inch screen. This material was sheared. The resulting fibrous material had a BET surface area of 1.6897 m$^2$/g+/−0.0155 m$^2$/g, a porosity of 87.7163 percent and a bulk density (@0.53 psia) of 0.1448 g/mL. An average length of the fibers was 0.824 mm and an average width of the fibers was 0.0262 mm, giving an average L/D of 32:1. A scanning electron micrograph of the fibrous material is shown in FIG. 31 at 25× magnification.

Example 5

Preparation of Densified Fibrous Material from Bleached Kraft Board without Added Binder Fibrous material was prepared according to Example 2. Approximately 1 lb of water was sprayed onto each 10 lb of fibrous material. The fibrous material was densified using a California Pellet Mill 1100 operating at 75° C. Pellets were obtained having a bulk density ranging from about 7 lb/ft$^3$ to about 15 lb/ft$^3$.

Example 6

Preparation of Densified Fibrous Material from Bleached Kraft Board with Binder

Fibrous material was prepared according to Example 2. A 2 weight percent stock solution of POLYOX™ WSR N10 (polyethylene oxide) was prepared in water.

Approximately 1 lb of the stock solution was sprayed onto each 10 lb of fibrous material. The fibrous material was densified using a California Pellet Mill 1100 operating at 75° C. Pellets were obtained having a bulk density ranging from about 15 lb/ft$^3$ to about 40 lb/ft$^3$.

Example 7

Reducing the Molecular Weight of Cellulose in Fibrous Kraft Paper by Gamma Radiation with Minimum Oxidation Fibrous material is prepared according to Example 4. The fibrous Kraft paper is densified according to Example 5.

The densified pellets are placed in a glass ampoule having a maximum capacity of 250 mL. The glass ampoule is evacuated under high vacuum (10$^{-5}$ torr) for 30 minutes, and then back-filled with argon gas. The ampoule is sealed under argon. The pellets in the ampoule are irradiated with gamma radiation for about 3 hours at a dose rate of about 1 Mrad per hour to provide an irradiated material in which the cellulose has a lower molecular weight than the fibrous Kraft starting material.

Example 8

Reducing the Molecular Weight of Cellulose in Fibrous Kraft Paper by Gamma Radiation with Maximum Oxidation Fibrous material is prepared according to Example 4. The fibrous Kraft paper is densified according to Example 5.

The densified pellets are placed in a glass ampoule having a maximum capacity of 250 mL. The glass ampoule is sealed under an atmosphere of air. The pellets in the ampoule are irradiated with gamma radiation for about 3 hours at a dose rate of about 1 Mrad per hour to provide an irradiated material in which the cellulose has a lower molecular weight than the fibrous Kraft starting material.

Example 9

Electron Beam Processing

Samples were treated with electron beam using a vaulted Rhodotron® TT200 continuous wave accelerator delivering 5 MeV electrons at 80 kW of output power. Table 1 describes the parameters used. Table 2 reports the nominal dose used for the Sample ID (in MRad) and the corresponding dose delivered to the sample (in kgy).

TABLE 1

| Rhodotron ® TT 200 Parameters | |
|---|---|
| Beam | |
| Beam Produced: | Accelerated electrons |
| Beam energy: | Nominal (fixed): 10 MeV (+0 keV-250 keV) |
| Energy dispersion at 10 Mev: | Full width half maximum (FWHM) 300 keV |
| Beam power at 10 MeV: | Guaranteed Operating Range 1 to 80 kW |
| Power Consumption | |
| Stand-by condition (vacuum and cooling ON): | <15 kW |
| At 50 kW beam power: | <210 kW |
| At 80 kW beam power: | <260 kW |

TABLE 1-continued

Rhodotron ® TT 200 Parameters

RF System

| | |
|---|---|
| Frequency: | 107.5 ± 1 MHz |
| Tetrode type: | Thomson TH781 |

Scanning Horn

| | |
|---|---|
| Nominal Scanning Length (measured at 25-35 cm from window): | 120 cm |
| Scanning Range: | From 30% to 100% of Nominal Scanning Length |
| Nominal Scanning Frequency (at max. scanning length): | 100 Hz ± 5% |
| Scanning Uniformity (across 90% of Nominal Scanning Length) | ±5% |

TABLE 2

Dosages Delivered to Samples

| Total Dosage (MRad) (Number Associated with Sample ID | Delivered Dose (kgy)[1] |
|---|---|
| 1 | 9.9 |
| 3 | 29.0 |
| 5 | 50.4 |
| 7 | 69.2 |
| 10 | 100.0 |
| 15 | 150.3 |
| 20 | 198.3 |
| 30 | 330.9 |
| 50 | 529.0 |
| 70 | 695.9 |
| 100 | 993.6 |

[1]For example, 9.9 kgy was delivered in 11 seconds at a beam current of 5 mA and a line speed of 12.9 feet/minute. Cool time between treatments was around 2 minutes.

Example 10

Methods of Determining Molecular Weight of Cellulosic and Lignocellulosic Materials by Gel Permeation Chromatography Cellulosic and lignocellulosic materials for analysis were treated according to Example 4. Sample materials presented in the following tables include Kraft paper (P), wheat straw (WS), alfalfa (A), cellulose (C), switchgrass (SG), grasses (G), and starch (ST), and sucrose (S). The number "132" of the Sample ID refers to the particle size of the material after shearing through a 1/32 inch screen. The number after the dash refers to the dosage of radiation (MRad) and "US" refers to ultrasonic treatment. For example, a sample ID "PI32-10" refers to Kraft paper that has been sheared to a particle size of 132 mesh and has been irradiated with 10 MRad.

For samples that were irradiated with e-beam, the number following the dash refers to the amount of energy delivered to the sample. For example, a sample ID "P-100e" refers to Kraft paper that has been delivered a dose of energy of about 100 MRad or about 1000 kgy (Table 2).

TABLE 3

Peak Average Molecular Weight of Irradiated Kraft Paper

| Sample Source | Sample ID | Dosage[1] (MRad) | Ultrasound[2] | Average MW ± Std Dev. |
|---|---|---|---|---|
| Kraft Paper | P132 | 0 | No | 32853 ± 10006 |
| | P132-10 | 10 | " | 61398 ± 2468** |
| | P132-100 | 100 | " | 8444 ± 580 |
| | P132-181 | 181 | " | 6668 ± 77 |
| | P132-US | 0 | Yes | 3095 ± 1013 |

**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

TABLE 4

Peak Average Molecular Weight of Irradiated Kraft Paper with E-Beam

| Sample Source | Sample ID | Dosage (MRad) | Average MW ± Std Dev. |
|---|---|---|---|
| Kraft Paper | P-1e | 1 | 63489 ± 595 |
| | P-5e | 5 | 56587 ± 536 |
| | P-10e | 10 | 53610 ± 327 |
| | P-30e | 30 | 38231 ± 124 |
| | P-70e | 70 | 12011 ± 158 |
| | P-100e | 100 | 9770 ± 2 |

TABLE 5

Peak Average Molecular Weight of Gamma Irradiated Materials

| Sample ID | Peak # | Dosage[1] (MRad) | Ultrasound[2] | Average MW ± Std Dev. |
|---|---|---|---|---|
| WS132 | 1 | 0 | No | 1407411 ± 175191 |
| | 2 | " | " | 39145 ± 3425 |
| | 3 | " | " | 2886 ± 177 |
| WS132-10* | 1 | 10 | " | 26040 ± 3240 |
| WS132-100* | 1 | 100 | " | 23620 ± 453 |
| A132 | 1 | 0 | " | 1604886 ± 151701 |
| | 2 | " | " | 37525 ± 3751 |
| | 3 | " | " | 2853 ± 490 |
| A132-10* | 1 | 10 | " | 50853 ± 1665 |
| | 2 | " | " | 2461 ± 17 |
| A132-100* | 1 | 100 | " | 38291 ± 2235 |
| | 2 | " | " | 2487 ± 15 |
| SG132 | 1 | 0 | " | 1557360 ± 83693 |
| | 2 | " | " | 42594 ± 4414 |
| | 3 | " | " | 3268 ± 249 |
| SG132-10* | 1 | 10 | " | 60888 ± 9131 |
| SG132-100* | 1 | 100 | " | 22345 ± 3797 |
| SG132-10-US | 1 | 10 | Yes | 86086 ± 43518 |
| | 2 | " | " | 2247 ± 468 |
| SG132-100-US | 1 | 100 | " | 4696 ± 1465 |

*Peaks coalesce after treatment
**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

TABLE 6

Peak Average Molecular Weight of Irradiated Material with E-Beam

| Sample ID | Peak # | Dosage | Average MW ± STD DEV. |
|---|---|---|---|
| A-1e | 1 | 1 | 1004783 ± 97518 |
| | 2 | | 34499 ± 482 |
| | 3 | | 2235 ± 1 |
| A-5e | 1 | 5 | 38245 ± 346 |
| | 2 | | 2286 ± 35 |
| A-10e | 1 | 10 | 44326 ± 33 |
| | 2 | | 2333 ± 18 |

TABLE 6-continued

Peak Average Molecular Weight of Irradiated Material with E-Beam

| Sample ID | Peak # | Dosage | Average MW ± STD DEV. |
|---|---|---|---|
| A-30e | 1 | 30 | 47366 ± 583 |
|  | 2 |  | 2377 ± 7 |
| A-50e | 1 | 50 | 32761 ± 168 |
|  | 2 |  | 2435 ± 6 |
| G-1e | 1 | 1 | 447362 ± 38817 |
|  | 2 |  | 32165 ± 779 |
|  | 3 |  | 3004 ± 25 |
| G-5e | 1 | 5 | 62167 ± 6418 |
|  | 2 |  | 2444 ± 33 |
| G-10e | 1 | 10 | 72636 ± 4075 |
|  | 2 |  | 3065 ± 34 |
| G-30e | 1 | 30 | 17159 ± 390 |
| G-50e | 1 | 50 | 18960 ± 142 |
| ST | 1 | 0 | 923336 ± 1883 |
|  | 2 |  | 150265 ± 4033 |
| ST-1e | 1 | 1 | 846081 ± 5180 |
|  | 2 |  | 131222 ± 1687 |
| ST-5e | 1 | 5 | 90664 ± 1370 |
| ST-10e | 1 | 10 | 98050 ± 255 |
| ST-30e | 1 | 30 | 41884 ± 223 |
| ST-70e | 1 | 70 | 9699 ± 31 |
| ST-100e | 1 | 100 | 8705 ± 38 |

Peak average molecular weights were measured for samples treated with either sodium bicarbonate (SBC) or tetrabutylammonium fluoride hydrate (TBAF). None of the samples reported in Table 6C showed any hydrolysis (a drop in average molecular weight.

TABLE 6C

Peak Average Molecular Weights (Mp) of Treated Samples

| Sample ID | Peak # | No-treatment | SBC treated | TBAF treated |
|---|---|---|---|---|
| A-10e | 1 | 53618 ± 484 | 53271 ± 503 | 52995 ± 832 |
|  | 2 | 2342 ± 4 | 2342 ± 1 | 2342 ± 12 |
| A-50e | 1 | 33011 ± 120 | 34469 ± 53 | 34830 ± 49 |
|  | 2 | 2443 ± 6 | 2500 ± 6 | 2529 ± 8 |
| G-10e | 1 | 47693 ± 173 | 48154 ± 535 | 51850 ± 1972 |
|  | 2 | 2354 ± 1 | 2408 ± 5 | 2481 ± 5 |
| G-50e | 1 | 33715 ± 33 | 35072 ± 78 | 32731 ± 64 |
| P-30e | 1 | 30313 ± 390 | 32809 ± 54 | 33000 ± 69 |
| P-70e | 1 | 14581 ± 134 | 15797 ± 12 | 15898 ± 161 |
| P-100e | 1 | 12448 ± 28 | 13242 ± 2 | 13472 ± 3 |

Gel Permeation Chromatography (GPC) is used to determine the molecular weight distribution of polymers. During GPC analysis, a solution of the polymer sample is passed through a column packed with a porous gel trapping small molecules. The sample is separated based on molecular size with larger molecules eluting sooner than smaller molecules. The retention time of each component is most often detected by refractive index (RI), evaporative light scattering (ELS), or ultraviolet (UV) and compared to a calibration curve. The resulting data is then used to calculate the molecular weight distribution for the sample.

A distribution of molecular weights rather than a unique molecular weight is used to characterize synthetic polymers. To characterize this distribution, statistical averages are utilized. The most common of these averages are the "number average molecular weight" ($M_n$) and the "weight average molecular weight" ($M_w$). Methods of calculating these values are described in Example 9 of PCT/US/2007/022719.

The polydispersity index or PI is defined as the ratio of $M_w/M_n$. The larger the PI, the broader or more disperse the distribution. The lowest value that a PI can be is 1. This represents a monodisperse sample; that is, a polymer with all of the molecules in the distribution being the same molecular weight.

The peak molecular weight value ($M_p$) is another descriptor defined as the mode of the molecular weight distribution. It signifies the molecular weight that is most abundant in the distribution. This value also gives insight to the molecular weight distribution.

Most GPC measurements are made relative to a different polymer standard. The accuracy of the results depends on how closely the characteristics of the polymer being analyzed match those of the standard used. The expected error in reproducibility between different series of determinations, calibrated separately, is ca. 5-10% and is characteristic to the limited precision of GPC determinations. Therefore, GPC results are most useful when a comparison between the molecular weight distributions of different samples is made during the same series of determinations.

The lignocellulosic samples required sample preparation prior to GPC analysis. First, a saturated solution (8.4% by weight) of lithium chloride (LiCl) was prepared in dimethyl acetamide (DMAc). Approximately 100 mg of the sample was added to approximately 10 g of a freshly prepared saturated LiCl/DMAc solution, and each mixture was heated to approximately 150° C.–170° C. with stirring for 1 hour. The resulting solutions were generally light- to dark-yellow in color. The temperature of the solutions was decreased to approximately 100° C. and the solutions were heated for an additional 2 hours. The temperature of the solutions was then decreased to approximately 50° C. and the sample solutions were heated for approximately 48 to 60 hours. Of note, samples irradiated at 100 Mrad were more easily solubilized as compared to their untreated counterpart. Additionally, the sheared samples (denoted by the number 132) had slightly lower average molecular weights as compared with uncut samples.

The resulting sample solutions were diluted 1:1 using DMAc as solvent and were filtered through a 0.45 µm PTFE filter. The filtered sample solutions were then analyzed by GPC using the parameters described in Table 7. The peak average molecular weights (Mp) of the samples, as determined by Gel Permeation Chromatography (GPC), are summarized in Tables 3-6. Each sample was prepared in duplicate and each preparation of the sample was analyzed in duplicate (two injections) for a total of four injections per sample. The EasiCal® polystyrene standards PS1A and PS1B were used to generate a calibration curve for the molecular weight scale from about 580 to 7,500,00 Daltons.

TABLE 7

GPC Analysis Conditions

| | |
|---|---|
| Instrument: | Waters Alliance GPC 2000 |
| Columns (3): | Plgel 10µ Mixed-B |
| | S/N's: 10M-MB-148-83; 10M-MB-148-84; 10M-MB-174-129 |
| Mobile Phase (solvent): | 0.5% LiCl in DMAc (1.0 mL/min.) |
| Column/Detector Temperature: | 70° C. |
| Injector Temperature: | 70° C. |
| Sample Loop Size: | 323.5 µL |

Example 11

Time-of-Flight Secondary Ion Mass Spectrometry (ToF-SIMS) Surface Analysis

Time-of-Flight Secondary Ion Mass Spectroscopy (ToF-SIMS) is a surface-sensitive spectroscopy that uses a pulsed ion beam (Cs or microfocused Ga) to remove molecules from the very outermost surface of the sample. The particles are removed from atomic monolayers on the surface (secondary ions). These particles are then accelerated into a "flight tube" and their mass is determined by measuring the exact time at which they reach the detector (i.e. time-of-flight). ToF-SIMS provides detailed elemental and molecular information about the surface, thin layers, interfaces of the sample, and gives a full three-dimensional analysis. The use is widespread, including semiconductors, polymers, paint, coatings, glass, paper, metals, ceramics, biomaterials, pharmaceuticals and organic tissue. Since ToF-SIMS is a survey technique, all the elements in the periodic table, including H, are detected. ToF-SIMS data is presented in Tables 8-11. Parameters used are reported in Table 12.

TABLE 8

Normalized Mean Intensities of Various Positive Ions of Interest
(Normalized relative to total ion counts × 10000)

| | | P132 | | P132-10 | | P132-100 | |
|---|---|---|---|---|---|---|---|
| m/z | species | Mean | σ | Mean | σ | Mean | σ |
| 23 | Na | 257 | 28 | 276 | 54 | 193 | 36 |
| 27 | Al | 647 | 43 | 821 | 399 | 297 | 44 |
| 28 | Si | 76 | 45.9 | 197 | 89 | 81.7 | 10.7 |
| 15 | $CH_3$ | 77.9 | 7.8 | 161 | 26 | 133 | 12 |
| 27 | $C_2H_3$ | 448 | 28 | 720 | 65 | 718 | 82 |
| 39 | $C_3H_3$ | 333 | 10 | 463 | 37 | 474 | 26 |
| 41 | $C_3H_5$ | 703 | 19 | 820 | 127 | 900 | 63 |
| 43 | $C_3H_7$ | 657 | 11 | 757 | 162 | 924 | 118 |
| 115 | $C_9H_7$ | 73 | 13.4 | 40.3 | 4.5 | 42.5 | 15.7 |
| 128 | $C_{10}H_8$ | 55.5 | 11.6 | 26.8 | 4.8 | 27.7 | 6.9 |
| 73 | $C_3H_9Si^*$ | 181 | 77 | 65.1 | 18.4 | 81.7 | 7.5 |
| 147 | $C_5H_{15}OSi_2^*$ | 72.2 | 33.1 | 24.9 | 10.9 | 38.5 | 4 |
| 207 | $C_5H_{15}O_3Si_3^*$ | 17.2 | 7.8 | 6.26 | 3.05 | 7.49 | 1.77 |
| 647 | $C_{42}H_{64}PO_3$ | 3.63 | 1.05 | 1.43 | 1.41 | 10.7 | 7.2 |

TABLE 9

Normalized Mean Intensities of Various Negative Ions of Interest
(Normalized relative to total ion counts × 10000)

| | | P132 | | P132-10 | | P132-100 | |
|---|---|---|---|---|---|---|---|
| m/z | species | Mean | σ | Mean | σ | Mean | σ |
| 19 | F | 15.3 | 2.1 | 42.4 | 37.8 | 19.2 | 1.9 |
| 35 | Cl | 63.8 | 2.8 | 107 | 33 | 74.1 | 5.5 |
| 13 | CH | 1900 | 91 | 1970 | 26 | 1500 | 6 |
| 25 | $C_2H$ | 247 | 127 | 220 | 99 | 540 | 7 |
| 26 | CN | 18.1 | 2.1 | 48.6 | 30.8 | 43.9 | 1.4 |
| 42 | CNO | 1.16 | 0.71 | 0.743 | 0.711 | 10.8 | 0.9 |
| 46 | $NO_2$ | 1.87 | 0.38 | 1.66 | 1.65 | 12.8 | 1.8 |

TABLE 10

Normalized Mean Intensities of Various Positive Ions of Interest
(Normalized relative to total ion counts × 10000)

| | | P-1e | | P-5e | | P-10e | | P-30e | | P-70e | | P-100e | |
|---|---|---|---|---|---|---|---|---|---|---|---|---|---|
| m/z | species | Mean | σ | Mean | σ | Mean | σ | Mean | σ | Mean | σ | Mean | σ |
| 23 | Na | 232 | 56 | 370 | 37 | 241 | 44 | 518 | 57 | 350 | 27 | 542 | 104 |
| 27 | Al | 549 | 194 | 677 | 86 | 752 | 371 | 761 | 158 | 516 | 159 | 622 | 166 |
| 28 | Si | 87.3 | 11.3 | 134 | 24 | 159 | 100 | 158 | 32 | 93.7 | 17.1 | 124 | 11 |
| 15 | $CH_3$ | 114 | 23 | 92.9 | 3.9 | 128 | 18 | 110 | 16 | 147 | 16 | 141 | 5 |
| 27 | $C_2H_3$ | 501 | 205 | 551 | 59 | 645 | 165 | 597 | 152 | 707 | 94 | 600 | 55 |
| 39 | $C_3H_3$ | 375 | 80 | 288 | 8 | 379 | 82 | 321 | 57 | 435 | 61 | 417 | 32 |
| 41 | $C_3H_5$ | 716 | 123 | 610 | 24 | 727 | 182 | 607 | 93 | 799 | 112 | 707 | 84 |
| 43 | $C_3H_7$ | 717 | 121 | 628 | 52 | 653 | 172 | 660 | 89 | 861 | 113 | 743 | 73 |
| 115 | $C_9H_7$ | 49.9 | 14.6 | 43.8 | 2.6 | 42.2 | 7.9 | 41.4 | 10.1 | 27.7 | 8 | 32.4 | 10.5 |
| 128 | $C_{10}H_8$ | 38.8 | 13.1 | 39.2 | 1.9 | 35.2 | 11.8 | 31.9 | 7.8 | 21.2 | 6.1 | 24.2 | 6.8 |
| 73 | $C_3H_9Si^*$ | 92.5 | 3.0 | 80.6 | 2.9 | 72.3 | 7.7 | 75.3 | 11.4 | 63 | 3.4 | 55.8 | 2.1 |
| 147 | $C_5H_{15}OSi_2^*$ | 27.2 | 3.9 | 17.3 | 1.2 | 20.4 | 4.3 | 16.1 | 1.9 | 21.7 | 3.1 | 16.3 | 1.7 |
| 207 | $C_5H_{15}O_3Si_3^*$ | 6.05 | 0.74 | 3.71 | 0.18 | 4.51 | 0.55 | 3.54 | 0.37 | 5.31 | 0.59 | 4.08 | 0.28 |
| 647 | $C_{42}H_{64}PO_3$ | 1.61 | 1.65 | 1.09 | 1.30 | 0.325 | 0.307 | nd | ~ | 0.868 | 1.31 | 0.306 | 0.334 |

TABLE 11

Normalized Mean Intensities of Various Negative Ions of Interest
(Normalized relative to total ion counts × 10000)

| | | P-1e | | P-5e | | P-10e | | P-30e | | P-70e | | P-100e | |
|---|---|---|---|---|---|---|---|---|---|---|---|---|---|
| m/z | species | Mean | σ | Mean | σ | Mean | σ | Mean | σ | Mean | σ | Mean | σ |
| 13 | CH | 1950 | 72 | 1700 | 65 | 1870 | 91 | 1880 | 35 | 2000 | 46 | 2120 | 102 |
| 25 | $C_2H$ | 154 | 47 | 98.8 | 36.3 | 157 | 4 | 230 | 17 | 239 | 22 | 224 | 19 |
| 19 | F | 25.4 | 1 | 24.3 | 1.4 | 74.3 | 18.6 | 40.6 | 14.9 | 25.6 | 1.9 | 21.5 | 2 |
| 35 | Cl | 39.2 | 13.5 | 38.7 | 3.5 | 46.7 | 5.4 | 67.6 | 6.2 | 45.1 | 2.9 | 32.9 | 10.2 |
| 26 | CN | 71.9 | 18.9 | 6.23 | 2.61 | 28.1 | 10.1 | 34.2 | 29.2 | 57.3 | 28.9 | 112 | 60 |
| 42 | CNO | 0.572 | 0.183 | 0.313 | 0.077 | 0.62 | 0.199 | 1.29 | 0.2 | 1.37 | 0.55 | 1.38 | 0.28 |
| 46 | $NO_2$ | 0.331 | 0.057 | 0.596 | 0.255 | 0.668 | 0.149 | 1.44 | 0.19 | 1.92 | 0.29 | 0.549 | 0.1 |

TABLE 12

ToF-SIMS Parameters
Instrument Conditions:

| | |
|---|---|
| Instrument: | PHI TRIFT II |
| Primary Ion Source: | $^{69}$Ga |
| Primary Ion Beam Potential: | 12 kV + ions |
| | 18 kV − ions |
| Primary Ion Current (DC): | 2 na for P#E samples |
| | 600 pA for P132 samples |
| Energy Filter/CD: | Out/Out |
| Masses Blanked: | None |
| Charge Compensation: | On |

ToF-SIMS uses a focused, pulsed particle beam (typically Cs or Ga) to dislodge chemical species on a materials surface. Particles produced closer to the site of impact tend to be dissociated ions (positive or negative). Secondary particles generated farther from the impact site tend to be molecular compounds, typically fragments of much larger organic macromolecules. The particles are then accelerated into a flight path on their way towards a detector. Because it is possible to measure the "time-of-flight" of the particles from the time of impact to detector on a scale of nanoseconds, it is possible to produce a mass resolution as fine as 0.00× atomic mass units (i.e. one part in a thousand of the mass of a proton). Under typical operating conditions, the results of ToF-SIMS analysis include: a mass spectrum that surveys all atomic masses over a range of 0-10,000 amu, the rastered beam produces maps of any mass of interest on a sub-micron scale, and depth profiles are produced by removal of surface layers by sputtering under the ion beam. Negative ion analysis showed that the polymer had increasing amounts of CNO, CN, and $NO_2$ groups.

Example 12

X-Ray Photoelectron Spectroscopy (XPS)/Electron Spectroscopy for Chemical Analysis (ESCA)

X-Ray Photoelectron Spectroscopy (XPS) (sometimes called "ESCA") measures the chemical composition of the top five nanometers of surface; XPS uses photo-ionization energy and energy-dispersive analysis of the emitted photoelectrons to study the composition and electronic state of the surface region of a sample. X-ray Photoelectron spectroscopy is based upon a single photon in/electron out. Soft x-rays stimulate the ejection of photoelectrons whose kinetic energy is measured by an electrostatic electron energy analyzer. Small changes to the energy are caused by chemically-shifted valence states of the atoms from which the electrons are ejected; thus, the measurement provides chemical information about the sample surface.

TABLE 13

Atomic Concentrations (in %)[a,b]

| | Atom | | | |
|---|---|---|---|---|
| Sample ID | C | O | Al | Si |
| P132 (Area 1) | 57.3 | 39.8 | 1.5 | 1.5 |
| P132 (Area 2) | 57.1 | 39.8 | 1.6 | 1.5 |
| P132-10 (Area 1) | 63.2 | 33.5 | 1.7 | 1.6 |
| P132-10 (Area 2) | 65.6 | 31.1 | 1.7 | 1.7 |
| P132-100 (Area 1) | 61.2 | 36.7 | 0.9 | 1.2 |
| P132-100 (Area 2) | 61 | 36.9 | 0.8 | 1.3 |

[a]Normalized to 100% of the elements detected. XPS does not detect H or He.

TABLE 14

Carbon Chemical State (in % C)

| Sample ID | C—C, C—H | C—O | C=O | O—C=O |
|---|---|---|---|---|
| P132 (Area 1) | 22 | 49 | 21 | 7 |
| P132 (Area 2) | 25 | 49 | 20 | 6 |
| P132-10 (Area 1) | 34 | 42 | 15 | 9 |
| P132-10 (Area 2) | 43 | 38 | 14 | 5 |
| P132-100 (Area 1) | 27 | 45 | 15 | 9 |
| P132-100 (Area 2) | 25 | 44 | 23 | 9 |

TABLE 15

Atomic Concentrations (in %)[a,b]

| | Atom | | | | |
|---|---|---|---|---|---|
| Sample ID | C | O | Al | Si | Na |
| P-1e (Area 1) | 59.8 | 37.9 | 1.4 | 0.9 | ~ |
| P-1e (Area 2) | 58.5 | 38.7 | 1.5 | 1.3 | ~ |
| P-5e (Area 1) | 58.1 | 39.7 | 1.4 | 0.8 | ~ |
| P-5e (Area 2) | 58.0 | 39.7 | 1.5 | 0.8 | ~ |
| P-10e (Area 1) | 61.6 | 36.7 | 1.1 | 0.7 | ~ |
| P-10e (Area 2) | 58.8 | 38.6 | 1.5 | 1.1 | ~ |
| P-50e (Area 1) | 59.9 | 37.9 | 1.4 | 0.8 | <0.1 |
| P-50e (Area 2) | 59.4 | 38.3 | 1.4 | 0.9 | <0.1 |
| P-70e (Area 1) | 61.3 | 36.9 | 1.2 | 0.6 | <0.1 |
| P-70e (Area 2) | 61.2 | 36.8 | 1.4 | 0.7 | <0.1 |
| P-100e (Area 1) | 61.1 | 37.0 | 1.2 | 0.7 | <0.1 |
| P-100e (Area 2) | 60.5 | 37.2 | 1.4 | 0.9 | <0.1 |

[a]Normalized to 100% of the elements detected. XPS does not detect H or He.
[b]A less than symbol "<" indicates accurate quantification cannot be made due to weak signal intensity.

TABLE 16

Carbon Chemical State Table (in % C)

| Sample ID | C—C, C—H | C—O | C=O | O—C=O |
|---|---|---|---|---|
| P-1e (Area 1) | 29 | 46 | 20 | 5 |
| P-1e (Area 2) | 27 | 49 | 19 | 5 |
| P-5e (Area 1) | 25 | 53 | 18 | 5 |
| P-5e (Area 2) | 28 | 52 | 17 | 4 |
| P-10e (Area 1) | 33 | 47 | 16 | 5 |
| P-10e (Area 2) | 28 | 51 | 16 | 5 |
| P-50e (Area 1) | 29 | 45 | 20 | 6 |
| P-50e (Area 2) | 28 | 50 | 16 | 5 |
| P-70e (Area 1) | 32 | 45 | 16 | 6 |
| P-70e (Area 2) | 35 | 43 | 16 | 6 |
| P-100e (Area 1) | 32 | 42 | 19 | 7 |
| P-100e (Area 2) | 30 | 47 | 16 | 7 |

TABLE 17

Analytical Parameters

| | |
|---|---|
| Instrument: | PHI Quantum 2000 |
| X-ray source: | Monochromated Alk$_\alpha$ 1486.6 eV |
| Acceptance Angle: | ±23° |
| Take-off angle: | 45° |
| Analysis area: | 1400 × 300 μm |
| Charge Correction: | C1s 284.8 eV |

XPS spectra are obtained by irradiating a material with a beam of aluminum or magnesium X-rays while simultaneously measuring the kinetic energy (KE) and number of electrons that escape from the top 1 to 10 nm of the material being analyzed (see analytical parameters, Table 17). The XPS technique is highly surface specific due to the short range of the photoelectrons that are excited from the solid. The energy of the photoelectrons leaving the sample is determined using a Concentric Hemispherical Analyzer (CHA) and this gives a spectrum with a series of photoelectron peaks. The binding energy of the peaks is characteristic of each element. The peak areas can be used (with appropriate sensitivity factors) to determine the composition of the materials surface. The shape of each peak and the binding energy can be slightly altered by the chemical state of the emitting atom. Hence XPS can provide chemical bonding information as well. XPS is not sensitive to hydrogen or helium, but can detect all other elements. XPS requires ultra-high vacuum (UHV) conditions and is commonly used for the surface analysis of polymers, coatings, catalysts, composites, fibers, ceramics, pharmaceutical/medical materials, and materials of biological origin. XPS data is reported in Tables 13-16.

Example 13

Raman Analysis

Raman spectra were acquired from the surface of fibers from samples: P132, P132-100, P-1e, and P-100e. The measurements were performed using a "LabRam" J-Y Spectrometer. A HeNe laser (632.8 nm wavelength) and 600 gr/mm grating were used for the measurements. The measurements were performed confocally using backscattering geometry) (180° under an Olympus BX40 microscope. The samples had a Raman spectrum typical of cellulose.

Example 14

Scanning Probe Microscopy (SPM) Surface Analysis Using an Atomic Force Microscope (AFM)

The purpose of this analysis was to obtain Atomic Force Microscope (AFM) images of the samples in Tables 18 and 19 to measure surface roughness.

Scanning probe microscopy (SPM) is a branch of microscopy that forms images of surfaces using a physical probe that scans the specimen. An image of the surface is obtained by mechanically moving the probe in a raster scan of the specimen, line by line, and recording the probe-surface interaction as a function of position. The atomic force microscope (AFM) or scanning force microscope (SFM) is a very high-resolution type of scanning probe microscope, with demonstrated resolution of fractions of a nanometer, more than 1000 times better than the optical diffraction limit. The probe (or the sample under a stationary probe) generally is moved by a piezoelectric tube. Such scanners are designed to be moved precisely in any of the three perpendicular axes (x,y,z). By following a raster pattern, the sensor data forms an image of the probe-surface interaction. Feedback from the sensor is used to maintain the probe at a constant force or distance from the object surface. For atomic force microscopy, the sensor is a position-sensitive photodetector that records the angle of reflection from a laser bean focused on the top of the cantilever.

TABLE 18

Roughness Results for Gamma-Irradiated Samples

| Sample ID | RMS (Å) | $R_a$ (Å) | $R_{max}$ (Å) |
|---|---|---|---|
| P132 | 927.2 | 716.3 | 8347.6 |
| P132-10 | 825.7 | 576.8 | 11500 |
| P132-100 | 1008 | 813.5 | 7250.7 |

TABLE 19

Roughness Results for Samples Irradiated with E-Beam

| Sample ID | RMS (Å) | $R_a$ (Å) | $R_{max}$ (Å) |
|---|---|---|---|
| P-1e | 1441.2 | 1147.1 | 8955.4 |
| P-5e | 917.3 | 727.5 | 6753.4 |
| P-10e | 805.6 | 612.1 | 7906.5 |
| P-30e | 919.2 | 733.7 | 6900 |
| P-70e | 505.8 | 388.1 | 5974.2 |
| P-100e | 458.2 | 367.9 | 3196.9 |

AFM images were collected using a NanoScope III Dimension 5000 (Digital Instruments, Santa Barbara, Calif., USA). The instrument was calibrated against a NIST traceable standard with an accuracy better than 2%. NanoProbe silicon tips were used. Image processing procedures involving auto-flattening, plane fitting or convolution were employed.

One 5 μm ×5 μm area was imaged at a random location on top of a single fiber. Perspective (3-D) views of these surfaces are included with vertical exaggerations noted on the plots (FIGS. 31A-31F). The roughness analyses were performed and are expressed in: (1) Root-Mean-Square Roughness, RMS; (2) Mean Roughness, Ra; and (3) Maximum Height (Peak-to-Valley), Rmax. Results are summarized in Tables 18 and 19.

Example 15

Determining Crystallinity of Irradiated Materials by X-Ray Diffraction

X-ray diffraction (XRD) is a method by which a crystalline sample is irradiated with monoenergetic x-rays. The interaction of the lattice structure of the sample with these x-rays is recorded and provides information about the crystalline structure being irradiated. The resulting characteristic "fingerprint" allows for the identification of the crystalline compounds present in the sample. Using a whole-pattern fitting analysis (the Rietvelt Refinement), it is possible to perform quantitative analyses on samples containing more than one crystalline compound.

TABLE 20

XRD Data Including Domain Size and % Crystallinity

| Sample ID | Domain Size (Å) | % Crystallinity |
|---|---|---|
| P132 | 55 | 55 |
| P132-10 | 46 | 58 |
| P132-100 | 50 | 55 |
| P132-181 | 48 | 52 |
| P132-US | 26 | 40 |
| A132 | 28 | 42 |
| A132-10 | 26 | 40 |
| A132-100 | 28 | 35 |
| WS132 | 30 | 36 |
| WS132-10 | 27 | 37 |
| WS132-100 | 30 | 41 |
| SG132 | 29 | 40 |
| SG132-10 | 28 | 38 |
| SG132-100 | 28 | 37 |
| SG132-10-US | 25 | 42 |
| SG132-100-US | 21 | 34 |

Each sample was placed on a zero background holder and placed in a Phillips PW 1800 diffractometer using Cu radiation. Scans were then run over the range of 5° to 50° with a step size of 0.05° and a counting time of 2 hours each.

Once the diffraction patterns were obtained, the phases were identified with the aid of the Powder Diffraction File published by the International Centre for Diffraction Data. In all samples the crystalline phase identified was cellulose—Ia, which has a triclinic structure.

The distinguishing feature among the 20 samples is the peak breadth, which is related to the crystallite domain size. The experimental peak breadth was used to compute the domain size and percent crystallinity, which are reported in Table 4.

Percent crystallinity ($X_c$ %) is measured as a ratio of the crystalline area to the total area under the x-ray diffraction peaks and equals $100\% \times (A_c/(A_a+A_c))$, where $A_c$=Area of crystalline phase
$A_a$=Area of amorphous phase
$X_c$=Percent of crystallinity To determine the percent crystallinity for each sample it was necessary to first extract the amount of the amorphous phase. This is done by estimating the area of each diffraction pattern that can be attributed to the crystalline phase (represented by the sharper peaks) and the non-crystalline phase (represented by the broad humps beneath the pattern and centered at 22° and 38°).

A systematic process was used to minimize error in these calculations due to broad crystalline peaks as well as high background intensity, First, a linear background was applied and then removed. Second, two Gaussian peaks centered at 22° and 38° with widths of 10-12° each were fitted to the humps beneath the crystalline peaks. Third, the area beneath the two broad Gaussian peaks and the rest of the pattern were determined. Finally, percent crystallinity was calculated by dividing the area beneath the crystalline peak by the total intensity (after background subtraction). Domain size and % crystallinity of the samples as determined by X-ray diffraction (XRD) are presented in Table 20.

Example 16

Porosimetry Analysis of Irradiated Materials

Mercury pore size and pore volume analysis (Table 21) is based on forcing mercury (a non-wetting liquid) into a porous structure under tightly controlled pressures. Since mercury does not wet most substances and will not spontaneously penetrate pores by capillary action, it must be forced into the voids of the sample by applying external pressure. The pressure required to fill the voids is inversely proportional to the size of the pores. Only a small amount of force or pressure is required to fill large voids, whereas much greater pressure is required to fill voids of very small pores.

TABLE 21

Pore Size and Volume Distribution by Mercury Porosimetry

| Sample ID | Total Intrusion Volume (mL/g) | Total Pore Area (m²/g) | Median Pore Diameter (Volume) (μm) | Median Pore Diameter (Area) (μm) | Average Pore Diameter (4 V/A) (μm) | Bulk Density @ 0.50 psia (g/mL) | Apparent (skeletal) Density (g/mL) | Porosity (%) |
|---|---|---|---|---|---|---|---|---|
| P132 | 6.0594 | 1.228 | 36.2250 | 13.7278 | 19.7415 | 0.1448 | 1.1785 | 87.7163 |
| P132-10 | 5.5436 | 1.211 | 46.3463 | 4.5646 | 18.3106 | 0.1614 | 1.5355 | 89.4875 |
| P132-100 | 5.3985 | 0.998 | 34.5235 | 18.2005 | 21.6422 | 0.1612 | 1.2413 | 87.0151 |
| P132-181 | 3.2866 | 0.868 | 25.3448 | 12.2410 | 15.1509 | 0.2497 | 1.3916 | 82.0577 |
| P132-US | 6.0005 | 14.787 | 98.3459 | 0.0055 | 1.6231 | 0.1404 | 0.8894 | 84.2199 |
| A132 | 2.0037 | 11.759 | 64.6308 | 0.0113 | 0.6816 | 0.3683 | 1.4058 | 73.7990 |
| A132-10 | 1.9514 | 10.326 | 53.2706 | 0.0105 | 0.7560 | 0.3768 | 1.4231 | 73.5241 |
| A132-100 | 1.9394 | 10.205 | 43.8966 | 0.0118 | 0.7602 | 0.3760 | 1.3889 | 72.9264 |
| SG132 | 2.5267 | 8.265 | 57.6958 | 0.0141 | 1.2229 | 0.3119 | 1.4708 | 78.7961 |
| SG132-10 | 2.1414 | 8.643 | 26.4666 | 0.0103 | 0.9910 | 0.3457 | 1.3315 | 74.0340 |
| SG132-100 | 2.5142 | 10.766 | 32.7118 | 0.0098 | 0.9342 | 0.3077 | 1.3590 | 77.3593 |
| SG132-10-US | 4.4043 | 1.722 | 71.5734 | 1.1016 | 10.2319 | 0.1930 | 1.2883 | 85.0169 |
| SG132-100-US | 4.9665 | 7.358 | 24.8462 | 0.0089 | 2.6998 | 0.1695 | 1.0731 | 84.2010 |
| WS132 | 2.9920 | 5.447 | 76.3675 | 0.0516 | 2.1971 | 0.2773 | 1.6279 | 82.9664 |

TABLE 21-continued

Pore Size and Volume Distribution by Mercury Porosimetry

| Sample ID | Total Intrusion Volume (mL/g) | Total Pore Area (m²/g) | Median Pore Diameter (Volume) (μm) | Median Pore Diameter (Area) (μm) | Average Pore Diameter (4 V/A) (μm) | Bulk Density @ 0.50 psia (g/mL) | Apparent (skeletal) Density (g/mL) | Porosity (%) |
|---|---|---|---|---|---|---|---|---|
| WS132-10 | 3.1138 | 2.901 | 57.4727 | 0.3630 | 4.2940 | 0.2763 | 1.9808 | 86.0484 |
| WS132-100 | 3.2077 | 3.114 | 52.3284 | 0.2876 | 4.1199 | 0.2599 | 1.5611 | 83.3538 |
| A-1e | 1.9535 | 3.698 | 25.3411 | 0.0810 | 2.1130 | 0.3896 | 1.6299 | 76.0992 |
| A-5e | 1.9697 | 6.503 | 29.5954 | 0.0336 | 1.2117 | 0.3748 | 1.4317 | 73.8225 |
| A-10e | 2.0897 | 12.030 | 45.5493 | 0.0101 | 0.6948 | 0.3587 | 1.4321 | 74.9545 |
| A-50e | 2.1141 | 7.291 | 37.0760 | 0.0304 | 1.1599 | 0.3577 | 1.4677 | 75.6264 |
| G-1e | 2.4382 | 7.582 | 58.5521 | 0.0201 | 1.2863 | 0.3144 | 1.3472 | 76.6610 |
| G-5e | 2.4268 | 6.436 | 44.4848 | 0.0225 | 1.5082 | 0.3172 | 1.3782 | 76.9831 |
| G-10e | 2.6708 | 6.865 | 62.8605 | 0.0404 | 1.5562 | 0.2960 | 1.4140 | 79.0638 |
| G-50e | 2.8197 | 6.798 | 56.5048 | 0.0315 | 1.6591 | 0.2794 | 1.3179 | 78.7959 |
| P-1e | 7.7692 | 1.052 | 49.8844 | 22.9315 | 29.5348 | 0.1188 | 1.5443 | 92.3065 |
| P-5e | 7.1261 | 1.212 | 46.6400 | 12.3252 | 23.5166 | 0.1268 | 1.3160 | 90.3644 |
| P-10e | 6.6096 | 1.113 | 41.4252 | 17.4375 | 23.7513 | 0.1374 | 1.4906 | 90.7850 |
| P-50e | 6.5911 | 1.156 | 40.7837 | 15.9823 | 22.7974 | 0.1362 | 1.3302 | 89.7616 |
| P-100e | 5.3507 | 1.195 | 35.3622 | 10.7400 | 17.9063 | 0.1648 | 1.3948 | 88.1840 |
| S | 0.4362 | 0.030 | 102.8411 | 42.5047 | 57.8208 | 0.9334 | 1.5745 | 40.7160 |
| S-1e | 0.3900 | 0.632 | 90.6808 | 0.0041 | 2.4680 | 0.9772 | 1.5790 | 38.1140 |
| S-5e | 0.3914 | 0.337 | 97.1991 | 0.0070 | 4.6406 | 0.9858 | 1.6052 | 38.5847 |
| S-10e | 0.4179 | 0.349 | 113.4360 | 0.0042 | 4.7873 | 0.9469 | 1.5669 | 39.5678 |
| S-30e | 0.4616 | 5.329 | 102.0559 | 0.0042 | 0.3464 | 0.9065 | 1.5585 | 41.8388 |
| S-50e | 0.5217 | 7.162 | 137.2124 | 0.0051 | 0.2914 | 0.8521 | 1.5342 | 44.4582 |
| S-100e | 0.8817 | 15.217 | 76.4577 | 0.0053 | 0.2318 | 0.6478 | 1.5105 | 57.1131 |
| St | 0.6593 | 17.631 | 4.2402 | 0.0053 | 0.1496 | 0.7757 | 1.5877 | 51.1438 |
| St-1e | 0.6720 | 18.078 | 4.3360 | 0.0052 | 0.1487 | 0.7651 | 1.5750 | 51.4206 |
| St-5e | 0.6334 | 19.495 | 4.2848 | 0.0051 | 0.1300 | 0.7794 | 1.5395 | 49.3706 |
| St-10e | 0.6208 | 16.980 | 4.3362 | 0.0056 | 0.1462 | 0.7952 | 1.5703 | 49.3630 |
| St-30e | 0.6892 | 18.066 | 4.4152 | 0.0050 | 0.1526 | 0.7475 | 1.5417 | 51.5165 |
| St-50e | 0.6662 | 18.338 | 4.3759 | 0.0054 | 0.1453 | 0.7637 | 1.5548 | 50.8778 |
| St-100e | 0.6471 | 23.154 | 5.4032 | 0.0048 | 0.1118 | 0.7229 | 1.3582 | 46.7761 |

The AutoPore 9520 can attain a maximum pressure of 414 MPa or 60,000 psia. There are four low pressure stations for sample preparation and collection of macropore data from 0.2 psia to 50 psia. There are two high pressure chambers, which collect data from 25 psia to 60,000 psia. The sample is placed in a bowl-like apparatus called a penetrometer, which is bonded to a glass capillary stem with a metal coating. As mercury invades the voids in and around the sample, it moves down the capillary stem. The loss of mercury from the capillary stem results in a change in the electrical capacitance. The change in capacitance during the experiment is converted to volume of mercury by knowing the stem volume of the penetrometer in use. A variety of penetrometers with different bowl (sample) sizes and capillaries are available to accommodate most sample sizes and configurations. Table 22 below defines some of the key parameters calculated for each sample.

TABLE 22

Definition of Parameters

| Parameter | Description |
|---|---|
| Total Intrusion Volume: | The total volume of mercury intruded during an experiment. This can include interstitial filling between small particles, porosity of sample, and compression volume of sample. |
| Total Pore Area: | The total intrusion volume converted to an area assuming cylindrical shaped pores. |
| Median Pore Diameter (volume): | The size at the 50$^{th}$ percentile on the cumulative volume graph. |
| Median Pore Diameter (area): | The size at the 50$^{th}$ percentile on the cumulative area graph. |
| Average Pore Diameter: | The total pore volume divided by the total pore area (4V/A). |
| Bulk Density: | The mass of the sample divided by the bulk volume. Bulk volume is determined at the filling pressure, typically 0.5 psia. |
| Apparent Density: | The mass of sample divided by the volume of sample measured at highest pressure, typically 60,000 psia. |
| Porosity: | (Bulk Density/Apparent Density) × 100% |

Example 17

Particle Size Analysis of Irradiated Materials

The technique of particle sizing by static light scattering is based on Mie theory (which also encompasses Fraunhofer theory). Mie theory predicts the intensity vs. angle relationship as a function of the size for spherical scattering particles provided that other system variables are known and held constant. These variables are the wavelength of incident light and the relative refractive index of the sample material.

Application of Mie theory provides the detailed particle size information. Table 23 summarizes particle size using median diameter, mean diameter, and modal diameter as parameters.

TABLE 23

Particle Size by Laser Light Scattering (Dry Sample Dispersion)

| Sample ID | Median Diameter (μm) | Mean Diameter (μm) | Modal Diameter (μm) |
|---|---|---|---|
| A132 | 380.695 | 418.778 | 442.258 |
| A132-10 | 321.742 | 366.231 | 410.156 |
| A132-100 | 301.786 | 348.633 | 444.169 |
| SG132 | 369.400 | 411.790 | 455.508 |
| SG132-10 | 278.793 | 325.497 | 426.717 |
| SG132-100 | 242.757 | 298.686 | 390.097 |
| WS132 | 407.335 | 445.618 | 467.978 |
| WS132-10 | 194.237 | 226.604 | 297.941 |
| WS132-100 | 201.975 | 236.037 | 307.304 |

Particle size was determined by Laser Light Scattering (Dry Sample Dispersion) using a Malvern Mastersizer 2000 using the following conditions:
Feed Rate: 35%
Disperser Pressure: 4 Bar
Optical Model: (2.610, 1.000i), 1.000

An appropriate amount of sample was introduced onto a vibratory tray. The feed rate and air pressure were adjusted to ensure that the particles were properly dispersed. The key component is selecting an air pressure that will break up agglomerations, but does not compromise the sample integrity. The amount of sample needed varies depending on the size of the particles. In general, samples with fine particles require less material than samples with coarse particles.

Example 18

Surface Area Analysis of Irradiated Materials

Surface area of each sample was analyzed using a Micromeritics ASAP 2420 Accelerated Surface Area and Porosimetry System. The samples were prepared by first degassing for 16 hours at 40° C. Next, free space (both warm and cold) with helium is calculated and then the sample tube is evacuated again to remove the helium. Data collection begins after this second evacuation and consists of defining target pressures which controls how much gas is dosed onto the sample. At each target pressure, the quantity of gas adsorbed and the actual pressure are determined and recorded. The pressure inside the sample tube, is measured with a pressure transducer. Additional doses of gas will continue until the target pressure is achieved and allowed to equilibrate. The quantity of gas adsorbed is determined by summing multiple doses onto the sample. The pressure and quantity define a gas adsorption isotherm and are used to calculate a number of parameters, including BET surface area (Table 24).

TABLE 24

Summary of Surface Area by Gas Adsorption

| Sample ID | Single point surface area ($m^2/g$) | | BET Surface Area ($m^2/g$) |
|---|---|---|---|
| P132 | @ P/Po = 0.250387771 | 1.5253 | 1.6897 |
| P132-10 | @ P/Po = 0.239496722 | 1.0212 | 1.2782 |
| P132-100 | @ P/Po = 0.240538100 | 1.0338 | 1.2622 |
| P132-181 | @ P/Po = 0.239166091 | 0.5102 | 0.6448 |
| P132-US | @ P/Po = 0.217359072 | 1.0983 | 1.6793 |
| A132 | @ P/Po = 0.240040610 | 0.5400 | 0.7614 |
| A132-10 | @ P/Po = 0.211218936 | 0.5383 | 0.7212 |
| A132-100 | @ P/Po = 0.238791097 | 0.4258 | 0.5538 |
| SG132 | @ P/Po = 0.237989353 | 0.6359 | 0.8350 |
| SG132-10 | @ P/Po = 0.238576905 | 0.6794 | 0.8689 |
| SG132-100 | @ P/Po = 0.241960361 | 0.5518 | 0.7034 |
| SG132-10-US | @ P/Po = 0.225692889 | 0.5693 | 0.7510 |
| SG132-100-US | @ P/Po = 0.225935246 | 1.0983 | 1.4963 |
| G-10-US | | | 0.751 |
| G100-US | | | 1.496 |
| G132-US | | | 1.679 |
| WS132 | @ P/Po = 0.237823664 | 0.6582 | 0.8663 |
| WS132-10 | @ P/Po = 0.238612476 | 0.6191 | 0.7912 |
| WS132-100 | @ P/Po = 0.238398832 | 0.6255 | 0.8143 |
| A-1e | @ P/Po = 0.238098138 | 0.6518 | 0.8368 |
| A-5e | @ P/Po = 0.243184477 | 0.6263 | 0.7865 |
| A-10e | @ P/Po = 0.243163236 | 0.4899 | 0.6170 |
| A-50e | @ P/Po = 0.243225512 | 0.4489 | 0.5730 |
| G-1e | @ P/Po = 0.238496102 | 0.5489 | 0.7038 |
| G-5e | @ P/Po = 0.242792602 | 0.5621 | 0.7086 |
| G-10e | @ P/Po = 0.243066031 | 0.5021 | 0.6363 |
| G-50e | @ P/Po = 0.238291132 | 0.4913 | 0.6333 |
| P-1e | @ P/Po = 0.240842223 | 1.1413 | 1.4442 |
| P-5e | @ P/Po = 0.240789274 | 1.0187 | 1.3288 |
| P-10e | @ P/Po = 0.240116967 | 1.1015 | 1.3657 |
| P-50e | @ P/Po = 0.240072114 | 1.0089 | 1.2593 |
| P-100e | @ P/Po = 0.236541386 | 0.9116 | 1.1677 |
| S | @ P/Po = 0.225335038 | 0.0147 | 0.0279 |
| S-1e | @ P/Po = 0.217142291 | 0.0193 | 0.0372 |
| S-5e | @ P/Po = 0.133107838 | 0.0201 | 0.0485 |
| S-10e | @ P/Po = 0.244886517 | 0.0236 | 0.0317 |
| S-30e | @ P/Po = 0.237929400 | 0.0309 | 0.0428 |
| S-50e | @ P/Po = 0.245494494 | 0.0262 | 0.0365 |
| S-100e | @ P/Po = 0.224698551 | 0.0368 | 0.0506 |
| St | @ P/Po = 0.238324949 | 0.3126 | 0.4013 |
| St-1e | @ P/Po = 0.238432726 | 0.3254 | 0.4223 |
| St-5e | @ P/Po = 0.238363587 | 0.3106 | 0.4071 |
| St-10e | @ P/Po = 0.238341099 | 0.3205 | 0.4268 |
| St-30e | @ P/Po = 0.238629889 | 0.3118 | 0.4189 |
| St-50e | @ P/Po = 0.244630980 | 0.3119 | 0.3969 |
| St-100e | @ P/Po = 0.238421621 | 0.2932 | 0.3677 |

The BET model for isotherms is a widely used theory for calculating the specific surface area. The analysis involves determining the monolayer capacity of the sample surface by calculating the amount required to cover the entire surface with a single densely packed layer of krypton. The monolayer capacity is multiplied by the cross sectional area of a molecule of probe gas to determine the total surface area. Specific surface area is the surface area of the sample aliquot divided by the mass of the sample.

Example 19

Fiber Length Determination of Irradiated Materials

Fiber length distribution testing was performed in triplicate on the samples submitted using the Techpap MorFi LB01 system. The average fiber length and width are reported in Table 25.

TABLE 25

Summary of Lignocellulosic Fiber Length and Width Data

| Sample ID | Arithmetic Average (mm) | Average Length Weighted in Length (mm) | Statistically Corrected Average Length Weighted in Length (mm) | Width (micrometers) (μm) |
|---|---|---|---|---|
| P132-10 | 0.484 | 0.615 | 0.773 | 24.7 |
| P132-100 | 0.369 | 0.423 | 0.496 | 23.8 |
| P132-181 | 0.312 | 0.342 | 0.392 | 24.4 |
| A132-10 | 0.382 | 0.423 | 0.650 | 43.2 |
| A132-100 | 0.362 | 0.435 | 0.592 | 29.9 |
| SG132-10 | 0.328 | 0.363 | 0.521 | 44.0 |
| SG132-100 | 0.325 | 0.351 | 0.466 | 43.8 |
| WS132-10 | 0.353 | 0.381 | 0.565 | 44.7 |
| WS132-100 | 0.354 | 0.371 | 0.536 | 45.4 |

Example 20

Ultrasonic Treatment of Irradiated and Un-Irradiated Switchgrass

Switchgrass was sheared according to Example 4. The switchgrass was treated by ultrasound alone or irradiation with 10 Mrad or 100 Mrad of gamma rays, and then sonicated. The resulting materials correspond to G132-BR (un-irradiated), G132-10-BR (10 Mrad and sonication) and G132-100-BR (100 Mrad and sonication), as presented in Table 1. Sonication was performed on each sample for 30 minutes using 20 kHz ultrasound from a 1000 W horn under re-circulating conditions. Each sample was dispersed in water at a concentration of about 0.10 g/mL.

Figure 32:
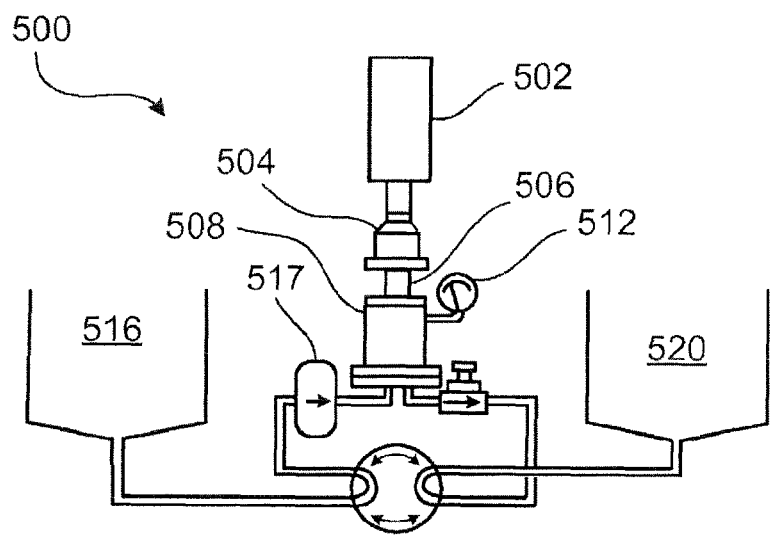
Figure 33:
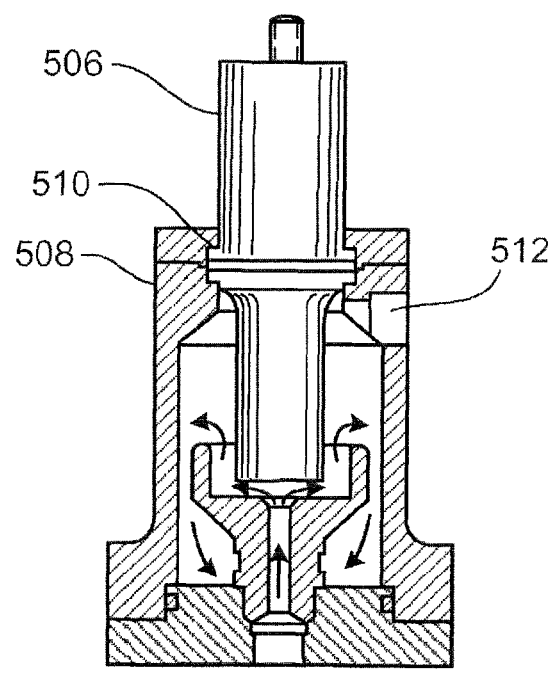
FIG. 33 is a cross-sectional view through the processing cell of FIG. 32.

FIGS. 32 and 33 show the apparatus used for sonication. Apparatus 500 includes a converter 502 connected to booster 504 communicating with a horn 506 fabricated from titanium or an alloy of titanium. The horn, which has a seal 510 made from VITON® about its perimeter on its processing side, forms a liquid tight seal with a processing cell 508. The processing side of the horn is immersed in a liquid, such as water, that has dispersed therein the sample to be sonicated. Pressure in the cell is monitored with a pressure gauge 512. In operation, each sample is moved by pump 517 from tank 516 through the processing cell and is sonicated. After, sonication, the sample is captured in tank 520. The process can be reversed in that the contents of tank 520 can be sent through the processing cell and captured in tank 516. This process can be repeated a number of times until a desired level of processing is delivered to the sample.

Example 21

Scanning Electron Micrographs of Un-Irradiated Switchgrass in Comparison to Irradiated and Irradiated and Sonicated Switchgrass Switchgrass samples for the scanning electron micrographs were applied to carbon tape and gold sputter coated (70 seconds). Images were taken with a JEOL 6500 field emission scanning electron microscope.

Figure 34:
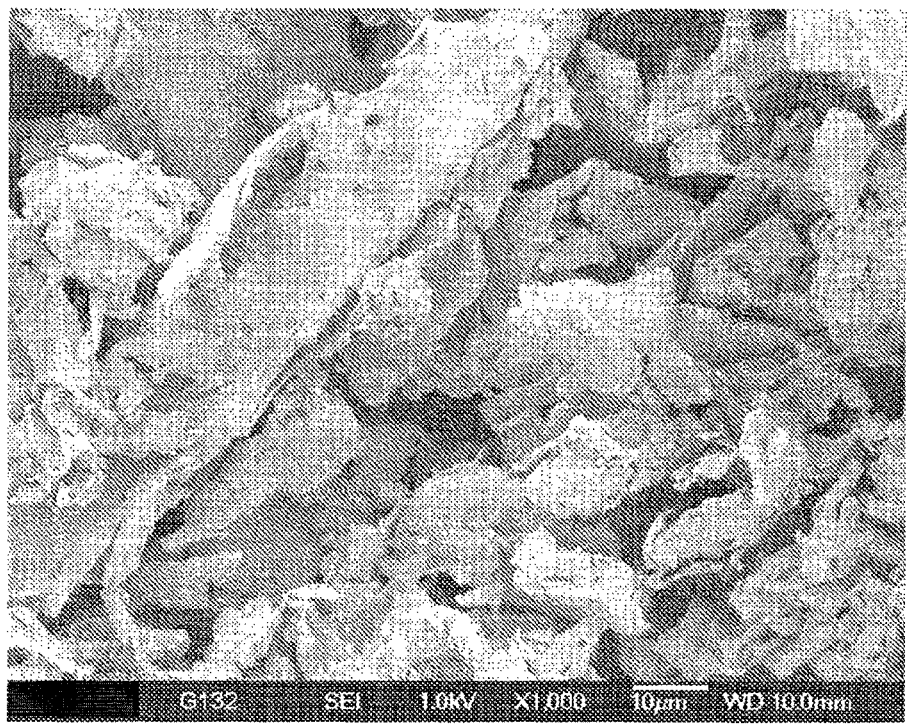
FIG. 34 is a scanning electron micrograph at 1000×
magnification of a fibrous material produced from shearing
switchgrass on a rotary knife cutter, and then passing the
sheared material through a ½₂ inch screen.

FIG. 34 is a scanning electron micrograph at 1000× magnification of a fibrous material produced from shearing switchgrass on a rotary knife cutter, and then passing the sheared material through a 1/32 inch screen.

Figure 35:
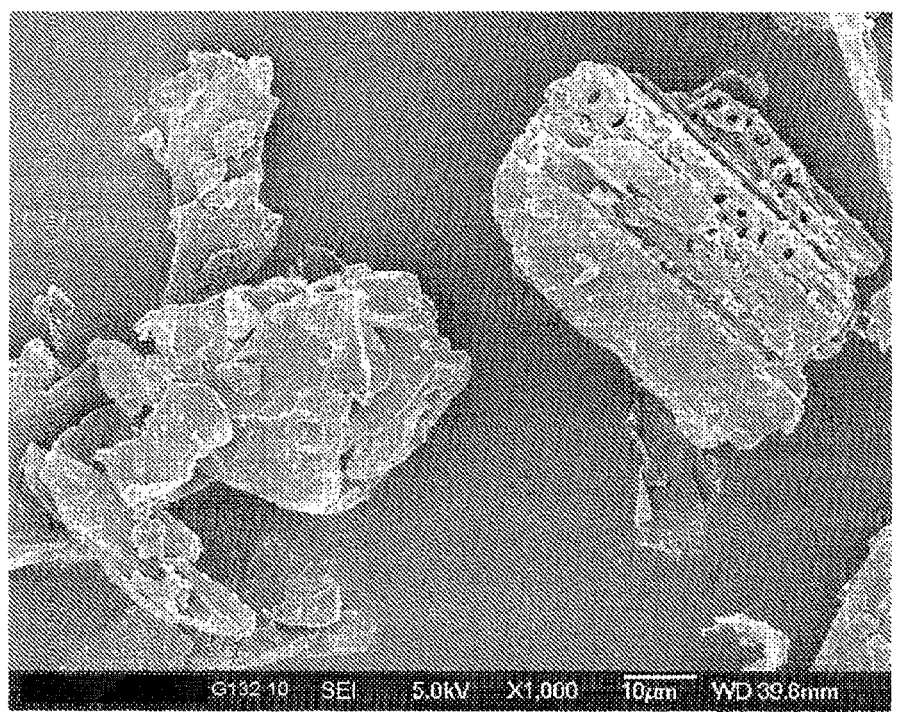
FIGS. 35 and 36 are scanning electron micrographs of the
fibrous material of FIG. 34 after irradiation with 10 Mrad
and 100 Mrad gamma rays, respectively, at 1000× magnification.
Figure 36:
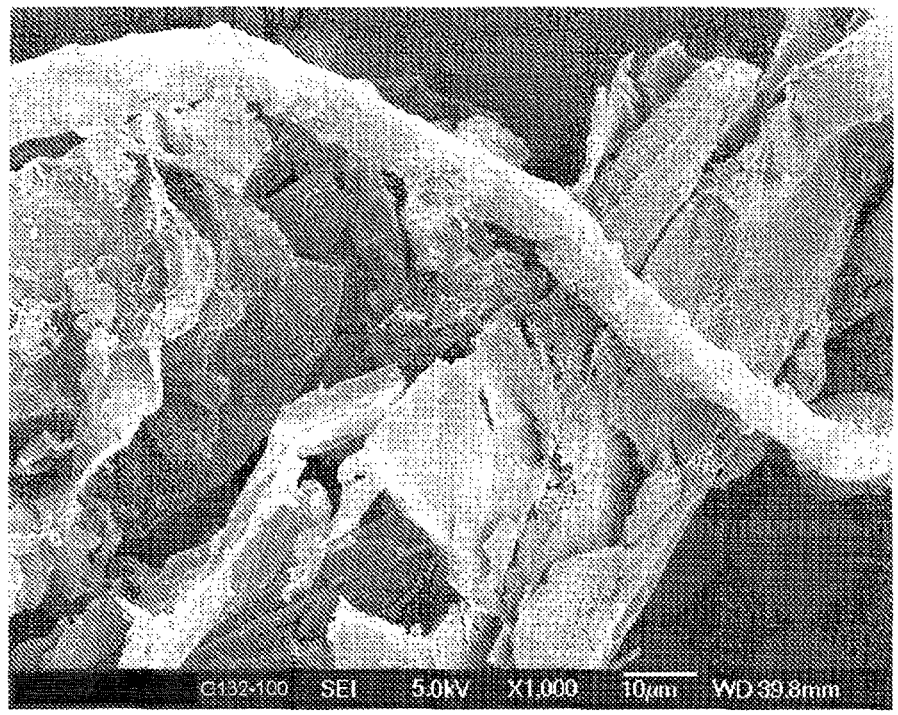

FIGS. 35 and 36 are scanning electron micrographs of the fibrous material of FIG. 34 after irradiation with 10 Mrad and 100 Mrad gamma rays, respectively, at 1000× magnification.

Figure 37:
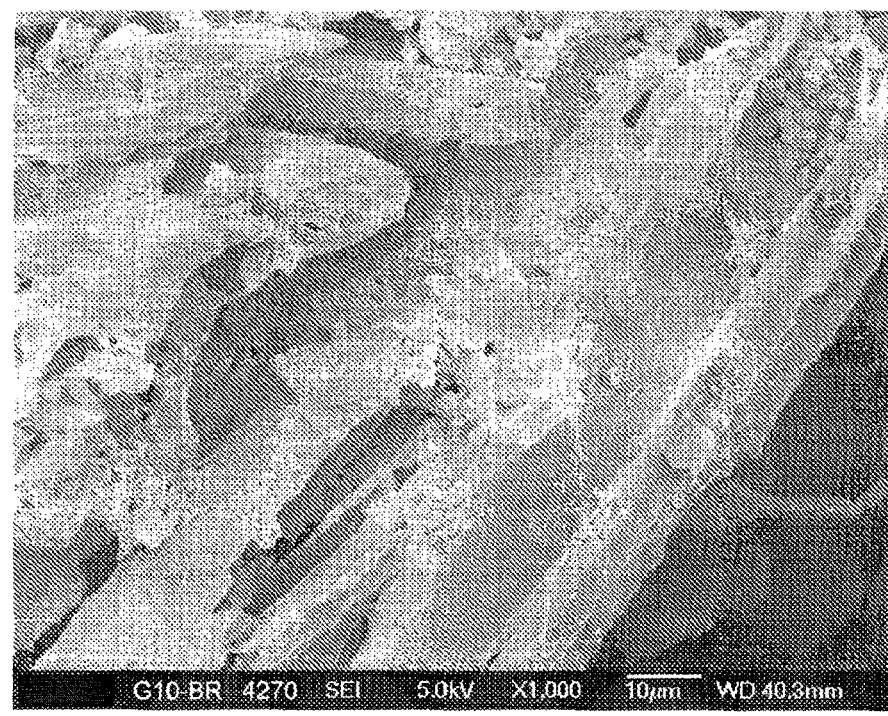
FIG. 37 is a scanning electron micrographs of the fibrous
material of FIG. 34 after irradiation with 10 Mrad and
sonication at 1000× magnification.

FIG. 37 is a scanning electron micrographs of the fibrous material of FIG. 34 after irradiation with 10 Mrad and sonication at 1000× magnification.

Figure 38:
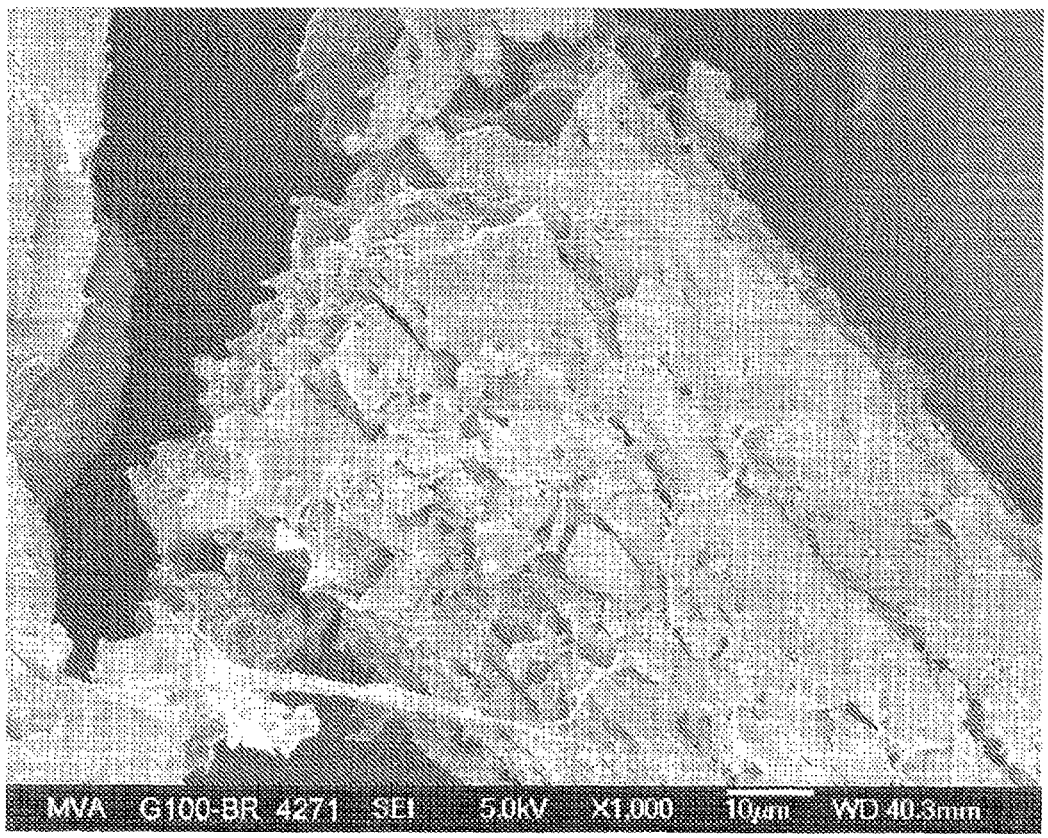
FIG. 38 is a scanning electron micrographs of the fibrous
material of FIG. 34 after irradiation with 100 Mrad and
sonication at 1000× magnification.

FIG. 38 is a scanning electron micrographs of the fibrous material of FIG. 34 after irradiation with 100 Mrad and sonication at 1000× magnification.

Example 22

Fourier Transform Infrared (FT-IR) Spectrum of Irradiated and Unirradiated Kraft Paper FT-IR analysis was performed on a Nicolet/Impact 400. The results indicate that samples P132, P132-10, P132-100, P-1e, P-5e, P-10e, P-30e, P-70e, and P-100e are consistent with a cellulose-based material.

Figure 39:
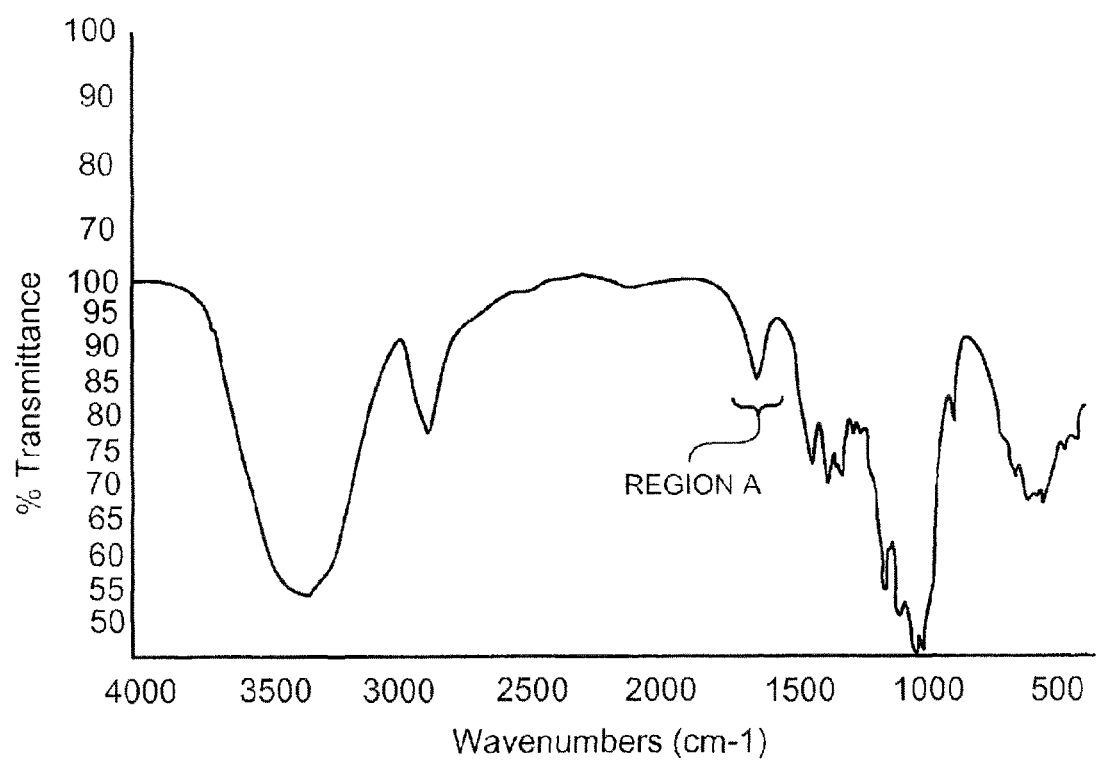
FIG. 39 is an infrared spectrum of Kraft board paper
sheared on a rotary knife cutter.
Figure 40:
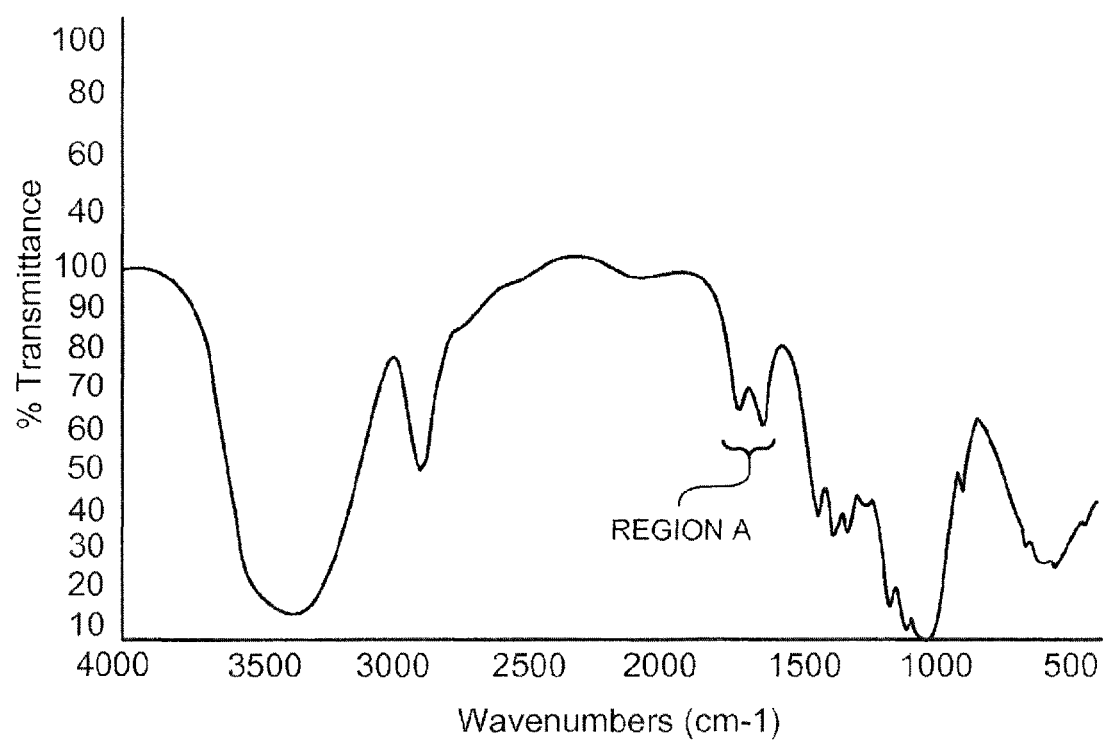
FIG. 40 is an infrared spectrum of the Kraft paper of FIG.
39 after irradiation with 100 Mrad of gamma radiation.
Figures 1, 40:
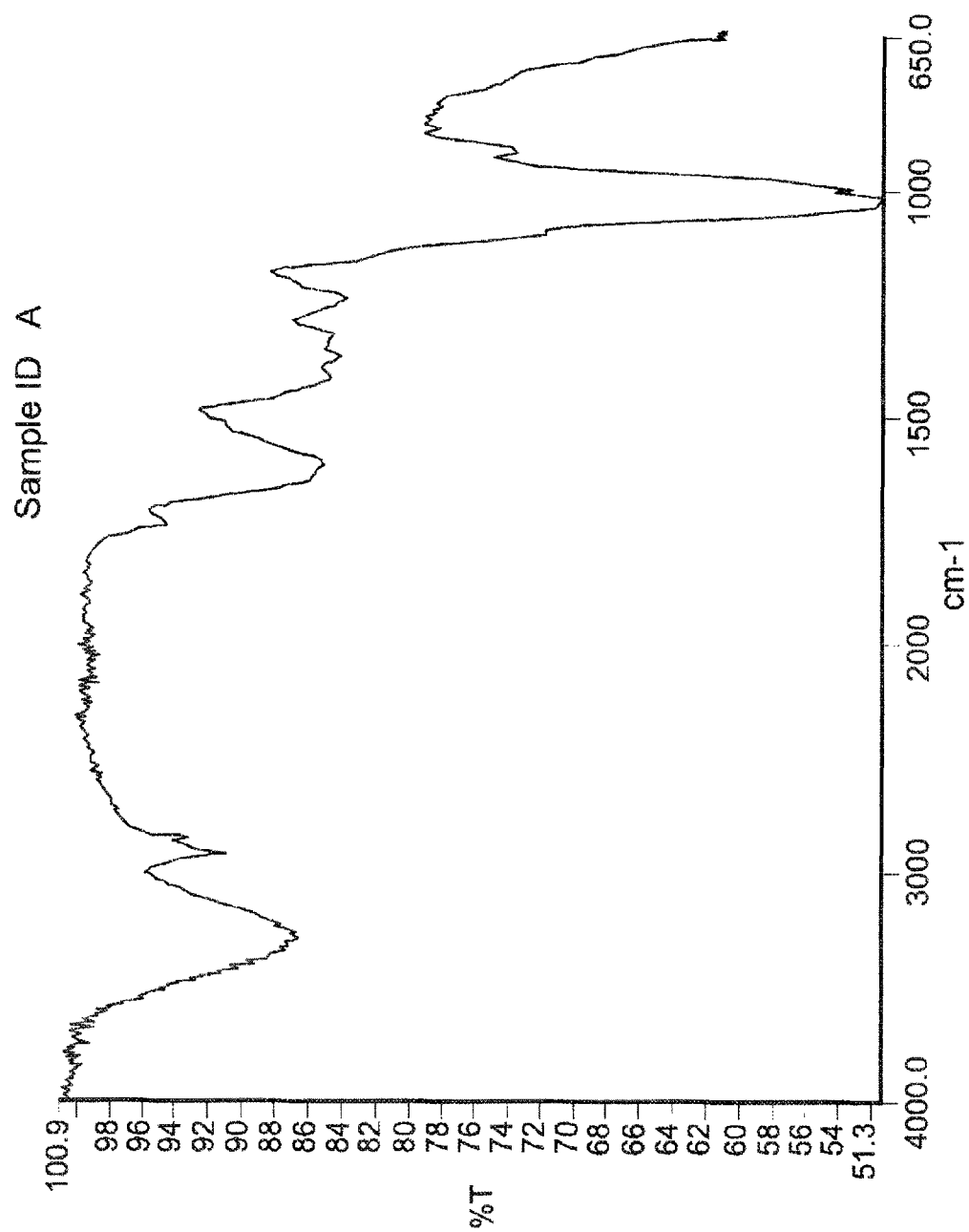
Figures 2, 40:
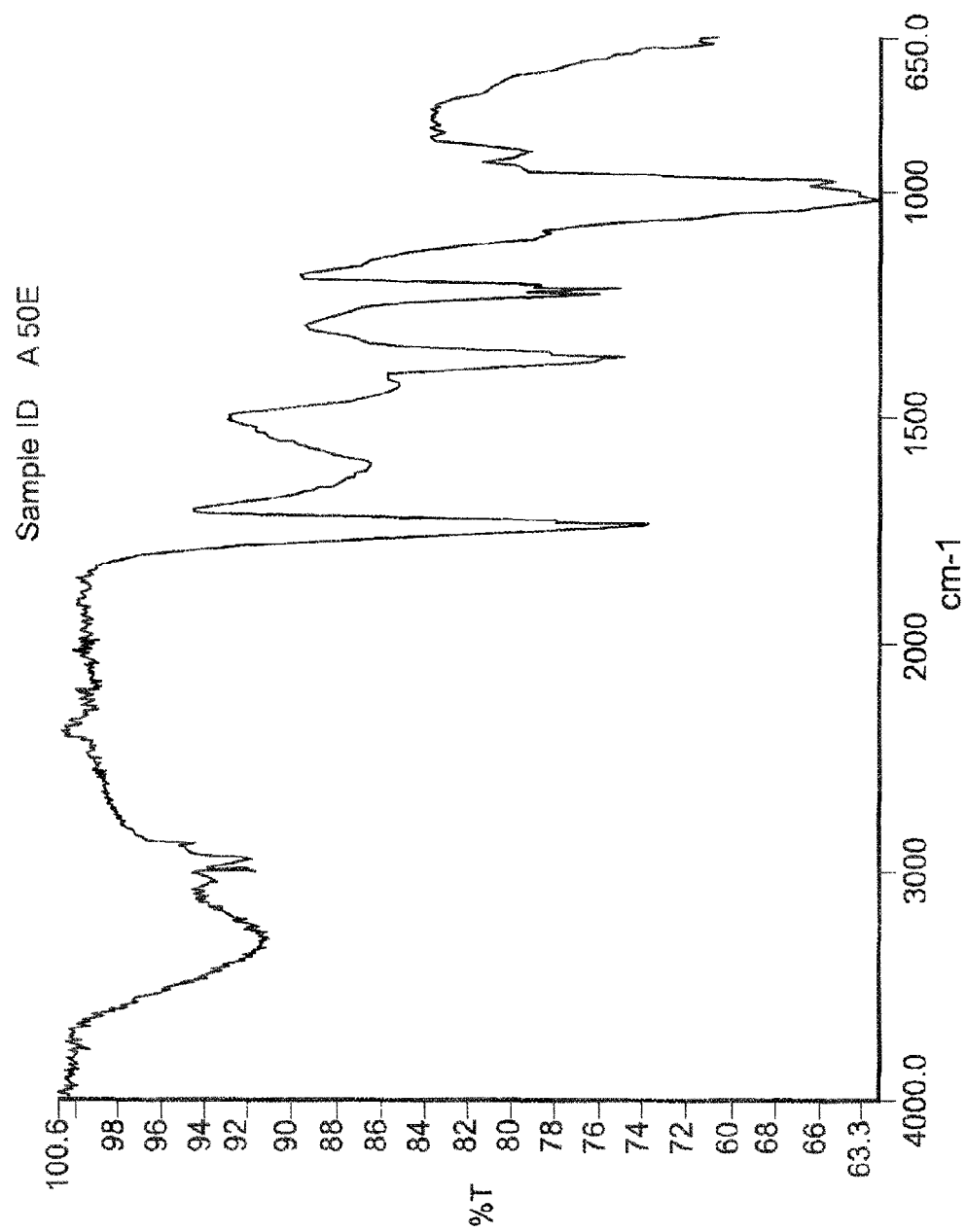
Figures 3, 40:
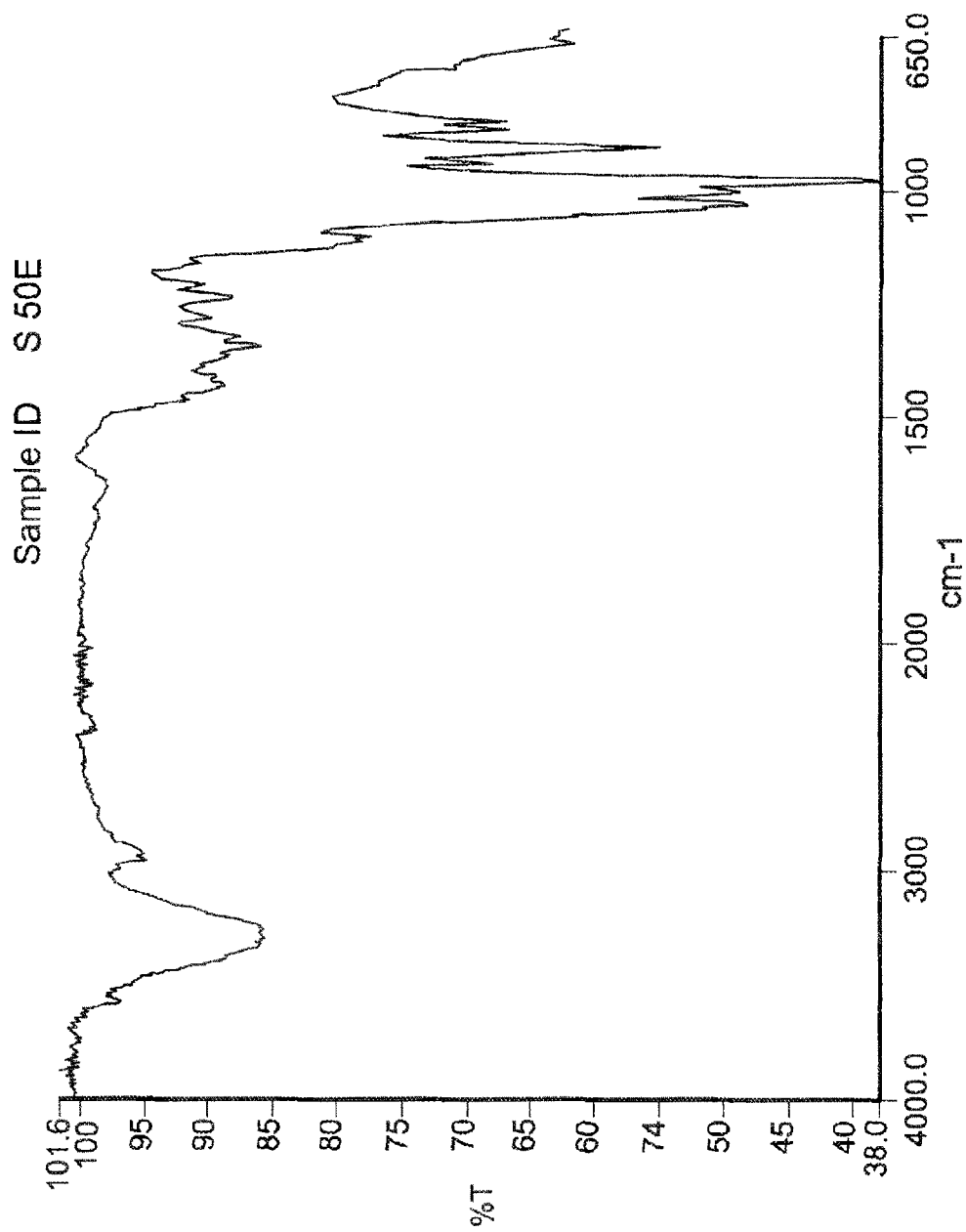
Figures 4, 40:
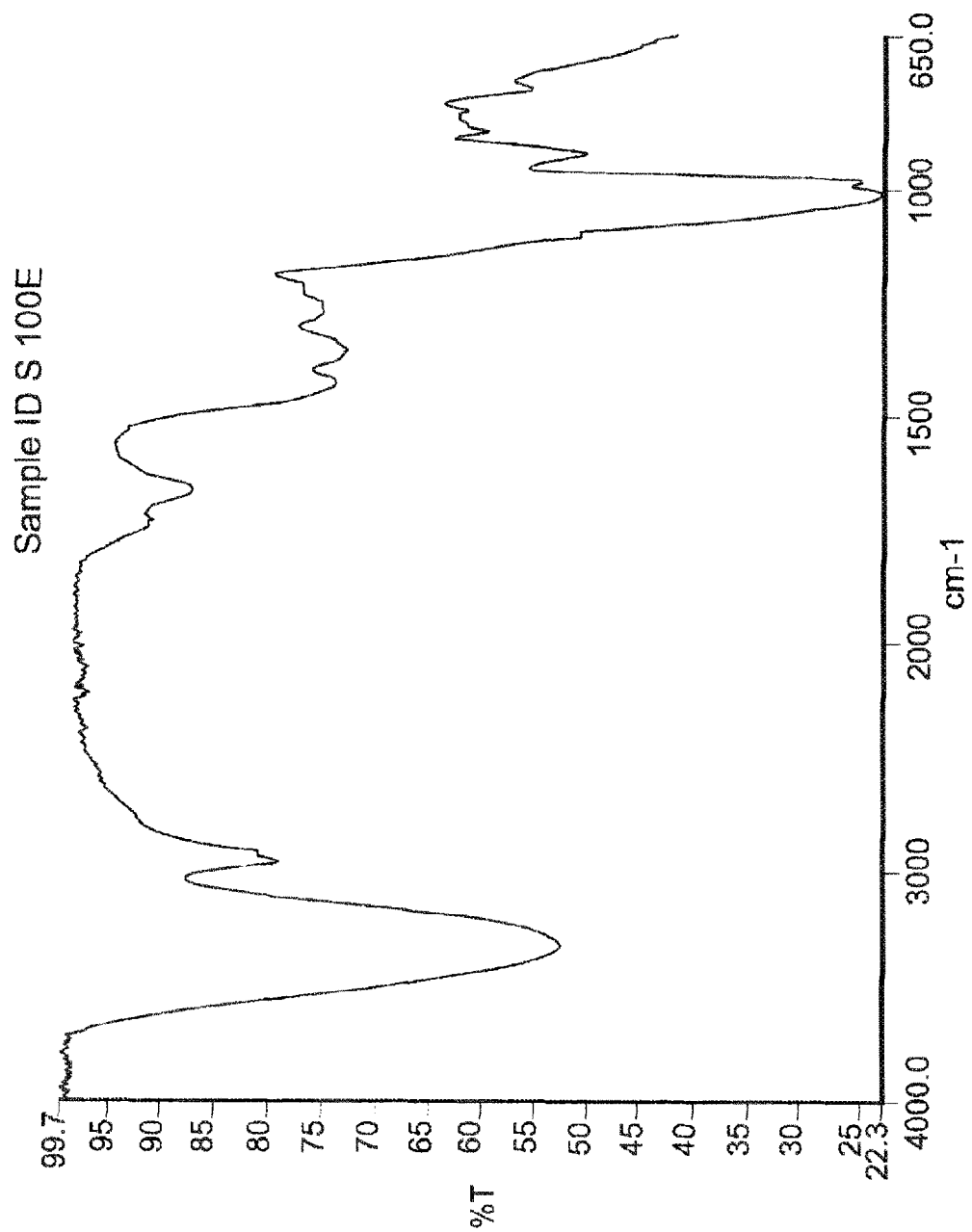
Figure 40A:
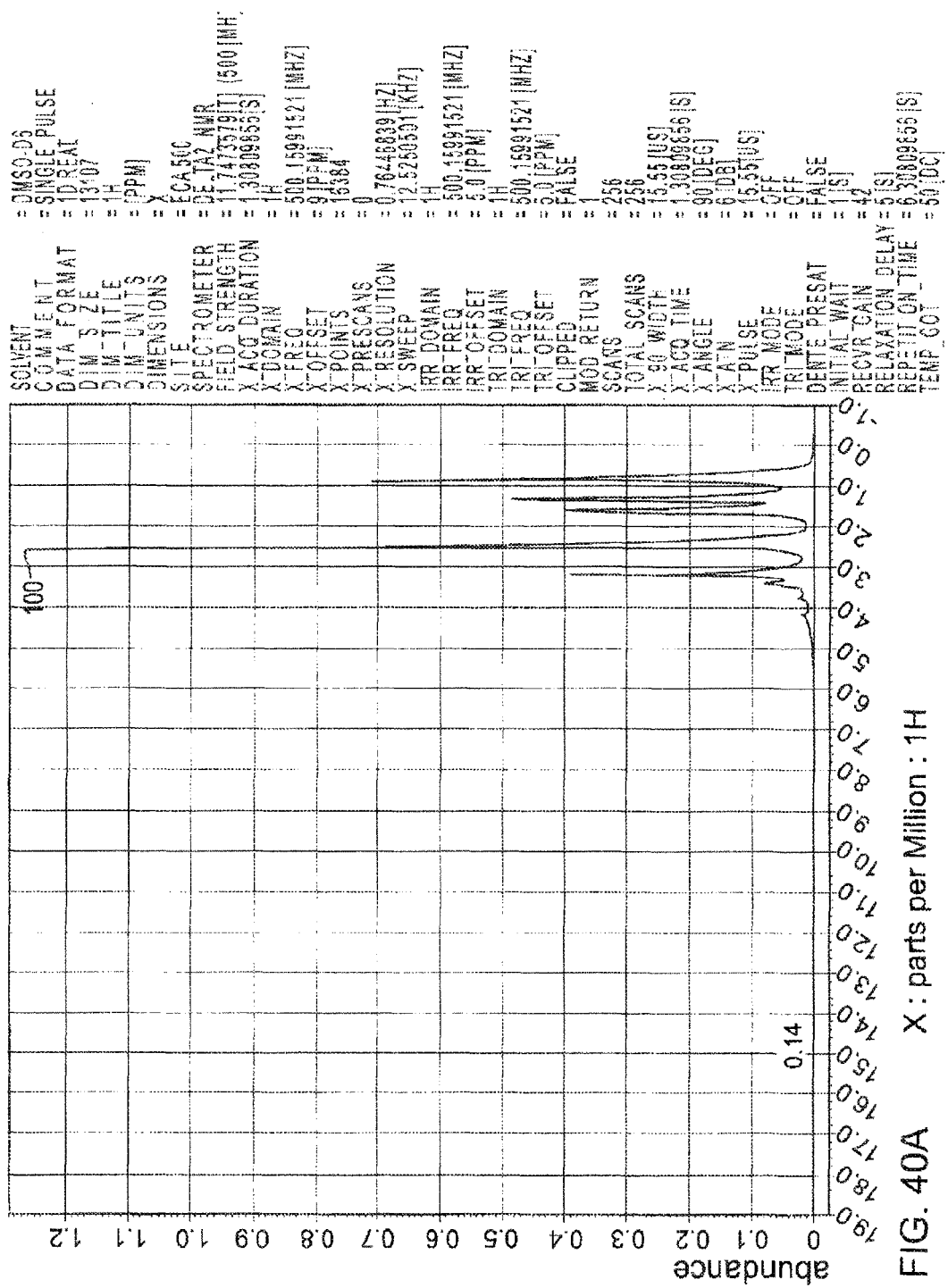
Figure 40B:
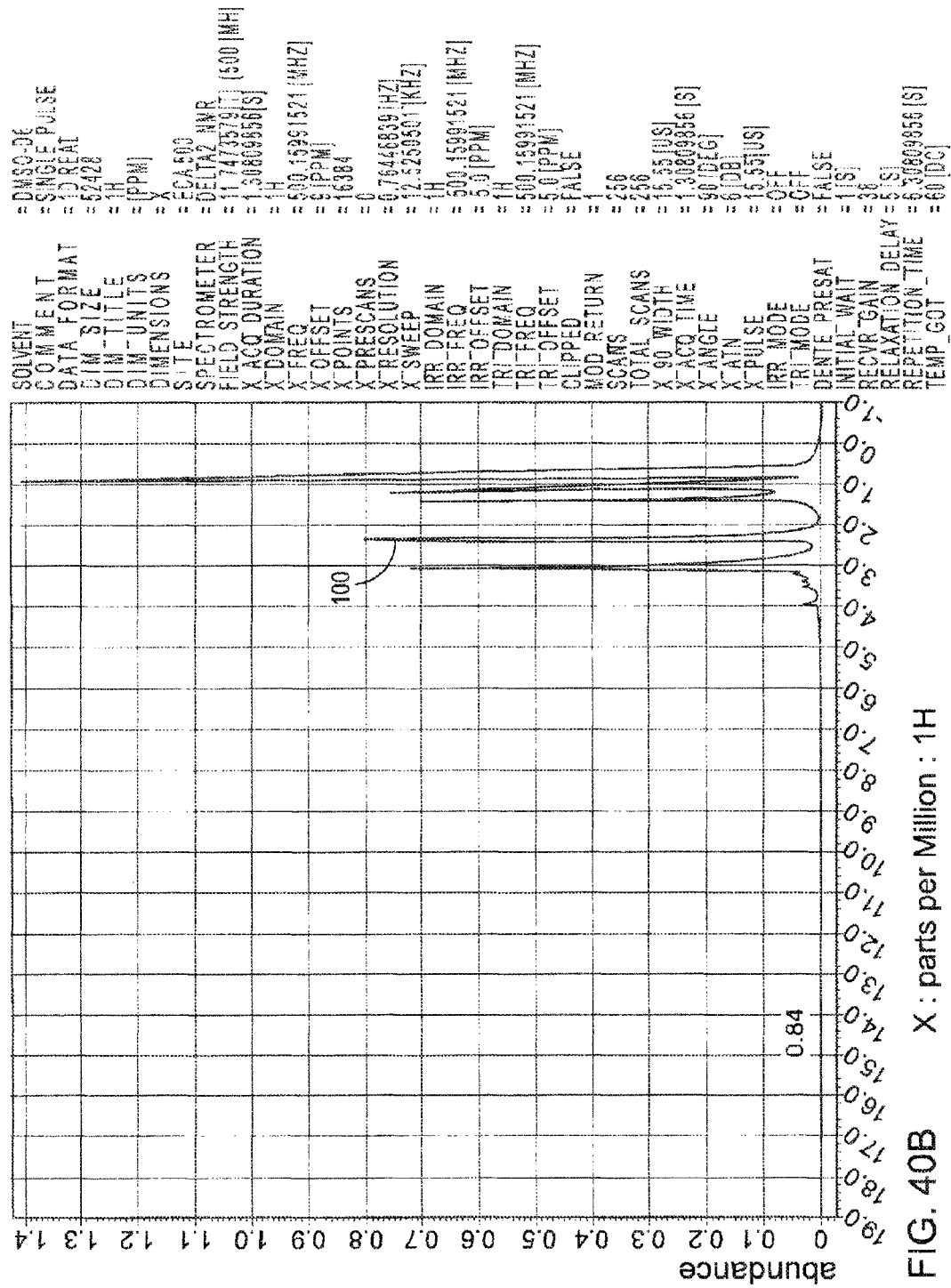
Figure 40C:
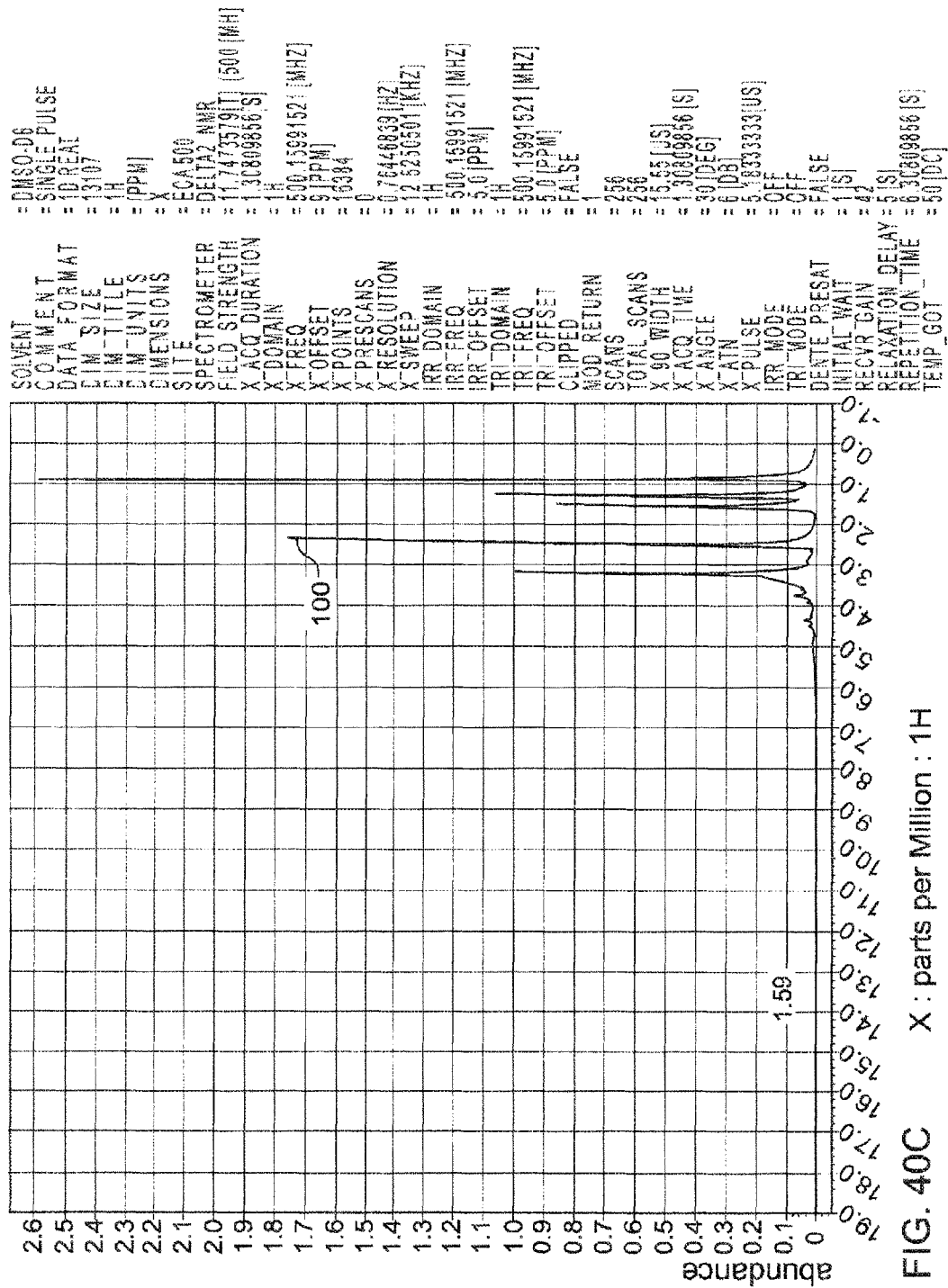
Figure 40D:
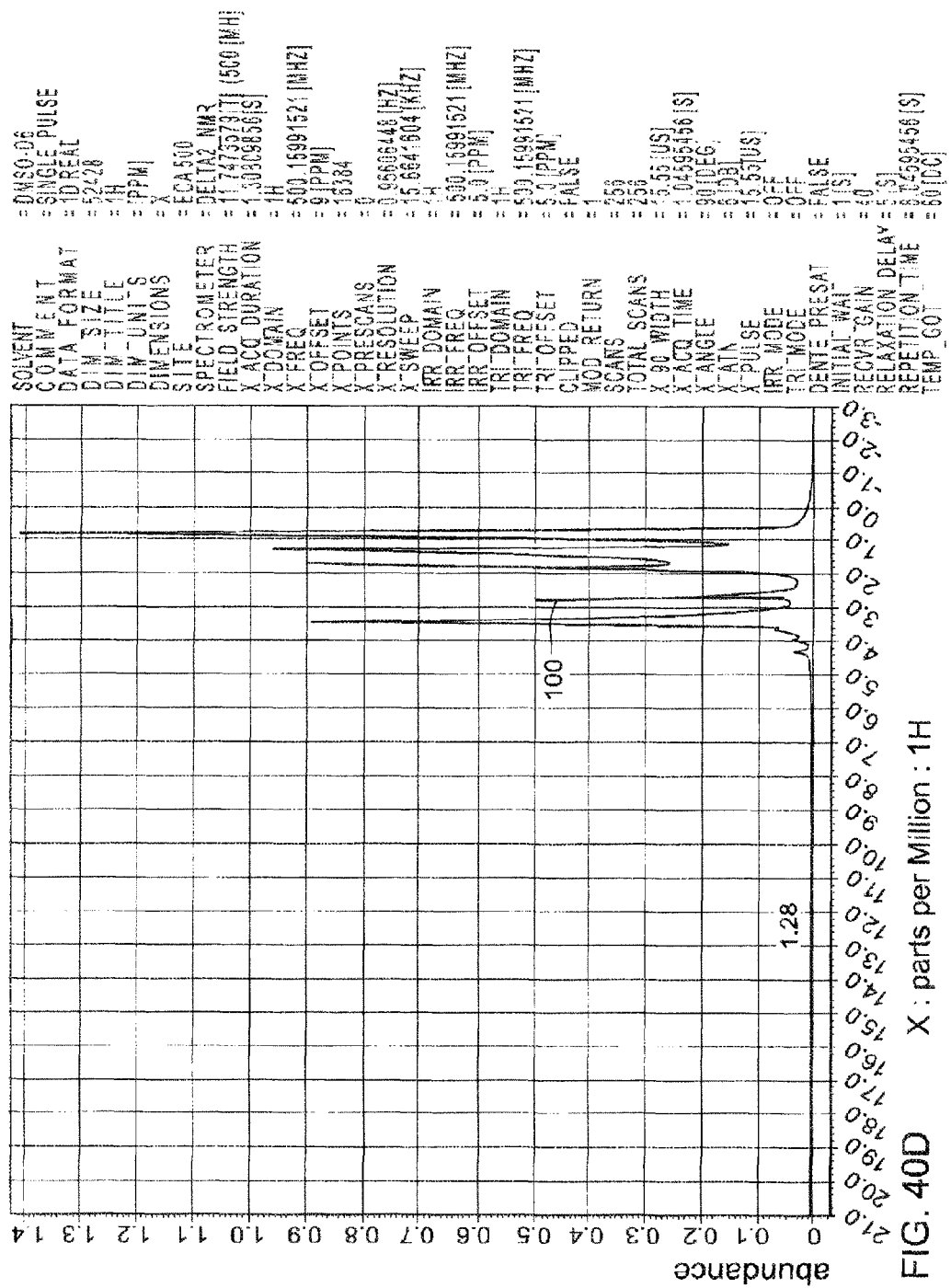
Figure 40E:
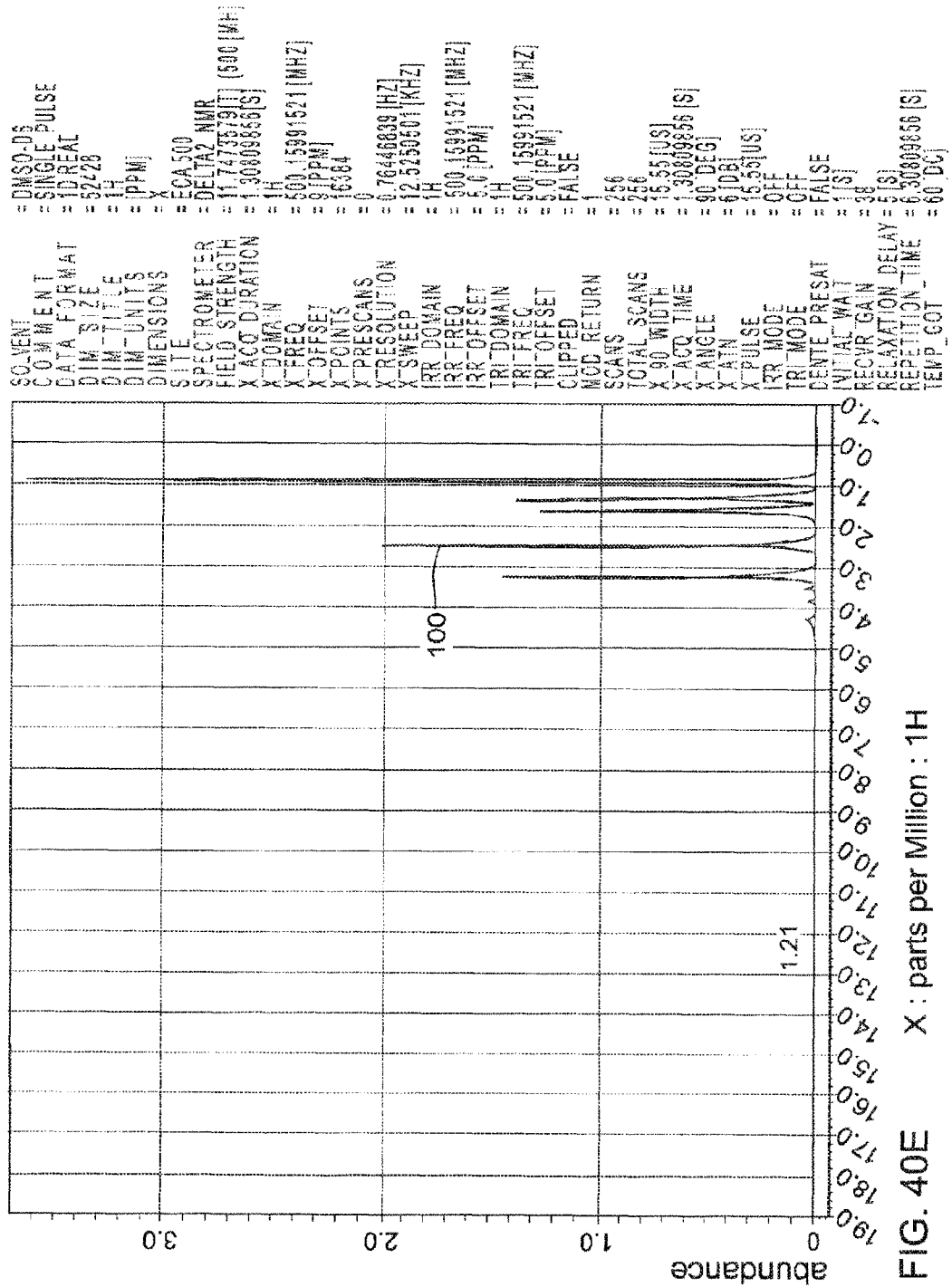
Figure 40F:
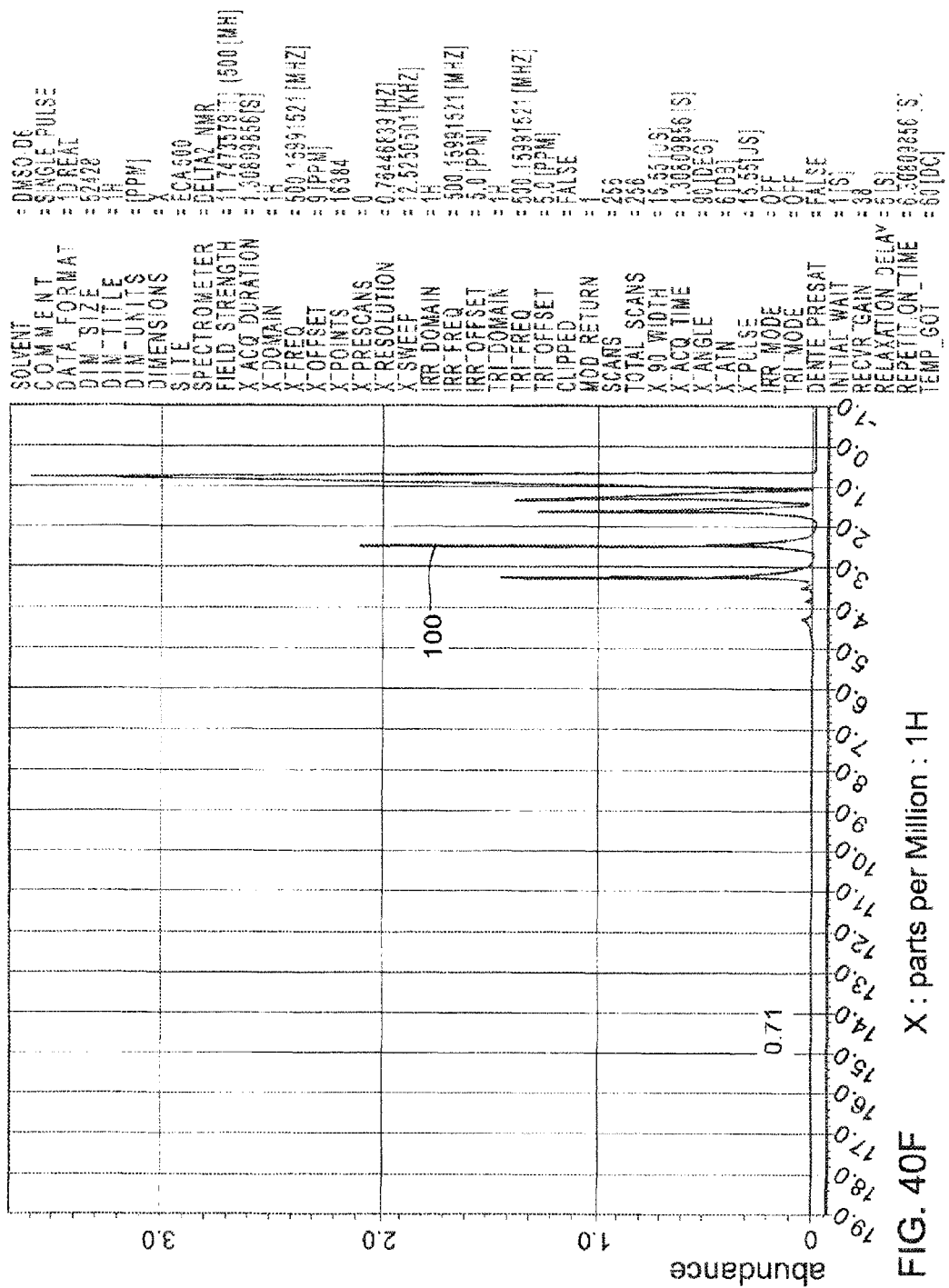
Figure 40G:
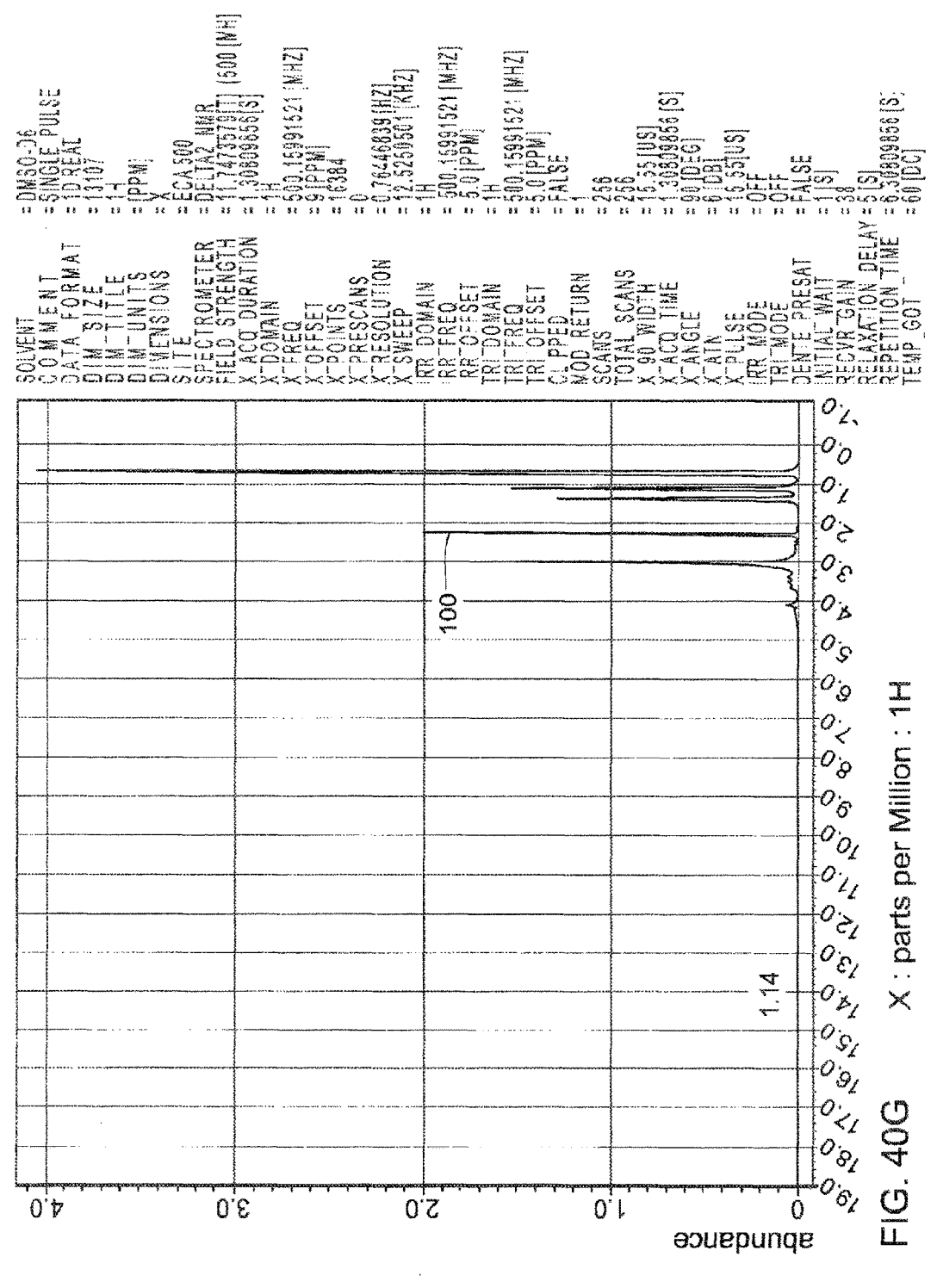
Figure 40H:
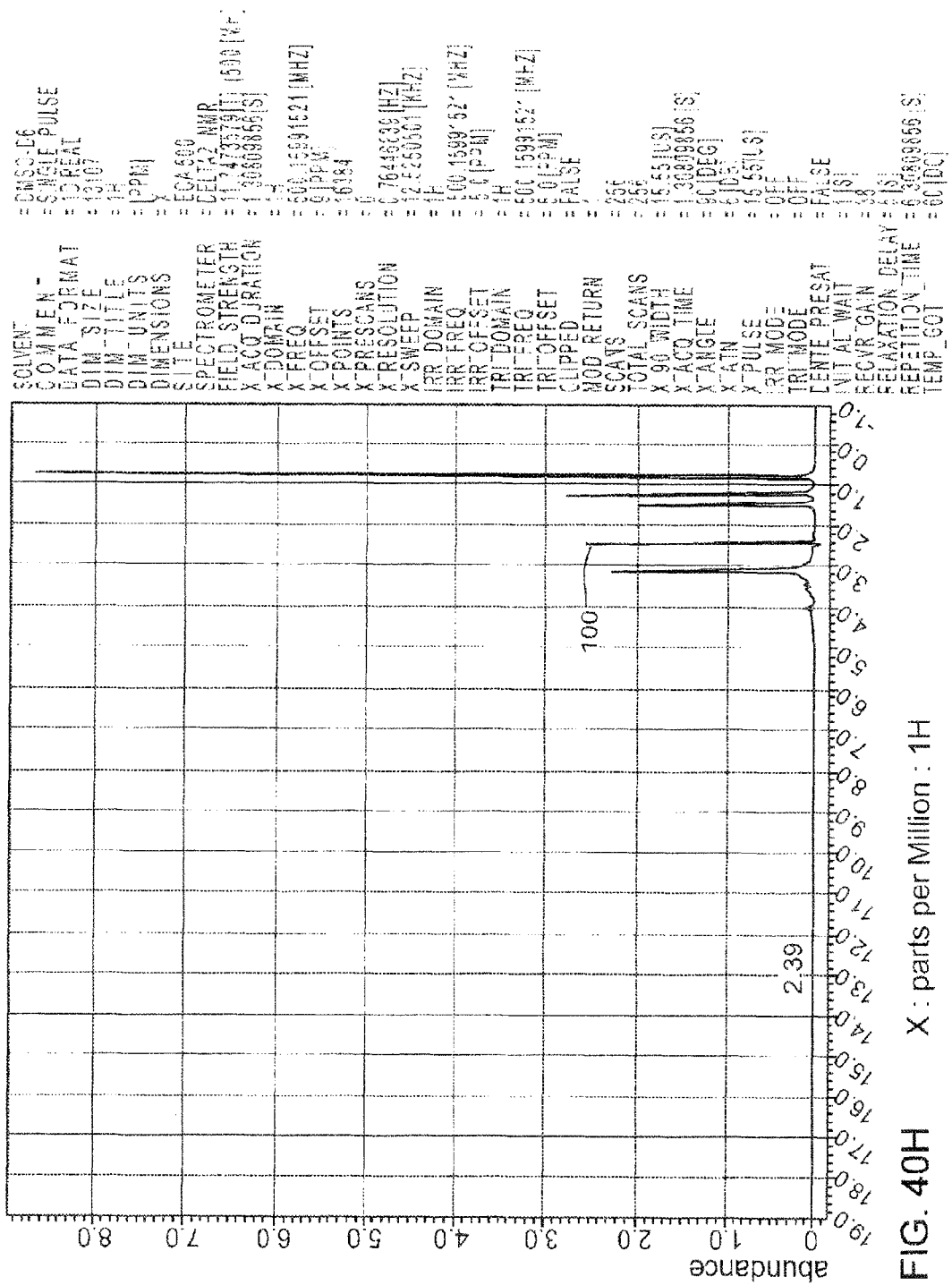
Figure 40:
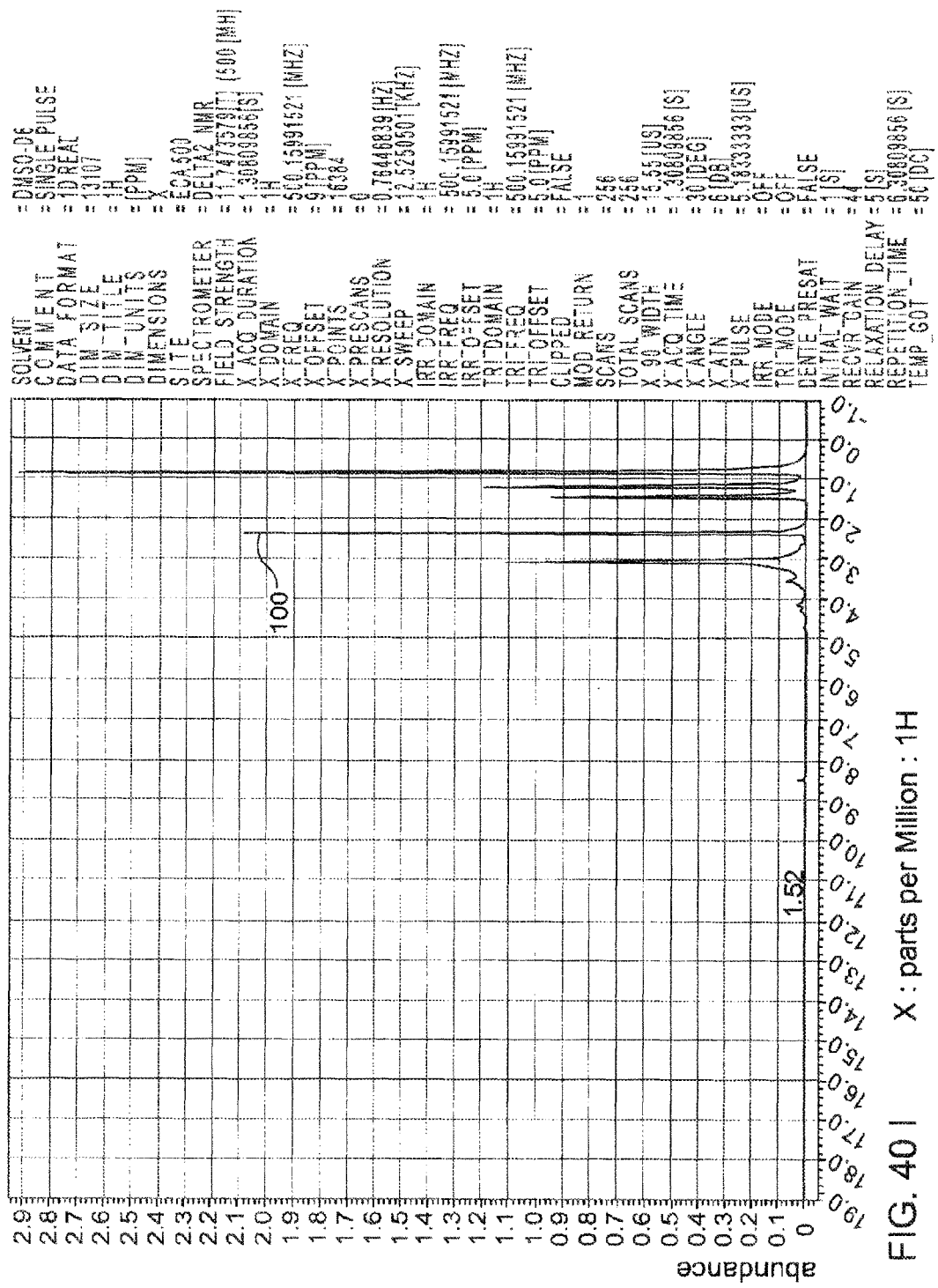
Figure 40:
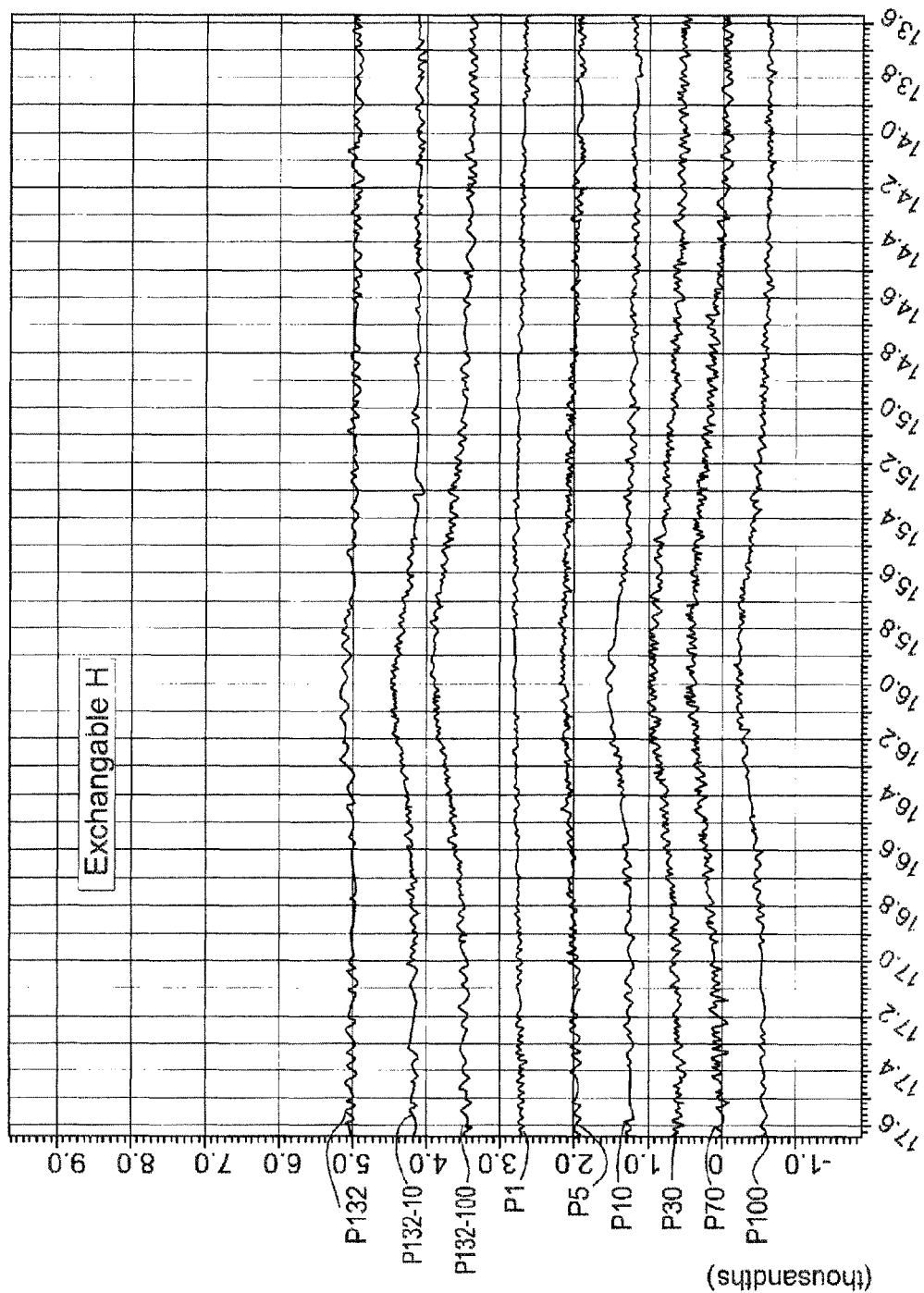

FIG. 39 is an infrared spectrum of Kraft board paper sheared according to Example 4, while FIG. 40 is an infrared spectrum of the Kraft paper of FIG. 39 after irradiation with 100 Mrad of gamma radiation. The irradiated sample shows an additional peak in region A (centered about 1730 cm$^{-1}$) that is not found in the unirradiated material. Of note, an increase in the amount of a carbonyl absorption at ~1650 cm$^{-1}$ was detected when going from P132 to P132-10 to P132-100. Similar results were observed for the samples P-1e, P-5e, P-10e, P-30e, P-70e, and P-100e.

FIGS. 40-1 to 40-4 are infrared spectra of alfalfa (A), alfalfa irradiated at 50e (A-50e), sucrose irradiated at 50e (S-50e), and sucrose irradiated at 100e (S-100e), respectively. Of note, an increase in the amount of a carbonyl absorption at ~1650 cm-1 was detected for sample A-50e, as well as S-100e.

The alfalfa samples showed a small peak present at 1720 cm$^{-1}$ in the untreated sample, which grows to the most dominant peak in the A-50e spectrum. There was no significant change in the IR spectrum for sucrose. S-100e was the only spectrum which showed two small new peaks at 1713 and 1647 cm$^{-1}$.

Example 23

Proton and Carbon-13 Nuclear Magnetic Resonance ($^1$H-NMR and $^{13}$C-NMR) Spectra of Irradiated and Unirradiated Kraft Paper Sample Preparation The samples P132, 132-10, P132-100, P-1e, P-5e, P-10e, P-30e , P-70e , and P-100e were prepared for analysis by dissolution with DMSO-d$_6$ with 2% tetrabutyl ammonium fluoride trihydrate. The samples which had undergone lower levels of irradiation were significantly less soluble than the samples with higher irradiation. Unirradiated samples formed a gel in this solvent mixture, but heating to 60° C. resolved the peaks in the NMR spectra. The samples having undergone higher levels of irradiation were soluble at a concentration of 10% wt/wt.

Analysis $^1$H-NMR spectra of the samples at 15 mg/mL showed a distinct very broad resonance peak centered at 16 ppm (FIGS. 40A-40J). This peak is characteristic of an exchangeable —OH proton for an enol and was confirmed by a "D$_2$O shake." Model compounds (acetylacetone, glucuronic acid, and keto-gulonic acid) were analyzed and made a convincing case that this peak was indeed an exchangeable enol proton. This proposed enol peak was very sensitive to concentration effects, and we were unable to conclude whether this resonance was due to an enol or possibly a carboxylic acid.

Figure 40K:
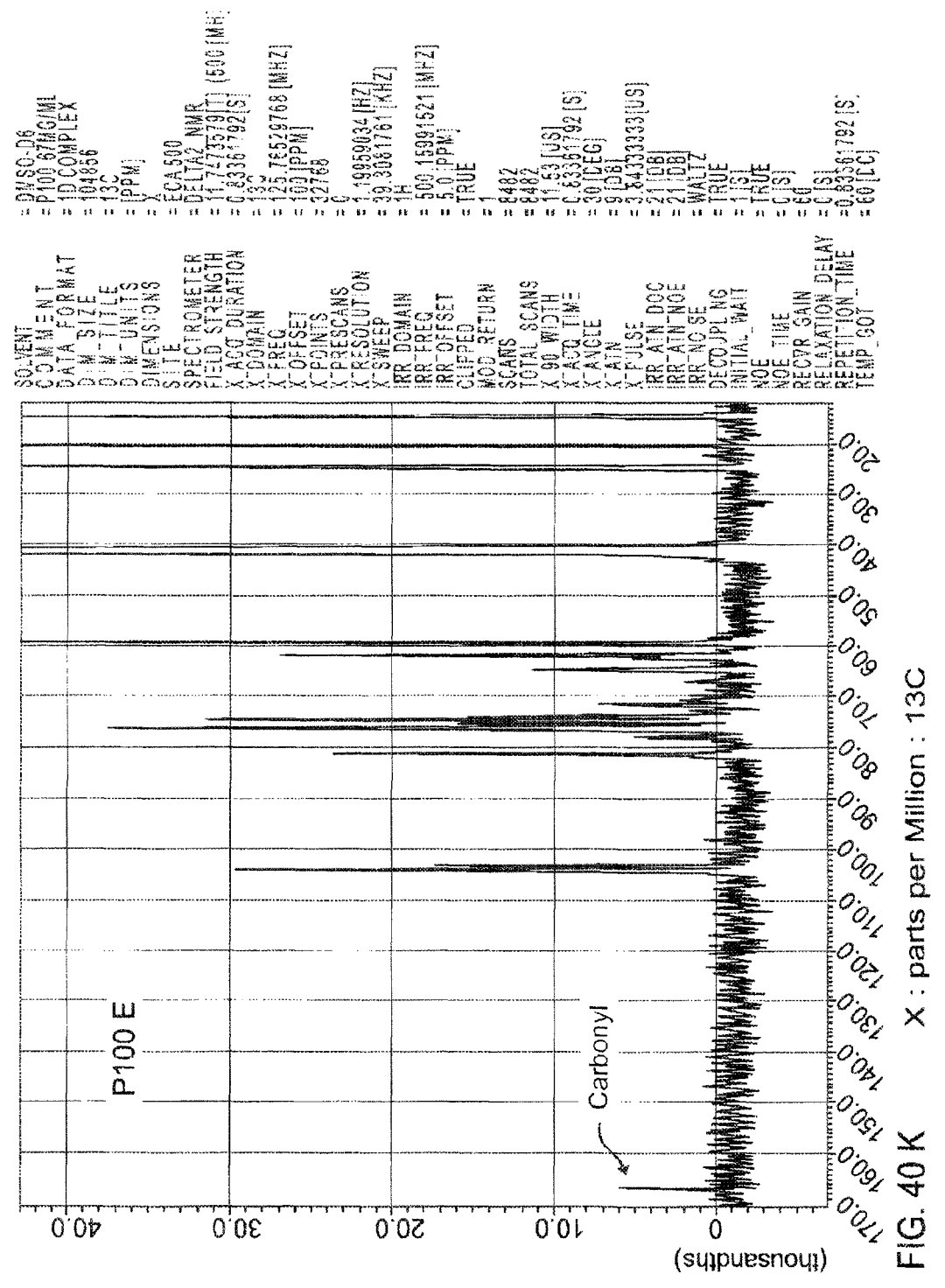
Figure 40L:
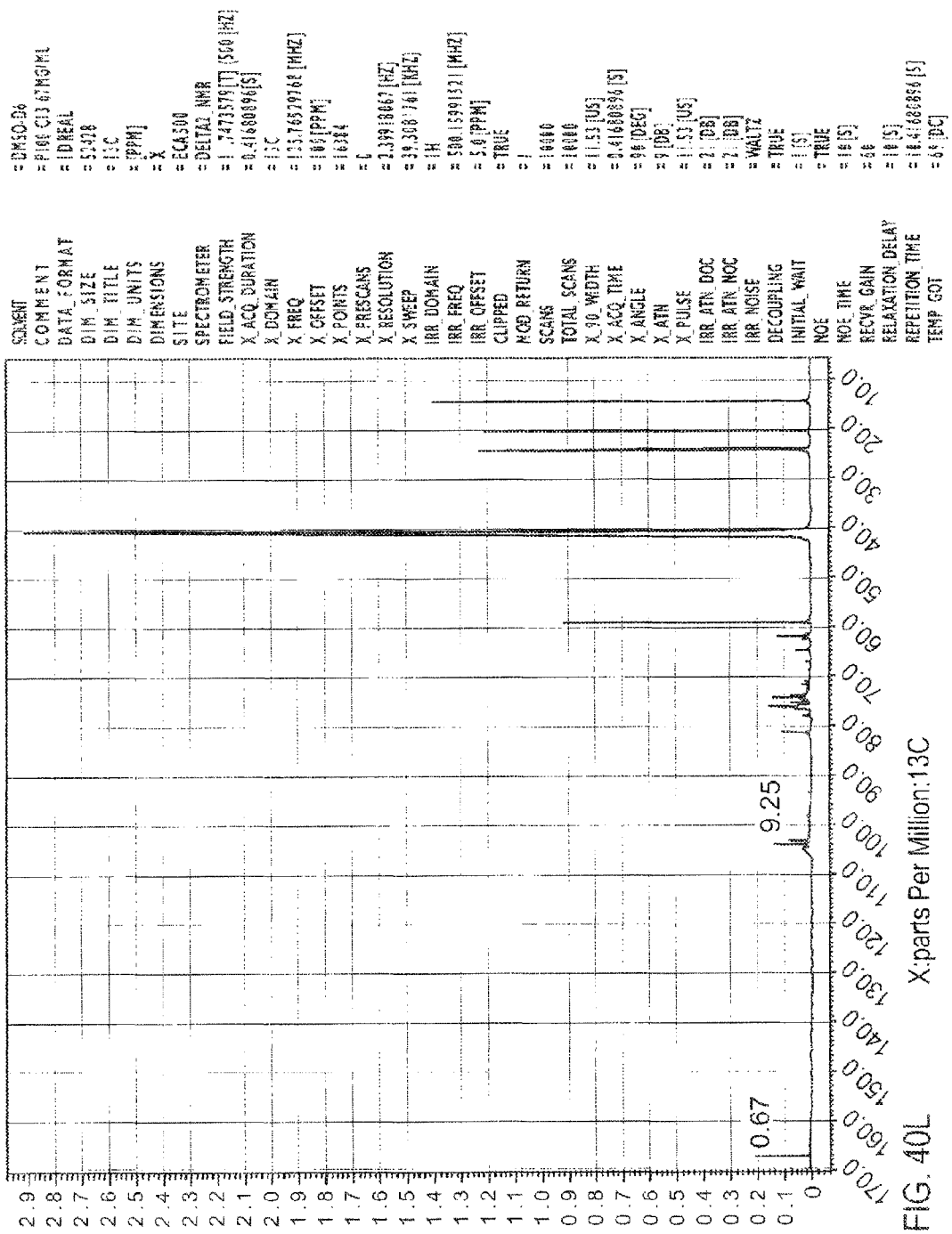
FIGS. 40L-40M are $^{13}$C-NMR
of sample P-100e with a delay time of 10 seconds.
Figure 40M:
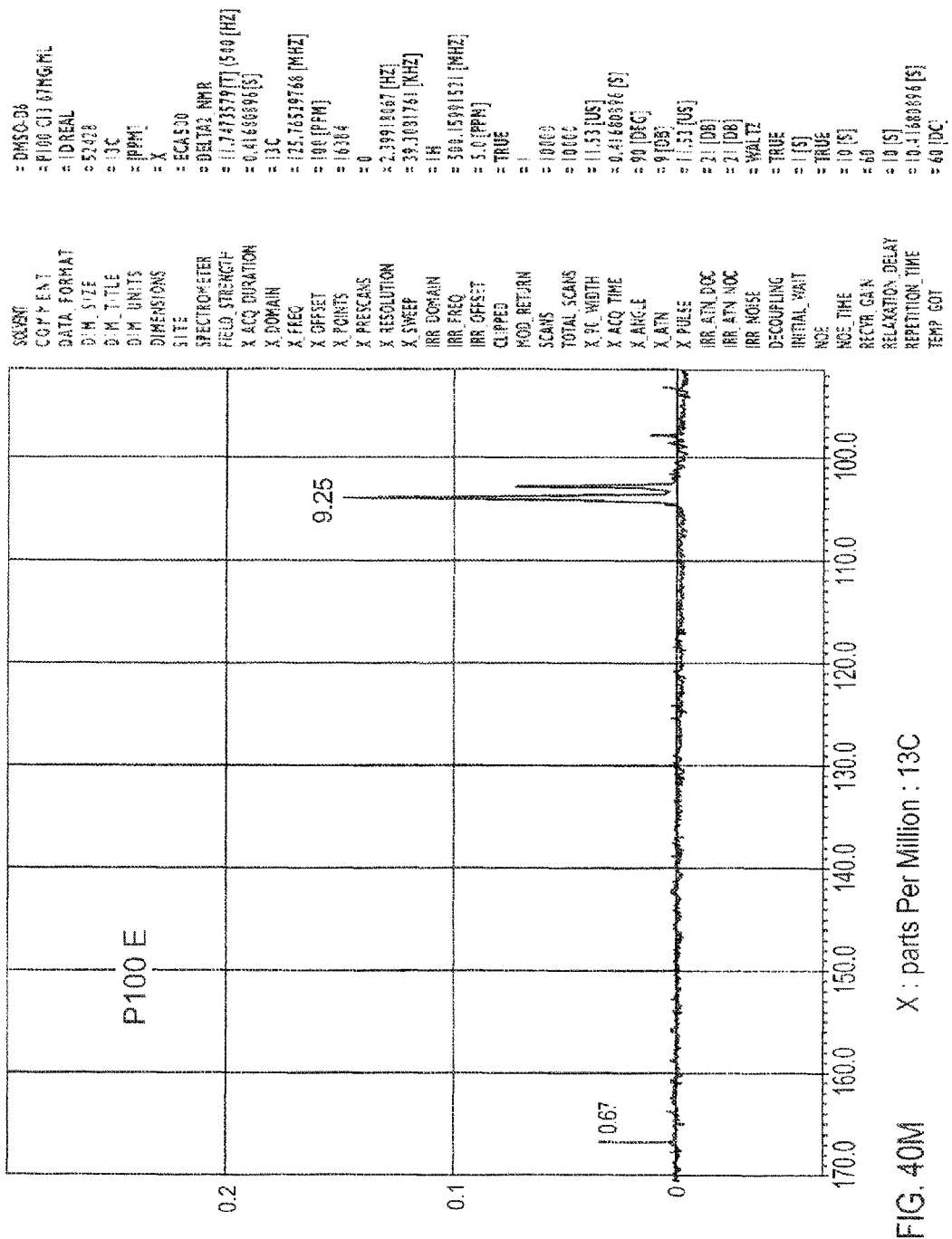
Figure 40N:
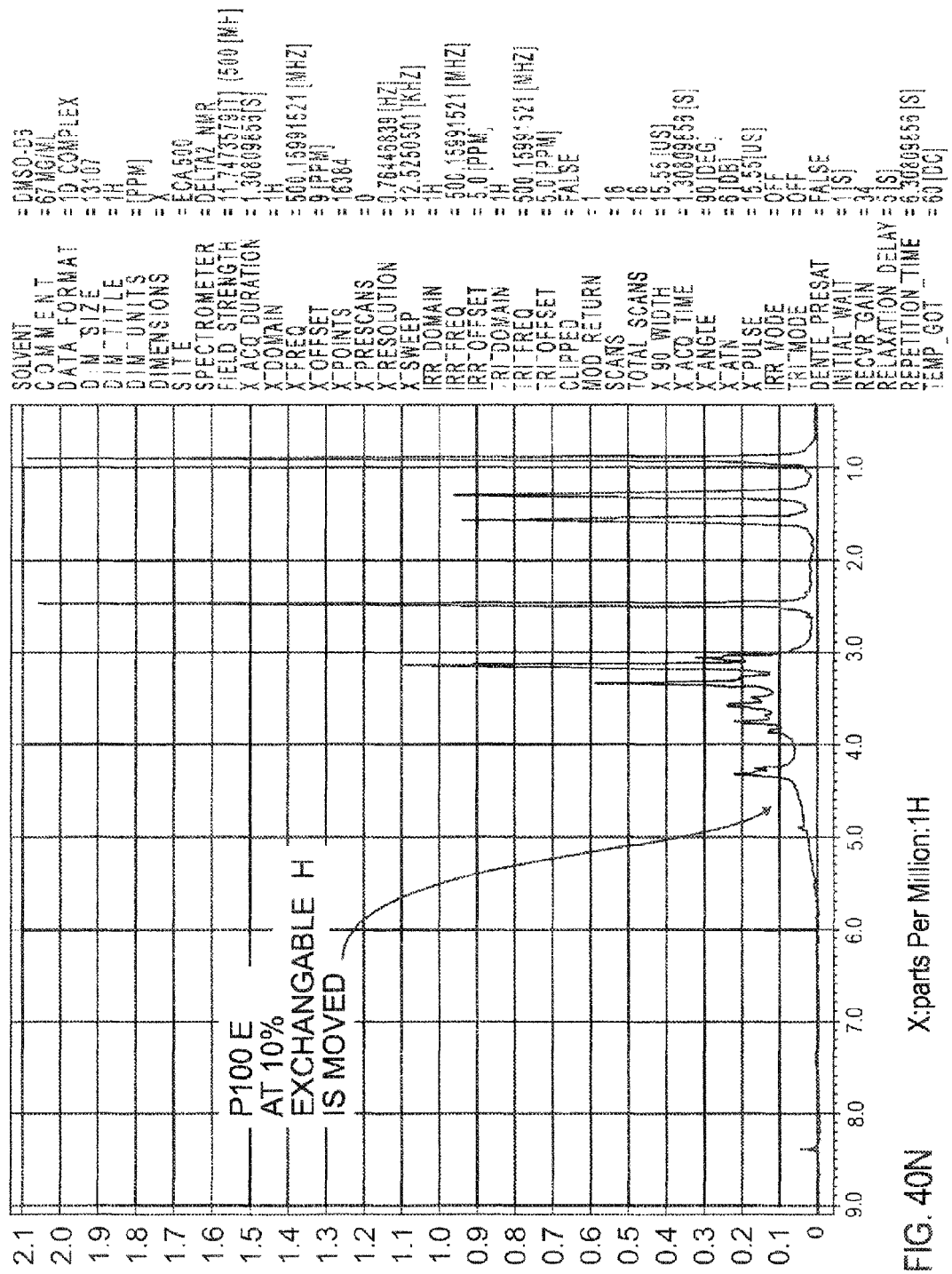
FIG. 40N
is a $^1$H-NMR at a concentration of 10% wt./wt. of sample
P-100e.

The carboxylic acid proton resonances of the model compounds were similar to what was observed for the treated cellulose samples. These model compounds were shifted up field to ~5-6 ppm. Preparation of P-100e at higher concentrations (~10% wt/wt) led to the dramatic down field shifting to where the carboxylic acid resonances of the model compounds were found (~6 ppm) (FIG. 40N). These results lead to the conclusion that this resonance is unreliable for characterizing this functional group, however the data suggests that the number of exchangeable hydrogens increases with increasing irradiation of the sample. Also, no vinyl protons were detected.

The $^{13}C$ NMR spectra of the samples confirm the presence of a carbonyl of a carboxylic acid or a carboxylic acid derivative. This new peak (at 168 ppm) is not present in the untreated samples (FIG. 40K). A $^{13}C$ NMR spectrum with a long delay allowed the quantitation of the signal for P-100e (FIGS. 40L-40M). Comparison of the integration of the carbonyl resonance to the resonances at approximately 100 ppm (the C1 signals) suggests that the ratio of the carbonyl carbon to C1 is 1:13.8 or roughly 1 carbonyl for every 14 glucose units. The chemical shift at 100 ppm correlates well with glucuronic acid.

more intense comparing the spectra from S-70E to S-100E. The $^1H$ NMR spectra have many overlapping peaks and are not easily interpreted.

Manual Titration

Samples P-100e and P132-100 (1 g) were suspended in deionized water (25 mL). The indicator alizarin yellow was added to each sample with stirring. P-100e was more difficult to wet. Both samples were titrated with a solution of 0.2M NaOH. The end point was very subtle and was confirmed by using pH paper. The starting pH of the samples was ~4 for both samples. PI32-100 required 0.4 milliequivalents of hydroxide, which gives a molecular weight for the carboxylic acid of 2500 amu. If 180 amu is used for a monomer, this suggests there is one carboxylic acid group for 13.9 monomer units. Likewise, P-100e required 3.2 milliequivalents of hydroxide, which calculates to be one carboxylic acid group for every 17.4 monomer units.

Conclusions

The C-6 carbon of cellulose appears to be oxidized to the carboxylic acid (a glucuronic acid derivative) in this oxidation is surprisingly specific. This oxidation is in agreement with the IR band that grows with irradiation at ~1740 cm$^{-1}$, which corresponds to an aliphatic carboxylic acid. The titration results are in agreement with the quantitative $^{13}C$ NMR. The increased solubility of the sample with the higher levels of irradiation correlates well with the increasing number of carboxylic acid protons. A proposed mechanism for the degradation of "C-6 oxidized cellulose" is provided below in Scheme 1.

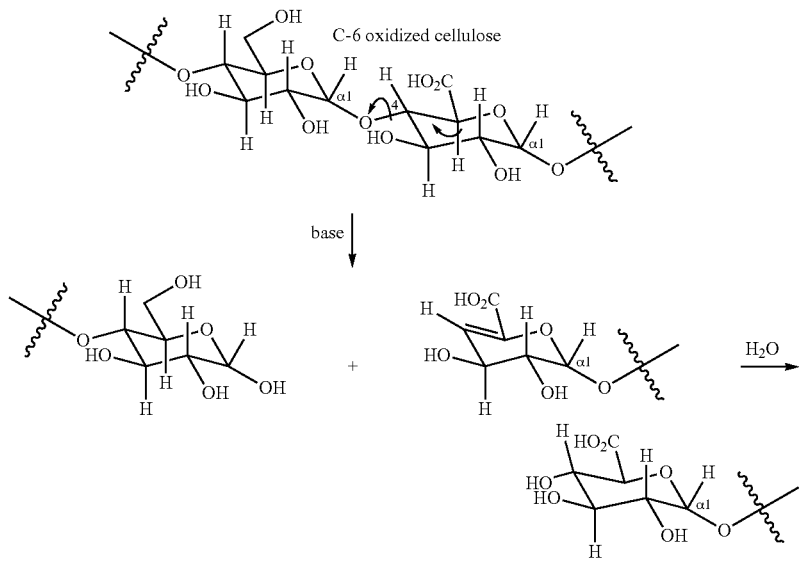

The $^{13}C$ NMR spectrum for A-50E (166,000 scans; 38 h) shows aromatic carbons of lignin (~130 ppm) and also shows multiple carbonyl resonances around 170 ppm (the P samples showed only one resonance). The $^1H$ NMR clearly shows the aromatic signals from lignin.

The $^{13}C$ NMR spectrum for S-100E does not show a carbonyl resonance at 170 ppm as the other treated samples do, but the $^{13}C$ NMR spectrum shows that there has been extensive reaction and there are now over 40 carbon resonances in the spectrum while untreated sucrose has only 12 signals (104.71, 93.20, 82.42 77.51 75.09, 73.68, 73.44, 72.14, 70.31, 63.44, 62.46, 61.24 ppm). These signals are Potentiometric Titration Analysis A potentiometer (Metrohm Ion Analysis 794 Basic Titrino) was used to measure the electrode potential of sample solutions and therefore an accurate titration analysis based on a redox reaction was achieved. The potential of the working electrode will suddenly change as the endpoint is reached.

Results

Figure 40O:
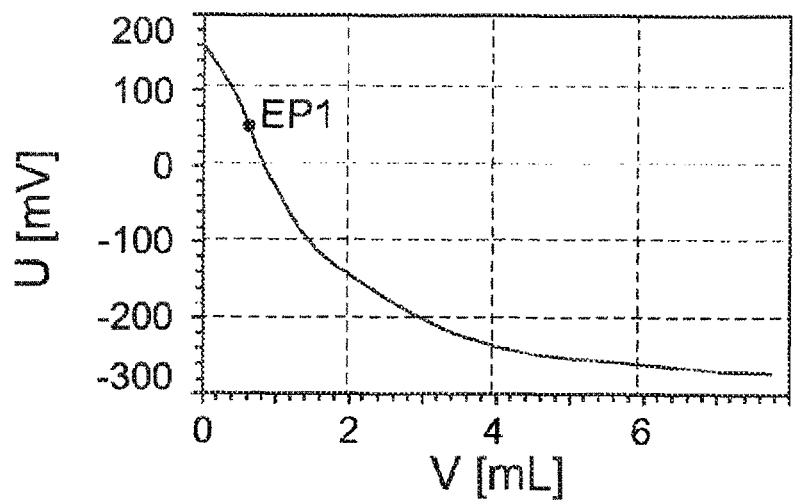
FIG. 40O is a titration curve of sample P-30e using a
potentiometer.
Figure 41:
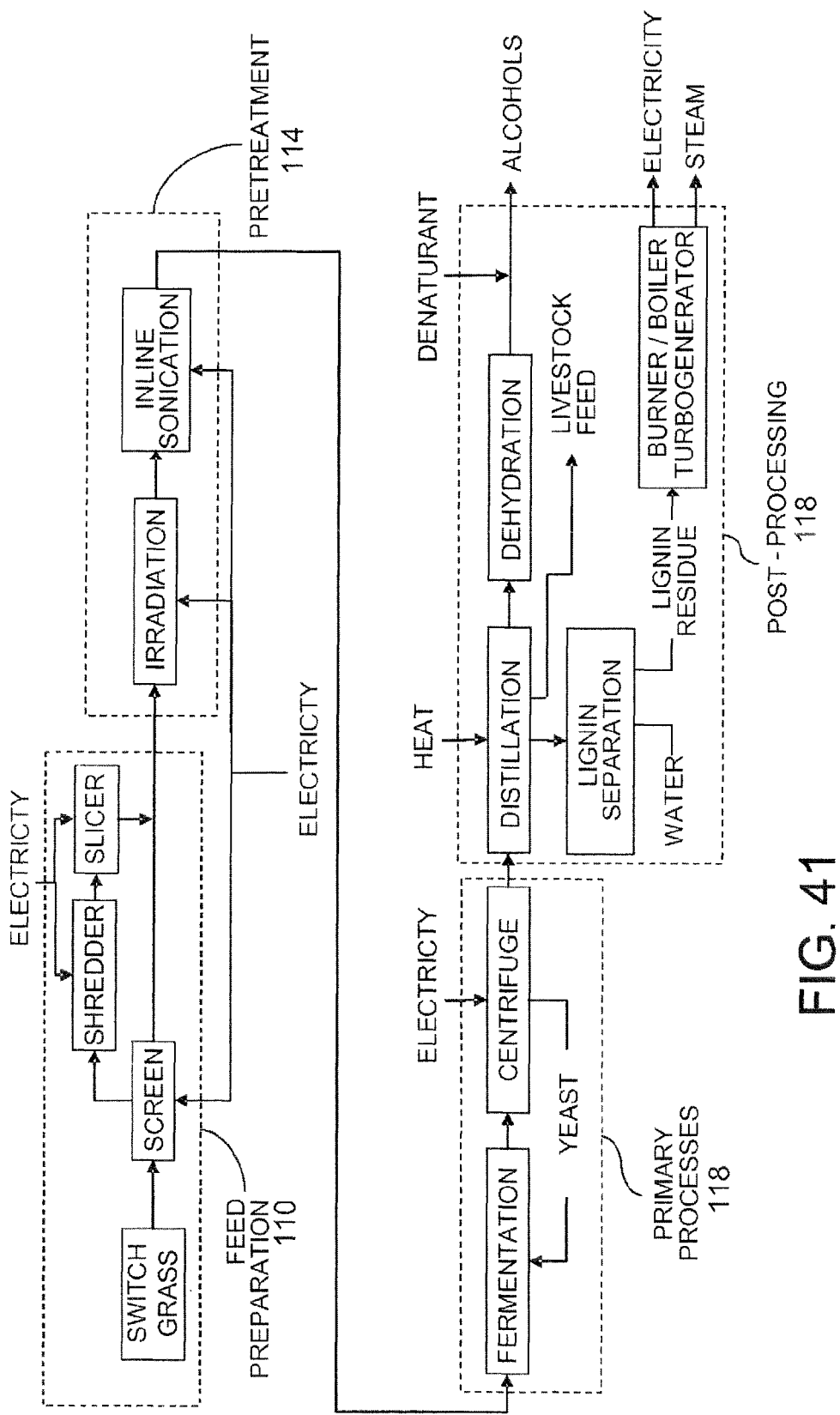
FIG. 41 is a schematic view of a process for biomass
conversion.
Figure 42:
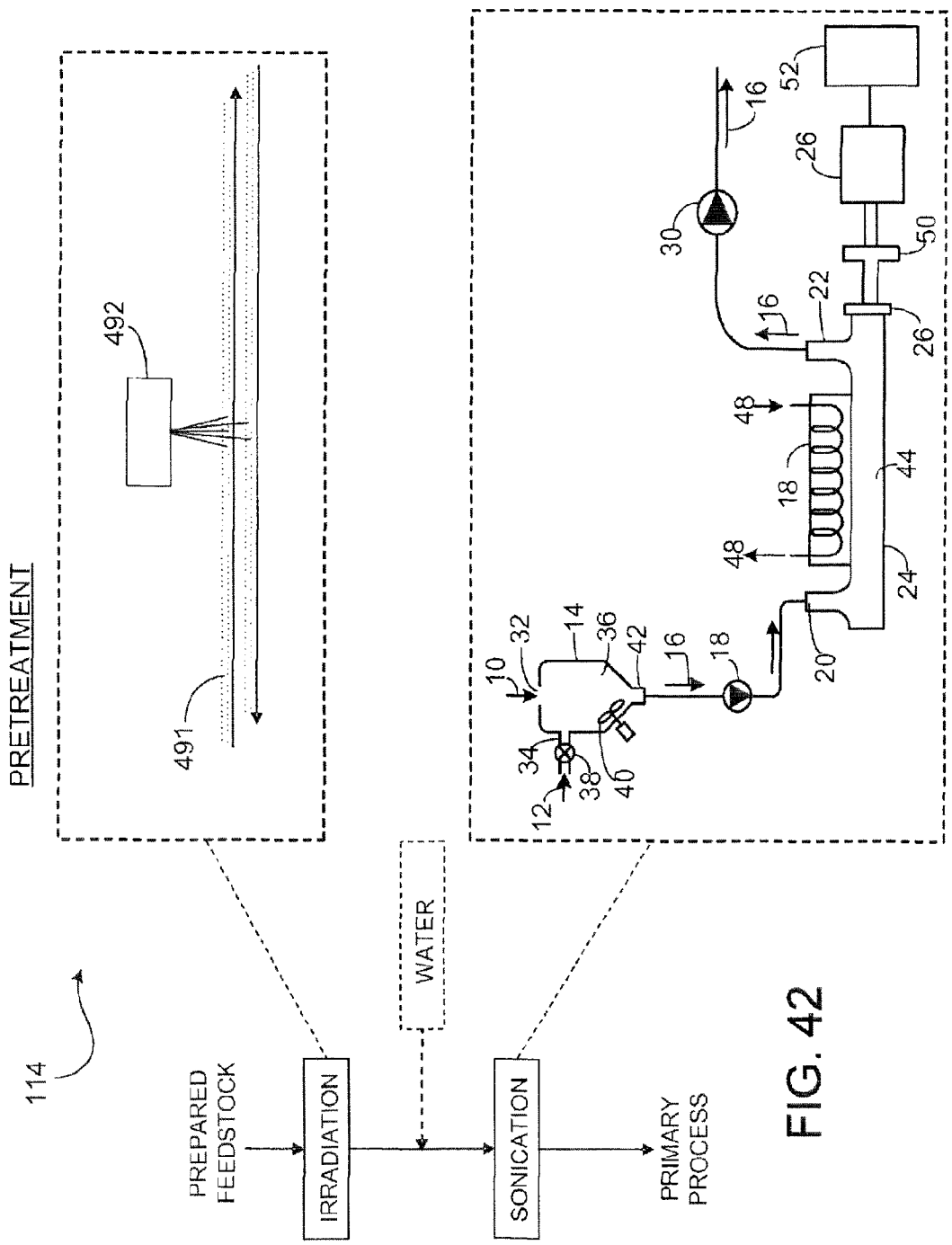
FIG. 42 is schematic view of another process for biomass
conversion.

P-30E had one carboxylic acid per 57 saccharide units. P-70E had one carboxylic acid unit per 27 saccharide units. P-100E had one carboxylic acid per 22 saccharide units. Of particular interest, the samples darkened significantly upon titration to a rusty red color. (This was not noticeable during the manual titrations). A titration curve for sample P-30e is presented in FIG. 40O.

Example 24

Combination of Electron Beam and Sonication Pretreatment

Switchgrass is used as the feedstock and is sheared with a Munson rotary knife cutter into a fibrous material. The fibrous material is then evenly distributed onto an open tray composed of tin with an area of greater than about 500 in$^2$. The fibrous material is distributed so that it has a depth of about 1-2 inches in the open tray. The fibrous material may be distributed in plastic bags at lower doses of irradiation (under 10 Mrad), and left uncovered on the metal tray at higher doses of radiation.

Separate samples of the fibrous material are then exposed to successive doses of electron beam radiation to achieve a total dose of 1 Mrad, 2 Mrad, 3, Mrad, 5 Mrad, 10 Mrad, 50 Mrad, and 100 Mrad. Some samples are maintained under the same conditions as the remaining samples, but are not irradiated, to serve as controls. After cooling, the irradiated fibrous material is sent on for further processing through a sonication device.

The sonication device includes a converter connected to booster communicating with a horn fabricated from titanium or an alloy of titanium. The horn, which has a seal made from VITON® about its perimeter on its processing side, forms a liquid tight seal with a processing cell. The processing side of the horn is immersed in a liquid, such as water, into which the irradiated fibrous material to be sonicated is immersed. Pressure in the cell is monitored with a pressure gauge. In operation, each sample is moved by pump through the processing cell and is sonicated.

To prepare the irradiated fibrous material for sonication, the irradiated fibrous material is removed from any container (e.g., plastic bags) and is dispersed in water at a concentration of about 0.10 g/mL. Sonication is performed on each sample for 30 minutes using 20 kHz ultrasound from a 1000 W horn under re-circulating conditions. After sonication, the irradiated fibrous material is captured in a tank. This process can be repeated a number of times until a desired level of processing is achieved based on monitoring the structural changes in the switchgrass. Again, some irradiated samples are kept under the same conditions as the remaining samples, but are not sonicated, to serve as controls. In addition, some samples that were not irradiated are sonicated, again to serve as controls. Thus, some controls are not processed, some are only irradiated, and some are only sonicated.

Example 25

Microbial Testing of Pretreated Biomass

Specific lignocellulosic materials pretreated as described herein are analyzed for toxicity to common strains of yeast and bacteria used in the biofuels industry for the fermentation step in ethanol production. Additionally, sugar content and compatibility with cellulase enzymes are examined to determine the viability of the treatment process. Testing of the pretreated materials is carried out in two phases as follows.

Phase 1: Toxicity and Sugar Content

Toxicity of the pretreated grasses and paper feedstocks is measured in yeast *Saccharomyces cerevisiae* (wine yeast) and *Pichia stipitis* (ATCC 66278) as well as the bacteria *Zymomonas mobilis* (ATCC 31821) and *Clostridium thermocellum* (ATCC 31924). A growth study is performed with each of the organisms to determine the optimal time of incubation and sampling.

Each of the feedstocks is then incubated, in duplicate, with *S. cerevisiae, P. stipitis, Z. mobilis*, and *C. thermocellum* in a standard microbiological medium for each organism. YM broth is used for the two yeast strains, *S. cerevisiae* and *P. stipitis*. RM medium is used for *Z. mobilis* and CM4 medium for *C. thermocellum*. A positive control, with pure sugar added, but no feedstock, is used for comparison. During the incubation, a total of five samples is taken over a 12 hour period at time 0, 3, 6, 9, and 12 hours and analyzed for viability (plate counts for *Z. mobilis* and direct counts for *S. cerevisiae*) and ethanol concentration.

Sugar content of the feedstocks is measured using High Performance Liquid Chromatography (HPLC) equipped with either a Shodex® sugar SP0810 or Biorad Aminex® HPX-87P column. Each of the feedstocks (approx. 5 g) is mixed with reverse osmosis (RO) water for 1 hour. The liquid portion of the mixture is removed and analyzed for glucose, galactose, xylose, mannose, arabinose, and cellobiose content. The analysis is performed according to National Bioenergy Center protocol Determination of Structural Carbohydrates and Lignin in Biomass.

Phase 2: Cellulase Compatibility

Feedstocks are tested, in duplicate, with commercially available Accellerase® 1000 enzyme complex, which contains a complex of enzymes that reduces lignocellulosic biomass into fermentable sugars, at the recommended temperature and concentration in an Erlenmeyer flask. The flasks are incubated with moderate shaking at around 200 rpm for 12 hours. During that time, samples are taken every three hours at time 0, 3, 6, 9, and 12 hours to determine the concentration of reducing sugars (Hope and Dean, *Biotech J*, 1974, 144:403) in the liquid portion of the flasks.

Example 26

Sugar Concentration Analysis Using HPLC 13 samples were analyzed for sugar concentration (HPLC) and toxicity against 3 microorganisms (*Pichia stipitis, Saccharomyces cerevisiae*, and *Zymomonas mobilis*. Table 26 lists the equipment used for these experiments. Table 27 and 28 provide a list of the sugars (including vendor and lot numbers) used to prepare the HPLC standard and the protocol used to prepare the HPLC standard, respectively.

TABLE 26

| Equipment Utilized in Experiments | |
|---|---|
| Equipment | Manufacturer, Name |
| pH meter | Orion |
| Shakers (2) | B. Braun Biotech, Certomat BS-1 |
| HPLC | Waters, 2690 HPLC Module |
| Spectrophotometer | Unicam, UV300 |
| YSI Biochem Analyzer | Interscience, YSI |

TABLE 27

Sugars used in HPLC analysis

| Sugar | Manufacturer | Ref # | Lot # |
|---|---|---|---|
| glucose | | 49140 | 1284892 |
| xylose | | 95731 | 1304473 51707231 |
| cellobiose | BioChemika | 22150 | 1303157 14806191 |
| arabinose | | 10840 | 1188979 24105272 |
| mannose | | 63582 | 363063/1 22097 |
| galactose | | 48259 | 46032/1 33197 |

TABLE 28

Preparation of HPLC standards

| Desired Concentration (mg/mL) | Volume of sugar solution | Volume of Nanopure Water (mL) | Total Volume (mL) |
|---|---|---|---|
| 4 | 50 mL of 4 mg/mL | 0 | 50 |
| 2 | 25 mL of 4 mg/mL | 25 | 50 |
| 1 | 25 mL of 2 mg/mL | 25 | 50 |
| 0.5 | 25 mL of 1 mg/mL | 25 | 50 |
| 0.1 | 5 ml of 1 mg/mL | 20 | 25 |
| Verification Standard 1.5 mg/mL | 18.75 mL of 4 mg/mL | 31.25 | 50 |

Analysis

Each sample (1 gram) was mixed with reverse osmosis water at 200 rpm and 50° C. overnight. The pH of the sample was adjusted to between 5 and 6 and filtered through a 0.2 μm syringe filter. Samples were stored at −20° C. prior to analysis to maintain integrity of the samples. The observations made during the preparation of the samples are presented in Table 29.

TABLE 29

Observations During HPLC Sample Preparation

| Sample | Amount used (g) | Water added (mL) | pH | Observations |
|---|---|---|---|---|
| P132 | 1 | 30 | 5.38 | Fluffy, difficult to mix |
| P132-10 | 1 | 25 | 6.77 | Fluffy, difficult to mix |
| P132-100 | 1 | 20 | 3.19 | pH is low, difficult to bring |
| P132-US | 0.3 | 5 | 6.14 | to pH 5.0, used 10N NaOH |
| A132 | 1 | 15 | 5.52 | |
| A132-10 | 1 | 15 | 4.9 | |
| A132-100 | 1 | 15 | 5.39 | |
| SG132 | 1 | 15 | 5.59 | |
| SG132-10 | 1 | 15 | 5.16 | |
| SG132-100 | 1 | 15 | 4.7 | |
| SG132-10-US | 0.3 | 5 | 5.12 | |
| SG132-100-US | 0.3 | 5 | 4.97 | |

TABLE 29-continued

Observations During HPLC Sample Preparation

| Sample | Amount used (g) | Water added (mL) | pH | Observations |
|---|---|---|---|---|
| WS132 | 1 | 15 | 5.63 | |
| WS132-10 | 1 | 15 | 5.43 | |
| WS132-100 | 1 | 15 | 5.02 | |

*pH of these samples was adjusted to pH using 1N NaOH

Standards were prepared fresh from a 4 mg/mL stock solution of the 6 combined sugars, glucose, xylose, cellobiose, arabinose, mannose, and galactose. The stock solution was prepared by dissolving 0.400 grams of each sugar into 75 mL of nanopure water (0.3 micron filtered). Once dissolved, the stock solution was diluted to 100 mL using a volumetric flask and stored at −20° C. Working standard solutions of 0.1, 0.5, 1, 2, and 4 mg/mL were prepared by serial dilution of the stock solution with nanopure water. In addition, a verification standard of 1.5 mg/mL was also prepared from the stock solution.

Sugar concentrations were analyzed according to the protocol *Determination of Structural Carbohydrates in Biomass* (NREL Biomass Program, 2006) and this protocol is incorporated herein by reference in its entirety. A SHODEX SUGAR SP0810 COLUMN with an Evaporative Light Scattering Detector was used. A verification standard (1.5 mg/mL of standard) was analyzed every 8 injections to ensure that the integrity of the column and detector were maintained during the experiment. The standard curve coefficient of variation ($R^2$ value) was at least 0.989 and the concentration of the verification standards were within 10% of the actual concentration. The HPLC conditions were as follows:

TABLE 30

HPLC Parameters

| | |
|---|---|
| Injection volume: | 20 μL |
| Mobile phase: | nanopure water*, 0.45 μm filtered and degassed |
| Flow rate: | 0.5 mL/min |
| Column temperature: | 85° C. |
| Detector temperature: | evaporator temperature 110° C., nebulizer temperature 90° C. |

*Initial tests noted that better separation was observed when using nanopure water than 15/85 acetonitrile:water in the mobile phase (manufacturer does not recommend using greater than 20% acetonitrile with this column).

Results

The results of the HPLC analysis are presented in Tables 31, 32, and 33.

TABLE 31

Sugar Concentration Expressed as mg/mL and mg/g of Extract

| Sample ID | Xylose mW~150 $C_5H_{10}O_5$ Mono | | Arabinose mW~150 $C_5H_{10}O_5$ Mono | | Glucose mW~180 $C_6H_{12}O_6$ Mono | | Galactose (see gluc) mg/mL:mg/g | | Mannose (see gluc) mg/mL:mg/g | | Cellobiose mW~342 $C_{12}H_{22}O_{11}$ Disacc | |
|---|---|---|---|---|---|---|---|---|---|---|---|---|
| | mg/mL | mg/g | mg/mL | mg/g | mg/mL | mg/g | mg/mL | mg/g | mg/mL | mg/g | mg/mL | mg/g |
| P | | | | | | | | | | | | |
| P-132 | 0.00 | 0.00 | 0.00 | 0.00 | 0.00 | 0.00 | 0.00 | 0.00 | 0.00 | 0.00 | 0.00 | 0.00 |
| P-132-10 | 0.00 | 0.00 | 0.00 | 0.00 | 0.34 | 8.60 | 0.00 | 0.00 | 0.00 | 0.00 | 00.33 | 8.13 |

TABLE 31-continued

Sugar Concentration Expressed as mg/mL and mg/g of Extract

| | Xylose mW~150 $C_5H_{10}O_5$ Mono | | Arabinose mW~150 $C_5H_{10}O_5$ Mono | | Glucose mW~180 $C_6H_{12}O_6$ Mono | | Galactose (see gluc) mg/mL:mg/g | | Mannose (see gluc) mg/mL:mg/g | | Cellobiose mW~342 $C_{12}H_{22}O_{11}$ Disacc | |
|---|---|---|---|---|---|---|---|---|---|---|---|---|
| Sample ID | mg/mL | mg/g | mg/mL | mg/g | mg/mL | mg/g | mg/mL | mg/g | mg/mL | mg/g | mg/mL | mg/g |
| P-132-100 | 0.35 | 7.04 | 0.00 | 0.00 | 0.34 | 6.14 | 0.00 | 0.00 | 0.00 | 0.00 | 0.36 | 7.20 |
| P-132-BR | 0.35 | 5.80 | 0.43 | 7.17 | 0.34 | 5.62 | 0.00 | 0.00 | 0.00 | 0.00 | 0.00 | 0.00 |
| G | | | | | | | | | | | | |
| G-132 | 0.39 | 5.88 | 0.38 | 5.73 | 0.84 | 12.66 | 0.34 | 5.04 | 0.92 | 13.76 | 0.00 | 0.00 |
| G-132-10 | 0.50 | 7.50 | 0.41 | 6.18 | 1.07 | 16.04 | 0.35 | 5.19 | 0.98 | 14.66 | 0.00 | 0.00 |
| G-132-100 | 0.00 | 0.00 | 0.37 | 5.54 | 0.41 | 6.14 | 0.00 | 0.00 | 0.55 | 8.28 | 0.45 | 6.71 |
| G-132-10-US | 0.34 | 5.73 | 0.39 | 6.45 | 0.33 | 5.43 | 0.00 | 0.00 | 0.00 | 0.00 | 0.00 | 0.00 |
| G-132-100-US | 0.00 | 0.00 | 0.37 | 6.22 | 0.35 | 5.90 | 0.33 | 5.43 | 0.40 | 6.70 | 0.39 | 6.45 |
| A | | | | | | | | | | | | |
| A-132 | 1.36 | 20.39 | 0.00 | 0.00 | 1.08 | 16.22 | 0.39 | 5.84 | 1.07 | 16.02 | 0.00 | 0.00 |
| A-132-10 | 1.19 | 17.87 | 0.00 | 0.00 | 0.00 | 0.00 | 0.00 | 0.00 | 0.37 | 5.52 | 0.00 | 0.00 |
| A-132-100 | 1.07 | 16.11 | 0.00 | 0.00 | 0.35 | 5.18 | 0.00 | 0.00 | 0.00 | 0.00 | 0.81 | 12.2 |
| WS | | | | | | | | | | | | |
| WS-132 | 0.49 | 7.41 | 0.41 | 6.15 | 0.39 | 5.90 | 0.00 | 0.00 | 0.00 | 0.00 | 0.00 | 0.00 |
| WS-132-10 | 0.57 | 8.49 | 0.40 | 5.99 | 0.73 | 10.95 | 0.34 | 5.07 | 0.50 | 7.55 | 0.00 | 0.00 |
| WS-132-100 | 0.43 | 6.39 | 0.37 | 5.51 | 0.36 | 5.36 | 0.00 | 0.00 | 0.36 | 5.33 | 0.35 | 5.25 |

TABLE 32

Sugar Concentration Expressed at % of Paper

| Sugar concentration (% of dry sample) | P132 | P132-10 | P132-100 | P132-US |
|---|---|---|---|---|
| cellobiose | 0.00 | 0.81 | 0.72 | 0.00 |
| glucose | 0.00 | 0.86 | 0.67 | 0.56 |
| xylose | 0.00 | 0.00 | 0.70 | 0.58 |
| galactose | 0.00 | 0.00 | 0.00 | 0.00 |
| arabinose | 0.00 | 0.00 | 0.00 | 0.72 |
| mannose | 0.00 | 0.00 | 0.00 | 0.00 |

TABLE 33

Sugar Concentration Expressed at % of Total Sample

| Sugar concentration (% of dry sample) | A132 | A132-10 | A132-100 | SG132 | SG132-10 | SG132-100 | SG132-10-US | SG132-100-US | WS132 | WS132-10 | WS132-100 |
|---|---|---|---|---|---|---|---|---|---|---|---|
| cellobiose | 0.00 | 0.00 | 1.22 | 0.00 | 0.00 | 0.67 | 0.00 | 0.65 | 0.00 | 0.00 | 0.53 |
| glucose | 1.62 | 0.00 | 0.52 | 1.27 | 1.60 | 0.61 | 0.54 | 0.59 | 0.59 | 1.10 | 0.54 |
| xylose | 2.04 | 1.79 | 1.61 | 0.59 | 0.75 | 0.00 | 0.57 | 0.00 | 0.74 | 0.85 | 0.64 |
| galactose | 0.58 | 0.00 | 0.00 | 0.50 | 0.52 | 0.00 | 0.00 | 0.54 | 0.00 | 0.51 | 0.00 |
| arabinose | 0.00 | 0.00 | 0.00 | 0.57 | 0.62 | 0.55 | 0.65 | 0.62 | 0.62 | 0.60 | 0.55 |
| mannose | 1.60 | 0.55 | 0.00 | 1.38 | 1.47 | 0.83 | 0.00 | 0.67 | 0.00 | 0.76 | 0.53 |

Example 27

Toxicity Study

Twelve samples were analyzed for toxicity against a panel of three ethanol-producing cultures. In this study, glucose was added to the samples in order to distinguish between starvation of the cultures and toxicity of the samples. A thirteenth sample was tested for toxicity against *Pichia stipitis*. A summary of the protocol used is listed in Table 32. A description of the chemicals and equipment used in the toxicity testing is reported in Tables 34-36.

TABLE 34

Conditions for Toxicity Testing

| Variable | Organism | | |
|---|---|---|---|
| | *Zymomonas mobilis* ATCC 31821 | *Saccharomyces cerevisiae* ATCC 24858 | *Pichia stipitis* NRRL Y-7124 |
| Test Repetition | | Duplicate | |
| Inoculation Volume (mL) | 1 | 0.1 | 1 |
| Incubation Temperature | 30° C. | 25° C. | 25° C. |
| Shaker Speed (rpm) | 125 | 200 | 125 |
| Erlenmeyer Flask Volume | 250 mL | 500 mL | 250 mL |
| Media volume | 100 mL | 100 mL | 100 mL |
| Total Incubation time (hours) | 36 | 36 | 48 |
| Ethanol Analysis (hours) | 24, 30, 36 | 24, 30, 36 | 24, 36, 48 |
| Cell Counts (hours) | 24, 36 | 24, 36 | 24, 48 |
| pH | 0 hours | 0 hours | 0 hours |

TABLE 35

Reagents Used for Toxicity Testing

| Media Component | Manufacturer | Reference # | Lot # |
|---|---|---|---|
| Urea | ScholAR Chemistry | 9472706 | AD-7284-43 |
| Yeast Nitrogen Base | Becton Dickinson | 291940 | 7128171 |
| Peptone | Becton Dickinson | 211677 | 4303198 |
| Xylose | Fluka | 95731 | 1304473 51707231 |
| Glucose | Sigma | G-5400 | 107H0245 |
| Yeast Extract (used for S. cerevisiae) | Becton Dickinson | 288620 | 4026828 |
| Yeast Extract (used for P. stipitis and Z. mobilis) | Becton Dickinson | 212750 | 7165593 |
| $MgSO_4 \cdot 7H_2O$ | Sigma | M5921 | 034K0066 |
| $(NH_4)_2SO_4$ | Sigma | A4418 | 117K5421 |
| $KH_2PO_4$ | Sigma | P5379 | 074K0160 |
| YM Broth | Becton Dickinson | 271120 | 6278265 |

TABLE 36

YSI Components Used in Shake Flask Study

| Component | Catalog # | Lot # |
|---|---|---|
| YSI Ethanol Membrane | 2786 | 07L100153 |
| YSI Ethanol Standard (3.2 g/L) | 2790 | 012711040 |
| YSI Ethanol Buffer | 2787 | 07M1000053, 07100215 |

Testing was performed using the three microorganisms as described below.

*Saccharomyces cerevisiae* ATCC 24858 (American Type Culture Collection)

A slant of *S. cerevisiae* was prepared from a rehydrated lyophilized culture obtained from ATCC. A portion of the slant material was streaked onto an YM Broth 20 g/L agar (pH 5.0) and incubated at 30° C. for 2 days. A 250 mL Erlenmeyer flask containing 50 mL of medium (20 g/L glucose, 3 g/L yeast extract, and 5.0 g/L peptone, pH 5.0) was inoculated with one colony from the YM plate and incubated for 24 hours at 25° C. and 200 rpm. After 23 hours of growth, a sample was taken and analyzed for optical density (600 nm in a UV spectrophotometer) and purity (Gram stain). Based on these results, two seed flasks, each having an optical density (OD) of between 4 and 8 and with a clean Gram stain, were combined to inoculate the growth flasks.

The test vessels were 500 mL Erlenmeyer flasks containing 100 mL of the sterile medium described above. All flasks were autoclaved at 121° C. and 15 psi prior to the addition of the test materials. The test materials were not sterilized, as autoclaving will change the content of the samples. The test samples were added at the time of inoculation (rather than prior to) to reduce the possibility of contamination. In addition to the test samples, 1 mL (1% v/v) of seed flask material was added to each flask. The flasks were incubated as described above for 36 hours.

*Pichia stipitis* NRRL Y-7124 (ARS Culture Collection)

A slant of *P. stipitis* was prepared from a rehydrated lyophilized culture obtained from ARS Culture Collection. A portion of the slant material was streaked onto an YM Broth+20 g/L agar (pH 5.0) and incubated at 30° C. for 2 days. A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) was inoculated with a small amount of plate material and incubated for 24 hours at 25° C. and 125 rpm. After 23 hours of growth, a sample was taken and analyzed for optical density (600 nm in a UV spectrophotometer) and purity (Gram stain). Based on these results, one flask (called the Seed Flask) at an optical density of 5.23 and with a clean Gram Stain was chosen to inoculate all of the test flasks.

The test vessels were 250 mL Erlenmeyer flasks containing 100 mL of the sterile medium described above. All flasks were autoclaved empty at 121° C. and 15 psi and filter sterilized (0.22 µm filter) media added to the flasks prior to the addition of the test materials. The test materials were not sterilized, as autoclaving will change the content of the samples and filter sterilization not appropriate for sterilization of solids. The test samples were added at the time of inoculation (rather than prior to) to reduce the possibility of contamination. In addition to the test samples, 1 mL (1% v/v) of seed flask material was added to each flask. The flasks were incubated as described above for 48 hours.

*Zymomonas mobilis* ATCC 31821 (American Type Culture)

A slant of *Z. mobilis* was prepared from a rehydrated lyophilized culture obtained from ATTC. A portion of the slant material was streaked onto an DYE plates (glucose 20 g/L, Yeast Extract 10 g/L, Agar 20 g/L, pH 5.4) and incubated at 30° C. and 5% $CO_2$ for 2 days. A 20 mL screw-cap test tube containing 15 mL of medium (25 g/L glucose, 10 g/L yeast extract, 1 g/L $MgSO_4'$ 7 $H_2O$, 1 g/L $(NH_4)_2SO_4$, 2 g/L $KH_2PO_4$, pH 5.4) was inoculated with one colony and incubated for 24 hours at 30° C. with no shaking. After 23 hours of growth, a sample was taken and analyzed for optical density (600 nm in a UV spectrophotometer) and purity (gram stain). Based on these results, one tube (OD 1.96) was chosen to inoculate the second seed flask. The second seed flask was a 125 ml flask containing 70 mL of the media described above and was inoculated with 700 µL (1% v/v) and incubated for 24 hours at 30° C. with no shaking. After 23 hours of growth, a sample was taken and analyzed for optical density (600 nm in a UV spectrophotometer) and purity (gram stain). Based on these results, one flask (called the Seed Flask) with an OD of 3.72 was chosen to inoculate all of the test flasks.

The test vessels were 250 mL Erlenmeyer flasks containing 100 mL of the sterile medium described above with the exception of yeast extract at 5 g/L. All flasks were autoclaved empty at 121° C. and 15 psi and filter sterilized (0.22 µm filter) media added to the flasks prior to the addition of the test materials. The test materials were not sterilized, as autoclaving will change the content of the samples and filter sterilization not appropriate for sterilization of solids. The test samples were added at the time of inoculation to reduce the possibility of contamination. In addition to the test samples, 1 mL (1% v/v) of seed flask material was added to each flask. The flasks were incubated as described above for 36 hours Analysis Two samples were analyzed for cell concentration (using spread plating for *Z. mobilis* and direct counts (haemocytometer and microscope for *S. cerevisiae* and *P. stipitis*). Appropriately diluted samples of *Z. mobilis* were spread on Dextrose Yeast Extract (glucose 20 g/L, Yeast Extract 10 g/L, Agar 20 g/L, pH 5.4) plates, incubated at 30° C. and 5% CO2 for 2 days, and the number of colonies counted. Appropriately diluted samples of *S. cerevisiae* and *P. stipitis* were mixed with 0.05% Trypan blue, loaded into a Neubauer haemocytometer. The cells were counted under 40× magnification.

Three samples were analyzed for ethanol concentration using the YSI Biochem Analyzer based on the alcohol dehydrogenase assay (YSI, Interscience). Samples were centrifuged at 14,000 rpm for 20 minutes and the supernatant stored at −20° C. to preserve integrity. The samples were diluted to between 0-3.2 g/L ethanol prior to analysis. A standard of 3.2 g/L ethanol was analyzed approximately every 30 samples to ensure the integrity of the membrane was maintained during analysis. The optical density (600 nm) of the samples is not reported because the solid test samples interfered with absorbance measurement by increasing the turbidity of the samples and are inaccurate.

Results of Ethanol Analysis

Performance was used to compare each sample to the control for each microorganism (Tables 37-39). However, the % performance cannot be used to compare between strains. When comparing strains, the total concentration of ethanol should be used. When analyzing the data, a % performance of less than 80% may indicate toxicity when accompanied by low cell number. The equation used to determine % performance is:

$$\% \text{ Performance} = (\text{ethanol in the sample/ethanol in control}) \times 100$$

TABLE 37

Ethanol Concentration and % Performance Using *Saccharomyces cerevisiae*

| Sample # | 24 hours Ethanol Concentration (g/L) | 24 hours % Performance | 30 hours Ethanol Concentration (g/L) | 30 hours % Performance | 36 hours Ethanol Concentration (g/L) | 36 hours % Performance |
|---|---|---|---|---|---|---|
| P132 | 4.0 | 140 | 5.2 | 127 | 3.26 | 176 |
| P132-10 | 4.2 | 147 | 5.1 | 125 | 3.86 | 209 |
| P132-100 | 4.3 | 149 | 5.6 | 136 | 3.47 | 187 |
| A132 | 5.5 | 191 | 6.5 | 160 | 5.24 | 283 |
| A132-10 | 1.9 | 67 | 6.3 | 153 | 5.54 | 299 |
| A132-100 | 4.4 | 154 | 5.6 | 137 | 4.04 | 218 |
| G132 | 5.3 | 186 | 6.0 | 146 | 3.99 | 215 |
| G132-10 | 5.2 | 180 | 6.4 | 156 | 4.63 | 250 |
| G132-100 | 5.5 | 191 | 6.3 | 155 | 4.60 | 248 |
| WS132 | 4.8 | 168 | 6.3 | 155 | 4.51 | 244 |
| WS132-10 | 4.9 | 172 | 6.0 | 146 | 4.55 | 246 |
| WS132-100 | 4.9 | 170 | 5.7 | 140 | 4.71 | 254 |
| Control | 2.9 | 100 | 4.1 | 100 | 1.85 | 100 |

TABLE 38

Ethanol Concentration and % Performance Using *Pichia stipites*

| Sample # | 24 hours Ethanol Concentration (g/L) | 24 hours % Performance | 36 hours Ethanol Concentration (g/L) | 36 hours % Performance | 48 hours Ethanol Concentration (g/L) | 48 hours % Performance |
|---|---|---|---|---|---|---|
| P132 | 2.8 | 130 | 3.4 | 188 | 8.1 | 176 |
| P132-10 | 7.3 | 344 | 11.9 | 655 | 15.8 | 342 |
| P132-100 | 5.2 | 247 | 8.6 | 472 | 13.3 | 288 |
| A132 | 12.2 | 575 | 14.7 | 812 | 14.9 | 324 |
| A132-10 | 15.1 | 710 | 18.7 | 1033 | 26.0 | 565 |
| A132-100 | 10.9 | 514 | 16.7 | 923 | 22.2 | 483 |
| G132 | 8.0 | 375 | 12.9 | 713 | 13.3 | 288 |
| G132-10 | 10.1 | 476 | 16.0 | 884 | 22.3 | 485 |
| G132-100 | 8.6 | 406 | 15.2 | 837 | 21.6 | 470 |
| WS132 | 9.8 | 460 | 14.9 | 820 | 17.9 | 389 |
| WS132-10 | 7.8 | 370 | 16.1 | 890 | 19.3 | 418 |
| WS132-100 | 9.1 | 429 | 15.0 | 829 | 15.1 | 328 |
| Sample A* | 13.2 | 156 | 19.0 | 166 | 20.6 | 160 |
| Control | 2.1 | 100 | 1.8 | 100 | 4.6 | 100 |

Samples in BOLD were the highest ethanol producers, over 20 g/L and similar to the concentrations in wood hydrolyzates (H. K. Sreenath and T. W. Jeffries Bioresource Technology 72 (2000) 253-260).
*Analyzed in later shake flask experiment.

TABLE 39

Ethanol Concentration and % Performance Using *Zymomonas mobilis*

| | 24 hours | | 30 hours | | 36 hours | |
|---|---|---|---|---|---|---|
| Sample # | Ethanol Concentration (g/L) | % Performance | Ethanol Concentration (g/L) | % Performance | Ethanol Concentration (g/L) | % Performance |
| P132 | 7.5 | 85 | 6.8 | 84 | 7.5 | 93 |
| P132-10 | 7.5 | 85 | 4.8 | 59 | 6.8 | 84 |
| P132-100 | 7.3 | 83 | 6.2 | 77 | 7.1 | 88 |
| A132 | 9.6 | 109 | 8.3 | 103 | 9.1 | 112 |
| A132-10 | 9.2 | 105 | 8.4 | 105 | 8.8 | 109 |
| A132-100 | 8.2 | 93 | 7.6 | 94 | 7.6 | 93 |
| WS132 | 7.9 | 89 | 7.1 | 88 | 7.7 | 94 |
| WS132-10 | 8.2 | 93 | 6.8 | 85 | 7.3 | 90 |
| WS132-100 | 8.7 | 98 | 6.9 | 86 | 8.3 | 102 |
| G132 | 8.7 | 99 | 7.1 | 88 | 8.1 | 99 |
| G132-10 | 7.8 | 88 | 7.0 | 88 | 7.3 | 90 |
| G132-100 | 8.6 | 98 | 7.8 | 98 | 8.3 | 102 |
| Control | 8.8 | 100 | 8.0 | 100 | 8.1 | 100 |

Results from Cell Concentration Analysis

% Cells is used to compare each sample to the control for each organism (Tables 40-42). However, the % cells cannot be used to compare between strains. When comparing strains, the total concentration of cells should be used. When analyzing the data, a % performance of less than 70% may indicate toxicity when accompanied by low ethanol concentration. The equation used to determine % performance is:

% cells=(number of cell in the sample/number of cells in control)×100

TABLE 40

Results from Cell Concentration Analysis for *Saccharomyces cerevisiae*

| | 24 hours | | 36 hours | |
|---|---|---|---|---|
| Sample # | Cell Concentration (×10$^8$/mL) | % Cells | Cell Concentration (×10$^8$/mL) | % Cells |
| P132 | 1.99 | 166 | 2.51 | 83 |
| P132-10 | 2.51 | 209 | 1.91 | 63 |
| P132-100 | 1.35 | 113 | 1.99 | 66 |
| A132 | 3.80 | 316 | 2.59 | 85 |
| A132-10 | 1.73 | 144 | 3.90 | 129 |
| A132-100 | 3.98 | 331 | 2.51 | 83 |
| G132 | 2.14 | 178 | 3.12 | 103 |
| G132-10 | 2.33 | 194 | 2.59 | 85 |
| G132-100 | 3.57 | 298 | 2.66 | 88 |
| WS132 | 4.10 | 341 | 2.66 | 88 |
| WS132-10 | 2.63 | 219 | 2.81 | 93 |
| WS132-100 | 2.29 | 191 | 2.40 | 79 |
| Control | 1.20 | 100 | 3.03 | 100 |

TABLE 41

Results from Cell Concentration Analysis for *Pichia stipitis*

| | 24 hours | | 48 hours | |
|---|---|---|---|---|
| Sample # | Cell Concentration (×10$^8$/mL) | % Cells | Cell Concentration (×10$^8$/mL) | % Cells |
| P132 | 16.4 | 108 | 20.3 | 87 |
| P132-10 | 11.5 | 76 | 9.5 | 41 |
| P132-100 | 6.5 | 43 | 17.8 | 76 |
| A132 | 7.1 | 47 | 10.2 | 44 |
| A132-10 | 12.7 | 84 | 9.3 | 40 |
| A132-100 | 11.8 | 78 | 18.3 | 78 |
| G132 | 4.5 | 30 | 4.8 | 21 |
| G132-10 | 22.8 | 151 | 9.8 | 42 |
| G132-100 | 10.1 | 67 | 21.7 | 93 |
| WS132 | 17.6 | 117 | 8.2 | 35 |
| WS132-10 | 5.3 | 35 | 10.8 | 46 |
| WS132-100 | 9.3 | 62 | 10.7 | 46 |
| Control | 15.1 | 100 | 23.4 | 100 |

TABLE 42

Results from Cell Concentration Analysis for *Zymomonas mobilis*

| | 24 hours | | 36 hours | |
|---|---|---|---|---|
| Sample # | Cell Concentration (×10$^8$/mL) | % Cells | Cell Concentration (×10$^8$/mL) | % Cells |
| P132 | 7.08 | 86 | 2.97 | 66 |
| P132-10 | 21.80 | 264 | 4.37 | 98 |
| P132-100 | 4.50 | 54 | 3.35 | 75 |
| A132 | 6.95 | 84 | 1.99 | 44 |
| A132-10 | 6.13 | 74 | 4.05 | 91 |
| A132-100 | 9.60 | 116 | 4.20 | 94 |
| G132 | 7.48 | 90 | 3.84 | 86 |
| G132-10 | 14.75 | 178 | 2.89 | 65 |
| G132-100 | 6.00 | 72 | 2.55 | 57 |
| WS132 | 9.70 | 117 | 4.55 | 102 |
| WS132-10 | 13.20 | 160 | 4.32 | 97 |
| WS132-100 | 5.15 | 62 | 2.89 | 65 |
| Control | 8.27 | 100 | 4.47 | 100 |

Example 28

Shake Flask Fermentation of Cellulose Samples Using *P. stipitis*

Summary

Thirteen samples were tested for ethanol production in *P. stipitis* culture without sugar added. They were tested in the presence and absence of cellulase (Accellerase® 1000, Genencor). Equipment and reagents used for the experiment are listed below in Tables 43-45.

TABLE 43

Equipment and frequency of maintenance

| Equipment | Manufacturer | Frequency of Maintenance |
|---|---|---|
| Shakers (2) | B. Braun Biotech, Certomat BS-1 | Quarterly |
| Spectrophotometer | Unicam, UV300 | Biannual |
| YSI Biochem Analyzer | Interscience, YSI | Monthly |

TABLE 44

YSI Components used in shake flask study

| Component | Catalog # | Lot # |
|---|---|---|
| YSI Ethanol Membrane | 2786 | 07L100153 |
| YSI Ethanol Standard (3.2 g/L) | 2790 | 012711040 |
| YSI Ethanol Buffer | 2787 | 07M1000053, 07100215 |

TABLE 45

Chemicals used for shake flask fermentation

| Media Component | Manufacturer | Reference # | Lot # |
|---|---|---|---|
| Urea | ScholAR Chemistry | 9472706 | AD-7284-43 |
| Yeast Nitrogen Base | Becton Dickinson | 291940 | 7128171 |
| Peptone | Becton Dickinson | 211677 | 4303198 |
| YM Broth | Becton Dickinson | 271120 | 6278265 |
| Accellerase ® Enzyme complex | Genencor | Accellerase ® 1000 | 1600794133 |
| Xylose | BioChemika | 95731 | 1304473 51707231 |
| Glucose | Sigma | G-5400 | 107H0245 |

A slant of *P. stipitis* NRRL Y-7124 was prepared from a rehydrated lyophilized culture obtained from ARS Culture Collection. A portion of the slant material was streaked onto a Yeast Mold (YM) Broth+20 g/L agar (pH 5.0) and incubated at 30° C. for 2 days. A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) was inoculated with one colony and incubated for 24 hours at 25° C. and 100 rpm. After 23 hours of growth, a sample was taken and analyzed for optical density (600 nm in a UV spectrophotometer) and purity (Gram stain). Based on these results, one flask (called the Seed Flask) at an optical density of 6.79 and with a clean Gram stain was chosen to inoculate all of the test flasks.

The test vessels were 250 mL Erlenmeyer flasks containing 100 mL of medium (1.7 g/L yeast nitrogen base, 2.27 g/L urea, and 6.56 g/L peptone). No sugar (glucose or xylose) was added to the growth flask medium. All flasks were autoclaved empty at 121° C. and 15 psi and filter sterilized (0.22 urn filter) media added to the flasks prior to the addition of the test materials. The test materials were not sterilized, as autoclaving will change the content of the samples and filter sterilization is not appropriate for sterilization of solids. The test samples (listed in Table 46) were added at the time of inoculation (rather than prior to) to reduce the possibility of contamination. In addition to the test samples, 1 mL (1% v/v) of seed flask material was added to each flask. Flasks containing sample P132-100 required the addition of 0.4 mL 1 M NaOH to bring the pH to 5.0. The flasks were incubated at 30° C. and 150 rpm above for 96 hours.

One set of duplicate flasks per feedstock contained Accellerase® enzyme complex (1.25 mL per flask, highest recommended dosage is 0.25 mL per gram of biomass, Genencor) to attempt simultaneous saccharification and fermentation (SSF). The other set of duplicate flasks did not contain Accellerase® enzyme complex. A total of 52 flasks were analyzed.

Six control flasks were also analyzed. Positive control flasks contained SolkaFloc 200 NF Powdered Cellulose (lot # UA158072, International Fiber Corporation) at a concentration of 2.5 grams per 100 mL flask (25 grams per L) with and without addition of Accellerase® enzyme complex. In addition, a control containing sugars (glucose and xylose) only was used.

TABLE 46

The amount of each feedstock added to each flask

| Xyleco Number | Amount added to Flask (g/100 mL) |
|---|---|
| P132 | 2.5 |
| P132-10 | 2.5 |
| P132-100 | 2.5 |
| A132 | 5 |
| A132-10 | 5 |
| A132-100 | 5 |
| G132 | 5 |
| G132-10 | 5 |
| G132-100 | 5 |
| WS132 | 5 |
| WS132-10 | 5 |
| WS132-100 | 5 |
| Sample A | 5 |

Analysis

Samples were analyzed for ethanol concentration (Tables 47, 48, and 49) using the YSI Biochem Analyzer based on the alcohol dehydrogenase assay (YSI, Interscience). Samples were centrifuged at 14,000 rpm for 20 minutes and the supernatant stored at −20° C. The samples were diluted to between 0-3.2 g/L ethanol prior to analysis. A standard of 2.0 g/L ethanol was analyzed approximately every 30 samples to ensure the integrity of the membrane was maintained during analysis.

Results

TABLE 47

Results of Control Flasks

| Control | Ethanol Concentration (g/L) | | | |
|---|---|---|---|---|
| | 24 hours | 36 hours | 48 hours | 96 hours |
| Containing Glucose, no cellulose, no enzyme | 13.20 | 19.00 | 20.60 | 21.60 |
| Containing Crystalline Cellulose (Solka Floc), no sugar, no enzyme | 0.00 | 0.00 | 0.00 | 0.00 |
| Containing Crystalline Cellulose (Solka Floc) at 25 g/L, no sugar, Accellerase ® added | 6.56 | 7.88 | 9.80 | 8.65 |

TABLE 48

Results of Shake Flasks without Accellerase ® 1000

| Sample Number | Ethanol Concentration (g/L) | | | |
|---|---|---|---|---|
| | 24 hours | 36 hours | 48 hours | 96 hours |
| P132 | 0.09 | 0.00 | 0.00 | 0.12 |
| P132-10 | 0.02 | 0.01 | 0.02 | 0.17 |
| P132-100 | 0.09 | 0.01 | 0.00 | 0.02 |
| A132 | 1.74 | 1.94 | 2.59 | 3.70 |
| A132-10 | 1.82 | 2.36 | 2.30 | 2.96 |
| A132-100 | 0.30 | 0.73 | 1.31 | 2.38 |
| G132 | 0.40 | 0.09 | 0.24 | 0.42 |
| G132-10 | 0.69 | 0.42 | 0.22 | 0.24 |
| G132-100 | 0.19 | 0.05 | 0.05 | 0.21 |
| WS132 | 0.47 | 0.50 | 0.68 | 0.65 |
| WS132-10 | 0.47 | 0.49 | 0.34 | 0.92 |
| WS132-100 | 0.14 | 0.07 | 0.08 | 0.22 |
| Sample A | 1.88 | 1.89 | 2.30 | 3.28 |

TABLE 49

Results of Shake Flasks with Accellerase ® 1000

| Sample Number | Ethanol Concentration (g/L) | | | |
|---|---|---|---|---|
| | 24 hours | 36 hours | 48 hours | 96 hours |
| P132 | 7.04 | 8.72 | 9.30 | 5.80 |
| P132-10 | 4.22 | 4.48 | 4.49 | 1.24 |
| P132-100 | 3.18 | 4.28 | 4.70 | 3.35 |
| A132 | 2.79 | 2.91 | 2.03 | 4.30 |
| A132-10 | 3.31 | 1.62 | 2.11 | 2.71 |
| A132-100 | 2.06 | 1.92 | 1.02 | 1.47 |
| G132 | 0.87 | 0.40 | 0.32 | 0.44 |
| G132-10 | 1.38 | 1.04 | 0.63 | 0.07 |
| G132-100 | 2.21 | 2.56 | 2.34 | 0.12 |
| WS132 | 1.59 | 1.47 | 1.07 | 0.99 |
| WS132-10 | 1.92 | 1.18 | 0.73 | 0.23 |
| WS132-100 | 2.90 | 3.69 | 3.39 | 0.27 |
| Sample A | 2.21 | 2.35 | 3.39 | 2.98 |

Example 29

Cellulase Assay

Summary

Thirteen samples were tested for cellulase susceptibility using an industry cellulase (Accellerase® 1000, Genencor) under optimum conditions of temperature and pH.

Protocol

The protocol is a modification of the NREL "Laboratory Analytical Procedure LAP-009 *Enzymatic Saccharification of Lignocellulosic Biomass*". A sample of material was added to 10 mL 0.1 M sodium citrate buffer (pH 4.8) and 40 mg/mL tetracycline (to prevent growth of bacteria) in a 50 mL tube in duplicate. The amount of sample added to each tube is listed in Table 50. Some samples were difficult to mix (P132, P132-10, P132-100), so were added at a lower concentration. A positive control of 0.2 grams SolkaFloc 200 NF Powdered Cellulose ( UA158072, International Fiber Corporation) and a negative control (no sample) were also included. Enough reverse osmosis (RO) water to bring the volume to a total of 20 mL was added to the tubes. Both the sodium citrate buffer and water were heated to 50° C. prior to use.

Accellerase® 1000 enzyme was added to each tube at a dosage of 0.25 mL per gram of biomass (highest dosage recommended by Genecor). The tubes were incubated at 45° angle at 150 rpm and 50 degrees C. (recommended by Genencor) for 72 hours. Samples were taken at 0, 3, 6, 9, 12, 18, 24, 48, and 72 hours (Table 52 and 53), centrifuged at 14,000 rpm for 20 minutes and the supernatant frozen at −20° C. The glucose concentration in the samples was analyzed using the YSI Biochem Analyzer (Interscience) using the conditions described in Table 51. A glucose standard solution of 2.5 g/L was prepared by dissolving 2.500 grams glucose (Sigma Cat# G7528-5KG, Lot#: 107H0245) in distilled water. Once dissolved, the total volume was brought to 1 L with distilled water in a volumetric flask. The standard was prepared fresh weekly and stored at 4° C.

TABLE 50

Amount of Each Sample Added

| Xyleco Number | Amount added to Tube (g/20 mL) |
|---|---|
| P132 | 0.5 |
| P132-10 | 0.5 |
| P132-100 | 0.5 |
| A132 | 0.75 |
| A132-10 | 0.75 |
| A132-100 | 0.75 |
| G132 | 0.75 |
| G132-10 | 0.75 |
| G132-100 | 0.75 |
| WS132 | 0.75 |
| WS132-10 | 0.75 |
| WS132-100 | 0.75 |
| Sample A | 0.75 |
| SolkaFloc 200NF (Control) | 0.2 |
| Negative Control | 0 |

TABLE 51

YSI Components Used in Shake Flask Study

| Component | Catalog # | Lot # |
|---|---|---|
| YSI Glucose Membrane | 2365 | 07D100124 |
| YSI Glucose Buffer | 2357 | 014614A |

Results

TABLE 52

Cellulase Assay Results

| Sample Number | Glucose Concentration (mg/mL) at Incubation Time (hours) | | | | | | | | |
|---|---|---|---|---|---|---|---|---|---|
| | 0 | 3 | 6 | 9 | 12 | 18 | 24 | 48 | 72 |
| P132 | 0.59 | 4.19 | 7.00 | 8.72 | 9.70 | 10.95 | 12.19 | 15.10 | 15.65 |
| P132-10 | 0.36 | 3.37 | 5.08 | 6.39 | 6.98 | 7.51 | 8.99 | 11.25 | 11.65 |
| P132-100 | 0.91 | 3.86 | 5.67 | 7.31 | 8.08 | 9.47 | 10.70 | 12.70 | 13.80 |
| A132 | 0.39 | 1.51 | 1.92 | 2.40 | 2.64 | 3.04 | 3.30 | 3.90 | 4.06 |
| A132-10 | 0.42 | 1.80 | 2.27 | 2.63 | 2.86 | 3.16 | 3.43 | 4.02 | 4.14 |

TABLE 52-continued

Cellulase Assay Results

| Sample Number | Glucose Concentration (mg/mL) at Incubation Time (hours) | | | | | | | | |
|---|---|---|---|---|---|---|---|---|---|
| | 0 | 3 | 6 | 9 | 12 | 18 | 24 | 48 | 72 |
| A132-100 | 0.46 | 2.09 | 2.72 | 3.16 | 3.43 | 3.78 | 4.09 | 4.84 | 5.26 |
| G132 | 0.40 | 1.16 | 1.35 | 1.52 | 1.60 | 1.67 | 1.85 | 2.10 | 2.21 |
| G132-10 | 0.34 | 1.34 | 1.64 | 1.95 | 2.03 | 2.09 | 2.36 | 2.77 | 3.02 |
| G132-100 | 0.61 | 1.84 | 2.32 | 2.89 | 3.14 | 3.52 | 3.97 | 4.81 | 5.44 |
| WS132 | 0.35 | 1.48 | 1.81 | 2.14 | 2.26 | 2.50 | 2.70 | 3.18 | 3.26 |
| WS132-10 | 0.44 | 1.77 | 2.22 | 2.60 | 2.76 | 2.61 | 3.15 | 3.62 | 3.82 |
| WS132-100 | 0.70 | 2.76 | 3.63 | 4.59 | 4.78 | 5.29 | 5.96 | 6.99 | 7.43 |
| Sample A | 0.42 | 1.09 | 1.34 | 1.55 | 1.69 | 1.66 | 2.17 | 2.96 | 3.71 |
| Negative Control (no sample) | 0.03 | 0.03 | 0.01 | 0.01 | 0.02 | 0.01 | 0.02 | 0.02 | 0.02 |
| Positive Control (SolkaFloc) | 0.17 | 2.38 | 3.65 | 4.71 | 5.25 | 5.98 | 7.19 | 9.26 | 9.86 |

Figure 65:
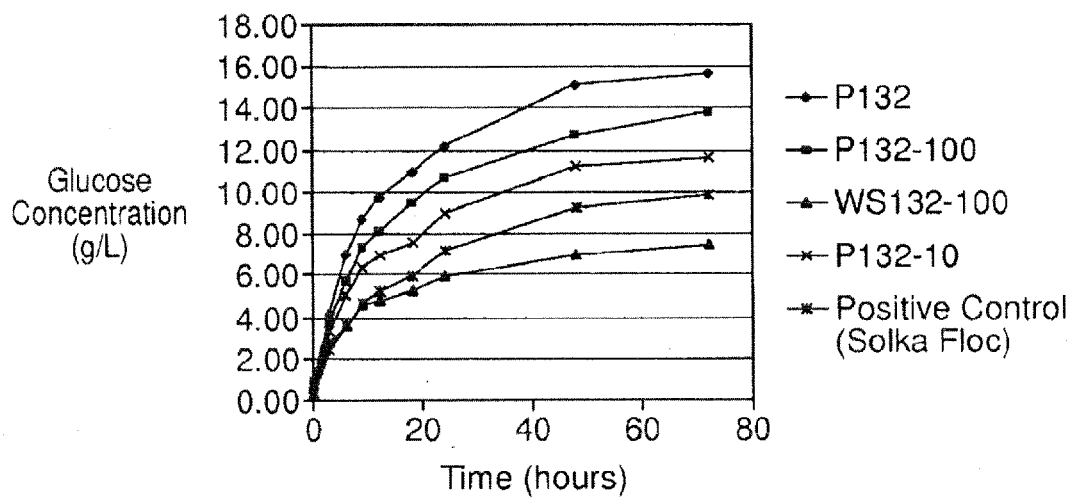
FIG. 65 is a chart showing glucose concentration (top 4
producers) in Example 29.

FIG. 65 shows a graph of glucose concentration (top 4 producers).

The amount of cellulose digested in the tube was calculated as follows:

g/mL glucose×20 mL (volume of sample)×0.9 (to correct for the water molecule added upon hydrolysis of cellulose)

The percent of the total sample released as glucose (in Table 53 below) was calculated as follows:

g of cellulose digested/g of sample added (see Table 5 for details)*100

TABLE 53

Cellulase Assay Results

| Sample Number | Percent of the Total Sample Released as Glucose (%) at Incubation Time (h) | | | | | | | | |
|---|---|---|---|---|---|---|---|---|---|
| | 0 | 3 | 6 | 9 | 12 | 18 | 24 | 48 | 72 |
| P132 | 2.02 | 14.98 | 25.16 | 31.36 | 34.85 | 39.38 | 43.81 | 54.29 | 56.27 |
| P132-10 | 1.19 | 12.02 | 18.25 | 22.97 | 25.06 | 27.00 | 32.29 | 40.43 | 41.87 |
| P132-100 | 3.17 | 13.79 | 20.38 | 26.28 | 29.02 | 34.06 | 38.45 | 45.65 | 49.61 |
| A132 | 0.86 | 3.55 | 4.58 | 5.74 | 6.29 | 7.27 | 7.87 | 9.31 | 9.70 |
| A132-10 | 0.94 | 4.25 | 5.42 | 6.29 | 6.82 | 7.56 | 8.18 | 9.60 | 9.89 |
| A132-100 | 1.03 | 4.94 | 6.50 | 7.56 | 8.18 | 9.05 | 9.77 | 11.57 | 12.58 |
| G132 | 0.89 | 2.71 | 3.22 | 3.62 | 3.79 | 3.98 | 4.39 | 4.99 | 5.26 |
| G132-10 | 0.74 | 3.14 | 3.91 | 4.66 | 4.82 | 4.99 | 5.62 | 6.60 | 7.20 |
| G132-100 | 1.39 | 4.34 | 5.54 | 6.91 | 7.49 | 8.42 | 9.48 | 11.50 | 13.01 |
| WS132 | 0.77 | 3.48 | 4.32 | 5.11 | 5.38 | 5.98 | 6.43 | 7.58 | 7.78 |
| WS132-10 | 0.98 | 4.18 | 5.30 | 6.22 | 6.58 | 6.24 | 7.51 | 8.64 | 9.12 |
| WS132-100 | 1.61 | 6.55 | 8.69 | 10.99 | 11.42 | 12.67 | 14.26 | 16.73 | 17.78 |
| Sample A | 0.94 | 2.54 | 3.19 | 3.70 | 4.01 | 3.96 | 5.16 | 7.06 | 8.86 |
| Positive Control (SolkaFloc) | 1.29 | 21.15 | 32.72 | 42.30 | 47.07 | 53.73 | 64.53 | 83.16 | 88.56 |

TABLE 54

Equipment and Frequency of Maintenance

| Equipment | Manufacturer, Name | Frequency of Maintenance |
|---|---|---|
| Shakers (2) | B. Braun Biotech, Certomat BS-1 | Quarterly |
| Spectrophotometer | Unicam, UV300 | Biannual |
| YSI Biochem Analyzer | Interscience, YSI | Monthly |

Example 30

Shake Flask Fermentation Using *Pichia stipitis*

Summary

Shake flask fermentation using *Pichia stipitis* was performed using four cellulosic materials having the highest % performance from Table 36.

Protocol

Experiments were run under the parameters outlined in Tables 54-56.

TABLE 55

YSI Components Used in Shake Flask Study

| Component | Reference # | Lot # |
|---|---|---|
| YSI Ethanol Membrane | 2786 | 07M100361 |
| YSI Ethanol Standard (3.2 g/L) | 2790 | 1271040 |
| YSI Ethanol Buffer | 2787 | 07J100215 |

TABLE 56

Chemicals Used for Shake Flask Fermentation

| Media Component | Manufacturer | Reference # | Lot # |
|---|---|---|---|
| Urea | ScholAR Chemistry | 9472706 | AD-7284-43 |
| Yeast Nitrogen Base | Becton Dickinson | 291940 | 7128171 |
| Peptone | Becton Dickinson | 211677 | 4303198 |
| YM Broth | Becton Dickinson | 271120 | 6278265 |
| Xylose | Alfa Aesar | A10643 | 10130919 |
| Glucose | Fisher Scientific | BP350-1 | 030064 |

Seed Development

For all the following shake flask experiments the seed flasks were prepared using the following procedure.

A working cell bank of *P. stipitis* NRRL Y-7124 was prepared from a rehydrated lyophilized culture obtained from ARS Culture Collection. Cryovials containing *P. stipitis* culture in 15% v/v glycerol were stored at −75° C. A portion of the thawed working cell bank material was streaked onto a Yeast Mold (YM) Broth+20 g/L agar (pH 5.0) and incubated at 30° C. for 2 days. The plates were held for 2 days at 4° C. before use. A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) was inoculated with one colony and incubated for 24 hours at 25° C. and 100 rpm. After 23 hours of growth, a sample was taken and analyzed for optical density (600 nm in a UV spectrophotometer) and purity (Gram stain). Based on these results, one flask (called the Seed Flask) at an optical density of between 4 and 8 and with a clean Gram stain was used to inoculate all of the test flasks.

Three experiments were run using samples A132-10, A132-100, G132-10, and G132-100. Experiment #1 tested these four samples for ethanol concentration at varying concentrations of xylose and at constant concentrations of glucose. Experiment #2 tested these four samples for ethanol concentration at double the concentration of feedstock used in the experiments of Table 36. Finally, experiment #3 tested these four samples for ethanol concentration while varying both the xylose and the glucose concentrations, simultaneously.

Experiment #1—Varying the Xylose Concentration

Four cellulosic samples (A132-10, A132-100, G132-10, and G132-100) were tested at varying xylose concentrations as listed in Table 57 below.

TABLE 57

Media Composition of Experiment #1 Flasks

| Treatment | Xylose Concentration (g/L) | Glucose Concentration (g/L) |
|---|---|---|
| 100% Xylose | 40.0 | 40.0 |
| 50% Xylose | 20.0 | 40.0 |
| 25% Xylose | 10.0 | 40.0 |
| 10% Xylose | 4.0 | 40.0 |
| 0% Xylose | 0.0 | 40.0 |

The test vessels (a total of 40, 250 mL Erlenmeyer flasks) contained 100 mL of medium. Five different types of media were prepared with the amount of xylose and glucose outlined in Table 57. In addition, the media contained 1.7 g/L yeast nitrogen base (Becton Dickinson #291940) 2.27 g/L urea (ScholAR Chemistry #9472706), and 6.56 g/L peptone (Becton Dickinson #211677). All flasks were autoclaved empty at 121° C. and 15 psi and filter sterilized (0.22 µm filter) media was added to the flasks prior to the addition of the test materials. Flasks were held at room temperature for 4 days and inspected for contamination (cloudiness) prior to use. The test materials were not sterilized, as autoclaving will change the content of the samples and filter sterilization not appropriate for sterilization of solids. The test samples (A132-10, A132-100, G0132-10, and G132-100 at 5 g per 100 mL) were added at the time of inoculation (rather than prior to) to reduce the possibility of contamination. In addition to the test samples, 1 mL (1% v/v) of seed flask material was added to each flask. The flasks were incubated at 30° C. and 150 rpm for 72 hours.

Unfortunately, one flask (sample A132-100 with 100% Xylose) was broken during the testing. Therefore, all results past 24 hours of incubation are reported as a single flask. After 72 hours of incubation, 100% of the original amount of cellulosic material (5.0 g) was added to the 100% Xylose flasks (7 flasks in total, one flask containing sample A132-100 was broken) and incubated as above for an additional 48 hours.

TABLE 58

Addition of Feedstock to 100% Xylose Flasks at Incubation Time 72 hours

| Feedstock | Added at 72 hours (grams) |
|---|---|
| A132-10 | 5 |
| A132-100 | 5 |
| G132-10 | 5 |
| G132-100 | 5 |

Analysis

Samples were taken from the 40 test flasks at incubation times of 0, 6, 12, 24, 36, 48, and 72 hours. In addition, samples were taken at 24 and 48 hours post-addition of the second feedstock amount in the 100% Xylose flasks (see Table 58).

A total of 292 samples were analyzed for ethanol concentration using a YSI Biochem Analyzer based on the alcohol dehydrogenase assay (YSI, Interscience). Samples were centrifuged at 14,000 rpm for 20 minutes and the supernatant stored at −20° C. Of note, time 0 samples required filtration through a 0.45 µm syringe filter. The samples will be diluted to between 0-3.2 g/L ethanol prior to analysis. A standard of 2.0 g/L ethanol was analyzed approximately every 30 samples to ensure the integrity of the membrane was maintained.

A total of 47 samples were analyzed for cell count. Samples will be taken at 72 hours incubation and 48 hours post-addition of more cellulosic material. Appropriately diluted samples were mixed with 0.05% Trypan blue and loaded into a Neubauer haemocytometer. The cells were counted under 40× magnification.

Experiment #2—Analysis of 2× Feedstock Concentration

The test vessels (a total of 8, 250 mL Erlenmeyer flasks) contained 100 mL of medium. The media contained 40 g/L glucose, 40 g/L xylose, 1.7 g/L yeast nitrogen base (Becton Dickinson #291940) 2.27 g/L urea (ScholAR Chemistry #9472706), and 6.56 g/L peptone (Becton Dickinson #211677). Flasks were prepared as in Experiment #1.

The test samples (A132-10, A132-100, G132-10, and G132-100 at 10 g per 100 mL) were added at the time of inoculation (rather than prior to) to reduce the possibility of contamination. In addition to the test samples, 1 mL (1% v/v) of seed flask material was added to each flask. The flasks were incubated at 30° C. and 150 rpm above for 72 hours.

Analysis

Samples were from the 8 test flasks at an incubation time of 0, 6, 12, 24, 36, 48, and 72 hours. Ethanol analyses of the 56 samples was performed as per experiment #1 and are reported in Table 59. A cell count was performed on the 72 hour sample as per experiment #1 and is presented in Table 60.

TABLE 59

Ethanol Concentration in Flasks with Double Feedstock

| Sample Time | Ethanol Concentration (g/L) | | | |
|---|---|---|---|---|
| | A132-10 | A132-100 | G132-10 | G132-100 |
| 0 | 1.38 | 0.26 | 0.12 | 0.11 |
| 6 | 1.75 | 0.21 | 0.20 | 0.10 |
| 12 | 2.16 | 0.73 | 0.69 | 0.31 |
| 24 | 19.05 | 15.35 | 16.55 | 12.60 |
| 36 | 21.75 | 17.55 | 18.00 | 15.30 |
| 48 | 26.35 | 23.95 | 24.65 | 20.65 |
| 72 | 26.95 | 27.35 | 28.90 | 27.40 |

TABLE 60

Cell Concentration at 72 hour Incubation Time in Flasks with Double Feedstock

| Sample | Cell Concentration (×10$^8$/mL) |
|---|---|
| A132-10 | 4.06 |
| A132-100 | 5.37 |
| G132-10 | 5.18 |
| G132-100 | 4.47 |

Experiment #3—Varying Xylose and Glucose Concentrations

Four cellulosic samples (A132-10, A132-100, G132-10, and G132-100) were tested at varying xylose and glucose concentrations as listed in the table below (Table 60).

TABLE 61

Media Composition of Experiment #3 Flasks

| Treatment | Xylose Concentration (g/L) | Glucose Concentration (g/L) |
|---|---|---|
| 50% Sugar | 20.0 | 20.0 |
| 25% Sugar | 10.0 | 10.0 |
| 10% Sugar | 4.0 | 4.0 |
| 0% Sugar | 0.0 | 0 |

The test vessels (a total of 32, 250 mL Erlenmeyer flasks) contained 100 mL of medium. Four different types of media were prepared with the amount of xylose and glucose outlined in Table 61. In addition, the media contained 1.7 g/L yeast nitrogen base (Becton Dickinson #291940) 2.27 g/L urea (ScholAR Chemistry #9472706), and 6.56 g/L peptone (Becton Dickinson #211677). The flasks were prepared as per Experiment #1. The test samples (A132-10, A132-100, G132-10, and G132-100) were added at the time of inoculation (rather than prior to) to reduce the possibility of contamination. In addition to the test samples, 1 mL (1% v/v) of seed flask material was added to each flask. The flasks were incubated at 30° C. and 150 rpm for 72 hours.

Analysis

Samples were taken from the 32 test flasks at an incubation time of 0, 6, 12, 24, 36, 48, and 72 hours (see Tables 62-65). A total of 224 samples were analyzed for ethanol concentration using the YSI Biochem Analyzer based on the alcohol dehydrogenase assay (YSI, Interscience). Samples were centrifuged at 14,000 rpm for 20 minutes and the supernatant stored at −20° C. Of note, some of the samples required centrifugation and then filtration through a 0.45 μm syringe filter. The samples were diluted to between 0-3.2 g/L ethanol prior to analysis. A standard of 2.0 g/L ethanol was analyzed approximately every 30 samples to ensure the integrity of the YSI membrane was maintained.

TABLE 62

Ethanol Results Sample A132-10

| Sample Time | Ethanol Concentration (g/L) | | | | | | | | |
|---|---|---|---|---|---|---|---|---|---|
| | 0% Xylose | 10% Xylose | 25% Xylose | 50% Xylose | 100% Xylose | 0% Sugars* | 10% Sugars* | 25% Sugars* | 50% Sugars* |
| 0 | 0.43 | 0.42 | 0.42 | 0.41 | 0.39 | 0.53 | 0.57 | 0.56 | 0.56 |
| 6 | 1.16 | 1.16 | 1.15 | 1.16 | 1.12 | 0.93 | 0.91 | 0.83 | 0.88 |
| 12 | 1.72 | 1.86 | 1.71 | 1.79 | 1.90 | 1.21 | 2.13 | 2.47 | 2.32 |
| 24 | 15.55 | 15.90 | 17.05 | 17.05 | 16.95 | 1.02 | 4.88 | 9.77 | 13.35 |
| 36 | 17.10 | 17.40 | 20.25 | 21.35 | 20.25 | 1.29 | 4.27 | 9.99 | 17.55 |
| 48 | 16.40 | 17.05 | 19.70 | 23.00 | 26.80 | 1.47 | 3.03 | 8.33 | 16.60 |
| 72 | 15.15 | 15.55 | 19.25 | 21.85 | 28.00 | 1.14 | 1.52 | 5.08 | 14.20 |
| 24 hours post-addition | — | — | — | — | 23.15 | — | — | — | — |
| 48 hours post-addition | — | — | — | — | 21.55 | — | — | — | — |

*Analysis from experiment #3.

TABLE 63

Ethanol Results Sample A132-100

Ethanol Concentration (g/L)

| Sample Time | 0% Xylose | 10% Xylose | 25% Xylose | 50% Xylose | 100% Xylose | 0% Sugars* | 10% Sugars* | 25% Sugars* | 50% Sugars* |
|---|---|---|---|---|---|---|---|---|---|
| 0 | 0.11 | 0.09 | 0.17 | 0.20 | 0.18 | 0.12 | 0.14 | 0.09 | 0.13 |
| 6 | 0.13 | 0.15 | 0.15 | 0.15 | 0.14 | 0.10 | 0.11 | 0.11 | 0.13 |
| 12 | 0.88 | 1.00 | 1.18 | 1.25 | 0.89 | 0.18 | 1.58 | 1.55 | 1.57 |
| 24 | 15.90 | 15.70 | 16.50 | 16.05 | 14.60** | 0.18 | 3.33 | 7.99 | 11.15 |
| 36 | 16.00 | 17.90 | 16.90 | 19.45 | 17.80** | 0.21 | 2.85 | 8.37 | 16.10 |
| 48 | 15.75 | 16.70 | 19.30 | 22.15 | 27.00** | 0.54 | 1.47 | 7.54 | 15.60 |
| 72 | 14.85 | 15.35 | 18.55 | 21.30 | 28.50** | 0.78 | 0.51 | 4.47 | 12.90 |
| 24 hours post-addition | — | — | — | — | 24.80** | — | — | — | — |
| 48 hours post-addition | — | — | — | — | 23.60** | — | — | — | — |

*Analysis from experiment #3.
**All results based on analysis of one flask.

TABLE 64

Ethanol Results Sample G132-10

Ethanol Concentration (g/L)

| Sample Time | 0% Xylose | 10% Xylose | 25% Xylose | 50% Xylose | 100% Xylose | 0% Sugars* | 10% Sugars* | 25% Sugars* | 50% Sugars* |
|---|---|---|---|---|---|---|---|---|---|
| 0 | 0.09 | 0.08 | 0.08 | 0.08 | 0.08 | 0.05 | 0.05 | 0.05 | 0.06 |
| 6 | 0.14 | 0.13 | 0.14 | 0.14 | 0.13 | 0.11 | 0.12 | 0.11 | 0.12 |
| 12 | 1.01 | 0.96 | 1.00 | 0.87 | 1.14 | 0.48 | 1.60 | 1.79 | 1.71 |
| 24 | 15.90 | 15.70 | 16.30 | 16.05 | 14.60 | 0.13 | 3.96 | 8.54 | 11.10 |
| 36 | 15.10 | 17.45 | 16.80 | 18.75 | 22.15 | 0.09 | 3.02 | 8.69 | 16.55 |
| 48 | 15.95 | 16.90 | 19.25 | 21.10 | 24.00 | 0.07 | 2.05 | 8.10 | 16.50 |
| 72 | 13.50 | 15.80 | 18.55 | 21.25 | 26.55 | 0.09 | 0.11 | 5.55 | 14.15 |
| 24 hours post-addition | — | — | — | — | 24.95 | — | — | — | — |
| 48 hours post-addition | — | — | — | — | 24.20 | — | — | — | — |

*Analysis from experiment #3.

TABLE 65

Ethanol Results Sample G132-100

Ethanol Concentration (g/L)

| Sample Time | 0% Xylose | 10% w/v Xylose | 25% w/v Xylose | 50% w/v Xylose | 100% w/v Xylose | 0% Sugars* | 10% Sugars* | 25% Sugars* | 50% Sugars* |
|---|---|---|---|---|---|---|---|---|---|
| 0 | 0.04 | 0.04 | 0.04 | 0.04 | 0.05 | 0.05 | 0.05 | 0.05 | 0.06 |
| 6 | 0.07 | 0.07 | 0.08 | 0.08 | 0.07 | 0.04 | 0.05 | 0.05 | 0.06 |
| 12 | 0.60 | 0.56 | 0.67 | 0.58 | 0.71 | 0.13 | 1.37 | 1.48 | 1.44 |
| 24 | 13.05 | 14.45 | 14.90 | 13.95 | 12.05 | 0.03 | 3.67 | 7.62 | 10.55 |
| 36 | 15.10 | 17.10 | 18.25 | 18.20 | 19.25 | 0.01 | 3.09 | 8.73 | 16.10 |
| 48 | 14.40 | 17.00 | 19.35 | 22.55 | 24.45 | 0.01 | 1.91 | 7.76 | 15.85 |
| 72 | 14.70 | 15.40 | 18.45 | 22.10 | 27.55 | 0.03 | 0.01 | 5.08 | 14.30 |
| 24 hours post-addition | — | — | — | — | 25.20 | — | — | — | — |
| 48 hours post-addition | — | — | — | — | 24.60 | — | — | — | — |

*Analysis from experiment #3.

Samples were taken at 72 hours incubation for cell counts (see Tables 66-67). Appropriately diluted samples were mixed with 0.05% Trypan blue and loaded into a Neubauer haemocytometer. The cells were counted under 40× magnification.

Results

One seed flask was used to inoculate all Experiment #1 and #2 test flasks. The optical density (600 nm) of the seed flask was measured to be 5.14 and the cell concentration was $4.65 \times 10^8$ cells/mL (Tables 65-66). Therefore, the initial concentration of cells in the test flasks was approximately $4.65 \times 10^6$ cells/mL.

A second seed flask was used to inoculate Experiment #3 flasks. The optical density (600 nm) of the seed flask was 5.78 and the cell concentration was $3.75 \times 10^8$ cells/mL. Therefore, the initial concentration of cells in the test flasks was approximately $3.75 \times 10^6$ cells/mL.

TABLE 66

Cell Counts at Incubation Time of 72 hour

Cell Concentration ($\times 10^8$/mL)

| Sample | 0% Xylose | 10% Xylose | 25% Xylose | 50% Xylose | 100% Xylose | 0% Sugar | 10% Sugar | 25% Sugar | 50% Sugar |
|---|---|---|---|---|---|---|---|---|---|
| A132-10 | 0.37 | 0.63 | 3.72 | 4.92 | 4.05 | 0.26 | 0.22 | 0.26 | 1.54 |
| A132-100 | 0.99 | 1.07 | 0.99 | 0.78 | 1.97 | 0.03* | 0.33 | 0.44 | 1.81 |
| G132-10 | 0.95 | 4.50 | 2.67 | 2.67 | 3.82 | 0.01* | 0.17 | 0.49 | 1.92 |
| G132-100 | 6.53 | 4.02 | 4.84 | 4.47 | 5.29 | 0.01* | 0.33 | 0.89 | 2.22 |

*Samples were heavily contaminated after 72 hours of growth. This is expected because the Pichia did not grow well without sugar added, and contaminants (from the non-sterile samples) were able to out-grow the Pichia.

TABLE 67

Cell Counts at Incubation Time of 48 hours Post-Addition (100% Xylose and Glucose)

| Sample | Cell Concentration ($\times 10^8$/mL) |
|---|---|
| A132-10 | 10.17 |
| A132-100 | 3.38 |
| G132-10 | 3.94 |
| G132-100 | 6.53 |

Example 31

Toxicity Testing of Lignocellulosic Samples Against *P. stipitis* and *S. cerevisiae*

Summary

Thirty-seven samples were analyzed for toxicity against two ethanol-producing cultures, *Saccharomyces cerevisiae* and *Pichia stipitis*. In this study, glucose was added to the samples in order to distinguish between starvation of the cultures and toxicity of the samples.

TABLE 68

Conditions for Toxicity Testing

| | Organism | |
|---|---|---|
| Variable | *Saccharomyces cerevisiae* ATCC 24858 | *Pichia stipitis* NRRL Y-7124 |
| Inoculation Volume (mL) | 0.5-1 (target $6-7 \times 10^5$ cells/mL) | 1 (target $3-4 \times 10^6$ cells/mL) |
| Test Repetition | Single Flasks | |
| Incubation Temperature ($\pm 1°$ C.) | 25° C. | 25° C. |
| Shaker Speed (rpm) | 200 | 125 |
| Type of Container | 500 mL Erlenmeyer Flask | 250 mL Erlenmeyer Flask |
| Media volume | 100 mL | 100 mL |
| Total Incubation time (hours) | 72 | 72 |
| Ethanol Analysis (hours) | 0, 6, 12, 24, 36, 48, 72 | 0, 6, 12, 24, 36, 48, 72 |
| Cell Counts (hours) | 24, 72 | 24, 72 |
| pH | 0 hours | 0 hours |

Protocol

A summary of the protocol used is listed in Table 68. A description of the chemicals used in toxicity testing is listed in Table 69. Two control flasks (no sample added) were performed for each microorganism for each week of testing. A total of 82 flasks were analyzed.

During the experiments, no ethanol or cells appeared in the *P. stipitis* flasks containing samples C, C-1e, C-5e, and C-10e in the first 24 hours of incubation. In order to confirm the results, the test was repeated. The second test confirmed some inhibition of *P. stipitis* growth when samples C, C1E, C5E, and C10E were added to the flasks.

TABLE 69

Chemicals and Materials Used for Toxicity Testing

| Media Component | Manufacturer | Reference # | Lot # |
|---|---|---|---|
| Urea | ScholAR Chemistry | 9472706 | AD-7284-43 |
| Yeast Nitrogen Base | Becton Dickinson | 291940 | 7128171 |

TABLE 69-continued

Chemicals and Materials Used for Toxicity Testing

| Media Component | Manufacturer | Reference # | Lot # |
|---|---|---|---|
| Peptone | Becton Dickinson | 211677 | 4303198 |
| Xylose | Alfa Aesar | A10643 | 10130919 |
| Glucose | Sigma | G-5400 | 107H0245 |
| Yeast Extract | Becton Dickinson | 288620 | 4026828 |
| YM Broth | Becton Dickinson | 271120 | 6278265 |

TABLE 70

YSI Components Used in Toxicity Study

| Component | Catalogue # |
|---|---|
| YSI Ethanol Membrane | 2786 |
| YSI Ethanol Standard (3.2 g/L) | 2790 |
| YSI Ethanol Buffer | 2787 |

Test Samples

Seven test samples (all with the C designation) were ground using a coffee grinder suitable for small samples. The samples were ground to a consistent particle size (between samples) with the naked eye. Sample number C-100e ground easily to a small particle size.

All samples were added to the flasks at a concentration of 50 grams per liter with the exception of the six P samples (25 grams per liter). These samples were white to off-white in color and visually fluffy and the flasks would not mix properly (not enough free liquid) at the 50 grams per liter concentration. Samples S dissolved easily and could in the future be added to the flasks at a higher concentration. Samples A and G could be added at 100 grams per Liter in the future.

Testing was performed using the two microorganisms as described below.

*Saccharomyces cerevisiae* ATCC 24858 (American Type Culture Collection)

A working cell bank of *S. cerevisiae* ATCC 24858 was prepared from a rehydrated lyophilized culture obtained from American Type Culture Collection. Cryovials containing *S. cerevisiae* culture in 15% v/v glycerol are stored at −75° C. A portion of the thawed working cell bank material will be streaked onto a Yeast Mold (YM) Broth+20 g/L agar (pH 5.0) and incubated at 30° C. for 2 days. A 250 mL Erlenmeyer flask containing 50 mL of medium (20 g/L glucose, 3 g/L yeast extract, and 5.0 g/L peptone, pH 5.0) was inoculated with one colony from the YM plate and incubated for 24 hours at 25° C. and 200 rpm. After 23 hours of growth, a sample was taken and analyzed for optical density (600 nm in a UV spectrophotometer) and purity (Gram stain). Based on these results, one flask (called the Seed Flask) with an OD of 9-15 and pure Gram stain was to be used for inoculating the growth flasks. After 23 hours of growth, the seed flask had a low OD (5.14) and cell count ($1.35 \times 10^8$ cells/mL). Of note, the colony taken from the seed plate was smaller than usual. Therefore, 0.5 mL of seed material (as opposed to the planned 0.1 mL) was added to each test vessel.

The test vessels were 500 mL Erlenmeyer flasks containing 100 mL of the sterile medium described above. All flasks were autoclaved at 121° C. and 15 psi prior to the addition of the test materials. The test materials were not sterilized, as autoclaving would change the content of the samples. The test samples were added at the time of inoculation (rather than prior to) to reduce the possibility of contamination. In addition to the test samples, 0.5-1.0 mL (0.5-1.0% v/v) of seed flask material was added to each flask. The flasks were incubated as described above for 72 hours.

*Pichia stipitis* (ARS Culture Collection)

A working cell bank of *P. stipitis* NRRL Y-7124 was prepared from a rehydrated lyophilized culture obtained from ARS Culture Collection. Cryovials containing *P. stipitis* culture in 15% v/v glycerol are stored at −75° C. A portion of the thawed working cell bank material was streaked onto a Yeast Mold (YM) Broth+20 g/L agar (pH 5.0) and incubated at 30° C. for 2 days. The plates were held for up to 5 days at 4° C. before use. A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) was inoculated with one colony and incubated for 24 hours at 25° C. and 125 rpm. After 23 hours of growth, a sample was taken and analyzed for optical density (600 nm in a UV spectrophotometer) and purity (Gram stain). Based on these results, one flask (called the Seed Flask) at an optical density of 5-9 and with a pure Gram Stain was used to inoculate all of the test flasks.

The test vessels were 250 mL Erlenmeyer flasks containing 100 mL of the sterile medium described above. All flasks were autoclaved empty at 121° C. and 15 psi and filter sterilized (0.22 μm filter) medium added to the flasks prior to the addition of the test materials. The test materials were not sterilized, as autoclaving would change the content of the samples and filter sterilization not appropriate for sterilization of solids. The test samples were added at the time of inoculation (rather than prior to) to reduce the possibility of contamination. In addition to the test samples, 1 mL (1% v/v) of seed flask material was added to each flask. The flasks were incubated as described above for 72 hours.

Analysis

Samples were taken from seed flasks just prior to inoculation and each test flask at 24 and 72 hours and analyzed for cell concentration using direct counts. Appropriately diluted samples of *S. cerevisiae* and *P. stipitis* were mixed with 0.05% Trypan blue, loaded into a Neubauer haemocytometer. The cells were counted under 40× magnification.

Samples were taken from each flask at 0, 6, 12, 24, 36, 48 and 72 hours and analyzed for ethanol concentration using the YSI Biochem Analyzer based on the alcohol dehydrogenase assay (YSI, Interscience). Samples were centrifuged at 14,000 rpm for 20 minutes and the supernatant stored at −20° C. The samples will be diluted to 0-3.2 g/L ethanol prior to analysis. A standard of 2.0 g/L ethanol was analyzed approximately every 30 samples to ensure the integrity of the membrane was maintained during analysis.

Calculations

The following calculations were used to compare the cell counts and ethanol concentration to the control flasks.

% performance=(concentration of ethanol in test flask/ethanol in control)*100% cells=(number of cells in test flask/number of cells in control flask)*100

Results

The *S. cerevisiae* seed flask had an optical density (600 nm) of 5.14 and a cell concentration of $1.35 \times 10^8$ cells/mL. One half mL of seed flask material was added to each of the test flasks. Therefore, the starting cell concentration in each flask was $6.75 \times 10^5$/mL. During the second week of testing, the *S. cerevisiae* seed flask had an optical density (600 nm) of 4.87 and a cell concentration of $3.15 \times 10^7$ cells/mL. One mL of seed flask material was added to each of the test flasks. Therefore, the starting cell concentration in each flask was 6.30×10$^5$/mL. The pH of the *S. cerevisiae* flasks at a sample time of 0 hours is presented in Table 71. The pH of the flask contents was within the optimal pH for *S. cerevisiae* growth (pH 4-6). No pH adjustment was required.

TABLE 71 pH of *S. cerevisiae* flasks at sample time 0 hours

| Sample Number | pH |
|---|---|
| P | 5.04 |
| P1E | 4.99 |
| P5E | 5.04 |
| P10E | 4.98 |
| P50E | 4.67 |
| P100E | 4.43 |
| G | 5.45 |
| G1E | 5.47 |
| G5E | 5.46 |
| G10E | 5.39 |
| G50E | 5.07 |
| A | 5.72 |
| A1E | 5.69 |
| A5E | 5.62 |
| A10E | 5.61 |
| A50E | 5.74 |
| S* | 5.10 |
| S1E | 5.08 |
| S5E | 5.07 |
| S10E | 5.04 |
| S30E | 4.84 |
| S50E | 4.57 |
| S100E | 4.33 |
| C | 5.46 |
| C1E | 5.54 |
| C5E | 5.50 |
| C10E | 5.33 |
| C30E | 5.12 |
| C50E | 4.90 |
| C100E | 4.66 |
| ST | 5.11 |
| ST1E | 5.06 |
| ST5E | 4.96 |
| ST10E | 4.94 |
| ST30E | 5.68 |
| ST50E | 4.48 |
| ST100E | 4.23 |
| control A | 5.02 |
| control B | 5.04 |

*"S" refers to sucrose
*"C" refers to corn
*"ST" refers to starch

The ethanol concentration and performance in the *S. cerevisiae* flasks are presented in Table 72 and 73. The highest ethanol concentrations were produced by the S (sucrose) samples.

TABLE 72

Ethanol Concentration in *S. cerevisiae* flasks

| Sample Number | Ethanol Concentration (g/L) at the following times (hours) | | | | | | |
|---|---|---|---|---|---|---|---|
| | 0 | 6 | 12 | 24 | 36 | 48 | 72 |
| P | 0.02 | 0.04 | 0.38 | 5.87 | 7.86 | 5.41 | 1.04 |
| P1E | 0.03 | 0.03 | 0.28 | 5.10 | 8.03 | 5.46 | 0.58 |
| P5E | 0.03 | 0.04 | 0.57 | 8.84 | 6.38 | 3.40 | 0.04 |
| P10E | 0.06 | 0.05 | 0.65 | 6.63 | 7.66 | 5.57 | 1.40 |
| P50E | 0.04 | 0.03 | 0.26 | 2.80 | 5.85 | 8.59 | 5.68 |
| P100E | 0.04 | 0.02 | 0.12 | 3.64 | 8.26 | 7.51 | 3.03 |
| G | 0.04 | 0.04 | 0.57 | 10.20 | 8.24 | 6.66 | 2.84 |
| G1E | 0.04 | 0.05 | 0.46 | 10.20 | 9.24 | 6.94 | 2.84 |
| G5E | 0.11 | 0.11 | 0.44 | 10.00 | 8.7 | 6.36 | 0.88 |
| G10E | 0.05 | 0.04 | 0.40 | 9.97 | 8.41 | 5.79 | 0.11 |
| G50E | 0.05 | 0.05 | 0.48 | 9.72 | 8.33 | 6.13 | 2.38 |
| A | 0.29 | 0.38 | 0.48 | 8.43 | 8.76 | 7.09 | 4.66 |
| A1E | 0.34 | 0.44 | 0.79 | 9.66 | 8.9 | 7.18 | 2.64 |
| A5E | 0.55 | 0.45 | 0.99 | 9.44 | 8.96 | 7.56 | 3.80 |
| A10E | 0.55 | 0.55 | 0.93 | 9.58 | 8.33 | 6.28 | 1.40 |
| A50E | 0.22 | 0.08 | 0.38 | 9.38 | 8.01 | 5.99 | 0.98 |
| S | 0.03 | 0.03 | 0.39 | 5.73 | 7.06 | 10.10 | 15.90 |
| S1E | 0.05 | 0.06 | 0.31 | 7.24 | 9.52 | 12.10 | 14.90 |
| S5E | 0.02 | 0.05 | 0.34 | 5.87 | 7.68 | 11.90 | 19.00 |
| S10E | 0.03 | 0.04 | 0.35 | 5.88 | 7.72 | 11.50 | 19.30 |
| S30E | 0.03 | 0.05 | 0.09 | 5.94 | 7.97 | 11.20 | 20.40 |
| S50E* | 0.13 | 0.19 | 0.47 | 5.46 | 7.96 | 13.00 | 18.30 |
| S100E | 0.11 | 0.10 | 0.21 | 7.00 | 10.6 | 13.80 | 12.70 |
| C | 0.01 | 0.04 | 0.32 | 8.47 | 7.57 | 5.48 | 6.40 |
| C1E | 0.00 | 0.06 | 0.37 | 8.93 | 7.86 | 5.99 | 1.37 |
| C5E | 0.03 | 0.05 | 0.48 | 9.32 | 7.92 | 5.69 | 1.41 |
| C10E | 0.02 | 0.04 | 0.52 | 9.14 | 7.67 | 5.34 | 0.35 |
| C30E | 0.02 | 0.05 | 0.28 | 9.15 | 8.15 | 5.84 | 2.47 |
| C50E | 0.03 | 0.06 | 0.44 | 9.31 | 7.79 | 5.78 | 1.79 |
| C100E | 0.03 | 0.06 | 0.58 | 9.06 | 6.85 | 5.95 | 1.09 |
| ST | 0.02 | 0.05 | 0.99 | 8.54 | 6.69 | 5.09 | 0.42 |
| ST1E | 0.03 | 0.04 | 0.70 | 8.87 | 7.29 | 4.81 | 1.04 |
| ST5E | 0.02 | 0.04 | 0.52 | 8.61 | 7.16 | 4.97 | 0.85 |
| ST10E | 0.02 | 0.05 | 0.33 | 8.97 | 7.05 | 5.26 | 0.68 |
| ST30E | 0.03 | 0.04 | 0.71 | 8.47 | 6.96 | 4.89 | 0.21 |
| ST50E | 0.04 | 0.07 | 0.34 | 8.46 | 8.19 | 7.04 | 3.20 |
| ST100E | 0.03 | 0.10 | 0.30 | 9.30 | 8.62 | 7.29 | 4.23 |
| control A | 0.01 | 0.07 | 0.85 | 5.92 | 8.18 | 7.81 | 6.26 |
| control B | 0.01 | 0.04 | 0.27 | 4.86 | 6.43 | 8.01 | 6.75 |
| control A* | 0.04 | 0.21 | 1.36 | 5.19 | 7.31 | 7.55 | 5.16 |
| control B* | 0.03 | 0.20 | 1.18 | 5.16 | 5.96 | 7.62 | 5.32 |

*analyzed week 2

TABLE 73

Performance in *S. cerevisiae* flasks

| Sample Number | Performance (%) at the following times (hours) | | | |
|---|---|---|---|---|
| | 24 | 36 | 48 | 72 |
| P | 108.9 | 107.6 | 68.4 | 16.0 |
| P1E | 94.6 | 109.9 | 69.0 | 8.9 |
| P5E | 164.0 | 87.3 | 43.0 | 0.6 |
| P10E | 123.0 | 104.9 | 70.4 | 21.5 |
| P50E | 51.9 | 80.1 | 108.6 | 87.3 |
| P100E | 67.5 | 113.1 | 94.9 | 46.5 |
| G | 189.2 | 112.8 | 84.2 | 43.6 |
| G1E | 189.2 | 126.5 | 87.7 | 43.6 |
| G5E | 185.5 | 119.1 | 80.4 | 13.5 |
| G10E | 185.0 | 115.1 | 73.2 | 1.7 |
| G50E | 180.3 | 114.0 | 77.5 | 36.6 |
| A | 156.4 | 119.9 | 89.6 | 71.6 |
| A1E | 179.2 | 121.8 | 90.8 | 40.6 |
| A5E | 175.1 | 122.7 | 95.6 | 58.4 |
| A10E | 177.7 | 114.0 | 79.4 | 21.5 |
| A50E | 174.0 | 109.7 | 75.7 | 15.1 |
| S | 106.3 | 96.6 | 127.7 | 244.2 |
| S1E | 134.3 | 130.3 | 153.0 | 228.9 |
| S5E | 108.9 | 105.1 | 150.4 | 291.9 |
| S10E | 109.1 | 105.7 | 145.4 | 296.5 |
| S30E | 110.2 | 109.1 | 141.6 | 313.4 |
| S50E* | 105.5 | 119.9 | 171.3 | 349.2 |
| S100E | 129.9 | 145.1 | 174.5 | 195.1 |
| C | 157.1 | 103.6 | 69.3 | 98.3 |
| C1E | 165.7 | 107.6 | 75.7 | 21.0 |
| C5E | 172.9 | 108.4 | 71.9 | 21.7 |
| C10E | 169.6 | 105.0 | 67.5 | 5.4 |
| C30E | 169.8 | 111.6 | 73.8 | 37.9 |
| C50E | 172.7 | 106.6 | 73.1 | 27.5 |

TABLE 73-continued

Performance in *S. cerevisiae* flasks

| Sample Number | Performance (%) at the following times (hours) | | | |
|---|---|---|---|---|
| | 24 | 36 | 48 | 72 |
| C100E | 168.1 | 93.8 | 75.2 | 16.7 |
| ST | 158.4 | 91.6 | 64.3 | 6.5 |
| ST1E | 164.6 | 99.8 | 60.8 | 16.0 |
| ST5E | 159.7 | 98.0 | 62.8 | 13.1 |
| ST10E | 166.4 | 96.5 | 66.5 | 10.4 |
| ST30E | 157.1 | 95.3 | 61.8 | 3.2 |
| ST50E | 157.0 | 112.1 | 89.0 | 49.2 |
| ST100E | 172.5 | 118.0 | 92.2 | 65.0 |
| control A | 109.8 | 112.0 | 98.7 | 96.2 |
| control B | 90.2 | 88.0 | 101.3 | 103.7 |
| control A* | 100.3 | 110.1 | 99.5 | 98.5 |
| control B* | 99.7 | 89.8 | 100.4 | 101.5 |

*analyzed week 2

The cell concentration and % cells in the *S. cerevisiae* flasks are presented in Table 74. High cell counts were observed in all flasks; however, not all of the cells appear to be making ethanol.

TABLE 74

*S cerevisiae* Cell Counts and % Cells

| Sample Number | Cell Count (cells × $10^8$/mL) | | % Cells (count/count control) *100 | |
|---|---|---|---|---|
| | 24 hours | 72 hours | 24 hours | 72 hours |
| P | 0.62 | 0.96 | 97.7 | 139.0 |
| P1E | 0.35 | 1.18 | 54.1 | 170.9 |
| P5E | 1.13 | 1.93 | 177.3 | 279.5 |
| P10E | 0.59 | 1.42 | 91.8 | 205.6 |
| P50E | 0.32 | 1.40 | 49.4 | 202.8 |
| P100E | 0.45 | 1.94 | 70.6 | 281.0 |
| G | 0.74 | 3.48 | 116.5 | 504.0 |
| G1E | 0.68 | 3.65 | 107.1 | 528.6 |
| G5E | 0.62 | 3.87 | 96.5 | 560.5 |
| G10E | 0.70 | 2.73 | 109.5 | 395.4 |
| G50E | 0.46 | 2.10 | 71.8 | 304.1 |
| A | 0.55 | 3.53 | 86.0 | 511.2 |
| A1E | 0.83 | 3.45 | 130.7 | 499.6 |
| A5E | 0.67 | 3.53 | 104.8 | 511.2 |
| A10E | 0.53 | 1.95 | 83.6 | 282.4 |
| A50E | 0.66 | 1.62 | 103.5 | 234.6 |
| S | 0.44 | 1.11 | 69.5 | 160.8 |
| S1E | 0.44 | 1.10 | 68.2 | 159.3 |
| S5E | 0.23 | 0.99 | 36.5 | 143.4 |
| S10E | 0.39 | 0.73 | 61.2 | 105.4 |
| S30E | 0.31 | 0.71 | 48.3 | 102.1 |
| S50E* | 0.44 | 0.90 | 86.5 | 196.5 |
| S100E | 0.53 | 0.84 | 82.4 | 121.7 |
| C | 0.45 | 1.81 | 70.6 | 262.1 |
| C1E | 0.71 | 2.40 | 110.6 | 347.6 |
| C5E | 0.53 | 2.33 | 83.6 | 337.4 |
| C10E | 0.77 | 1.55 | 120.0 | 224.5 |
| C30E | 0.75 | 1.80 | 117.6 | 260.7 |
| C50E | 0.64 | 1.70 | 100.1 | 246.2 |
| C100E | 0.81 | 1.51 | 127.1 | 218.7 |
| ST | 0.75 | 1.75 | 117.6 | 253.4 |
| ST1E | 0.57 | 1.36 | 89.4 | 197.0 |
| ST5E | 0.58 | 1.49 | 90.7 | 215.8 |
| ST10E | 0.61 | 1.32 | 95.4 | 191.2 |
| ST30E | 0.59 | 0.60 | 91.8 | 86.9 |
| ST50E | 0.59 | 1.30 | 91.8 | 188.3 |
| ST100E | 0.41 | 1.24 | 63.5 | 179.6 |
| control A | 0.81 | 0.79 | 127.1 | 114.1 |
| control B | 0.47 | 0.59 | 72.9 | 85.9 |
| control A* | 0.66 | 0.42 | 131.2 | 91.7 |
| control B* | 0.35 | 0.50 | 69.0 | 108.1 |

The *P. stipitis* seed flask had an optical density (600 nm) of 5.01 and a cell concentration of $3.30 \times 10^8$ cells/mL. One mL of seed flask material was added to each of the test flasks. Therefore, the starting cell concentration in each flask was $3.30 \times 10^6$/mL. During the second week of testing, the *P. stipitis* seed flask had an optical density (600 nm) of 5.45 and a cell concentration of $3.83 \times 10^8$ cells/mL. One mL of seed flask material was added to each of the test flasks. Therefore, the starting cell concentration in each flask was $3.83 \times 10^6$/mL. The pH of the *P. stipitis* flasks at a sample time of 0 hours is presented in Table 75. The pH of the flask contents was within the optimal pH for *P. stipitis* growth (pH 4-7). No pH adjustment was required.

TABLE 75 pH of *P. stipitis* Flasks at Sample Time 0 Hours

| Sample Number | pH |
|---|---|
| P | 4.91 |
| P1E | 4.87 |
| P5E | 4.90 |
| P10E | 4.78 |
| P50E | 4.46 |
| P100E | 4.24 |
| G | 5.45 |
| G1E | 5.43 |
| G5E | 5.48 |
| G10E | 5.32 |
| G50E | 4.99 |
| A | 5.69 |
| A1E | 5.66 |
| A5E | 5.60 |
| A10E | 5.58 |
| A50E | 5.69 |
| S | 5.00 |
| S1E | 4.94 |
| S5E | 4.86 |
| S10E | 4.78 |
| S30E | 4.51 |
| S50E | 4.27 |
| S100E | 4.08 |
| C | 5.36 |
| C1E | 5.30 |
| C5E | 5.29 |
| C10E | 5.06 |
| C30E | 4.89 |
| C50E | 4.70 |
| C100E | 4.59 |
| ST | 4.93 |
| ST1E | 4.90 |
| ST5E | 4.81 |
| ST10E | 4.83 |
| ST30E | 4.91 |
| ST50E | 4.24 |
| ST100E | 4.07 |
| control A | 4.93 |
| control B | 4.91 |

The ethanol concentration and performance in the *P. stipitis* flasks are presented in Table 76 and 77. The highest ethanol concentrations were the G and A series. Flasks C-30e, C-50e, and C-100e also contained high concentrations of ethanol. The cell concentration and % cells in the *P. stipitis* flasks are presented in Table 78. Low cell concentrations were observed in the flasks with the S designations. Low cell counts were also observed in flasks containing samples C, C1E, C5E, and C10E at the 24 hour sample time.

TABLE 76

Ethanol concentration in *P. stipitis* flasks

| Sample Number | Ethanol Concentration (g/L) at the following times (hours) | | | | | | |
|---|---|---|---|---|---|---|---|
| | 0 | 6 | 12 | 24 | 36 | 48 | 72 |
| P | 0.01 | 0.05 | 0.26 | 4.98 | 8.57 | 14.10 | 17.00 |
| P1E | 0.02 | 0.03 | 0.04 | 4.24 | 9.03 | 12.40 | 17.30 |
| P5E | 0.02 | 0.03 | 0.42 | 6.72 | 12.40 | 15.60 | 18.60 |
| P10E | 0.02 | 0.02 | 0.01 | 1.38 | 8.69 | 13.00 | 17.00 |
| P50E | 0.01 | 0.02 | 0.02 | 0.03 | 3.77 | 10.50 | 16.90 |
| P100E | 0.02 | 0.03 | 0.02 | 3.75 | 10.50 | 15.60 | 18.80 |
| G | 0.02 | 0.08 | 0.20 | 10.80 | 17.70 | 19.40 | 25.40 |
| G1E | 0.04 | 0.12 | 0.50 | 12.20 | 19.60 | 23.80 | 28.60 |
| G5E | 0.07 | 0.14 | 0.73 | 12.50 | 19.10 | 24.50 | 27.50 |
| G10E | 0.04 | 0.19 | 0.42 | 10.20 | 19.10 | 22.90 | 28.20 |
| G50E | 0.05 | 0.22 | 0.25 | 8.73 | 18.40 | 22.20 | 28.00 |
| A | 0.13 | 0.28 | 0.82 | 16.10 | 19.40 | 19.30 | 18.60 |
| A1E | 0.22 | 0.59 | 1.08 | 16.10 | 22.40 | 27.60 | 27.70 |
| A5E | 0.32 | 0.43 | 0.43 | 10.60 | 22.10 | 27.10 | 28.10 |
| A10E | 0.33 | 0.61 | 1.15 | 14.90 | 22.00 | 27.10 | 27.90 |
| A50E | 0.30 | 0.10 | 0.47 | 13.40 | 20.20 | 24.80 | 27.10 |
| S | 0.01 | 0.01 | 0.26 | 3.68 | 7.50 | 10.20 | 13.30 |
| S1E | 0.02 | 0.02 | 0.22 | 4.98 | 9.22 | 11.60 | 14.20 |
| S5E | 0.02 | 0.02 | 0.19 | 4.25 | 8.50 | 11.70 | 14.70 |
| S10E | 0.03 | 0.02 | 0.17 | 2.98 | 8.87 | 11.90 | 14.70 |
| S30E | 0.08 | 0.05 | 0.03 | 2.96 | 8.73 | 12.60 | 16.50 |
| S50E | 0.08 | 0.05 | 0.04 | 2.24 | 6.13 | 7.95 | 12.50 |
| S100E | 0.11 | 0.10 | 0.08 | 3.36 | 7.82 | 10.50 | 13.90 |
| C* | 0.02 | 0.03 | 0.05 | 0.23 | 1.66 | 2.68 | 6.57 |
| C1E* | 0.03 | 0.03 | 0.03 | 0.07 | 0.95 | 1.85 | 10.20 |
| C5E* | 0.03 | 0.02 | 0.04 | 0.05 | 0.37 | 1.59 | 4.80 |
| C10E* | 0.03 | 0.04 | 0.04 | 0.05 | 3.91 | 15.20 | 28.30 |
| C30E | 0.01 | 0.03 | 0.60 | 12.30 | 21.20 | 26.00 | 27.20 |
| C50E | 0.02 | 0.02 | 0.45 | 12.30 | 19.50 | 23.80 | 29.20 |
| C100E | 0.05 | 0.04 | 0.38 | 11.40 | 18.70 | 22.90 | 27.70 |
| ST | 0.03 | 0.03 | 0.37 | 6.69 | 10.70 | 13.50 | 10.90 |
| ST1E | 0.01 | 0.00 | 0.48 | 5.24 | 9.37 | 12.50 | 15.70 |
| ST5E | 0.02 | 0.03 | 0.29 | 5.45 | 10.10 | 11.90 | 14.70 |
| ST10E | 0.02 | 0.02 | 0.42 | 5.60 | 9.44 | 12.20 | 14.90 |
| ST30E | 0.05 | 0.04 | 0.73 | 5.70 | 9.50 | 12.10 | 15.20 |
| ST50E | 0.02 | 0.05 | 0.19 | 5.16 | 9.47 | 12.70 | 15.20 |
| ST100E* | 0.07 | 0.15 | 0.11 | 4.98 | 10.70 | 15.40 | 18.80 |
| control A | 0.02 | 0.03 | 0.37 | 4.05 | 7.50 | 9.24 | 11.50 |
| control B | 0.02 | 0.02 | 0.30 | 4.22 | 7.44 | 9.44 | 11.50 |
| Control A* | 0.02 | 0.05 | 0.69 | 4.86 | 8.69 | 11.10 | 16.40 |
| Control B* | 0.02 | 0.05 | 0.74 | 5.96 | 10.80 | 13.00 | 14.00 |

*analyzed week 2

TABLE 77

Performance in *P. stipitis* flasks

| Sample Number | Performance (%) at the following times (hours) | | | |
|---|---|---|---|---|
| | 24 | 36 | 48 | 72 |
| P | 120.3 | 114.7 | 151.0 | 147.8 |
| P1E | 102.4 | 120.9 | 132.8 | 150.4 |
| P5E | 162.3 | 166.0 | 167.0 | 161.7 |
| P10E | 33.3 | 116.3 | 139.2 | 147.8 |
| P50E | 0.7 | 50.5 | 112.4 | 147.0 |
| P100E | 90.6 | 140.6 | 167.0 | 163.5 |
| G | 260.9 | 236.9 | 207.9 | 220.9 |
| G1E | 294.7 | 262.4 | 254.8 | 248.7 |
| G5E | 301.9 | 255.7 | 262.3 | 239.1 |
| G10E | 246.4 | 255.7 | 245.2 | 245.2 |
| G50E | 210.9 | 246.3 | 237.7 | 243.5 |
| A | 388.9 | 259.7 | 206.6 | 161.7 |
| A1E | 388.9 | 299.9 | 295.5 | 240.9 |
| A5E | 256.0 | 295.9 | 290.1 | 244.3 |
| A10E | 359.9 | 294.5 | 290.1 | 242.6 |
| A50E | 323.7 | 270.4 | 265.5 | 235.7 |
| S | 88.9 | 100.4 | 109.2 | 115.7 |
| S1E | 120.3 | 123.4 | 124.2 | 123.5 |
| S5E | 102.7 | 113.8 | 125.3 | 127.8 |
| S10E | 72.0 | 118.7 | 127.4 | 127.8 |
| S30E | 71.5 | 116.9 | 134.9 | 143.5 |
| S50E | 54.1 | 82.1 | 85.1 | 108.7 |
| S100E | 81.2 | 104.7 | 112.4 | 120.9 |
| C* | 4.2 | 17.0 | 22.2 | 43.2 |
| C1E* | 1.4 | 9.7 | 15.4 | 67.1 |
| C5E* | 0.9 | 3.8 | 13.2 | 31.6 |
| C10E* | 0.9 | 40.1 | 126.1 | 246.1 |
| C30E | 297.1 | 283.8 | 278.4 | 236.5 |
| C50E | 297.1 | 261.0 | 254.8 | 253.9 |
| C100E | 275.4 | 250.3 | 245.2 | 240.9 |
| ST | 161.6 | 143.2 | 144.5 | 94.8 |
| ST1E | 126.6 | 125.4 | 133.8 | 136.5 |
| ST5E | 131.6 | 135.2 | 127.4 | 127.8 |
| ST10E | 135.3 | 126.4 | 130.6 | 129.6 |
| ST30E | 137.7 | 127.2 | 129.6 | 132.2 |
| ST50E | 124.6 | 126.8 | 136.0 | 132.2 |
| ST100E* | 120.3 | 109.7 | 127.8 | 123.7 |
| control A | 97.8 | 100.4 | 98.9 | 100.0 |
| control B | 101.9 | 99.6 | 101.1 | 100.0 |
| control A* | 89.8 | 89.1 | 92.1 | 107.9 |
| control B* | 110.2 | 110.8 | 107.9 | 92.1 |

*analyzed in week 2

TABLE 78

*P. stipitis* Cell Counts and % Cells

| Sample Number | Cell Count (cells × 10⁸/mL) | | % Cells (count/count control) *100 | |
|---|---|---|---|---|
| | 24 hours | 72 hours | 24 hours | 72 hours |
| P | 2.78 | 11.00 | 80.6 | 148.0 |
| P1E | 2.10 | 7.20 | 60.9 | 96.9 |
| P5E | 2.93 | 9.68 | 84.9 | 130.3 |
| P10E | 1.42 | 7.73 | 41.2 | 104.0 |
| P50E | 0.33 | 8.63 | 9.6 | 116.2 |
| P100E | 1.58 | 8.25 | 45.8 | 111.0 |
| G | 1.50 | 14.20 | 43.5 | 191.1 |
| G1E | 3.90 | 8.10 | 113.0 | 109.0 |
| G5E | 2.93 | 6.45 | 84.9 | 86.8 |
| G10E | 4.35 | 13.30 | 126.1 | 179.0 |
| G50E | 3.75 | 11.60 | 108.7 | 156.1 |
| A | 7.43 | 8.55 | 215.4 | 115.1 |
| A1E | 4.13 | 9.53 | 119.7 | 128.3 |
| A5E | 3.68 | 9.75 | 106.7 | 131.2 |
| A10E | 4.50 | 7.50 | 130.4 | 100.9 |
| A50E | 6.23 | 5.33 | 180.6 | 71.7 |
| S | 3.53 | 5.55 | 102.3 | 74.7 |
| S1E | 3.00 | 3.30 | 87.0 | 44.4 |
| S5E | 3.68 | 3.00 | 106.7 | 40.4 |
| S10E | 1.73 | 5.78 | 50.1 | 77.8 |
| S30E | 2.55 | 5.48 | 73.9 | 73.8 |
| S50E | 2.63 | 6.15 | 76.2 | 82.8 |
| S100E | 2.25 | 4.43 | 65.2 | 59.6 |
| C* | 0.00 | 0.26 | 0.00 | 7.2 |
| C1E* | 0.00 | 0.36 | 0.00 | 9.9 |
| C5E* | 0.00 | 0.08 | 0.00 | 2.1 |
| C10E* | 0.00 | 5.85 | 0.00 | 160.7 |
| C30E | 5.78 | 4.20 | 167.5 | 56.5 |
| C50E | 3.40 | 7.35 | 98.6 | 98.9 |
| C100E | 1.98 | 6.60 | 57.4 | 88.8 |
| ST | 2.55 | 7.65 | 73.9 | 103.0 |
| ST1E | 2.00 | 8.70 | 58.0 | 117.1 |
| ST5E | 1.85 | 6.75 | 53.6 | 90.8 |
| ST10E | 1.83 | 5.40 | 53.0 | 72.7 |
| ST30E | 2.78 | 6.15 | 80.6 | 82.8 |
| ST50E | 1.33 | 3.45 | 38.6 | 46.4 |
| ST100E* | 4.35 | 3.83 | 59.8 | 105.2 |
| control A | 3.60 | 7.13 | 104.3 | 96.0 |
| control B | 3.30 | 7.73 | 95.7 | 104.0 |

TABLE 78-continued

P. stipitis Cell Counts and % Cells

| Sample Number | Cell Count (cells × 10⁸/mL) | | % Cells (count/count control) *100 | |
|---|---|---|---|---|
| | 24 hours | 72 hours | 24 hours | 72 hours |
| control A* | 7.50 | 3.23 | 103.0 | 88.7 |
| control B* | 7.05 | 4.05 | 96.8 | 111.3 |

*analyzed week 2

Cell Toxicity Results Summary
Zymomonas mobilis

Figure 65A:
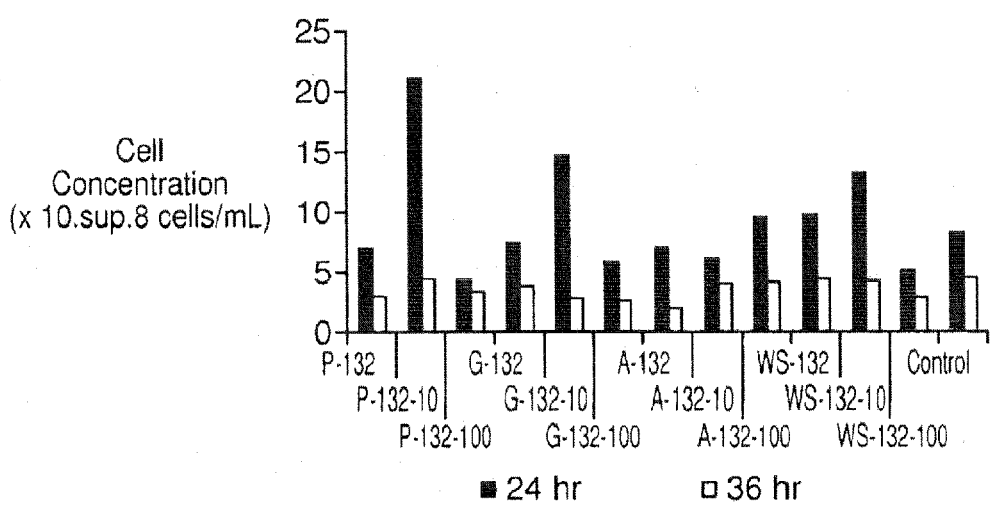
FIG. 65A is a chart showing cell concentrations for *Z. mobilis* in Example 31.

As shown in FIG. 65A, elevated cell numbers (e.g., greater than the control) were observed in samples containing P-132-10, G-132-10, and WS-132-10 at the 24 hour time point. Cell numbers in the presence of all other samples were comparable to the control. This observation indicates that the substrates were not toxic towards Z. mobilis for up to 24 hours after seeding.

At the 36 hour time point, a decrease in cell numbers (e.g., due to a loss of cells or cell death) was observed for all samples, including the control. The greatest decrease in cell numbers was observed for those samples containing P-132-10, G-132-10. The likely cause of this effect is common to all samples, including the control. Thus, the cause of this effect is not the test substrates, as these vary in each sample, and are not present in the control. Possible explanations for this observation include inappropriate culture conditions (e.g., temperature, media compositions), or ethanol concentrations in the sample.

Figure 65B:
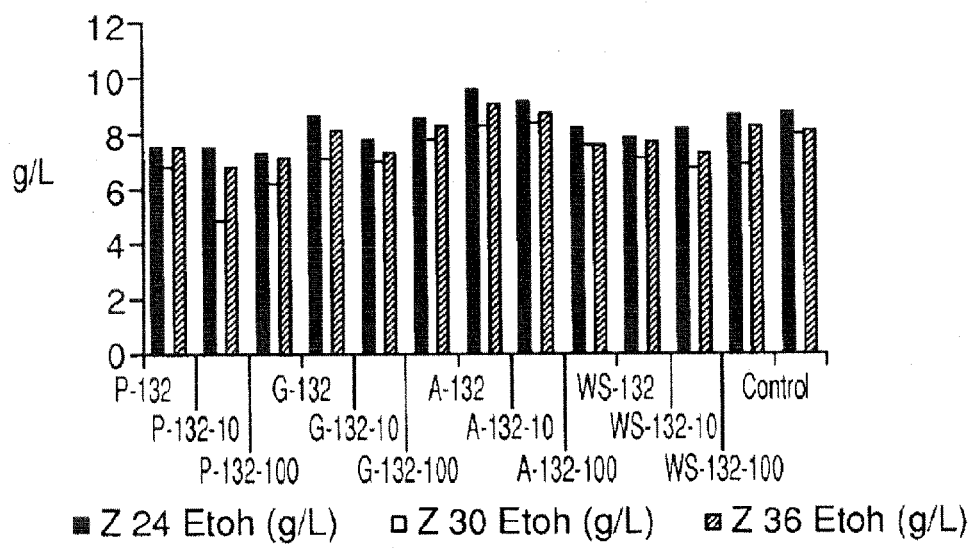
FIG. 65B is a chart showing ethanol concentrations for *Z. mobilis* in Example 31.

As shown in FIG. 65B, all cells produced comparable amounts of ethanol (e.g., 5-10 g/L) at each time point, irrespective of the substrate. Consistent with the cell number data presented in FIG. 65A, ethanol concentration in each sample peaked at the 24 hour time point. In contrast to the cell number data, ethanol concentration did not decrease at subsequent time points. This was expected as ethanol was not removed from the system. In addition, this data suggests that ethanol production in these samples may have resulted from fermentation of glucose in the culture media. None of the substrates tested appeared to increase ethanol production.

Figure 65C:
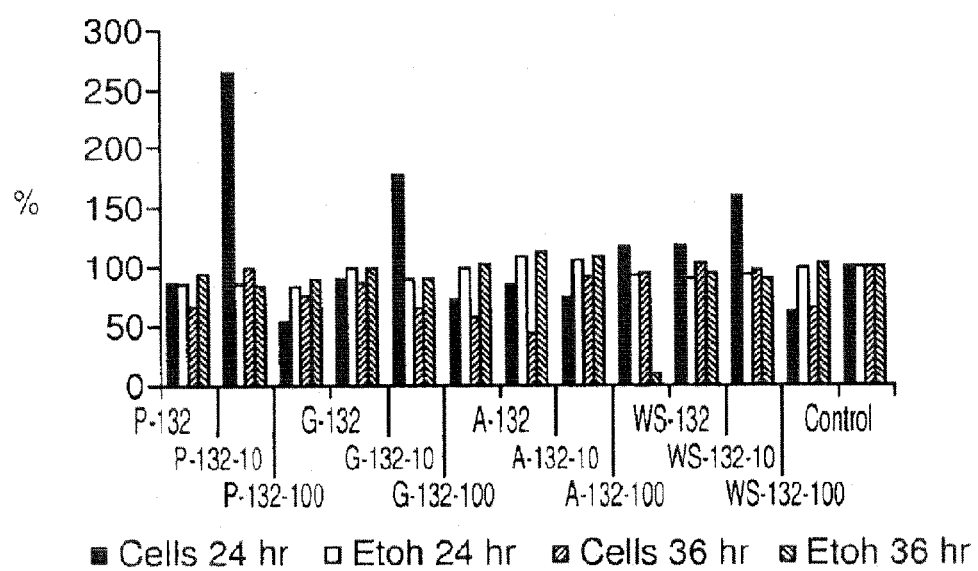
FIG. 65C is a chart showing % growth and ethanol
production for *Z. mobilis* in Example 31.

Together, FIGS. 65A and 65B suggest that ethanol concentrations above about 6 g/L may be toxic to Z. mobilis. This data is also presented as a percentage normalized against the control, as shown in FIG. 65C.

Pichia stipitis

Figure 66:
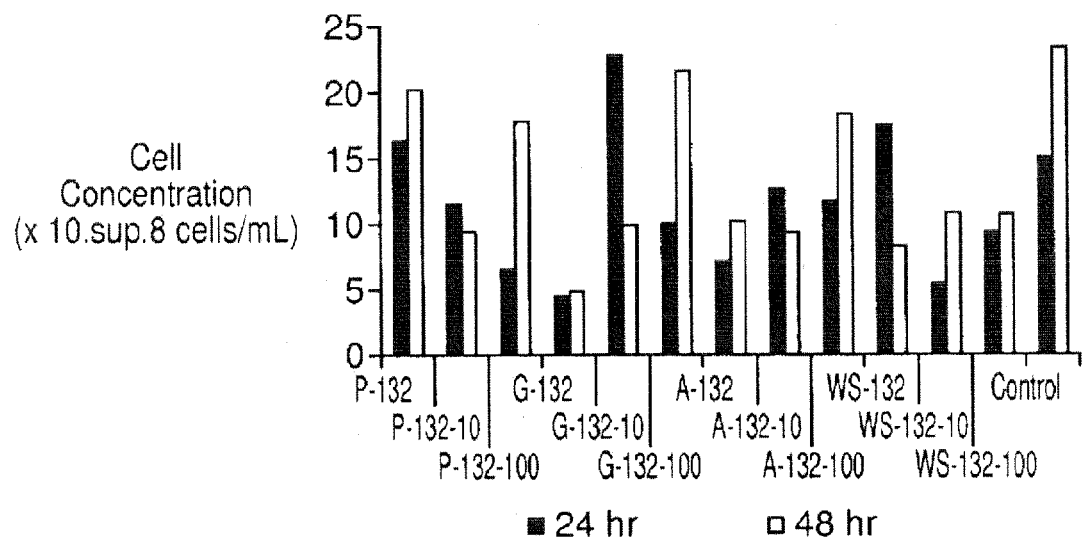
FIG. 66 is a chart showing cell concentrations for *P. stivitus* in Example 31.

As shown in FIG. 66, cell numbers were comparable to the control. Furthermore, although slightly reduced cell numbers were present in samples containing G-132 and WS-132, reduced cell numbers were not observed for G-132-10, G-132-100, A-132-10, or A-132-100. Thus, it is unlikely that substrates G or A are toxic. Rather, the reduced cell numbers observed for G-132 and WS-132 are likely to have been caused by an experimental anomaly or by the presence of unprocessed substrate somehow impeding cell growth. Overall, this data suggests that glucose present in the control and experimental samples is likely to be sufficient to promote optimal P. stipitis growth, and that the presence of an additional substrate in the sample does not increase this growth rate. These results also suggest that none of the samples are toxic in P. stipitis.

Figure 66A:
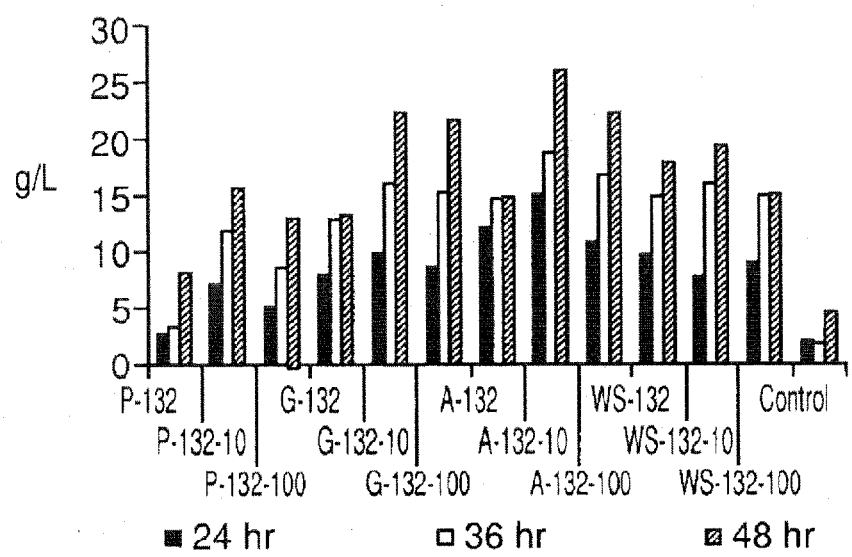
FIG. 66A is a chart showing ethanol concentrations for *P. stivitus* in Example 31.

As shown in FIG. 66A, despite the similar cell numbers reported in FIG. 66A, greatly increased ethanol production was observed in all samples containing an experimental substrate. Ethanol concentrations increased over time for each of the three time points tested. The highest concentration of ethanol was observed for A-132-10 at the 48 hour time point (e.g., approximately 26.0 g/L). By comparing the substrate concentrations with the highest levels of ethanol production with the cell number data presented in FIG. 66A, it can be seen that P. stipitis do not appear to be sensitive to increasing ethanol concentrations. Furthermore, ethanol production does not appear to be related to cell number, but rather appears to be related to the type of substrate present in the sample.

Figure 66B:
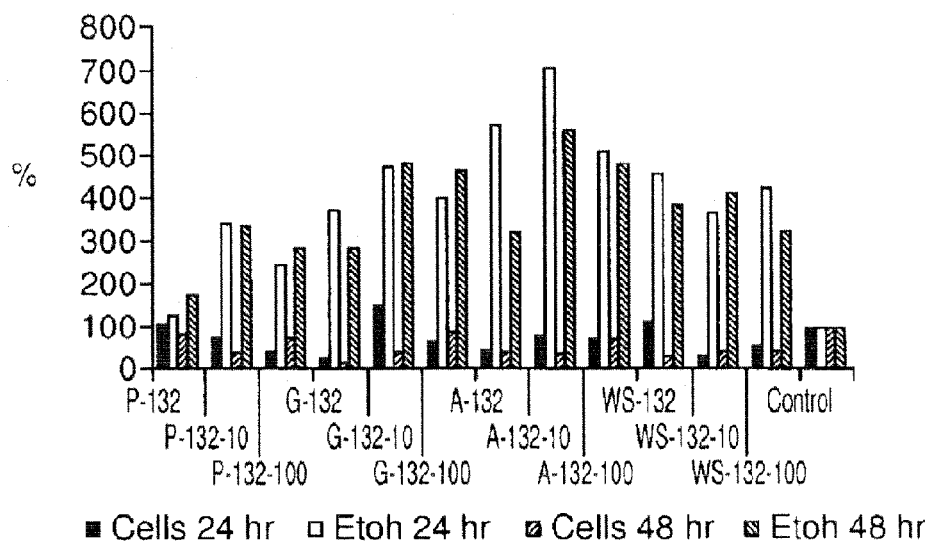
FIG. 66B is a chart showing % growth and ethanol
production for *P. stivitus* in Example 31.

Together, the results presented in FIGS. 66 and 66A suggest that the experimental substrates do not promote increased P. stipitis growth, however, they greatly increase the amount of ethanol produced by this cell type. This data is also presented as a percentage normalized against the control, as shown in FIG. 66B.

Saccharomyces cerevisiae

Figure 67:
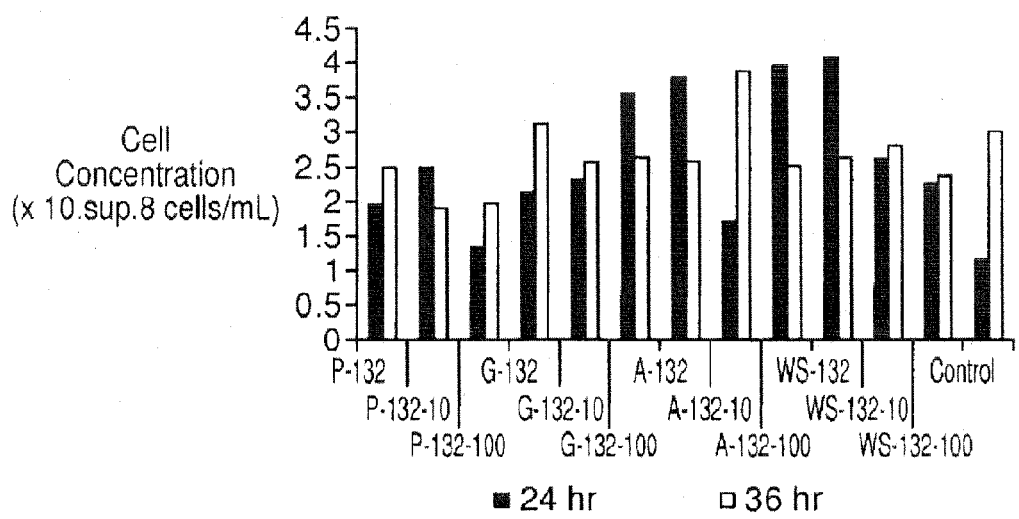
FIG. 67 is a chart showing cell concentrations for *S. cerevisiae* in Example 31.

As shown in FIG. 67, G-132-100, A-132, A-132-10, A-132-100, and WS-132, promoted slightly elevated cell numbers compared to the control. No significant reductions in cell number were observed for any sample. These results suggest that none of the samples are toxic in S. cerevisiae.

Figure 67A:
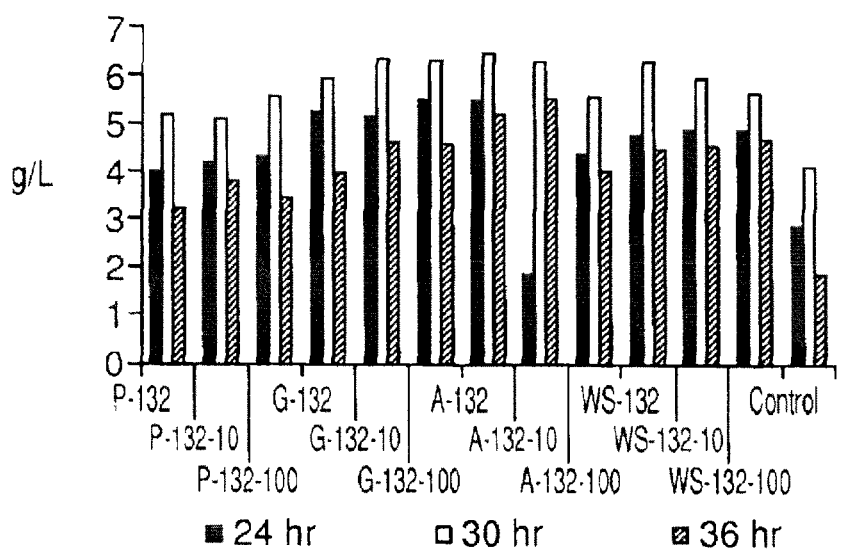
FIG. 67A is a chart showing ethanol concentrations for *S. cerevisiae* in Example 31.

As shown in FIG. 67A, increased ethanol production was observed in cells treated with each cell type compared to the control. Comparison of those samples containing the highest amount of ethanol with the cell number data presented in FIG. 67 suggests that ethanol concentrations in excess of 5 g/L may have had an adverse effect on cell numbers. However, this observation is not the case for all samples.

Figure 67B:
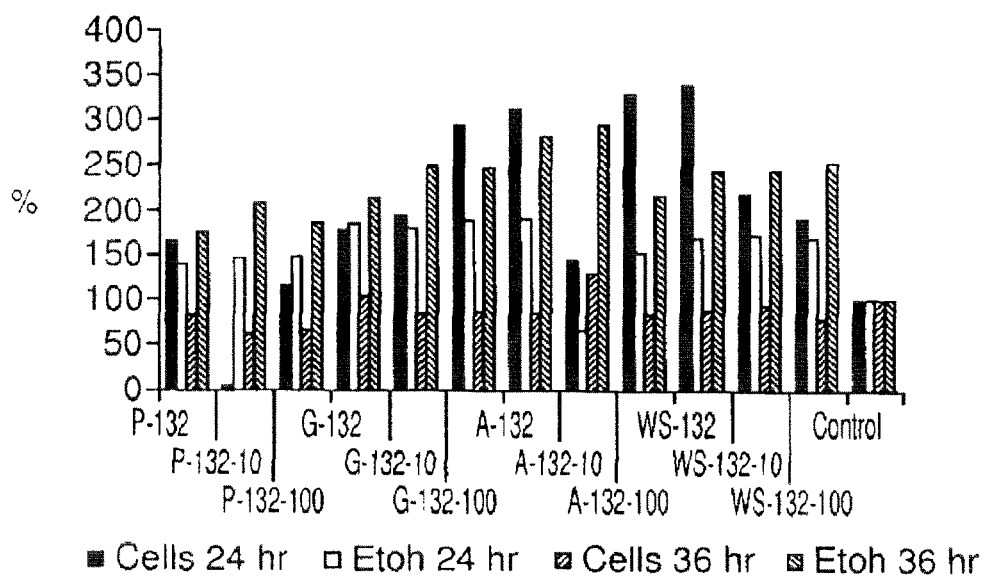
FIG. 67B is a chart showing % growth and ethanol
production for *S. cerevisiae* in Example 31.

This data is also presented as a percentage normalized against the control, as shown in FIG. 67B.

In conclusion, none of the samples tested appeared to be toxic in Z. mobilis, P. stipitis, and S. cerevisiae. Furthermore, P. stipitis appeared to be the most efficient of the three cell types for producing ethanol from the experimental substrates tested.

Example 32

Shake Flask Fermentation Studies Using P. stipitis

Summary

Shake flask fermentation studies using various enzymes, physical treatments, and Pichia stipitis were performed.

Protocol

Experiments were performed under the parameters outlined in Table 79.

TABLE 79

Chemicals and Materials Used for the Shake Flask Experiment

| Media Component | Manufacturer | Reference # |
|---|---|---|
| Urea | ScholAR Chemistry | 9472706 |
| Yeast Nitrogen Base | Becton Dickinson | 291940 |
| Peptone | Becton Dickinson | 211677 |
| Xylose | Alfa Aesar | A10643 |
| Glucose | Sigma | G-5400 |
| Yeast Extract | Becton Dickinson | 288620 |
| YM Broth | Becton Dickinson | 271120 |
| Novozyme ® 188 | Novozymes | Sigma #C6105 |
| Celluclast 1,5 FG | Novozymes | Sigma #C2730 |
| Solka Floc | International Fibre Corporation | 200 NF |
| Pluronic F-68 | Sigma | P1300 |
| Accellerase ® 1000 | Genencore | N/A |

Seed Development

A working cell bank of *P. stipitis* NRRL Y-7124 was prepared from a rehydrated lyophilized culture obtained from ARS Culture Collection. Cryovials containing *P. stipitis* culture in 15% v/v glycerol were stored at −75° C. A portion of the thawed working cell bank material were streaked onto a Yeast Mold (YM) Broth+20 g/L agar (pH 5.0) and incubated at 30° C. for 2 days. The plates were held for up to seven days at 4° C. before use.

A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) were inoculated with one colony and incubated for 24 hours at 25° C. and 150 rpm. After 23 hours of growth, a sample was taken and analyzed for optical density (OD 600 nm in a UV spectrophotometer) and purity (Gram stain). Based on these results, two flasks (called the Seed Flask I at an OD of between 4 and 8 and with a clean Gram stain was combined to inoculate the growth flasks.

Exemplary Experiments

Experiments were performed to 1) determine the correct sonifier output and temperature regulation (below 60° C.) and 2) confirm the concentration of Celluclast 1,5 FG and Novozyme 188 with and without Pluronic F-68.

Five hundred milliliters of water were added to a 1 L glass beaker. The horn of a Branson Model 450 Sonifier was placed ½ inch into the surface of the beaker and set at a maximum constant output for 60 minutes. The temperature of the water was measured every 10 minutes for 60 minutes of sonication.

An experiment was performed to determine if 1) the concentration of Celluclast 1,5 FG and Novozyme 188 (0.5 mL and 0.1 mL per gram of biomass, respectively) was sufficient for the shake flask experiments and 2) if the addition of Pluronic F68 augmented the hydrolysis of cellulose. Four 250 mL flasks were prepared with 100 mL of sterile broth (1.7 g/L yeast nitrogen base, 2.27 g/L urea, 6.56 g/L peptone, pH 5.0). Duplicate flasks contained 1% w/v Pluronic F-68. Solka Floe Crystalline Cellulose (6 g) was added to the flasks and allowed to soak at room temperature for 14 hours. Celluclast 1,5 FG and Novozyme 188 (0.5 mL and 0.1 mL per gram of Solka Floe, respectively) were added and each flask incubated at 50° C. for 24 hours at 100 rpm. Samples were taken prior to the addition of enzyme and 24 hours post enzyme addition from all four flasks and analyzed for glucose concentration using the YSI Biochem Analyzer (YSI, Interscience). One milliliter of *Pichia stipitis* seed flask contents was added to the four flasks and incubated at 25° C. and 125 rpm for 24 hours. Samples were taken from each flask prior to inoculation and after 24 hours incubation and analyzed for ethanol concentration using the YSI Biochem Analyzer (YSI, Interscience).

Test Flasks

The test flasks were 2.8 L Fernbach flasks holding 900 mL of broth (1.7 g/L yeast nitrogen base, 2.27 g/L urea, 6.56 g/L peptone, pH 5.0). Control flasks were 250 mL flasks containing 100 mL of broth (40 g/L glucose, 1.7 g/L yeast nitrogen base, 2.27 g/L urea, 6.56 g/L peptone, 40 g/L xylose, pH 5.0). The exact nature of each flask was decided by Xyleco and is described in Table 80 below.

Samples were not sterilized prior to the start of the experiment. All samples were added to the flasks and allowed to soak for 15 hours at room temperature. Some of the samples were sonicated for one hour using a Branson Model 450 Sonifier equipped with a ½ inch disruptor horn. The original plan was to split the flask contents into two, and sonicate each half continuously at the maximum output for the equipment up to 450 watts, (the allowable output depends on the viscosity of the sample) for 1 hour. An output setting of 3 and a Duty cycle of Pulse 90% were sufficient for the mixing of the beaker contents. At an output setting of 3, the meter read between 30 and 40. The output was calculated to be 40-60 watts.

Originally, the plan was to mix some samples (see Table 80) for various times using a POLYTRON PT 10/35 laboratory homogenizer (or rotor/stator) at 25,000 rpm for various times. Samples #22 and #23 were split into two beakers and treated for 30 minutes using the large Kinematica Polytron PT 10/35. The generator (tip) was a PTA 20 with a stator diameter of 20 mm. The instrument was operated at a speed of 11,000 rpm. Operation above 11,000 rpm caused splattering of beaker contents, movement of the beaker, and over-heating of the equipment. After samples #23 and #24, the Polytron PT 10/35 stopped working, presumably from over-use with quite viscous samples. Therefore, the hand-held Polytron PT1200C was used. The generator (tip) was a PT-DA 1212 with a stator diameter of 12 mm. The instrument could be operated at 25,000 rpm. It was noted by the operator that a similar degree of mixing was observed with the hand-held at 25,000 rpm as compared to the larger model at 11,000 rpm. The sample was periodically mixed by the operator to ensure even mixing. Samples 19 through 22 were mixed with the hand-held Polytron PT1200C.

Enzyme pretreatments included: 1) E1=Accelerase™ 1000 at a loading density of 0.25 mL per gram of substrate and 2) E2=Celluclast 1,5 FG and Novozyme 188 at a loading concentration of 0.5 and 0.1 mL per gram of substrate, respectively. After physical pretreatment (see Table 80 below), the appropriate enzyme(s) were added and the flasks held at 50° C. and 125 rpm for 20 hours. After 20 hours, the flasks were cooled to room temperature for 1 hour prior to the addition of *P. stipitis*.

TABLE 80

Summary of Test Treatments

| Test Number | Sample Number | Sample Concentration (g/900 mL) | Physical Treatment | Enzyme Treatment (50° C., 21 hours) |
|---|---|---|---|---|
| Control (250 mL flask performed in duplicate each week) | None | — | — | — |
| Week 1 | | | | |
| 1 | SP | 35 | 15 h r.t. soak | None |
| 2 | XP | 35 | 15 h r.t. soak | None |
| 3 | SP | 35 | 15 h r.t. soak | E1 |
| 4 | SP | 35 | 15 h r.t. soak | E2 |
| 5 | XP | 35 | 15 h r.t. soak | E1 |
| 6 | XP | 35 | 15 h r.t. soak | E2 |
| 7 | XP-10e | 35 | 15 h r.t. soak | E2 |
| 8 | XP-30e | 35 | 15 h r.t. soak | E2 |
| 9 | XP-50e | 35 | 15 h r.t. soak | E2 |
| 10 | XP-10e | 35 | 15 h r.t. soak, 1 hour sonication | E2 |
| 11 | XP-30e | 35 | 15 h r.t. soak, 1 hour sonication | E2 |
| 12 | XP-50e | 35 | 15 h r.t. soak, 1 hour sonication | E2 |
| Week 2 | | | | |
| 13 | XP-10e | 35 | 15 h r.t. soak, 10 min sonication | E2 |
| 14 | XP-30e | 35 | 15 h r.t. soak, 10 min sonication | E2 |

TABLE 80-continued

Summary of Test Treatments

| Test Number | Sample Number | Sample Concentration (g/900 mL) | Physical Treatment | Enzyme Treatment (50° C., 21 hours) |
|---|---|---|---|---|
| 15 | XP-50e | 35 | 15 h r.t. soak, 10 min sonication | E2 |
| 16 | XP-10e | 35 | 15 h r.t. soak, 30 min sonication | E2 |
| 17 | XP-30e | 35 | 15 h r.t. soak, 30 min sonication | E2 |
| 18 | XP-50e | 35 | 15 h r.t. soak, 30 min sonication | E2 |
| 19 | XP-10e | 35 | 15 h r.t. soak, 10 min rotor/stator | E2 |
| 20 | XP-30e | 35 | 15 h r.t. soak, 10 min rotor/stator | E2 |
| 21 | XP-50e | 35 | 15 h r.t. soak, 10 min rotor/stator | E2 |
| 22 | XP-10e | 35 | 15 h r.t. soak, 30 min rotor/stator | E2 |
| 23 | XP-30e | 35 | 15 h r.t. soak, 30 min rotor/stator | E2 |
| 24 | XP-50e | 35 | 15 h r.t. soak, 30 min rotor/stator | E2 |

Analysis

A sample was taken from each flask after physical and/or enzyme pretreatment (just prior to the addition of *P. stipitis*) and analyzed for glucose concentration using the YSI Biochem Analyzer (YSI, Interscience). Samples were centrifuged at 14,000 rpm for 20 minutes and the supernatant stored at −20° C. The samples were diluted to between 0-25.0 g/L glucose prior to analysis. A glucose standard was analyzed approximately every 30 samples to ensure the integrity of the membrane was maintained.

A total of five samples were taken from each flask at 0, 12, 24, 48, and 72 hours and analyzed for ethanol concentration using the YSI Biochem Analyzer based on the alcohol dehydrogenase assay (YSI, Interscience). Samples were centrifuged at 14,000 rpm for 20 minutes and the supernatant stored at −20° C. and diluted to between 0-3.0 g/L ethanol prior to analysis. A standard of 2.0 g/L ethanol was analyzed approximately every 30 samples to ensure the integrity of the membrane was maintained.

A sample of the seed flask was analyzed in order to determine the initial cell concentration in the test flasks. In addition one sample at 72 hours of incubation was taken from each flask and analyzed for cell concentration. Appropriately diluted samples were mixed with 0.05% Trypan blue and loaded into a Neubauer haemocytometer. The cells were counted under 40× magnification.

Results

Experiments

The results of a sonifier experiment are presented in Table 81. There were no problems with over-heating of the water.

TABLE 81

Sonifier Experiment

| Time | Temperature (° C.) |
|---|---|
| 0 | 18 |
| 10 | 18 |
| 20 | 19 |
| 30 | 19 |
| 40 | 19 |
| 50 | 19 |
| 60 | 19 |

The results of the experiment to confirm the concentration of Celluclast 1,5 FG and Novozyme 188 with and without Pluronic F-68 are presented in Table 82 and 83. A concentration of 60 g/L cellulose (Solka Floe) was added to each flask. After 24 hours of incubation, 33.7 to 35.7 g/L glucose was generated (30.3 to 32.1 g/L cellulose digested).

After 24 hours of incubation with *P. stipitis*, 23.2-25.7 g/L of glucose remained in the flasks. This indicates that not all of the glucose was used within 24 hours of incubation.

There was no evidence of Pluronic F-68 toxicity toward *P. stipitis*. However, there was no increase in the amount of glucose generated after a 24 hour enzyme treatment with the addition of Pluronic F-68.

TABLE 82

Glucose Results

| Flask | Glucose Concentration (g/L) | | |
|---|---|---|---|
| | Prior to Enzyme Treatment | After Enzyme Treatment (50° C., 24 hours, 100 rpm) | After *P. stipitis* for 24 hours |
| Control A | 0.28 | 34.3 | 23.2 |
| Control B | 0.64 | 35.7 | 25.3 |
| Containing Pluronic A | 0.48 | 34.8 | 25.6 |
| Containing Pluronic B | 0.93 | 33.7 | 25.7 |

TABLE 83

Ethanol Results

| Flask | Ethanol Concentration (g/L) at times (hours) | |
|---|---|---|
| | 0 (inoculation, after enzyme treatment) | 24 hours of *P. stipitis* |
| Control A | 0.01 | 7.23 |
| Control B | 0.01 | 5.75 |
| Containing Pluronic A | 0.01 | 7.57 |
| Containing Pluronic B | 0.00 | 7.36 |

During week one of testing, the seed flask had an optical density (600 nm) of 9.74 and a cell concentration of $4.21 \times 10^8$ cells/mL. Nine mL of seed flask material was added to each of the test flasks and 1 mL to the control flasks (1% v/v). Therefore, the starting cell concentration in each flask was $\times 4.21 \times 10^6$/mL.

During week two of testing, the seed flask had an optical density (600 nm) of 3.02 and a cell concentration of $2.85 \times 10^8$ cells/mL. To account for differences in cell counts and OD, 12 mL of seed flask material was added to each of the test flasks and 1.5 mL to the control flasks (1.5% v/v). Therefore, the starting cell concentration in each flask was $3.80 \times 10^6$/mL.

The ethanol concentration in the flasks is presented in Table 84. The highest concentration of ethanol was observed in Flask #6 (Sample XP, Overnight Soak, treatment with E2 at 50° C. for 21 hours). A concentration of 19.5 g/L (17.55 g/per flask) was generated from an original 35 grams of substrate in 48 hours. The yield of ethanol (grams of ethanol/gram of substrate) in flask #6 was 0.50.

TABLE 84

Ethanol Concentration

| Sample Number | Ethanol Concentraton (g/L) at Incubation Time (hours) | | | | |
|---|---|---|---|---|---|
| | 0 | 12 | 24 | 48 | 72 |
| Control A | 0.249 | 1.57 | 9.31 | 13.60 | 14.20 |
| Control B | 0.237 | 1.04 | 7.97 | 11.40 | 13.90 |
| 1 | 0.247 | 0.16 | 0.10 | 0.11 | 0.06 |
| 2 | 0.175 | 0.12 | 0.10 | 0.17 | 0.29 |
| 3 | 0.284 | 2.73* | 8.88 | 9.72 | 10.40 |
| 4 | 0.398 | 0.43 | 8.02 | 14.40 | 12.10 |
| 5 | 0.312 | 0.31 | 10.30 | 11.30 | 18.80 |
| 6 | 0.399 | 0.73 | 7.55 | 19.50* | 19.00 |
| 7 | 0.419 | 0.38 | 4.73 | 16.80* | 15.40 |
| 8 | 0.370 | 0.46 | 0.56 | 9.86 | 13.50 |
| 9 | 0.183 | 0.47 | 0.53 | 12.00 | 14.10 |
| 10 | 0.216 | 0.35 | 6.11 | 13.80 | 15.60 |
| 11 | 0.199 | 0.33 | 0.88 | 9.02 | 8.52 |
| 12 | 0.264 | 0.43 | 0.41 | 8.76 | 13.80 |
| Control A | 0.49 | 0.84 | 7.93 | 13.00 | 15.00 |
| Control B | 0.50 | 0.93 | 8.39 | 13.40 | 15.00 |
| 13 | 0.86 | 0.99 | 8.42 | 10.50 | 14.20 |
| 14 | 0.95 | 0.88 | 3.79 | 10.90 | 12.40 |
| 15 | 1.18 | 0.42 | 1.12 | 9.26 | 12.60 |
| 16 | 0.88 | 0.42 | 5.41 | 6.78 | 12.80 |
| 17 | 0.99 | 0.45 | 1.73 | 10.60 | 12.00 |
| 18 | 1.17 | 0.46 | 1.12 | 10.60 | 12.10 |
| 19 | 0.78 | 0.50 | 9.75 | 12.60 | 13.40 |
| 20 | 0.94 | 0.39 | 2.54 | 11.10 | 12.20 |
| 21 | 1.28 | 0.43 | 1.46 | 11.50 | 11.30 |
| 22 | 0.84 | 1.09 | 10.00 | 14.00 | 10.10 |
| 23 | 0.96 | 0.57 | 6.77 | 11.10 | 12.10 |
| 24 | 1.20 | 0.42 | 1.91 | 12.10 | 13.10 |

*Samples analyzed twice with the same result.
Flasks with a concentration of greater than 15 g/L ethanol are in BOLD.

Flasks with a concentration of greater than 15 g/L ethanol are in BOLD.

The results of the glucose analysis are presented in Table 85. After 21 hours of enzyme treatment, the highest concentration of glucose was 19.6 g/L (17.6 grams per flask) in flask #6 (Sample XP, Overnight Soak, treatment with E2 at 50° C. for 21 hours). This was also the flask with the highest ethanol concentration (see Table 84). After 72 hours, very little glucose remained in the flasks. No glucose was detected in Flasks 1 and 2.

TABLE 85

Glucose Concentration

| Sample Number | Glucose Concentration (g/L) at Incubation Time (hours) | |
|---|---|---|
| | 0 | 72 |
| 1 | 0.0 | 0.00 |
| 2 | 0.0 | 0.00 |
| 3 | 7.2 | 0.02 |
| 4 | 13.3 | 0.03 |
| 5 | 15.9 | 0.05 |
| 6 | 19.6 | 0.05 |
| 7 | 13.9 | 0.04 |
| 8 | 15.4 | 0.06 |
| 9 | 18.3 | 0.09 |
| 10 | 17.1 | 0.05 |
| 11 | 13.0 | 0.04 |
| 12 | 17.0 | 0.08 |
| 13 | 14.4 | 0.03 |
| 14 | 13.7 | 0.04 |
| 15 | 16.3 | 0.08 |
| 16 | 13.2 | 0.03 |
| 17 | 13.4 | 0.04 |
| 18 | 15.8 | 0.06 |
| 19 | 15.3 | 0.04 |
| 20 | 14.3 | 0.04 |
| 21 | 15.5 | 0.06 |
| 22 | 14.7 | 0.04 |
| 23 | 13.5 | 0.04 |
| 24 | 16.6 | 0.07 |

The results of the direct cell counts are presented in Table 86. The concentration of viable cells was higher in the control flasks. The lowest counts were observed in flasks 1 through 4.

TABLE 86

Cell Counts

| Sample Number | Number of Cells (×106/mL) after 72 hours of incubation |
|---|---|
| Control A | 38.30 |
| Control B | 104.00 |
| 1 | 0.02 |
| 2 | 0.08 |
| 3 | 0.07 |
| 4 | 0.06 |
| 5 | 0.15 |
| 6 | 1.05 |
| 7 | 1.50 |
| 8 | 1.95 |
| 9 | 1.05 |
| 10 | 3.60 |
| 11 | 1.28 |
| 12 | 0.90 |
| Control A | 39.80 |
| Control B | 30.80 |
| 13 | 0.98 |
| 14 | 0.40 |
| 15 | 0.63 |
| 16 | 0.71 |
| 17 | 1.15 |
| 18 | 0.83 |
| 19 | 1.25 |
| 20 | 1.02 |
| 21 | 0.53 |
| 22 | 0.56 |
| 23 | 0.59 |
| 24 | 0.59 |

Example 32

Alcohol Production Using Irradiation-Sonication Pretreatment

The optimum size for biomass conversion plants is affected by factors including economies of scale and the type and availability of biomass used as feedstock. Increasing plant size tends to increase economies of scale associated with plant processes. However, increasing plant size also tends to increase the costs (e.g., transportation costs) per unit of biomass feedstock. Studies analyzing these factors suggest that the appropriate size for biomass conversion plants can range from 2000 to 10,000 dried tons of biomass feedstock per day. The plant described below is sized to process 2000 tons of dry biomass feedstock per day.

FIG. 39 shows a process schematic of a biomass conversion system configured to process switchgrass. The feed preparation subsystem processes raw biomass feedstock to remove foreign objects and provide consistently sized particles for further processing. The pretreatment subsystem changes the molecular structure (e.g., reduces the average molecular weight and the crystallinity) of the biomass feedstock by irradiating the biomass feedstock, mixing the irradiated the biomass feedstock with water to form a slurry, and applying ultrasonic energy to the slurry. The irradiation and sonication convert the cellulosic and lignocellulosic components of the biomass feedstock into fermentable materials. The primary process subsystem ferments the glucose and other low weight sugars present after pretreatment to form alcohols.

Example 32

Proton Irradiation of Cellulosic Material

The fibrous material of Example 4 is irradiated in vacuum with a beam of protons from a tandem Pelletron® accelerator 5SDH-2 (National Electrostatics Corporation). The energy of each proton and the current density can range from 2.0 to 3.12 MeV and from 0.3 to 140 nA/cm$^2$, respectively, which corresponds to a fluence rate of about $10^9$-$10^{12}$ cm$^{-2}$ s$^{-1}$. Molecular weight breakdown can start to occur from about 1 Mrad. Cross-linking can occur below this level.

Feed Preparation

The selected design feed rate for the plant is 2,000 dry tons per day of switchgrass biomass. The design feed is chopped and/or sheared switchgrass.

Biomass feedstock in the form of bales of switchgrass is received by the plant on truck trailers. As the trucks are received, they are weighed and unloaded by forklifts. Some bales are sent to on-site storage while others are taken directly to the conveyors. From there, the bales are conveyed to an automatic unwrapping system that cuts away any plastic wrapping and/or net surrounding the bales. The biomass feedstock is then conveyed past a magnetic separator to remove tramp metal, after which it is introduced to shredder-shearer trains where the material is reduced in size. Finally, the biomass feedstock is conveyed to the pretreatment subsystem.

In some cases, the switchgrass bales are wrapped with plastic net to ensure they don't break apart when handled, and may also be wrapped in plastic film to protect the bale from weather. The bales are either square or round. The bales are received at the plant from off-site storage on large truck trailers.

Since switchgrass is only seasonally available, long-term storage is required to provide feed to the plant year-round. Long-term storage will likely consist of 400-500 acres of uncovered piled rows of bales at a location (or multiple locations) reasonably close to the ethanol plant. On-site short-term storage is provided equivalent to 72 hours of production at an outside storage area. Bales and surrounding access ways as well as the transport conveyors will be on a concrete slab. A concrete slab is used because of the volume of traffic required to deliver the large amount of biomass feedstock required. A concrete slab will minimize the amount of standing water in the storage area, as well as reduce the biomass feedstock's exposure to dirt. The stored material provides a short-term supply for weekends, holidays, and when normal direct delivery of material into the process is interrupted.

The bales are off-loaded by forklifts and are placed directly onto bale transport conveyors or in the short-term storage area. Bales are also reclaimed from short-term storage by forklifts and loaded onto the bale transport conveyors.

Bales travel to one of two bale unwrapping stations. Unwrapped bales are broken up using a spreader bar and then discharged onto a conveyor which passes a magnetic separator to remove metal prior to shredding. A tramp iron magnet is provided to catch stray magnetic metal and a scalping screen removes gross oversize and foreign material ahead of multiple shredder-shearer trains, which reduce the biomass feedstock to the proper size for pretreatment. The shredder-shearer trains include shredders and rotary knife cutters. The shredders reduce the size of the raw biomass feedstock and feed the resulting material to the rotary knife cutters. The rotary knife cutters concurrently shear the biomass feedstock and screen the resulting material.

Three storage silos are provided to limit overall system downtime due to required maintenance on and/or breakdowns of feed preparation subsystem equipment. Each silo can hold approximately 55,000 cubic feet of biomass feedstock (~3 hours of plant operation).

Pretreatment

A conveyor belt carries the biomass feedstock from the feed preparation subsystem 110 to the pretreatment subsystem 114. As shown in FIG. 40, in the pretreatment subsystem 114, the biomass feedstock is irradiated using electron beam emitters, mixed with water to form a slurry, and subjected to the application of ultrasonic energy. As discussed above, irradiation of the biomass feedstock changes the molecular structure (e.g., reduces the average molecular weight and the crystallinity) of the biomass feedstock. Mixing the irradiated biomass feedstock into a slurry and applying ultrasonic energy to the slurry further changes the molecular structure of the biomass feedstock. Application of the radiation and sonication in sequence may have synergistic effects in that the combination of techniques appears to achieve greater changes to the molecular structure (e.g., reduces the average molecular weight and the crystallinity) than either technique can efficiently achieve on its own. Without wishing to be bound by theory, in addition to reducing the polymerization of the biomass feedstock by breaking intramolecular bonds between segments of cellulosic and lignocellulosic components of the biomass feedstock, the irradiation may make the overall physical structure of the biomass feedstock more brittle. After the brittle biomass feedstock is mixed into a slurry, the application of ultrasonic energy further changes the molecular structure (e.g., reduces the average molecular weight and the crystallinity) and also can reduce the size of biomass feedstock particles.

Electron Beam Irradiation

The conveyor belt 491 carrying the biomass feedstock into the pretreatment subsystem distributes the biomass feedstock into multiple feed streams (e.g., 50 feed streams) each leading to separate electron beam emitters 492. In this embodiment, the biomass feedstock is irradiated while it is dry. Each feed stream is carried on a separate conveyor belt to an associated electron beam emitter. Each irradiation feed conveyor belt can be approximately one meter wide. Before reaching the electron beam emitter, a localized vibration is induced in each conveyor belt to evenly distribute the dry biomass feedstock over the cross-sectional width of the conveyor belt.

Electron beam emitter 492 (e.g., electron beam irradiation devices commercially available from Titan Corporation, San Diego, Calif.) are configured to apply a 100 kilo-Gray dose of electrons applied at a power of 300 kW. The electron beam emitters are scanning beam devices with a sweep width of 1 meter to correspond to the width of the conveyor belt. In some embodiments, electron beam emitters with large, fixed beam widths are used. Factors including belt/beam width, desired dose, biomass feedstock density, and power applied govern the number of electron beam emitters required for the plant to process 2,000 tons per day of dry feed.

Sonication

The irradiated biomass feedstock is mixed with water to form a slurry before ultrasonic energy is applied. There can be a separate sonication system associated with each electron beam feed stream or several electron beam streams can be aggregated as feed for a single sonication system.

In each sonication system, the irradiated biomass feedstock is fed into a reservoir 1214 through a first intake 1232 and water is fed into the reservoir 1214 through second intake 1234. Appropriate valves (manual or automated) control the flow of biomass feedstock and the flow of water to produce a desired ratio of biomass feedstock to water (e.g., 10% cellulosic material, weight by volume). Each reservoir 1214 includes a mixer 1240 to agitate the contents of volume 1236 and disperse biomass feedstock throughout the water.

In each sonication system, the slurry is pumped (e.g., using a recessed impeller vortex pump 1218) from reservoir 1214 to and through a flow cell 1224 including an ultrasonic transducer 1226. In some embodiments, pump 1218 is configured to agitate the slurry 1216 such that the mixture of biomass feedstock and water is substantially uniform at inlet 1220 of the flow cell 1224. For example, the pump 1218 can agitate the slurry 1216 to create a turbulent flow that persists throughout the piping between the first pump and inlet 1220 of flow cell 1224.

Within the flow cell 1224, ultrasonic transducer 1226 transmits ultrasonic energy into slurry 1216 as the slurry flows through flow cell 1224. Ultrasonic transducer 1226 converts electrical energy into high frequency mechanical energy (e.g., ultrasonic energy) which is then delivered to the slurry through booster 48. Ultrasonic transducers are commercially available (e.g., from Hielscher USA, Inc. of Ringwood, N.J.) that are capable of delivering a continuous power of 16 kilowatts.

The ultrasonic energy traveling through booster 1248 in reactor volume 1244 creates a series of compressions and rarefactions in process stream 1216 with an intensity sufficient to create cavitation in process stream 1216. Cavitation disaggregates components of the biomass feedstock including, for example, cellulosic and lignocellulosic material dispersed in process stream 1216 (e.g., slurry). Cavitation also produces free radicals in the water of process stream 1216 (e.g., slurry). These free radicals act to further break down the cellulosic material in process stream 1216. In general, about 250 MJ/m$^3$ of ultrasonic energy is applied to process stream 1216 containing fragments of poplar chips. Other levels of ultrasonic energy (between about 5 and about 4000 MJ/m$^3$, e.g., 10, 25, 50, 100, 250, 500, 750, 1000, 2000, or 3000) can be applied to other biomass feedstocks After exposure to ultrasonic energy in reactor volume 1244, process stream 1216 exits flow cell 24 through outlet 1222.

Flow cell 1224 also includes a heat exchanger 1246 in thermal communication with at least a portion of reactor volume 1244. Cooling fluid 1248 (e.g., water) flows into heat exchanger 1246 and absorbs heat generated when process stream 1216 (e.g., slurry) is sonicated in reactor volume 1244. In some embodiments, the flow of cooling fluid 1248 into heat exchanger 1246 is controlled to maintain an approximately constant temperature in reactor volume 1244. In addition or in the alternative, the temperature of cooling fluid 1248 flowing into heat exchanger 1246 is controlled to maintain an approximately constant temperature in reactor volume 1244.

The outlet 1242 of flow cell 1224 is arranged near the bottom of reservoir 1214 to induce a gravity feed of process stream 1216 (e.g., slurry) out of reservoir 1214 towards the inlet of a second pump 1230 which pumps process stream 1216 (e.g., slurry) towards the primary process subsystem.

Sonication systems can include a single flow path (as described above) or multiple parallel flow paths each with an associated individual sonication units. Multiple sonication units can also be arranged to series to increase the amount of sonic energy applied to the slurry.

Primary Processes

A vacuum rotary drum type filter removes solids from the slurry before fermentation. Liquid from the filter is pumped cooled prior to entering the fermentors. Filtered solids are passed to passed to the post-processing subsystem for further processing.

The fermentation tanks are large, low pressure, stainless steel vessels with conical bottoms and slow speed agitators. Multiple first stage fermentation tanks can be arranged in series. The temperature in the first stage fermentation tanks is controlled to 30 degrees centigrade using external heat exchangers. Yeast is added to the first stage fermentation tank at the head of each series of tanks and carries through to the other tanks in the series.

Second stage fermentation consists of two continuous fermentors in series. Both fermentors are continuously agitated with slow speed mechanical mixers. Temperature is controlled with chilled water in external exchangers with continuous recirculation. Recirculation pumps are of the progressive cavity type because of the high solids concentration.

Off gas from the fermentation tanks and fermentors is combined and washed in a counter-current water column before being vented to the atmosphere. The off gas is washed to recover ethanol rather than for air emissions control.

Post-Processing

Distillation

Distillation and molecular sieve adsorption are used to recover ethanol from the raw fermentation beer and produce 99.5% ethanol. Distillation is accomplished in two columns—the first, called the beer column, removes the dissolved $CO_2$ and most of the water, and the second concentrates the ethanol to a near azeotropic composition.

All the water from the nearly azeotropic mixture is removed by vapor phase molecular sieve adsorption. Regeneration of the adsorption columns requires that an ethanol water mixture be recycled to distillation for recovery.

Fermentation vents (containing mostly $CO_2$, but also some ethanol) as well as the beer column vent are scrubbed in a water scrubber, recovering nearly all of the ethanol. The scrubber effluent is fed to the first distillation column along with the fermentation beer.

The bottoms from the first distillation contain all the unconverted insoluble and dissolved solids. The insoluble solids are dewatered by a pressure filter and sent to a combustor. The liquid from the pressure filter that is not recycled is concentrated in a multiple effect evaporator using waste heat from the distillation. The concentrated syrup from the evaporator is mixed with the solids being sent to the combustor, and the evaporated condensate is used as relatively clean recycle water to the process.

Because the amount of stillage water that can be recycled is limited, an evaporator is included in the process. The total amount of the water from the pressure filter that is directly recycled is set at 25%. Organic salts like ammonium acetate or lactate, steep liquor components not utilized by the organism, or inorganic compounds in the biomass end up in this stream. Recycling too much of this material can result in levels of ionic strength and osmotic pressures that can be detrimental to the fermenting organism's efficiency. For the water that is not recycled, the evaporator concentrates the dissolved solids into a syrup that can be sent to the combustor, minimizing the load to wastewater treatment.

Wastewater Treatment

The wastewater treatment section treats process water for reuse to reduce plant makeup water requirements. Wastewater is initially screened to remove large particles, which are collected in a hopper and sent to a landfill. Screening is followed by anaerobic digestion and aerobic digestion to digest organic matter in the stream. Anaerobic digestion produces a biogas stream that is rich in methane that is fed to the combustor. Aerobic digestion produces a relatively clean water stream for reuse in the process as well as a sludge that is primarily composed of cell mass. The sludge is also burned in the combustor. This screening/anaerobic digestion/aerobic digestion scheme is standard within the current ethanol industry and facilities in the 1-5 million gallons per day range can be obtained as "off-the-shelf units" from vendors.

Combustor, Boiler, and Turbo-Generator

The purpose of the combustor, boiler, and turbo-generator subsystem is to burn various by-product streams for steam and electricity generation. For example, some lignin, cellulose, and hemicellulose remains unconverted through the pretreatment and primary processes. The majority of wastewater from the process is concentrated to a syrup high in soluble solids. Anaerobic digestion of the remaining wastewater produces a biogas high in methane. Aerobic digestion produces a small amount of waste biomass (sludge). Burning these by-product streams to generate steam and electricity allows the plant to be self sufficient in energy, reduces solid waste disposal costs, and generates additional revenue through sales of excess electricity.

Three primary fuel streams (post-distillate solids, biogas, and evaporator syrup) are fed to a circulating fluidized bed combustor. The small amount of waste biomass (sludge) from wastewater treatment is also sent to the combustor. A fan moves air into the combustion chamber. Treated water enters the heat exchanger circuit in the combustor and is evaporated and superheated to 510° C. (950° F.) and 86 atm (1265 psia) steam. Flue gas from the combustor preheats the entering combustion air then enters a baghouse to remove particulates, which are landfilled. The gas is exhausted through a stack.

A multistage turbine and generator are used to generate electricity. Steam is extracted from the turbine at three different conditions for injection into the pretreatment reactor and heat exchange in distillation and evaporation. The remaining steam is condensed with cooling water and returned to the boiler feedwater system along with condensate from the various heat exchangers in the process. Treated well water is used as makeup to replace steam used in direct injection.

OTHER EMBODIMENTS

A number of embodiments of the invention have been described. Nevertheless, it will be understood that various modifications may be made without departing from the spirit and scope of the invention.

In some embodiments, relatively low doses of radiation, optionally, combined with acoustic energy, e.g., ultrasound, are utilized to crosslink, graft, or otherwise increase the molecular weight of a natural or synthetic carbohydrate-containing material, such as any of those materials in any form (e.g., fibrous form) described herein, e.g., sheared or un-sheared cellulosic or lignocellulosic materials, such as cellulose. The cross-linking, grafting, or otherwise increasing the molecular weight of the natural or synthetic carbohydrate-containing material can be performed in a controlled and predetermined manner by selecting the type or types of radiation employed (e.g., e-beam and ultraviolet or e-beam and gamma) and/or dose or number of doses of radiation applied. Such a material having increased molecular weight can be useful in making a composite, such as a fiber-resin composite, having improved mechanical properties, such as abrasion resistance, compression strength, fracture resistance, impact strength, bending strength, tensile modulus, flexural modulus and elongation at break. Cross-linking, grafting, or otherwise increasing the molecular weight of a selected material can improve the thermal stability of the material relative to an un-treated material. Increasing the thermal stability of the selected material can allow it to be processed at higher temperatures without degradation. In addition, treating materials with radiation can sterilize the materials, which can reduce their tendency to rot, e.g., while in a composite. The cross-linking, grafting, or otherwise increasing the molecular weight of a natural or synthetic carbohydrate-containing material can be performed in a controlled and predetermined manner for a particular application to provide optimal properties, such as strength, by selecting the type or types of radiation employed and/or dose or doses of radiation applied.

When used, the combination of radiation, e.g., low dose radiation, and acoustic energy, e.g., sonic or ultrasonic energy, can improve material throughput and/or minimize energy usage.

The resin can be any thermoplastic, thermoset, elastomer, adhesive, or mixtures of these resins. Suitable resins include any resin, or mixture of resins described herein.

In addition to the resin alone, the material having the increased molecular weight can be combined, blended, or added to other materials, such as metals, metal alloys, ceramics (e.g., cement), various inorganic and organic additives, such as lignin, elastomers, asphalts, glass, and mixtures of any of these and/or resins. When added to cement, fiber-reinforced cements can be produced having improved mechanical properties, such as the properties described herein, e.g., compression strength and/or fracture resistance.

Cross-linking, grafting, or otherwise increasing the molecular weight of a natural or synthetic carbohydrate-containing material utilizing radiation can provide useful materials in many forms and for many applications. For example, the carbohydrate-containing material can be in the form of a paper product, such as paper, paper pulp, or paper effluent, particle board, glued lumber laminates, e.g., veneer, or plywood, lumber, e.g., pine, poplar, oak, or even balsa wood lumber. Treating paper, particle board, laminates or lumber, can increase their mechanical properties, such as their strength. For example, treating pine lumber with radiation can make a high strength structural material.

When paper is made using radiation, radiation can be utilized at any point in its manufacture. For example, the pulp can be irradiated, a pressed fiber preform can be irradiated, or the finished paper itself can be irradiated. In some embodiments, radiation is applied at more than one point during the manufacturing process.

For example, a fibrous material that includes a first cellulosic and/or lignocellulosic material having a first molecular weight can be irradiated in a manner to provide a second cellulosic and/or lignocellulosic material having a second molecular weight higher than the first molecular weight. For example, if gamma radiation is utilized as the radiation source, a dose of from about 0.2 Mrad to about 10 Mrad, e.g., from about 0.5 Mrad to about 7.5 Mrad, or from about 2.0 Mrad to about 5.0 Mrad, can be applied. If e-beam radiation is utilized, a smaller dose can be utilized (relative to gamma radiation), such as a dose of from about 0.1 Mrad to about 5 Mrad, e.g., between about 0.2 Mrad to about 3 Mrad, or between about 0.25 Mrad and about 2.5 Mrad. After the relatively low dose of radiation, the second cellulosic and/or lignocellulosic material can be combined with a material, such as a resin, and formed into a composite, e.g., by compression molding, injection molding or extrusion. Forming resin-fiber composites is described in WO 2006/102543. Once composites are formed, they can be irradiated to further increase the molecular weight of the carbohydrate-containing material while in the composite.

Alternatively, a fibrous material that includes a first cellulosic and/or lignocellulosic material having a first molecular weight can be combined with a material, such as a resin, to provide a composite, and then the composite can be irradiated with a relatively low dose of radiation so as to provide a second cellulosic and/or lignocellulosic material having a second molecular weight higher than the first molecular weight. For example, if gamma radiation is utilized as the radiation source, a dose of from about 1 Mrad to about 10 Mrad can be applied. Using this approach increases the molecular weight of the material while it is with a matrix, such as a resin matrix. In some embodiments, the resin is a cross-linkable resin, and, as such, it cross-links as the carbohydrate-containing material increases in molecular weight, which can provide a synergistic effect to provide maximum mechanical properties to a composite. For example, such composites can have excellent low temperature performance, e.g., having a reduced tendency to break and/or crack at low temperatures, e.g., temperatures below 0° C., e.g., below −10° C., −20° C., −40° C., −50° C., −60° C. or even below −100° C., and/or excellent performance at high temperatures, e.g., capable of maintaining their advantageous mechanical properties at relatively high temperature, e.g., at temperatures above 100° C., e.g., above 125° C., 150° C., 200° C., 250° C., 300° C., 400° C., or even above 500° C. In addition, such composites can have excellent chemical resistance, e.g., resistance to swelling in a solvent, e.g., a hydrocarbon solvent, resistance to chemical attack, e.g., by strong acids, strong bases, strong oxidants (e.g., chlorine or bleach) or reducing agents (e.g., active metals such as sodium and potassium).

In some embodiments, the resin, or other matrix material, does not crosslink during irradiation. In some embodiments, additional radiation is applied while the carbohydrate-containing material is within the matrix to further increase the molecular weight of the carbohydrate-containing material. In some embodiments, the radiation causes bonds to form between the matrix and the carbohydrate-containing material.

In some embodiments, the carbohydrate-containing material is in the form of fibers. In such embodiments, when the fibers are utilized in a composite, the fibers can be randomly oriented within the matrix. In other embodiments, the fibers can be substantially oriented, such as in one, two, three or four directions. If desired, the fibers can be continuous or discrete.

Any of the following additives can added to the fibrous materials, densified fibrous materials a or any other materials and composites described herein. Additives, e.g., in the form of a solid, a liquid or a gas, can be added, e.g., to the combination of a fibrous material and resin. Additives include fillers such as calcium carbonate, graphite, wollastonite, mica, glass, fiber glass, silica, and talc; inorganic flame retardants such as alumina trihydrate or magnesium hydroxide; organic flame retardants such as chlorinated or brominated organic compounds; ground construction waste; ground tire rubber; carbon fibers; or metal fibers or powders (e.g., aluminum, stainless steel). These additives can reinforce, extend, or change electrical, mechanical or compatibility properties. Other additives include lignin, fragrances, coupling agents, compatibilizers, e.g., maleated polypropylene, processing aids, lubricants, e.g., fluorinated polyethylene, plasticizers, antioxidants, opacifiers, heat stabilizers, colorants, foaming agents, impact modifiers, polymers, e.g., degradable polymers, photostabilizers, biocides, antistatic agents, e.g., stearates or ethoxylated fatty acid amines. Suitable antistatic compounds include conductive carbon blacks, carbon fibers, metal fillers, cationic compounds, e.g., quaternary ammonium compounds, e.g., N-(3-chloro-2-hydroxypropyl)-trimethylammonium chloride, alkanolamides, and amines. Representative degradable polymers include polyhydroxy acids, e.g., polylactides, polyglycolides and copolymers of lactic acid and glycolic acid, poly(hydroxybutyric acid), poly(hydroxyvaleric acid), poly[lactide-co-(e-caprolactone)], poly[glycolide-co-(e-caprolactone)], polycarbonates, poly(amino acids), poly(hydroxyalkanoate)s, polyanhydrides, polyorthoesters and blends of these polymers.

When described additives are included, they can be present in amounts, calculated on a dry weight basis, of from below 1 percent to as high as 80 percent, based on total weight of the fibrous material. More typically, amounts range from between about 0.5 percent to about 50 percent by weight, e.g., 5 percent, 10 percent, 20 percent, 30, percent or more, e.g., 40 percent.

Any additives described herein can be encapsulated, e.g., spray dried or microencapsulated, e.g., to protect the additives from heat or moisture during handling.

The fibrous materials, densified fibrous materials, resins or additives may be dyed. For example, the fibrous material can be dyed before combining with the resin and compounding to form composites. In some embodiments, this dyeing can be helpful in masking or hiding the fibrous material, especially large agglomerations of the fibrous material, in molded or extruded parts, when this is desired. Such large agglomerations, when present in relatively high concentrations, can show up as speckles in the surfaces of the molded or extruded parts.

For example, the desired fibrous material can be dyed using an acid dye, direct dye or a reactive dye. Such dyes are available from Spectra Dyes, Kearny, N.J. or Keystone Aniline Corporation, Chicago, Ill. Specific examples of dyes include SPECTRA™ LIGHT YELLOW 2G, SPECTRACID™ YELLOW 4GL CONC 200, SPECTRANYL™ RHODAMINE 8, SPECTRANYL™ NEUTRAL RED B, SPECTRAMINE™ BENZOPERPURINE, SPECTRADIAZO™ BLACK OB, SPECTRAMINE™ TURQUOISE G, and SPECTRAMINE™ GREY LVL 200%, each being available from Spectra Dyes.

In some embodiments, resin color concentrates containing pigments are blended with dyes. When such blends are then compounded with the desired fibrous material, the fibrous material may be dyed in-situ during the compounding. Color concentrates are available from Clariant.

It can be advantageous to add a scent or fragrance to the fibrous materials, densified fibrous or composites. For example, it can be advantageous for the composites smell and/or look like natural wood, e.g., cedar wood. For example, the fragrance, e.g., natural wood fragrance, can be compounded into the resin used to make the composite. In some implementations, the fragrance is compounded directly into the resin as an oil. For example, the oil can be compounded into the resin using a roll mill, e.g., a Banbury® mixer or an extruder, e.g., a twin-screw extruder with counter-rotating screws. An example of a Banbury® mixer is the F-Series Banbury® mixer, manufactured by Farrel. An example of a twin-screw extruder is the WP ZSK 50 MEGAcompunder™, manufactured by Krupp Werner & Pfleiderer. After compounding, the scented resin can be added to the fibrous material and extruded or molded. Alternatively, master batches of fragrance-filled resins are available commercially from International Flavors and Fragrances, under the tradename PolyIff™ or from the RTP Company. In some embodiments, the amount of fragrance in the composite is between about 0.005% by weight and about 10% by weight, e.g., between about 0.1% and about 5% or 0.25% and about 2.5%.

Other natural wood fragrances include evergreen or redwood. Other fragrances include peppermint, cherry, strawberry, peach, lime, spearmint, cinnamon, anise, basil, bergamot, black pepper, camphor, chamomile, citronella, eucalyptus, pine, fir, geranium, ginger, grapefruit, jasmine, juniperberry, lavender, lemon, mandarin, marjoram, musk, myrhh, orange, patchouli, rose, rosemary, sage, sandalwood, tea tree, thyme, wintergreen, ylang ylang, vanilla, new car or mixtures of these fragrances. In some embodiments, the amount of fragrance in the fibrous material-fragrance combination is between about 0.005% by weight and about 20% by weight, e.g., between about 0.1% and about 5% or 0.25% and about 2.5%.

While fibrous materials have been described, such as cellulosic and lignocellulosic fibrous materials, other fillers may be used for making the composites. For example, inorganic fillers such as calcium carbonate (e.g., precipitated calcium carbonate or natural calcium carbonate), aragonite clay, orthorhombic clays, calcite clay, rhombohedral clays, kaolin, clay, bentonite clay, dicalcium phosphate, tricalcium phosphate, calcium pyrophosphate, insoluble sodium metaphosphate, precipitated calcium carbonate, magnesium orthophosphate, trimagnesium phosphate, hydroxyapatites, synthetic apatites, alumina, silica xerogel, metal aluminosilicate complexes, sodium aluminum silicates, zirconium silicate, silicon dioxide or combinations of the inorganic additives may be used. The fillers can have, e.g., a particle size of greater than 1 micron, e.g., greater than 2 micron, 5 micron, 10 micron, 25 micron or even greater than 35 microns.

Nanometer scale fillers can also be used alone, or in combination with fibrous materials of any size and/or shape. The fillers can be in the form of, e.g., a particle, a plate, or a fiber. For example, nanometer sized clays, silicon and carbon nanotubes, and silicon and carbon nanowires can be used. The filler can have a transverse dimension less than 1000 nm, e.g., less than 900 nm, 800 nm, 750 nm, 600 nm, 500 nm, 350 nm, 300 nm, 250 nm, 200 nm, less than 100 nm, or even less than 50 nm.

In some embodiments, the nano-clay is a montmorillonite. Such clays are available from Nanocor, Inc. and Southern Clay products, and have been described in U.S. Pat. Nos. 6,849,680 and 6,737,464. The clays can be surface treated before mixing into, e.g., a resin or a fibrous material. For example, the clay can be surface is treated so that its surface is ionic in nature, e.g., cationic or anionic.

Aggregated or agglomerated nanometer scale fillers, or nanometer scale fillers that are assembled into supramolecular structures, e.g., self-assembled supramolecular structures can also be used. The aggregated or supramolecular fillers can be open or closed in structure, and can have a variety of shapes, e.g., cage, tube or spherical.

Mobile Biomass Processing

Stationary processing facilities for processing biomass have been described. However, depending upon the source of biomass feedstock and the products produced therefrom, it can be advantageous to process or partially process biomass in mobile facilities that can be located close to the source of the feedstock and/or close to target markets for products produced from the feedstock. As an example, in some embodiments, various grasses such as switchgrass are used as biomass feedstock. Transporting large volumes of switchgrass from fields where it grows to processing facilities hundreds or even thousands of miles away may be both wasteful energetically and economically costly (for example, transportation of feedstock by train is estimated to cost between $3.00 and $6.00 per ton per 500 miles). Moreover, some of the products of processing switchgrass feedstock may be suitable for markets in regions where biomass feedstock is grown (e.g., ruminant feed for livestock). Once again, transporting ruminant feed hundreds or thousands of miles to market may not be economically viable.

Figure 63:
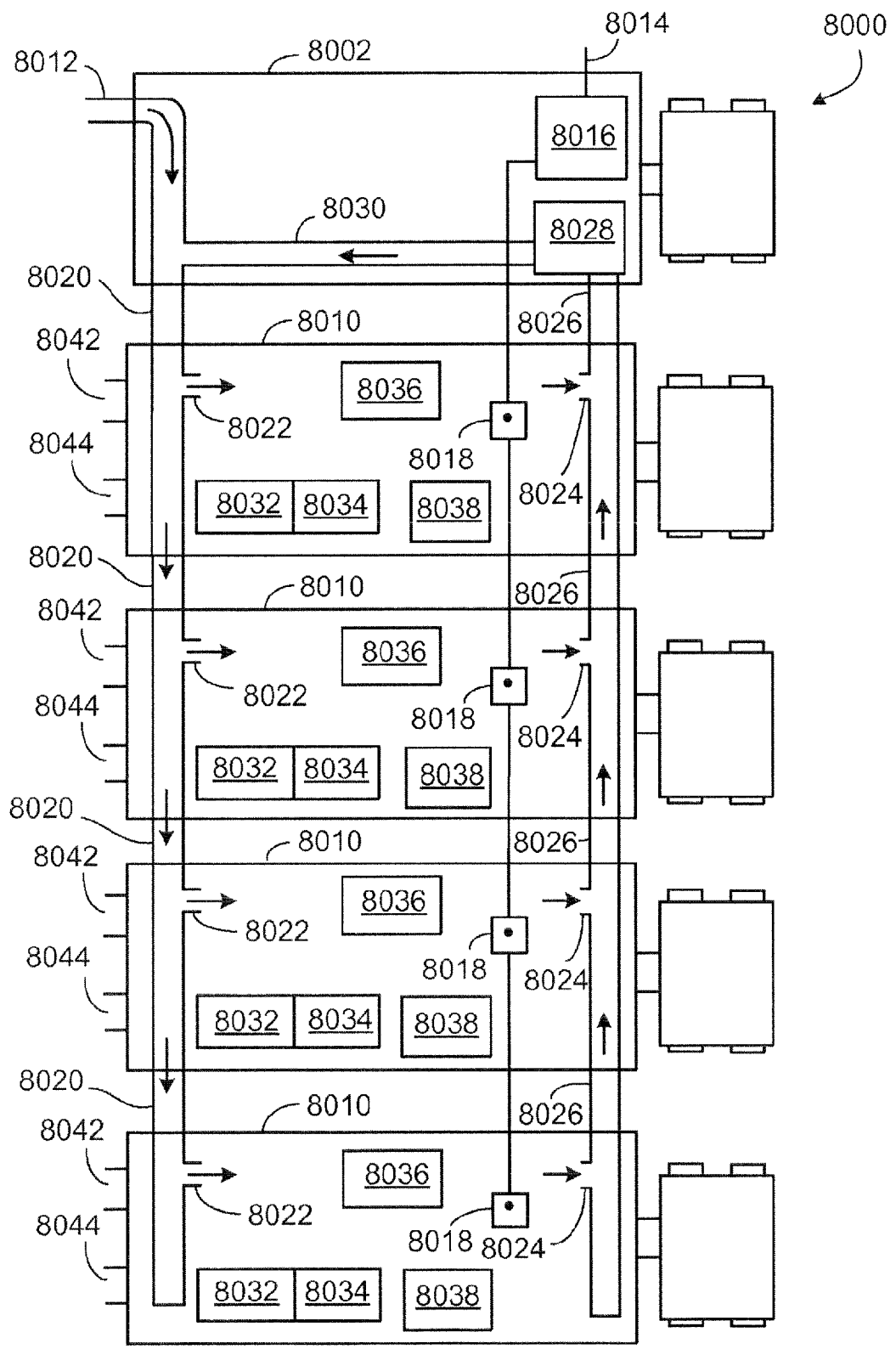
FIG. 63 is a schematic diagram of a truck-based mobile
biomass processing facility.

Accordingly, in some embodiments, the processing systems disclosed herein are implemented as mobile, reconfigurable processing facilities. One embodiment of such a mobile facility is shown in FIG. 63. Processing facility 8000 includes five transport trucks 8002, 8004, 8006, 8008, and 8010 (although five trucks are shown in FIG. 63, in general, any number of trucks may be used). Truck 8002 includes water supply and processing systems and electrical supply systems for the other trucks. Trucks 8004, 8006, 8008, and 8010 are each configured to process biomass feedstock in parallel.

Truck 8002 includes a water supply inlet 8012 for receiving water from a continuous supply (such as a water main) or a reservoir (e.g., a tank on another truck, or a tank or other reservoir located at the processing site). Process water is circulated to each of trucks 8004, 8006, 8008, and 8010 through a water supply conduit 8020. Each of trucks 8004, 8006, 8008, and 8010 includes a portion of conduit 8020. When the trucks are positioned next to one another to set up the mobile processing facility, the portions of conduit 8020 are connected to form a continuous water transport conduit. Each of trucks 8004, 8006, 8008, and 8010 includes a water inlet 8022 to supply process water, and a water outlet 8024 to remove used process water. The water outlets 8024 in each of trucks 8004, 8006, 8008, and 8010 lead to a piecewise continuous water disposal conduit 8026, which is similarly joined into a continuous conduit when the trucks are positioned next to one another. Waste process water is circulated to water processor 8028 in truck 8002, which treats the water to remove harmful waste materials and then recycles the treated water via conduit 8030 back into supply conduit 8020. Waste materials removed from the used process water can be disposed of on site, or stored (e.g., in another truck, not shown) and transported to a storage facility.

Truck 8002 also includes an electrical supply station 8016 that provides electrical power to each of trucks 8004, 8006, 8008, and 8010. Electrical supply station 8016 can be connected to an external power source via connection 8014. Alternatively, or in addition, electrical supply station can be configured to generate power (e.g., via combustion of a fuel source). Electrical power is supplied to each of trucks 8004, 8006, 8008, and 8010 via electrical supply conduit 8040. Each of trucks 8004, 8006, 8008, and 8010 includes an electrical power terminal 8018 to which devices on the truck requiring electrical power are connected.

Each of trucks 8004, 8006, 8008, and 8010 includes a feedstock inlet 8042 and a waste outlet 8044. Biomass feedstock enters each of trucks 8004, 8006, 8008, and 8010 through inlet 8042, where it is processed according to the methods disclosed herein. Following processing, waste material is discharged through outlet 8044. Alternatively, in some embodiments, each of trucks 8004, 8006, 8008, and 8010 can be connected to a common feedstock inlet (e.g., positioned in truck 8002), and each truck can discharge waste material through a common outlet (e.g., also positioned in truck 8002).

Each of trucks 8004, 8006, 8008, and 8010 can include various types of processing units; for example, in the configuration shown in FIG. 63, each of trucks 8004, 8006, 8008, and 8010 includes an ion accelerator 8032 (e.g., a horizontal Pelletron-based tandem folded accelerator), a heater/pyrolysis station 8034, a wet chemical processing unit 8036, and a biological processing unit 8038. In general, each of trucks 8004, 8006, 8008, and 8010 can include any of the processing systems disclosed herein. In certain embodiments, each of trucks 8004, 8006, 8008, and 8010 will include the same processing systems. In some embodiments, however, one or more trucks may have different processing systems.

In addition, some or all trucks may have certain processing systems onboard, but which are not used, depending upon the nature of the feedstock. In general, the layout of the various onboard processing systems on each of trucks 8004, 8006, 8008, and 8010 is reconfigurable according to the type of material that is processed.

Figure 64:
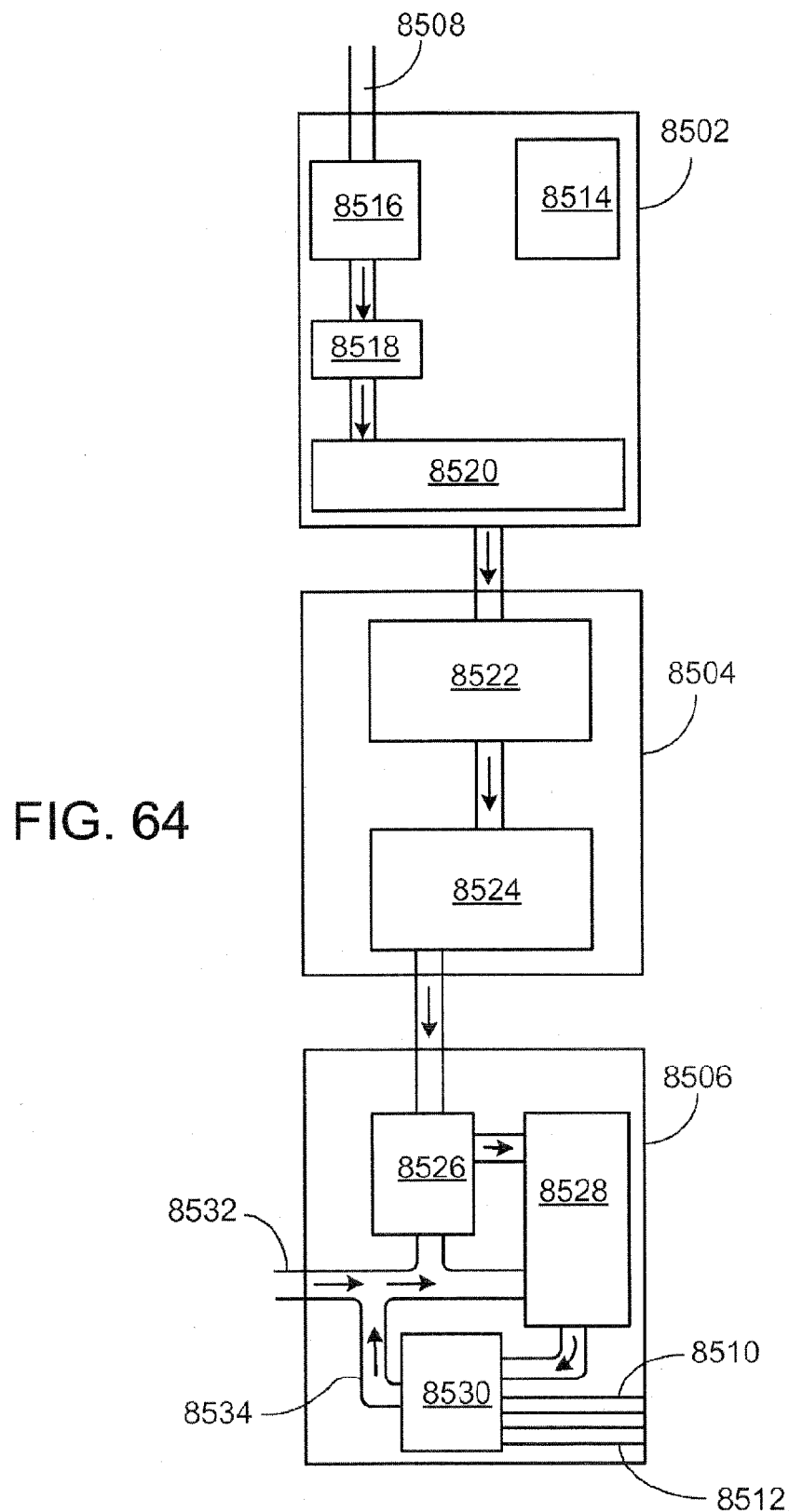
FIG. 64 is a schematic diagram of a train-based mobile
biomass processing facility.

Processing facility 8000 is an exemplary parallel processing facility; each of trucks 8004, 8006, 8008, and 8010 processes biomass feedstock in parallel. In certain embodiments, mobile processing facilities are implemented as serial processing facilities. An embodiment of train-based serial mobile processing facility 8500 is shown in FIG. 64. Processing facility 8500 includes three rail cars 8502, 8504, and 8506 (in general, any number of rail cars can be used), each configured to perform one or more processing steps in an overall biomass processing procedure. Rail car 8502 includes a feedstock inlet for receiving feedstock from a storage repository (e.g., a storage building, or another rail car). Feedstock is conveyed from one processing unit to another among the three rail cars via a continuous conveyor system. Rail car 8502 also includes an electrical supply station 8514 for supplying electrical power to each of rail cars 8502, 8504, and 8506.

Rail car 8502 includes a coarse mechanical processor 8516 and a fine mechanical processor 8518 for converting raw feedstock to a finely divided fibrous material. A third mechanical processor 8520 rolls the fibrous material into a flat, continuous mat. The mat of fibrous material is then transported to an ion accelerator 8522 on rail car 8504 that exposes the fibrous material to an ion beam. Following exposure to the ion beam, the fibrous material is transported to a low energy electron accelerator 8524.

The fibrous material is subsequently transported to a chemical processing unit 8526 on rail car 8506 for one or more chemical treatment steps. Rail car 8506 includes a process water inlet 8532 which receives process water from an external reservoir (e.g., a tank or another rail car).

Following chemical treatment in processing unit 8526, the material is transported to a biological processing unit 8528 to initiate fermentation of liberated sugars from the material. After biological processing is complete, the material is transported to a separator 8530, which diverts useful products into conduit 8510 and waste materials into conduit 8512. Conduit 8510 can be connected to a storage unit (e.g., a tanker car or an external storage tank). Similarly, waste products can be conveyed through conduit 8512 to a storage unit such as a tanker car, and/or to an external storage facility. Separator 8530 also recycles clean process water for subsequent delivery to chemical processing unit 8536 and/or biological processing unit 8528.

As discussed previously, processing facility 8500 is an example of a sequential configuration of a mobile processing facility; each of rail cars 8502, 8504, and 8506 includes a different subset of processing systems; and the feedstock process flow from each car is connected to the next car in series to complete the processing sequence.

In general, a wide variety of different mobile processing configurations can be used to process biomass feedstock. Both truck-based and train-based mobile processing facilities can be configured for either serial operation or parallel operation. Generally, the layout of the various processing units is reconfigurable, and not all processing units can be used for particular feedstocks. When a particular processing unit is not used for a certain feedstock, the processing unit can be withdrawn from the process flow. Alternatively, the processing unit can remain in the overall process flow, but can be deactivated so that feedstock passes through the deactivated unit rapidly without being modified.

Mobile processing facilities can include one or more electronic control devices that automate some or all aspects of the biomass processing procedure and/or the mobile facility setup procedure. For example, an electronic control device can be configured to receive input information about a feedstock material that is to be processed, and can generate a variety of output information including a suggested configuration of the mobile processing facility, and/or values for one or more process parameters involved in the biomass processing procedure that will be implemented.

Treatment of Hydrocarbon-Containing Materials

In some embodiments, the methods and systems disclosed herein for treating biomass can be used to process hydrocarbon-containing materials such as tar or oil sands, oil shale, crude oil (e.g., heavy crude oil and/or light crude oil), bitumen, coal, petroleum gases (e.g., methane, ethane, propane, butane, isobutane), liquefied natural and/or synthetic gas, asphalt, and other natural materials that include various types of hydrocarbons. For example, a processing facility for hydrocarbon-containing materials receives a supply of material. The material can be delivered directly from a mine, e.g., by conveyor belt and/or rail car system, and in certain embodiments, the processing facility can be constructed in relatively close proximity to, or even atop, the mine. In some embodiments, the material can be transported to the processing facility via railway freight car or another motorized transport system, and/or pumped to the processing facility via pipeline.

When the material enters the processing facility, the material can be broken down mechanically and/or chemically to yield starting material. As an example, the material can include material derived from oil sands and containing crude bitumen. Bitumen can then be processed into one or more hydrocarbon products using the methods disclosed herein. In some embodiments, the oil sands material can be extracted from surface mines such as open pit mines. In certain embodiments, sub-surface oil sands material can be extracted using a hot water flotation process that removes oil from sand particles, and then adding naphtha to allow pumping of the oil to the processing facility.

Bitumen processing generally includes two stages. In a first stage, relatively large bitumen hydrocarbons are cracked into smaller molecules using coking, hydrocracking, or a combination of the two techniques. In the coking process, carbon is removed from bitumen hydrocarbon molecules at high temperatures (e.g., 400° C. or more), leading to cracking of the molecules. In hydrocracking, hydrogen is added to bitumen molecules, which are then cracked over a catalyst system (e.g., platinum).

In a second stage, the cracked bitumen molecules are hydrotreated. In general, hydrotreating includes heating the cracked bitumen molecules in a hydrogen atmosphere to remove metals, nitrogen (e.g., as ammonia), and sulfur (e.g., as elemental sulfur).

The overall bitumen processing procedure typically produces approximately one barrel of synthetic crude oil for every 2.5 tons of oil sand material processed. Moreover, an energy equivalent of approximately one barrel of oil is used to produce three barrels of synthetic crude oil from oil sand-derived bitumen sources.

As another example, oil shale typically includes fine-grained sedimentary rock that includes significant amounts of kerogen (a mixture of various organic compounds in solid form). By heating oil shale, a vapor is liberated which can be purified to yield a hydrocarbon rich shale oil and a combustible hydrocarbon shale gas. Typically, the oil shale is heated to between 250° C. and 550° C. in the absence of oxygen to liberate the vapor.

The efficiency and cost-effectiveness with which usable hydrocarbon products can be extracted from oil sands material, oil shale, crude oil, and other oil-based materials can be improved by applying the methods disclosed herein. In addition, a variety of different hydrocarbon products (including various hydrocarbon fractions that are present in the material, and other types of hydrocarbons that are formed during processing) can be extracted from the materials.

In some embodiments, for example, ion beams can be used to process materials (and/or intermediate materials derived from the materials). For example, ion beams that include one or more different types of ions (e.g., protons, carbon ions, oxygen ions, hydride ions) can be used to process materials. The ion beams can include positive ions and/or negative ions, in doses that vary from 1 Mrad to 2500 Mrad or more, e.g., 50, 100, 250, 350, 500, 1000, 1500, 2000, or 2500 Mrad, or even higher levels.

In some embodiments, metal ions can be used to treat biomass material in addition to, or as alternatives to, the various types of ions disclosed above. For example, ions of metals that function as catalysts in hydrocarbon cracking, reforming, and alkylation processes, such as ions of rhodium, iridium, and platinum, can be generated, and biomass materials can be exposed to such ions to initiate degradation reactions in the biomass. Processing steps such as hydrocarbon cracking can also be used before, during, and/or after exposure to metal ions.

In certain embodiments, other methods can also be used to process raw and/or intermediate materials. For example, raw and/or intermediate materials can be exposed to electron beams. In general, the electron beams can have any of the properties discussed previously with regard to biomass processing. In some embodiments, additional processing methods can be used, including oxidation, pyrolysis, and sonication. In general, process parameters for each of these techniques when treating hydrocarbon-based raw and/or intermediate materials can be the same as those disclosed above in connection with biomass materials. Various combinations of these techniques can also be used to process raw or intermediate materials.

Generally, the various techniques can be used in any order, and any number of times, to treat raw and/or intermediate materials. For example, to process bitumen from oil sands, one or more of the techniques disclosed herein can be used prior to any mechanical breakdown steps, following one or more mechanical breakdown steps, prior to cracking, after cracking and/or prior to hydrotreatment, and after hydrotreatment. As another example, to process oil shale, one or more of the techniques disclosed herein can be used prior to either or both of the vaporization and purification steps discussed above. Products derived from the hydrocarbon-based materials can be treated again with any combination of techniques prior to transporting the products out of the processing facility (e.g., either via motorized transport, or via pipeline).

The techniques disclosed herein can be applied to process raw and/or intermediate material in dry form, in a solution or slurry, or in gaseous form (e.g., to process hydrocarbon vapors at elevated temperature). The solubility of raw or intermediate products in solutions and slurries can be controlled through selective addition of one or more agents such as acids, bases, oxidizing agents, reducing agents, and salts. In general, the methods disclosed herein can be used to initiate and/or sustain the reaction of raw and/or intermediate hydrocarbon-containing materials, extraction of intermediate materials from materials (e.g., extraction of hydrocarbon components from other solid or liquid components), distribution of raw and/or intermediate materials, and separation of intermediate materials from materials (e.g., separation of hydrocarbon-containing components from other solid matrix components to increase the concentration and/or purity and/or homogeneity of the hydrocarbon components).

In addition, microorganisms can be used for processing raw or intermediate materials, either prior to or following the use of ion beam exposure, electron beam exposure, pyrolysis, oxidation, sonication, and/or chemical processing. Suitable microorganisms include various types of bacteria, yeasts, and mixtures thereof, as disclosed previously. The processing facility can be equipped to remove harmful byproducts that result from the processing of raw or intermediate materials, including gaseous products that are harmful to human operators, and chemical byproducts that are harmful to humans and/or various microorganisms.

In some embodiments, the use of one or more of the techniques disclosed herein results in a molecular weight reduction of one or more components of the raw or intermediate material that is processed. As a result, various lower weight hydrocarbon substances can be produced from one or more higher weight hydrocarbon substances. In certain embodiments, the use of one or more of the techniques disclosed herein results in an increase in molecular weight of one or more components of the raw or intermediate material that is processed. For example, the various techniques disclosed herein can induce bond-formation between molecules of the components, leading to the formation of increased quantities of certain products, and even to new, larger weight products. In addition to hydrocarbon products, various other compounds can be extracted from the materials, including nitrogen based compounds (e.g., ammonia), sulfur-based compounds, and silicates and other silicon-based compounds. In certain embodiments, one or more products extracted from the materials can be combusted to generate process heat for heating water, raw or intermediate materials, generating electrical power, or for other applications.

In some embodiments, processing raw and/or intermediate materials via one or more of ion beam exposure, electron beam exposure, pyrolysis, oxidation, sonication, microorganisms, and/or chemical processing can lead to improvements in the efficiency (and even the elimination) of other processing steps. For example, processing oil sand materials (including bitumen) using one or more of the techniques disclosed herein can lead to more efficient cracking and/or hydrotreatment of the bitumen. As another example, processing oil shale can lead to more efficient extraction of various products, including shale oil and/or shale gas, from the oil shale. In certain embodiments, steps such as cracking or vaporization may not even be necessary if the techniques disclosed herein are first used to treat the material. Further, in some embodiments, by treating raw and/or intermediate materials, the products can be made more soluble in certain solvents, in preparation for subsequent processing steps in solution (e.g., steam blasting, sonication). Improving the solubility of the products can improve the efficiency of subsequent solution-based treatment steps. By improving the efficiency of other processing steps (e.g., cracking and/or hydrotreatment of bitumen, vaporization of oil shale), the overall energy consumed in processing the materials can be reduced, making extraction and processing of the materials economically feasible.

In certain embodiments, ion beams can be particularly efficient at processing raw hydrocarbon-containing materials. For example, due to the ability of ion beams to initiate both polymerization and depolymerization reactions, to deposit heat in the irradiated material, and to sputter or otherwise displace atoms of the irradiated material, hydrocarbon materials such as oil sands, oil shale, crude oil, asphalt, and other materials can be treated to improve additional processing steps for these materials and/or to extract useful products from the materials.

Products derived from processing hydrocarbon-containing materials can include one or more compounds suitable for use as fuels. The fuel compounds can be used on-site (e.g., combusted to generate electrical power) and/or can be transported to another facility for storage and/or use.

Processing of Crude Oil

The methods and systems disclosed herein can be used to process crude oil in addition to, or as an alternative to, conventional oil refining technologies. In particular, ion beam treatment methods—alone or in combination with any of the other methods disclosed herein—can be used for low temperature oil cracking, reforming, functionalization, and other processes.

Crude oils typically include large numbers of different hydrocarbon species, ranging from relatively light, volatile, low molecular weight hydrocarbons, to heavy, dense, highly viscous fractions (e.g., heavy oil, bitumen) of high molecular weight. The heavy crudes typically contain more sulfur and/or nitrogen and/or metals, relative to lighter, sweeter crudes such as the West Texas Intermediate which is traded on the New York Mercantile Exchange. In general, sweet crudes include relatively low amounts of sulfur-containing compounds; the sour crudes include larger amounts of sulfur-containing compounds. Simple refineries are generally designed to handle sweet crudes, while more complex deep conversion refineries are required for the processing of heavy, sour crude oils.

The large number of different hydrocarbon (and other) species in crude oil typically establish a relatively delicately balanced colloidal solubility system. When certain properties of the crude oil are changed (e.g., temperature, pressure, composition), the solubility balance can be destabilized, causing a single-phase crude oil feedstock to change to a multiphase, multicomponent mixture (which can include one or more gas, liquid, and solid phases). At room temperature and pressure, various components of crude oil are in different physical states. For example, lighter hydrocarbons (e.g., methane, ethane, propane, butane) are gases at room temperature and pressure. Components of intermediate molecular weight (e.g., pentane, hexane, octane, gasoline, kerosene, diesel fuel) are liquids under these conditions. Heavy fractions (e.g., asphalt, wax) are solids at standard temperature and pressure. Due to this range of physical states, conventional refineries typically process crude oil at elevated temperatures and/or pressures to ensure that most (or all) of the hydrocarbon fractions in the crude are either liquids or gases.

In some embodiments, one or more of the pretreatment methods disclosed herein, include ion beam pretreatment alone or in combination with one or more of the other techniques disclosed herein, can be used to enable processing of crude oil at reduced temperature and/or pressure. For example, the crude oil can be exposed to an ion beam, which assists in breaking molecular bonds in heavy crude oil fractions, producing lower molecular weight products as a result. While the heavy fractions are typically highly viscous liquids or even solids, the lower molecular weight products are typically less viscous liquids. As a result, the products can be further processed and/or refined at lower temperature and/or pressure. In certain embodiments, for example, following ion beam exposure, the exposed crude oil can be processed at a temperature of 800° F. or less (e.g., 700° F. or less, 600° F. or less, 500° F. or less, 400° F. or less, 300° F. or less, 200° F. or less, 150° F. or less, 100° F. or less, 50° F. or less).

In some embodiments, following ion beam exposure, the exposed crude oil can be processed at a pressure of 100 atmospheres or less (e.g., 90 atmospheres or less, 80 atmospheres or less, 70 atmospheres or less, 60 atmospheres or less, 50 atmospheres or less, 40 atmospheres or less, 30 atmospheres or less, 20 atmospheres or less, 10 atmospheres or less, 5 atmospheres or less, 2 atmospheres or less).

Crude oil refining comprises processes that separate various hydrocarbon and other components in the oil and, in some cases, convert certain hydrocarbons to other hydrocarbon species via molecular rearrangement (e.g., chemical reactions that break bonds). In some embodiments, a first step in the refining process is a water washing step to remove soluble components such as salts from the crude oil. Typically, the washed crude oil is then directed to a furnace for preheating. As discussed above, the crude oil can include a large number of different components with different viscosities; some components may even be solid at room temperature. By heating the crude oil, the component mixture can be converted to a mixture that can be flowed from one processing system to another (and from one end of a processing system to the other) during refining.

Preheated crude is then sent to a distillation tower, where fractionation of various components in the crude oil mixture occurs with heating in a distillation column. The amount of heat energy supplied to the crude oil mixture in the distillation process depends in part upon the composition of the oil; in general, however, significant energy is expended in heating the crude oil during distillation, cooling the distillates, pressurizing the distillation column, and in other such steps. Within limits, certain refineries are capable of reconfiguration to handle differing crude oil feedstocks and products. In general, however, due to the relatively specialized refining apparatus, the ability of refineries to handle significantly different crude oil feedstocks is restricted.

In some embodiments, pretreatment of crude oil feedstocks using methods disclosed herein, such as ion beam pretreatment (and/or one or more additional pretreatments), can enhance the ability of a refining apparatus to accept crude oils having different compositions. For example, by exposing a crude oil stream to incident ions from an ion beam, various chemical and/or physical properties of the crude oil mixture can be changed. Incident ions can cause chemical bonds to break, leading to the production of lighter molecular weight components with lower viscosities from heavier components with higher viscosities. Alternatively, or in addition, exposure of certain components to ions can lead to isomerization of the exposed components. The newly formed isomers can have lower viscosities than the components from which they are formed. The lighter molecular weight components and/or isomers with lower viscosities can then be introduced into the refinery, enabling processing of crude oil feedstock while may not have been suitable for processing initially.

In general, the various components of crude oil distill at different temperature ranges, corresponding to different vertical heights in a distillation column. Typically, for example, a refinery distillation column will include product streams at a large number of different temperature cut ranges, with the lowest boiling point (and, generally, smallest molecular weight) components drawn from the top of the column, and the highest boiling point, heaviest molecular weight components drawn from lower levels of the column. As an example, light distillates extracted from upper regions of the column typically include one or more of aviation gasoline, motor gasoline, napthas, kerosene, and refined oils. Intermediate distillates, removed from the middle region of the column, can include one or more of gas oil, heavy furnace oil, and diesel fuel oil. Heavy distillates, which are generally extracted from lower levels of the column, can include one or more of lubricating oil, grease, heavy oils, wax, and cracking stock. Residues remaining in the still can include a variety of high boiling components such as lubricating oil, fuel oil, petroleum jelly, road oils, asphalt, and petroleum coke. Certain other products can also be extracted from the column, including natural gas (which can be further refined and/or processed to produce components such as heating fuel, natural gasoline, liquefied petroleum gas, carbon black, and other petrochemicals), and various by-products (including, for example, fertilizers, ammonia, and sulfuric acid).

Generally, treatment of crude oil and/or components thereof using the methods disclosed herein (including, for example, ion beam treatment, alone or in combination with one or more other methods) can be used to modify molecular weights, chemical structures, viscosities, solubilities, densities, vapor pressures, and other physical properties of the treated materials. Typical ions that can be used for treatment of crude oil and/or components thereof can include protons, carbon ions, oxygen ions, and any of the other types of ions disclosed herein. In addition, ions used to treat crude oil and/or its components can include metal ions; in particular, ions of metals that catalyze certain refinery processes (e.g., catalytic cracking) can be used to treat crude oil and/or components thereof. Exemplary metal ions include, but are not limited to, platinum ions, palladium ions, iridium ions, rhodium ions, ruthenium ions, aluminum ions, rhenium ions, tungsten ions, and osmium ions.

In some embodiments, multiple ion exposure steps can be used. A first ion exposure can be used to treat crude oil (or components thereof) to effect a first change in one or more of molecular weight, chemical structure, viscosity, density, vapor pressure, solubility, and other properties. Then, one or more additional ion exposures can be used to effect additional changes in properties. As an example, the first ion exposure can be used to convert a substantial fraction of one or more high boiling, heavy components to lower molecular weight compounds with lower boiling points. Then, one or more additional ion exposures can be used to cause precipitation of the remaining amounts of the heavy components from the component mixture.

In general, a large number of different processing protocols can be implemented, according to the composition and physical properties of the feedstock. In certain embodiments, the multiple ion exposures can include exposures to only one type of ion. In some embodiments, the multiple ion exposures can include exposures to more than one type of ion. The ions can have the same charges, or different charge magnitudes and/or signs.

In certain embodiments, the crude oil and/or components thereof can be flowed during exposure to ion beams. Exposure during flow can greatly increase the throughput of the exposure process, enabling straightforward integration with other flow-based refinery processes.

In some embodiments, the crude oil and/or components thereof can be functionalized during exposure to ion beams. For example, the composition of one or more ion beams can be selected to encourage the addition of particular functional groups to certain components (or all components) of a crude oil feedstock. One or more functionalizing agents (e.g., ammonia) can be added to the feedstock to introduce particular functional groups. By functionalizing the crude oil and/or components thereof, ionic mobility within the functionalized compounds can be increased (leading to greater effective ionic penetration during exposure), and physical properties such as viscosity, density, and solubility of the crude oil and/or components thereof can be altered. By altering one or more physical properties of the crude oil and/or crude oil components, the efficiency and selectivity of subsequent refining steps can be adjusted, and the available product streams can be controlled. Moreover, functionalization of crude oil and/or crude oil components can lead to improved activating efficiency of catalysts used in subsequent refining steps.

In general, the methods disclosed herein—including ion beam exposure of crude oil and crude oil components—can be performed before, during, or after any of the other refining steps disclosed herein, and/or before, during, or after any other steps that are used to refine crude oil. The methods disclosed herein can also be used after refining is complete, and/or before refining begins. In certain embodiments, the methods disclosed herein, including ion beam exposure, can be used to process crude oil even during extraction of the crude oil from oil fields.

In some embodiments, when crude oil and/or components thereof are exposed to one or more ion beams, the exposed material can also be exposed to one or more gases concurrent with ion beam exposure. Certain components of crude oil, such as components that include aromatic rings, may be relatively more stable to ion beam exposure than nonaromatic components. Typically, for example, ion beam exposure leads to the formation of reactive intermediates such as radicals from hydrocarbons. The hydrocarbons can then react with other less reactive hydrocarbons. To reduce the average molecular weight of the exposed material, reactions between the reactive products and less reactive hydrocarbons lead to molecular bond-breaking events, producing lower weight fragments from longer chain molecules. However, more stable reactive intermediates (e.g., aromatic hydrocarbon intermediates) may not react with other hydrocarbons, and can even undergo polymerization, leading to the formation of heavier weight compounds. To reduce the extent of polymerization in ion beam exposed crude oil and/or crude oil components, one or more radical quenchers can be introduced during ion beam exposure. The radical quenchers can cap reactive intermediates, preventing the re-formation of chemical bonds that have been broken by the incident ions. Suitable radical quenchers include hydrogen donors such as hydrogen gas.

In certain embodiments, reactive compounds can be introduced during ion beam exposure to further promote degradation of crude oil and/or crude oil components. The reactive compounds can assist various degradation (e.g., bond-breaking) reactions, leading to a reduction in molecular weight of the exposed material. An exemplary reactive compound is ozone, which can be introduced directly as a gas, or generated in situ via application of a high voltage to an oxygen-containing supply gas (e.g., oxygen gas, air) or exposure of the oxygen-containing supply gas to an ion beam and/or an electron beam. In some embodiments, ion beam exposure of crude oil and/or crude oil components in the presence of a fluid such as oxygen gas or air can lead to the formation of ozone gas, which also assists the degradation of the exposed material.

Prior to and/or following distillation in a refinery, crude oil and/or components thereof can undergo a variety of other refinery processes to purify components and/or convert components into other products. In the following sections, certain additional refinery steps are outlined, and use of the methods disclosed herein in combination with the additional refinery steps will be discussed.

(i) Catalytic Cracking

Catalytic cracking is a widely used refinery process in which heavy oils are exposed to heat and pressure in the presence of a catalyst to promote cracking (e.g., conversion to lower molecular weight products). Originally, cracking was accomplished thermally, but catalytic cracking has largely replaced thermal cracking due to the higher yield of gasoline (with higher octane) and lower yield of heavy fuel oil and light gases. Most catalytic cracking processes can be classified as either moving-bed or fluidized bed processes, with fluidized bed processes being more prevalent. Process flow is generally as follows. A hot oil feedstock is contacted with the catalyst in either a feed riser line or the reactor. During the cracking reaction, the formation of coke on the surface of the catalyst progressively deactivates the catalyst. The catalyst and hydrocarbon vapors undergo mechanical separation, and oil remaining on the catalyst is removed by steam stripping. The catalyst then enters a regenerator, where it is reactivated by carefully burning off coke deposits in air. The hydrocarbon vapors are directed to a fractionation tower for separation into product streams at particular boiling ranges.

Older cracking units (e.g., 1965 and before) were typically designed with a discrete dense-phase fluidized catalyst bed in the reactor vessel, and operated so that most cracking occurred in the reactor bed. The extent of cracking was controlled by varying reactor bed depth (e.g., time) and temperature. The adoption of more reactive zeolite catalysts had led to improved modern reactor designs in which the reactor is operated as a separator to separate the catalyst and the hydrocarbon vapors, and control of the cracking process is achieved by accelerating the regenerated catalyst to a particular velocity in a riser-reactor before introducing it into the riser and injecting the feedstock into the riser.

The methods disclosed herein can be used before, during, and/or after catalytic cracking to treat components of crude oil. In particular, ion beam exposure (alone, or in combination with other methods) can be used to pre-treat feedstock prior to injection into the riser, to treat hydrocarbons (including hydrocarbon vapors) during cracking, and/or to treat the products of the catalytic cracking process.

Cracking catalysts typically include materials such as acid-treated natural aluminosilicates, amorphous synthetic silica-alumina combinations, and crystalline synthetic silica-alumina catalysts (e.g., zeolites). During the catalytic cracking process, components of crude oil can be exposed to ions from one or more ion beams to increase the efficiency of these catalysts. For example, the crude oil components can be exposed to one or more different types of metal ions that improve catalyst activity by participating in catalytic reactions. Alternatively, or in addition, the crude oil components can be exposed to ions that scavenge typical catalyst poisons such as nitrogen compounds, iron, nickel, vanadium, and copper, to ensure that catalyst efficiency remains high. Moreover, the ions can react with coke that forms on catalyst surfaces to remove the coke (e.g., by processes such as sputtering, and/or via chemical reactions), either during cracking or catalyst regeneration.

(ii) Alkylation

In petroleum terminology, alkylation refers to the reaction of low molecular weight olefins with an isoparaffin (e.g., isobutane) to form higher molecular weight isoparaffins. Alkylation can occur at high temperature and pressure without catalysts, but commercial implementations typically include low temperature alkylation in the presence of either a sulfuric acid or hydrofluoric acid catalyst. Sulfuric acid processes are generally more sensitive to temperature than hydrofluoric acid based processes, and care is used to minimize oxidation-reduction reactions that lead to the formation of tars and sulfur dioxide. In both processes, the volume of acid used is typically approximately equal to the liquid hydrocarbon charge, and the reaction vessel is pressurized to maintain the hydrocarbons and acid in a liquid state. Contact times are generally from about 10 to 40 minutes, with agitation to promote contact between the acid and hydrocarbon phases. If acid concentrations fall below about 88% by weight sulfuric acid or hydrofluoric acid, excessive polymerization can occur in the reaction products. The use of large volumes of strong acids makes alkylation processes expensive and potentially hazardous.

The methods disclosed herein can be used before, during, and/or after alkylation to treat components of crude oil. In particular, ion beam exposure (alone, or in combination with other methods) during alkylation can assist the addition reaction between olefins and isoparaffins. In some embodiments, ion beam exposure of the crude oil components can reduce or even eliminate the need for sulfuric acid and/or hydrofluoric acid catalysts, reducing the cost and the hazardous nature of the alkylation process. The types of ions, the number of ion beam exposures, the exposure duration, and the ion beam current can be adjusted to preferentially encourage 1+1 addition reactions between the olefins and isoparaffins, and to discourage extended polymerization reactions from occurring.

(iii) Catalytic Reforming and Isomerization

In catalytic reforming processes, hydrocarbon molecular structures are rearranged to form higher-octane aromatics for the production of gasoline; a relatively minor amount of cracking occurs. Catalytic reforming primarily increases the octane of motor gasoline.

Typical feedstocks to catalytic reformers are heavy straight-run naphthas and heavy hydrocracker naphthas, which include paraffins, olefins, naphthenes, and aromatics. Paraffins and naphthenes undergo two types of reactions during conversion to higher octane components: cyclization, and isomerization. Typically, paraffins are isomerized and converted, to some extent, to naphthenes. Naphthenes are subsequently converted to aromatics. Olefins are saturated to form paraffins, which then react as above. Aromatics remain essentially unchanged.

During reforming, the major reactions that lead to the formation of aromatics are dehydrogenation of naphthenes and dehydrocyclization of paraffins. The methods disclosed herein can be used before, during, and/or after catalytic reformation to treat components of crude oil. In particular, ion beam exposure (alone, or in combination with other methods) can be used to initiate and sustain dehydrogenation reactions of naphthenes and/or dehydrocyclization reactions of paraffins to form aromatic hydrocarbons. Single or multiple exposures of the crude oil components to one or more different types of ions can be used to improve the yield of catalytic reforming processes. For example, in certain embodiments, dehydrogenation reactions and/or dehydrocyclization reactions proceed via an initial hydrogen abstraction. Exposure to negatively charged, basic ions can increase the rate at which such abstractions occur, promoting more efficient dehydrogenation reactions and/or dehydrocyclization reactions. In some embodiments, isomerization reactions can proceed effectively in acidic environments, and exposure to positively charged, acidic ions (e.g., protons) can increase the rate of isomerization reactions.

Catalysts used in catalytic reformation generally include platinum supported on an alumina base. Rhenium can be combined with platinum to form more stable catalysts that permit lower pressure operation of the reformation process. Without wishing to be bound by theory, it is believed that platinum serves as a catalytic site for hydrogenation and dehydrogenation reactions, and chlorinated alumina provides an acid site for isomerization, cyclization, and hydrocracking reactions. In general, catalyst activity is reduced by coke deposition and/or chloride loss from the alumina support. Restoration of catalyst activity can occur via high temperature oxidation of the deposited coke, followed by chlorination of the support.

In some embodiments, ion beam exposure can improve the efficiency of catalytic reformation processes by treating catalyst materials during and/or after reformation reactions occur. For example, catalyst particles can be exposed to ions that react with and oxidize deposited coke on catalyst surfaces, removing the coke and maintaining/returning the catalyst in/to an active state. The ions can also react directly with undeposited coke in the reformation reactor, preventing deposition on the catalyst particles. Moreover, the alumina support can be exposed to suitably chosen ions (e.g., chlorine ions) to re-chlorinate the surface of the support. By maintaining the catalyst in an active state for longer periods and/or scavenging reformation by-products, ion beam exposure can lead to improved throughput and/or reduced operating costs of catalytic reformation processes.

(iv) Catalytic Hydrocracking

Catalytic hydrocracking, a counterpart process to ordinary catalytic cracking, is generally applied to crude oil components that are resistant to catalytic cracking. A catalytic cracker typically receives as feedstock more easily cracked paraffinic atmospheric and vacuum gas oils as charge stocks. Hydrocrackers, in contrast, typically receive aromatic cycle oils and coker distillates as feedstock. The higher pressures and hydrogen atmosphere of hydrocrackers make these components relatively easy to crack.

In general, although many different simultaneous chemical reactions occur in a catalytic hydrocracker, the overall chemical mechanism is that of catalytic cracking with hydrogenation. In general, the hydrogenation reaction is exothermic and provides heat to the (typically) endothermic cracking reactions; excess heat is absorbed by cold hydrogen gas injected into the hydrocracker. Hydrocracking reactions are typically carried out at temperatures between 550 and 750° F., and at pressures of between 8275 and 15,200 kPa. Circulation of large quantities of hydrogen with the feedstock helps to reduce catalyst fouling and regeneration. Feedstock is typically hydrotreated to remove sulfur, nitrogen compounds, and metals before entering the first hydrocracking stage; each of these materials can act as poisons to the hydrocracking catalyst.

Most hydrocracking catalysts include a crystalline mixture of silica-alumina with a small, relatively uniformly distributed amount of one or more rare earth metals (e.g., platinum, palladium, tungsten, and nickel) contained within the crystalline lattice. Without wishing to be bound by theory, it is believed that the silica-alumina portion of the catalyst provides cracking activity, and the rare earth metals promote hydrogenation. Reaction temperatures are generally raised as catalyst activity decreases during hydrocracking to maintain the reaction rate and product conversion rate. Regeneration of the catalyst is generally accomplished by burning off deposits which accumulate on the catalyst surface.

The methods disclosed herein can be used before, during, and/or after catalytic hydrocracking to treat components of crude oil. In particular, ion beam exposure (alone, or in combination with other methods) can be used to initiate hydrogenation and/or cracking processes. Single or multiple exposures of the crude oil components to one or more different types of ions can be used to improve the yield of hydrocracking by tailoring the specific exposure conditions to various process steps. For example, in some embodiments, the crude oil components can be exposed to hydride ions to assist the hydrogenation process. Cracking processes can be promoted by exposing the components to reactive ions such as protons and/or carbon ions.

In certain embodiments, ion beam exposure can improve the efficiency of hydrocracking processes by treating catalyst materials during and/or after cracking occurs. For example, catalyst particles can be exposed to ions that react with and oxidize deposits on catalyst surfaces, removing the deposits and maintaining/returning the catalyst in/to an active state. The crude oil components can also be exposed to ions that correspond to some or all of the metals used for hydrocracking, including platinum, palladium, tungsten, and nickel. This exposure to catalytic ions can increase the overall rate of the hydrocracking process.

(v) Other Processes

A variety of other processes that occur during the course of crude oil refining can also be improved by, or supplanted by, the methods disclosed herein. For example, the methods disclosed herein, including ion beam treatment of crude oil components, can be used before, during, and/or after refinery processes such as coking, thermal treatments (including thermal cracking), hydroprocessing, and polymerization to improve the efficiency and overall yields, and reduce the waste generated from such processes.

Other embodiments are within the scope of the following claims.

The invention claimed is:

1. A method comprising:
    converting a starchy material, comprising at least 5% by weight of starch, into a fuel by:
    irradiating the starchy material to change the molecular and/or supramolecular structure of the starchy material and thereby reduce its molecular weight;
    saccharifying the irradiated starchy material to produce a composition comprising sugars; and
    converting the sugars to a product comprising a hydrocarbon.

2. The method of claim 1, wherein the starchy material comprises amylose and amylopectin in a weight ratio of between 20:80 to 30:70.

3. The method of claim 1, wherein the starchy material is selected from the group consisting of maltodextrin, acid-modified starch, base-modified starch, bleached starch, oxidized starch, acetylated-starch, phosphate-modified starch, corn starch, wheat starch, potato starch, rice starch and combinations thereof.

4. The method of claim 1, wherein the starchy material comprises at least one starch selected from the group consisting of arracacha, buckwheat, banana, barley, cassava, kudzu, oca, sago, sorghum, regular household potatoes, sweet potato, taro, yams, bean, lentils, and peas.

5. The method of claim 1, wherein the hydrocarbon is selected from the group consisting of methane, ethane, propane, pentane, n-hexane, and combinations thereof.

6. The method of claim 1, wherein the fuel is an aviation fuel.

7. The method of claim 1, wherein the fuel is a motor fuel.

8. The method of claim 1, wherein the fuel is suitable for use in powering cars, trucks, tractors, ships, or trains.

9. The method of claim 1, wherein the fuel is suitable for use in an internal combustion engine.

10. The method of claim 1, wherein converting comprises contacting the sugars with a fermenting microorganism.

* * * * *